United States Patent
Davis et al.

(10) Patent No.: US 7,105,529 B2
(45) Date of Patent: *Sep. 12, 2006

(54) SUBSTITUTED OXINDOLE DERIVATIVES AS PROTEIN TYROSINE AND AS PROTEIN SERINE/THREONINE KINASE INHIBITORS AND COMPOSITIONS AND METHODS OF TREATING CHEMOTHERAPY AND RADIATION THERAPY SIDE EFFECTS

(75) Inventors: Stephen Thomas Davis, Durham, NC (US); Scott Howard Dickerson, Chapel Hill, NC (US); Stephen Vernon Frye, Durham, NC (US); Philip Anthony Harris, Raleigh, NC (US); Robert Neil Hunter, III, Raleigh, NC (US); Lee Frederick Kuyper, Durham, NC (US); Karen Elizabeth Lackey, Hillsborough, NC (US); Michael Joseph Luzzio, Groton, CT (US); James Marvin Veal, Apex, NC (US); Duncan Herrick Walker, Summit, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 556 days.

This patent is subject to a terminal disclaimer.

(21) Appl. No.: 09/999,331

(22) Filed: Nov. 30, 2001

(65) Prior Publication Data

US 2003/0069430 A1  Apr. 10, 2003

Related U.S. Application Data

(60) Division of application No. 09/262,351, filed on Mar. 4, 1999, now Pat. No. 6,369,086, which is a continuation-in-part of application No. PCT/EP98/05559, filed on Sep. 3, 1998.

(30) Foreign Application Priority Data

Sep. 5, 1997 (GB) ................................. 9718913.8

(51) Int. Cl.
*A61K 31/505* (2006.01)
*A61K 31/44* (2006.01)
*A61K 31/425* (2006.01)

(52) U.S. Cl. ........................ 514/272; 291/365; 291/366

(58) Field of Classification Search ................ 514/272, 514/291, 365, 366
See application file for complete search history.

(56) References Cited

U.S. PATENT DOCUMENTS

| 5,051,417 A | 9/1991 | Nadler et al. |
| 5,057,538 A | 10/1991 | Shiraishi et al. |
| 5,089,516 A | 2/1992 | Shiraishi et al. |
| 5,124,342 A | 6/1992 | Kerdesky et al. |
| 5,202,341 A | 4/1993 | Shiraishi et al. |
| 5,374,652 A | 12/1994 | Buzzetti et al. |
| 5,441,880 A | 8/1995 | Beach et al. |
| 5,443,962 A | 8/1995 | Draetta et al. |
| 5,449,755 A | 9/1995 | Roberts et al. |
| 5,488,057 A | 1/1996 | Buzzetti et al. |
| 5,496,828 A * | 3/1996 | Cullinan ..................... 514/324 |
| 5,627,207 A | 5/1997 | Buzzetti et al. |
| 5,672,508 A | 9/1997 | Gyruis et al. |
| 5,756,335 A | 5/1998 | Beach et al. |
| 5,770,423 A | 6/1998 | Beach et al. |
| 6,319,918 B1 | 11/2001 | Heckel et al. |
| 6,369,086 B1 | 4/2002 | Davis et al. |
| 6,387,919 B1 | 5/2002 | Davis et al. |
| 6,541,503 B1 | 4/2003 | Davis et al. |
| 6,620,818 B1 * | 9/2003 | Davis ....................... 514/228.2 |

FOREIGN PATENT DOCUMENTS

| EP | 0 436 333 A2 | 12/1990 |
| EP | 0 503 49 A1 | 2/1992 |
| EP | 0 503 349 B1 | 2/1992 |
| EP | 0 788 890 A1 | 2/1996 |
| WO | 93/01182 | 7/1992 |
| WO | 92/20796 A2 | 11/1992 |
| WO | 93/10242 | 11/1992 |
| WO | 94/28914 | 6/1993 |
| WO | 93/24514 | 12/1993 |
| WO | 94/23029 | 3/1994 |

(Continued)

OTHER PUBLICATIONS

Rozengurt, Current Opinion in Cell Biology, 1992, 4, pp. 161-165.

(Continued)

*Primary Examiner*—Kevin E. Weddington
(74) *Attorney, Agent, or Firm*—Jennifer L. Fox

(57) ABSTRACT

Compounds of formula (I): wherein X is N, CH, $CCF_3$, or $C(C_{1-12}$ aliphatic); $R^4$ is sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, $R^7$-sulfonyl, $R^7$ sulfonyl-$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Aryl-aminosulfonyl, $(R^8)_{1-3}$-Aryl-sulfonylamino, Het-amino, Het-sulfonyl, Het-aminosulfonyl, aminoiminoamino, or aminoiminoaminosulfonyl, $R^5$ is hydrogen; and further wherein $R^4$ and $R^5$ are optionally joined to form a fused ring, pharmaceutical formulations comprising them and their use in therapy, especially in the treatment of diseases mediated by CDK2 activity, such as alopecia induced by cancer chemotherapy or radiotherapy.

5 Claims, No Drawings

FOREIGN PATENT DOCUMENTS

| WO | 95/01349 | 5/1994 |
|---|---|---|
| WO | 96/00226 | 6/1994 |
| WO | 96/16964 | 10/1995 |
| WO | 96/22976 | 12/1995 |
| WO | 96/32380 | 3/1996 |
| WO | 96/12506 | 5/1996 |
| WO | 96/40116 | 6/1996 |
| WO | 97/25986 | 1/1997 |
| WO | 97/36867 | 2/1997 |
| WO | 97/27297 | 7/1997 |
| WO | 98/07695 | 8/1997 |
| WO | 98/07835 | 8/1997 |

OTHER PUBLICATIONS

Wilks, Progress in Growth Factor Research, 1990, 2, pp. 97-111.
Hanks et al., Science, 1988, 241, pp. 42-52.
Crews and Erikson, Cell, 1993, 74, pp. 215-217.
Ihle et al., Trends in Biochemical Sciences, 1994, 19, pp. 222-227.
Pelech and Sanghera, Trends in Biochemical Sciences, 1992, 17, pp. 233-238.
Massague and Roberts, Current Opinion in Cell Biology, 1995, 7, pp. 769-772.
Myerson et al., EMBO Journal, 1992, 11, pp. 2909-2917.
Draetta, Trends in Cell Biology, 1993, 3, pp. 287-289.
Murray and Kirschner, Nature, 1989, 339, pp. 275-280.
Solomon et al., Molecular Biology of the Cell, 1992, 3, pp. 13-27.
Ducommun et al., EMBO Journal, 1991, 10, pp. 3311-3319.
Gautier et al., Nature, 1989, 339, pp. 626-629.
Gould and Nurse, Nature, 1989, 342, pp. 39-45.
Krek and Nigg, EMBO Journal, 1991, 10, pp. 3331-3341.
Solomon et al., Cell, 1990, 63, pp. 1013-1024.
Pines, Trends in Biochemical Sciences, 1993, 18, pp. 195-197.
Sherr, Cell, 1993, 73, pp. 1059-1065.
Matsushime et al., Molecular & Cellular Biology, 1994, 14, pp. 2066-2076.
Ohtsubo and Roberts, Science, 1993, 259, pp. 1908-1912.
Quelle et al., Genes & Development, 1993, 7, pp. 1559-1571.
Resnitzky et al., Molecular & Cellular Biology, 1994, 14, pp. 1669-1679.
Girard et al., Cell, 1991, 67, pp. 1169-1179.
Pagano et al., EMBO Journal, 1992, 11, pp. 961-971.
Rosenblatt et al., Proceedings of the National Academy of Science USA, 1992, 89, pp. 2824-2828.
Walker and Maller, Nature, 1991, 354, pp. 314-317.
Pines, Current Opinion in Cell Biology, 1992, 4, pp. 144-148.
Lees, Current Opinion in Cell Biology, 1995, 7, pp. 773-780.
Hunter and Pines, Cell, 1994, 79, pp. 573-582.
Brickell, Critical Reviews in Oncogensis, 1992, 3, pp. 401-446.
Courtneidge, Seminars in Cancer Biology, 1994, 5, pp. 239-246.
Powis, Pharmacology & Therapeutics, 1994, 62, pp. 57-95.
Buchdunger et al., Proc. Nat. Acad. Sci. USA, vol. 92, 1995, pp. 2258-2262.
Hosoi et al., Journal of Biochemistry (Tokyo), 1995, 117, pp. 741-749.
Aplin et al., Journal of Neurochemistry, 1996, 67, pp. 699-707.
Tanaka et al., Nature, 1996, 383, pp. 528-531.
Borthwick et al., Biochemical & Biophysical Researc Communications, 1995, 210, pp. 738-745.
Badger et al., The Journal of Pharmacology and Experimental Therapeutics, 1996, 279, pp. 1453-1461.
Shawyer et al., Drug Discovery Today, 1997, 2, pp. 50-63.
He et al., Journal of Virology, 1997, 71, pp. 405-411.
Myers et al., Bioorganic & Medicinal Chemistry Letters, 1997, 7, pp. 421-424.
Vousden, FASEB Journal, 1993, 7, pp. 872-879.
Stone et al., Cancer Research, 1996, 56, pp. 440-452.
Perkins et al., Science, 1997, 275, pp. 523-527.
Baeuerle and Henkel, Annual Review of Immunology, 1994, 12, pp. 141-179.
Beg and Baltimore, Science, 1996, 274, pp. 782-784.
Wang et al., Science, 1996, 274, pp. 784-787.
Van Antwerp et al., Science, 1996, 274, pp. 787-789.
Armstrong, Clinical Infectious Diseases, 1993, 16, pp. 1-7.
Osmani et al., EMBO Journal, 1991, 10, pp. 2669-2679.
Kohn et al., Journal of Cellular Biochemistry, 54, 1994, pp. 440-452.
Osmani et al., Cell, vol. 67, Oct. 18, 1991, pp. 283-291.
Mohammed Kamel, et al., "Monoazo Metal Complex Forming Dyes Part v Dyes Derived from Isatin", J Chem. U. A. R. 9, No. 2, 139-144 (1966).
Vishnu J. Ram, et al., "Pesticidal mannich Bases Derived from Isatinimines", J Heterocycle Chem.; pp. 1367-1369, vol. 23, Sep.-Oct. 1986.
Xiaoyun Wu, et al., "Chemical Constituents of Isatis Indigotica", Planta Medica, pp. 55-57, 1997.
*Physicians Desk Reference*, 55th Edition, 2001, p. 1717.

* cited by examiner

SUBSTITUTED OXINDOLE DERIVATIVES AS PROTEIN TYROSINE AND AS PROTEIN SERINE/THREONINE KINASE INHIBITORS AND COMPOSITIONS AND METHODS OF TREATING CHEMOTHERAPY AND RADIATION THERAPY SIDE EFFECTS

This is a Divisional Application of prior U.S. application Ser. No. 09/262,351 filed on Mar. 4, 1999 now U.S. Pat. No. 6,369,086 which is Continuation-in-Part Application of International Application No. PCT/EP98/05559 filed Sep. 3, 1998, which claims priority from GB 9718913.8 filed Sep. 5, 1997.

The present application is a continuation-in-part application that claims the benefit of our pending application Patent Cooperation Treaty International Application Number PCT/EP/98/05559, International Filing Date Sep. 3, 1998, designating the United States of America, among others, which is a continuation application that claims the benefit of our United Kingdom Patent Application Number GB 9718913.8, filed Sep. 5, 1997. The benefit of priority is claimed pursuant to 35 U.S.C. Sections 120, and 365 and 37 C.F.R. Rules 1.78(a)(1), 494 and 495.

PART I, THE ORIGINAL DISCLOSURE

The present invention provides novel compounds, novel compositions, method of their use and methods of their manufacture, such compounds generally useful pharmacologically as agents in those disease states alleviated by the alteration of mitogen activated signalling pathways in general, and in particular in the inhibition or antagonism of protein kinases, which pathologically involve aberrant cellular proliferation, such disease states including tumor growth, restenosis, atherosclerosis, and thrombosis. In particular, the present invention relates to a series of substituted oxindole compounds, which exhibit protein tyrosine kinase and protein serine/threonine kinase inhibition, and which are useful in protecting a patient undergoing chemotherapy from chemotherapy-induced alopecia.

BACKGROUND OF THE INVENTION

Cell growth, differentiation, metabolism and function are extremely tightly controlled in higher eukaryotes. The ability of a cell to rapidly and appropriately respond to the array of external and internal signals it continually receives is of critical importance in maintaining a balance between these processes (Rozengurt, Current Opinion in Cell Biology 1992, 4, 161–5; Wilks, Progress in Growth Factor Research 1990, 2, 97–111). The loss of control over cellular regulation can often lead to aberrant cell function or death, often resulting in a disease state in the parent organism.

The protein kinases represent a large family of proteins which play a central role in the regulation of a wide variety of cellular processes and maintaining control over cellular function (Hanks, et al., Science 1988, 241, 42–52). A partial list of such kinases includes abl, ATK, bcr-abl, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, flt-1, Fps, Frk, Fyn, Hck, IGF-1R, INS-R, Jak, KDR, Lck, Lyn, MEK, p38, PDGFR, PIK, PKC, PYK2, ros, $tie_1$, $tie_2$, TRK, Yes, and Zap70.

One of the most commonly studied pathways involving kinase regulation is cellular signalling from receptors at the cell surface to the nucleus (Crews and Erikson, Cell 1993, 74, 215–7). One example of this pathway includes a cascade of kinases in which members of the Growth Factor receptor Tyrosine Kinases (such as EGF-R, PDGF-R, VEGF-R, IGF1-R, the Insulin receptor), deliver signals through phosphorylation to other kinases such as Src Tyrosine kinase, and the Raf, Mek and Erk serine/threonine kinase families (Crews and Erikson, Cell 1993, 74, 215–7; Ihle, et al., Trends in Biochemical Sciences 1994, 19, 222–7). Each of these kinases is represented by several family members (Pelech and Sanghera, Trends in Biochemical Sciences 1992, 17, 233–8) which play related, but functionally distinct roles. The loss of regulation of the growth factor signalling pathway is a frequent occurence in cancer as well as other disease states.

The signals mediated by kinases have also been shown to control growth, death and differentiation in the cell by regulating the processes of the cell cycle (Massague and Roberts, Current Opinion in Cell Biology 1995, 7, 769–72). Progression through the eukaryotic cell cycle is controlled by a family of kinases called cyclin dependent kinases (CDKs) (Myerson, et al., EMBO Journal 1992, 11, 2909–17). The regulation of CDK activation is complex, but requires the association of the CDK with a member of the cyclin family of regulatory subunits (Draetta, Trends in Cell Biology 1993, 3, 287–9; Murray and Kirschner, Nature 1989, 339, 275–80; Solomon, et al., Molecular Biology of the Cell. 1992, 3, 13–27). A further level of regulation occurs through both activating and inactivating phosphorylations of the CDK subunit (Draetta, Trends in Cell Biology 1993, 3, 287–9; Murray and Kirschner, Nature 1989, 339, 275–80; Solomon, et al., Molecular Biology of the Cell. 1992, 3, 13–27; Ducommun, et al., EMBO Journal 1991, 10, 3311–9; Gautier, et al., Nature 1989, 339, 626–9; Gould and Nurse, Nature 1989, 342, 3945; Krek and Nigg, EMBO Journal 1991, 10, 3331–41; Solomon, et al., Cell 990, 63, 1013–24). The coordinate activation and inactivation of different cyclin/CDK complexes is necessary for normal progression through the cell cycle (Pines, Trends in Biochemical Sciences 1993, 18, 195–7; Sherr, Cell 1993, 73, 1059–65). Both the critical G1-S and G2-M transitions are controlled by the activation of different cyclin/CDK activities. In G1, both cyclin D/CDK4 and cyclin E/CDK2 are thought to mediate the onset of S-phase (Matsushime, et al., Molecular & Cellular Biology 1994, 14, 2066–76; Ohtsubo and Roberts, Science 1993, 259, 1908–12; Quelle, et al., Genes & Development 1993, 7, 1559–71; Resnitzky, et al., Molecular & Cellular Biology 1994, 14, 1669–79). Progression through S-phase requires the activity of cyclin NACDK2 (Girard, et al., Cell 1991, 67, 1169–79; Pagano, et al., EMBO Journal 1992, 11, 961–71; Rosenblatt, et al., Proceedings of the National Academy of Science USA 1992, 89, 2824–8; Walker and Mailer, Nature 1991, 354, 314–7; Zindy, et al., Biochemical & Biophysical Research Communications 1992, 182, 1144–54) whereas the activation of cyclin A/cdc2 (CDK1) and cyclin B/cdc2 are required for the onset of metaphase (Draetta, Trends in Cell Biology 1993, 3, 287–9; Murray and Kirschner, Nature 1989, 339, 275–80; Solomon, et al., Molecular Biology of the Cell. 1992, 3, 13–27; Girard, et al., Cell 1991, 67, 1169–79; Pagano, et al., EMBO Journal 1992, 11, 961–71; Rosenblatt, et al., Proceedings of the National Academy of Science USA 1992, 89, 2824–8; Walker and Mailer, Nature 1991, 354, 314–7; Zindy, et al., Biochemical & Biophysical Research Communications 1992, 182, 1144–54). It is not surprising, therefore, that the loss of control of CDK regulation is a frequent event in hyperproliferative diseases and cancer. (Pines, Current Opinion in Cell Biology 1992, 4, 144–8; Lees, Current Opinion in Cell Biology 1995, 7, 773–80; Hunter and Pines, Cell 1994, 79, 573–82). The selective inhibition of CDKs is therefore an object of the present invention.

The compounds of the present invention are additionally useful in the treatment of one or more diseases afflicting mammals which are characterized by cellular proliferation in the areas of blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, diabetic nephropathy, malignant nephrosclerosis, thrombotic microangiopathy syndromes, organ transplant rejection and glomerulopathies. Metabolic disorders include psoriasis, diabetes mellitus, chronic wound healing, inflammation, neurodegenerative diseases, macular degeneration, and diabetic retinopathy.

Inhibitors of kinases involved in mediating or maintaining these disease states represent novel therapies for these disorders. Examples of such kinases include, but are not limited to: (1) inhibition of c-Src (Brickell, Critical Reviews in Oncogenesis 1992, 3, 401–46; Courtneidge, Seminars in Cancer Biology 1994, 5, 239–46), raf (Powis, Pharmacology & Therapeutics 1994, 62, 57–95) and the cyclin-dependent kinases (CDKs) 1, 2 and 4 in cancer (Pines, Current Opinion in Cell Biology 1992, 4, 144–8; Lees, Current Opinion in Cell Biology 1995, 7, 773–80; Hunter and Pines, Cell 1994, 79, 573–82), (2) inhibition of CDK2 or PDGF-R kinase in restenosis (Buchdunger, et al., Proceedings of the National Academy of Science USA 1995, 92, 2258–62), (3) inhibition of CDK5 and GSK3 kinases in Alzheimers (Hosoi, et al., Journal of Biochemistry (Tokyo) 1995, 117, 741–9; Aplin, et al., Journal of Neurochemistry 1996, 67, 699–707), (4) inhibition of c-Src kinase in osteoporosis (Tanaka, et al., Nature 1996, 383, 528–31), (5) inhibition of GSK-3 kinase in type-2 diabetes (Borthwick, et al., Biochemical & Biophysical Research Communications 1995, 210, 738–45); (6) inhibition of the p38 kinase in inflammation (Badger, et al., The Journal of Pharmacology and Experimental Therapeutics 1996, 279, 1453–61); (7) inhibition of VEGF-R 1-3 and TIE-1 and -2 kinases in diseases which involve angiogenesis (Shawver, et al., Drug Discovery Today 1997, 2, 50–63); (8) inhibition of UL97 kinase in viral infections (He, et al., Journal of Virology 1997, 71, 405–11); (9) inhibition of CSF-1R kinase in bone and hematopoetic diseases (Myers, et al., Bioorganic & Medicinal Chemistry Letters 1997, 7, 421–4), and (10) inhibition of Lck kinase in autoimmune diseases and transplant rejection (Myers, et al., Bioorganic & Medicinal Chemistry Letters 1997, 7, 417–20).

It is additionally possible that inhibitors of certain kinases may have utility in the treatment of diseases when the kinase is not misregulated, but is nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, FASEB Journal 1993, 7, 872–9). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone, et al., Cancer Research 1996, 56, 3199–202; Kohn, et al., Journal of Cellular Biochemistry 1994, 54, 440–52). Inhibition of CDKs 2 or 4 will prevent progression into the cycle in normal cells and limit the toxicity of cytotoxics which act in S-phase, G2 or mitosis. Furthermore, CDK2/cyclin E activity has also been shown to regulate NF-kB: Inhibition of CDK2 activity stimulates NF-kB-dependent gene expression, an event mediated through interactions with the p300 coactivator (Perkins, et al., Science 1997, 275, 523–7). NF-kB regulates genes involved in inflammatory responses, (such as hematopoietic growth factors chemokines and leukocyte adhesion molecules) (Baeuerle and Henkel, Annual Review of Immunology 1994, 12, 141–79) and may be involved in the suppression of apoptotic signals within the cell (Beg and Baltimore, Science 1996, 274, 782–4; Wang, et al., Science 1996, 274, 784–7; Van Antwerp, et al., Science 1996, 274, 787–9). Thus, inhibition of CDK2 may suppress apoptosis induced by cytotoxic drugs via a mechanism which involves NF-kB. This therefore suggests that inhibition of CDK2 activity may also have utility in other cases where regulation of NF-kB plays a role in etiology of disease. A further example may be taken from fungal infections: Aspergillosis is a common infection in immune-compromised patients (Armstrong, Clinical Infectious Diseases 1993, 16, 1–7). Inhibition of the *Aspergillus* kinases Cdc2/CDC28 or Nim A (Osmani, et al., EMBO Journal 1991, 10, 2669–79; Osmani, et al., Cell 1991, 67, 283–91) may cause arrest or death in the fungi, improving the therapeutic outcome for patients with these infections.

SUMMARY OF THE INVENTION

In brief summary, the invention comprises compounds of the formula (I):

A compound of formula (I):

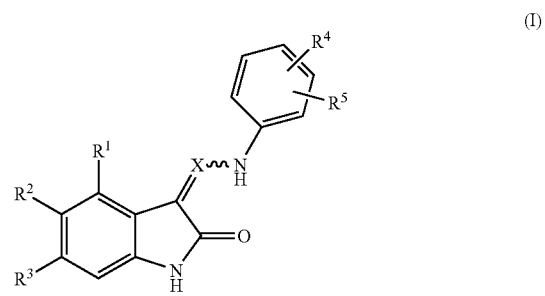

wherein
X is N, CH, CCF$_3$, or C(C$_{1-12}$ aliphatic);
R$^1$ is hydrogen, C$_{1-12}$ aliphatic, thiol, hydroxy, hydroxy-C$_{1-12}$ aliphatic, Aryl, Aryl-C$_{1-12}$ aliphatic, R$^6$-Aryl-C$_{1-12}$ aliphatic, Cyc, Cyc-C$_{1-6}$ aliphatic, Het, Het-C$_{1-12}$ aliphatic, C$_{1-12}$ alkoxy, Aryloxy, amino, C$_{1-12}$ aliphatic amino, di-C$_{1-12}$ aliphatic amino, di-C$_{1-12}$ aliphatic aminocarbonyl, di-C$_{1-12}$ aliphatic aminosulfonyl, C$_{1-12}$ alkoxycarbonyl, halogen, cyano, sulfonamide, or nitro, where R$^6$, Aryl, Cyc and Het are as defined below;

$R^2$ is hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Aryloxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl, or $C_{1-12}$ aliphatic-aminosulfonyl, where Aryl and Het are as defined below;

further wherein $R^1$ and $R^2$ are optionally joined to form a fused ring, said fused ring selected from the group as defined for Het below, or any of said fused rings optionally substituted by $C_{1-12}$ aliphatic, halogen, nitro, cyano, $C_{1-12}$ alkoxy, carbonyl-$C_{1-12}$ alkoxy or oxo;

$R^3$ is hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

further wherein $R^2$ and $R^3$ are optionally joined to form a fused ring, said fused ring selected from the group as defined for Het below, or any of said fused rings optionally substituted by $C_{1-6}$ aliphatic or $C_{1-6}$ aliphatic-carbonyl;

with the proviso that $R^1$, $R^2$, and $R^3$ cannot simultaneously be H;

$R^4$ is sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, $R^7$-sulfonyl, $R^7$-sulfonyl-$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Arylaminosulfonyl, $(R^8)_{1-3}$-Aryl-sulfonylamino, Het-amino, Het-sulfonyl, Het-aminosulfonyl, aminoiminoamino, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring selected from the group as defined for Het below, or any of said used rings optionally substituted by $C_{1-12}$ aliphatic, oxo or dioxo;

$R^6$ is $C_{1-12}$ aliphatic, hydroxy, $C_{1-12}$ alkoxy, or halogen;

$R^7$ is hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-2}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic, or hydroxyl where Het and Aryl are as defined below;

$R^8$ is hydrogen, nitro, cyano, $C_{1-12}$ alkoxy, halo, carbonyl-$C_{1-12}$ alkoxy or halo-$C_{1-12}$ aliphatic;

Aryl is phenyl, naphthyl, phenanthryl or anthracenyl;

Cyc is cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, quinoline, tetrahydrofuran, tetrazine, thidiazine, thiadiazole, thiatriazole, thiazine, thiazole, thiomorpholine, thiophene, thiopyran, triazine and triazole, with the proviso that when $R^2$ is thiadiazine, then $R^4$ cannot be methylsulfone;

and the pharmaceutically acceptable salts, biohydrolyzable esters, biohydrolyzable amides, biohydrolyzable carbamates solvates, hydrates, affinity reagents or prodrugs thereof in either crystalline or amorphous form.

A more preferred genus of compounds of the present invention includes compounds of formula (I), defined as follows:

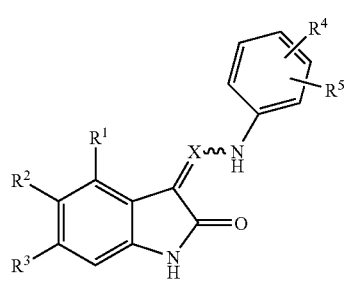

(I)

wherein

X is N, CH, or C($C_{1-6}$ aliphatic);

$R^1$ is hydrogen, $C_{1-6}$ aliphatic, hydroxy-$C_{1-6}$ aliphatic, Aryl-$C_{1-6}$ aliphatic, $R^6$-Aryl-$C_{1-6}$ aliphatic, Cyc-$C_{1-6}$ aliphatic, Het-$C_{1-6}$ aliphatic, $C_{1-6}$ alkoxy, Aryloxy, aminocarbonyl, di-$C_{1-6}$ aliphatic amino, di-$C_{1-6}$ aliphatic aminocarbonyl, di-$C_{1-6}$ aliphatic aminosulfonyl, $C_{1-6}$ alkoxycarbonyl, halogen, or nitro, where $R^6$, Aryl, Cyc and Het are as defined below;

$R^2$ is hydrogen, $C_{1-6}$ aliphatic, $R^7$-$C_{1-6}$ aliphatic, $C_{1-6}$ alkoxy, hydroxy-$C_{1-6}$ aliphatic, $C_{1-6}$ alkoxycarbonyl, carboxyl $C_{1-6}$ aliphatic, Aryl, $R^6$-Aryl-oxycarbonyl, $R^6$-oxycarbonyl-Aryl, Het, aminocarbonyl, $C_{1-6}$ aliphatic-aminocarbonyl, Aryl-$C_{1-6}$ aliphatic-aminocarbonyl, $R^6$-Aryl-$C_{1-6}$ aliphatic-aminocarbonyl, Het-$C_{1-6}$ aliphatic-aminocarbonyl, hydroxy-$C_{1-6}$ aliphatic-aminocarbonyl, $C_{1-6}$-alkoxy-$C_{1-6}$ aliphatic-aminocarbonyl, $C_{1-6}$ alkoxy-$C_{1-6}$ aliphatic-amino, di-$C_{1-6}$ aliphatic amino, di-$C_{1-6}$ aliphatic aminocarbonyl, di-$C_{1-6}$ aliphatic aminosulfonyl, halogen, hydroxy, nitro, sulfo, $C_{1-6}$ aliphatic-sulfonyl, aminosulfonyl, $C_{1-6}$ aliphatic-aminosulfonyl, or quaternary ammonium, where $R^7$, Aryl and Het are as defined below;

further wherein $R^1$ and $R^2$ are optionally joined to form a fused ring, said fused ring selected from the group as defined for Het above, or any of said fused rings optionally substituted by halogen or oxo;

$R^3$ is hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-6}$ aliphatic aminosulfonyl, $C_{1-6}$ alkoxy, Aryl, Aryloxy, hydroxy-Aryl, Het, hydroxy-Het, Het-oxy, or halogen, where Aryl and Het are as defined below;

further wherein $R^2$ and $R^3$ are optionally joined to form a fused ring, said fused ring selected from the group as defined for Het above, or any of said fused rings optionally substituted by $C_{1-6}$ aliphatic or $C_{1-6}$ aliphatic-carbonyl;

with the proviso that $R^1$, $R^2$ and $R^3$ cannot simultaneously be H;

$R^4$ is sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, $R^7$-sulfonyl, $R^7$-sulfonyl-$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Arylaminosulfonyl, $(R^8)_{1-3}$-Aryl-sulfonylamino, Het-amino, Het-sulfonyl, Het-aminosulfonyl, aminoiminoamino, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring selected from the group as defined for Het above, or any of said used rings optionally substituted by oxo or dioxo;

$R^6$ is hydrogen, $C_{1-6}$ aliphatic, hydroxy, $C_{1-6}$ alkoxy, or halogen;

$R^7$ is hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxy-alkoxyalkoxyaliphatic, or hydroxyl where Het and Aryl are as defined below;

$R^8$ is hydrogen or halo-$C_{1-6}$ aliphatic;

Aryl is phenyl, or naphthyl;

Cyc is cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole with the proviso that when $R^2$ is thiadiazine, then $R^4$ cannot be methylsulfone; and the pharmaceutically acceptable salts, biohydrolyzable esters, biohydrolyzable amides, biohydrolyzable carbamates, solvates, hydrates, affinity reagents or prodrugs thereof in either crystalline or amorphous form.

A highly preferred genus of compounds of the present invention includes compounds of formula (I), defined as follows:

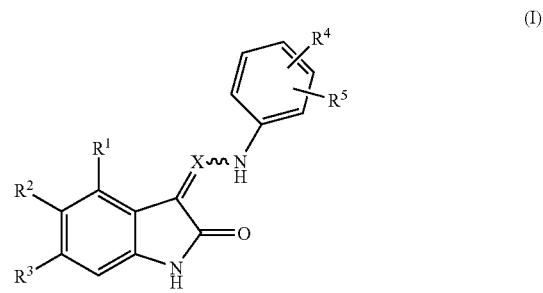

(I)

wherein

X is N, CH, or $CCH_3$, $R^1$ is hydrogen, $C_{1-6}$ aliphatic, hydroxy-$C_{1-6}$ aliphatic, di-$C_{1-6}$ aliphatic amino, di-$C_{1-6}$ aliphatic aminocarbonyl, di-$C_{1-6}$ aliphatic aminosulfonyl, Aryl-$C_{1-6}$ aliphatic, $R^6$-Aryl-$C_{1-6}$ aliphatic, Cyc-$C_{1-6}$ aliphatic, Het-$C_{1-6}$ aliphatic, $C_{1-6}$ alkoxy, Aryloxy, aminocarbonyl, $C_{1-6}$ alkoxycarbonyl, halogen, or nitro, where $R^6$, Aryl, Cyc and Het are as defined below;

$R^2$ is hydrogen, $C_{1-6}$ aliphatic, N-hydroxyimino-$C_{1-6}$ aliphatic, $C_{1-6}$ alkoxy, $C_{1-6}$ alkoxycarbonyl, Aryl, $R^6$-Aryloxycarbonyl, Het, aminocarbonyl, $C_{1-6}$ aliphatic aminocarbonyl, Aryl-$C_{1-6}$ aliphatic aminocarbonyl, $R^6$-Aryl-$C_{1-6}$ aliphatic aminocarbonyl, Het-$C_{1-6}$ aliphatic aminocarbonyl, di-$C_{1-6}$ aliphatic amino, di-$C_{1-6}$ aliphatic aminocarbonyl, di-$C_{1-6}$ aliphatic aminosulfonyl, hydroxy-$C_{1-6}$ aliphatic aminocarbonyl, $C_{1-16}$-alkoxy-$C_{1-6}$ aliphatic aminocarbonyl, $C_{1-6}$ alkoxy-$C_{1-6}$ aliphatic amino, halogen, hydroxy, nitro, $C_{1-6}$ aliphatic sulfonyl, or aminosulfonyl, $C_{1-6}$ aliphatic aminosulfonyl, where Aryl and Het are as defined below;

further wherein $R^1$ and $R^2$ are optionally joined to form a fused ring, said fused ring selected from the group as defined for Het below, or any of said fused rings optionally substituted by halogen or oxo;

$R^3$ is hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-16}$ aliphatic aminosulfonyl $C_{1-16}$ alkoxy, Aryloxy, Het, or halogen, where Aryl and Het are as defined below;

further wherein $R^2$ and $R^3$ are optionally joined to form a fused ring, said fused ring selected from the group as defined for Het below, or any of said fused rings optionally substituted by $C_{1-6}$ alkyl or $C_{1-6}$ alkylcarbonyl;

with the proviso that $R^1$, $R^2$ and $R^3$ cannot simultaneously be H;

$R^4$ is $R^7$-sulfonyl, $R^7$-sulfonyl $C_{1-6}$ aliphatic, $C_{1-6}$ aliphatic sulfonyl-$C_{1-6}$ aliphatic, $R^7$-aminosulfonyl, di-$C_{1-6}$ aliphatic amino, di-$C_{1-6}$ aliphatic aminocarbonyl, di-$C_{1-6}$ aliphatic aminosulfonyl, di-$C_{1-6}$ aliphatic aminosulfonyl-$C_{1-6}$ aliphatic, $R^7$-aminosulfonyl $C_{1-6}$ aliphatic, aminosulfonylamino, $R^7$-$C_{1-6}$ aliphatic aminosulfonyl-$C_{1-16}$ aliphatic, Aryl, Het, $R^8$-Aryl-aminosulfonyl, Het-aminosulfonyl, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring selected from the group as defined for Het below, or any of said used rings optionally substituted by oxo or dioxo;

$R^6$ is hydroxy, $C_{1-6}$ alkoxy, or halogen;

$R^7$ is hydrogen, $C_{1-6}$ aliphatic, hydroxy $C_{1-6}$-alkoxy, hydroxy-$C_{1-6}$ aliphatic, $C_{1-6}$ aliphatic carbonyl, Aryl-carbonyl, $C_{1-12}$ alkoxyalkoxyalkoxyalkoxyalkyl, hydroxyl, Aryl, Aryl-$C_{1-16}$-alkoxy, Aryl-$C_{1-6}$-aliphatic, Het, Het-$C_{1-6}$-alkoxy, di-Het-$C_{1-6}$-alkoxy, Het-$C_{1-6}$-aliphatic, di-Het-$C_{1-6}$-aliphatic;

$R^8$ is trifluoromethyl;

Aryl is phenyl;

Cyc is cyclobutyl;

Het is a saturated or unsaturated heteroatom ring system selected from the group consisting of benzimidazole, dihydrothiophene, dioxolane, furan, imidazole, morpholine, oxazole, pyridine, pyrrole, pyrrolidine, thiadiazole, thiazole, thiophene, and triazole, with the proviso that when $R^2$ is thiadiazine, then $R^4$ cannot be methylsulfone;

and the pharmaceutically acceptable salts, biohydrolyzable esters, biohydrolyzable amides, biohydrolyzable carbamates, solvates, hydrates, affinity reagents or prodrugs thereof in either crystalline or amorphous form.

A preferred group of compounds of the present invention with respect to the substitutions at $R^4$ are compounds of formula (I):

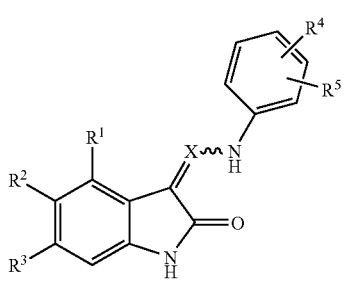

(I)

wherein

X is NH;

$R^1$ is hydrogen, $C_{1-12}$ aliphatic, thiol, hydroxy, hydroxy-$C_{1-12}$ aliphatic, Aryl, Aryl-$C_{1-12}$ aliphatic, $R^6$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, halogen, cyano, sulfonamide, or nitro, where $R^6$, Aryl, Cyc and Het are as defined below;

$R^2$ is hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Aryloxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl, or $C_{1-12}$ aliphatic-aminosulfonyl, where Aryl and Het are as defined below;

further wherein $R^1$ and $R^2$ are optionally joined to form a fused ring, said fused ring selected from the group as defined for Het below, or any of said fused rings optionally substituted by halogen, nitro, cyano, $C_{1-12}$ alkoxy, carbonyl-$C_{1-12}$ alkoxy or oxo;

$R^3$ is hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

further wherein $R^2$ and $R^3$ are optionally joined to form a fused ring, said fused ring selected from the group as defined for Het below, or any of said fused rings optionally substituted by $C_{1-6}$ aliphatic or $C_{1-6}$ aliphatic-carbonyl;

with the proviso that $R^1$, $R^2$ and $R^3$ cannot simultaneously be H;

$R^4$ is $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic aminosulfonyl, di-$C_{1-12}$ aliphatic aminosulfonyl-$C_{1-12}$ aliphatic, $(R^8)_{1-3}$-Aryl-aminosulfonyl, $(R^8)_{1-3}$-Aryl-sulfonylamino, or aminoiminoaminosulfonyl, where $R^7$, $R^8$, Aryl and Het are as defined below;

$R^5$ is hydrogen;

$R^6$ is $C_{1-12}$ aliphatic, hydroxy, $C_{1-12}$ alkoxy, or halogen;

$R^7$ is hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic, or hydroxyl where Het and Aryl are as defined below;

$R^8$ is hydrogen, nitro, cyano, $C_{1-12}$ alkoxy, halo, carbonyl-$C_{1-12}$ alkoxy or halo-$C_{1-12}$ aliphatic;

Aryl is phenyl, naphthyl, phenanthryl or anthracenyl;

Cyc is cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole with the proviso that when $R^2$ is thiadiazine, then $R^4$ cannot be methylsulfone;

and the pharmaceutically acceptable salts, biohydrolyzable esters, biohydrolyzable amides, biohydrolyzable carbamates solvates, hydrates, affinity reagents or prodrugs thereof in either crystalline or amorphous form.

Due to the presence of an oxindole exocyclic double bond, also included in the compounds of the invention are their respective pure E and Z geometric isomers as well as mixtures of E and Z isomers. The invention as described and claimed does not set any limiting ratios on prevalence of Z to E isomers. Thus compound number 104 in the tables below is disclosed and claimed as the E geometric thereof, the Z geometric isomer thereof and a mixture of the E and Z geometric isomers thereof, but not limited by any given ratio(s).

Likewise, it is understood that compounds of formula (I) may exist in tautomeric forms other than that shown in the formula.

Certain of the compounds as described will contain one or more chiral, or asymmetric, centers and will therefore be capable of existing as optical isomers that are either dextrorotatory or levorotatory. Also included in the compounds of the invention are the respective dextrorotatory or levorotatory pure preparations, and mixtures thereof.

Certain compounds of formula (I) above may exist in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) may exist in tautomeric forms other than that shown in the formula and these are also included within the scope of the present invention.

The present invention also provides compounds of formula (I) and pharmaceutically acceptable salts thereof (hereafter identified as the 'active compounds') for use in medical therapy, and particularly in the treatment of disorders mediated by CDK2 activity, such as alopecia induced by cancer chemotherapy.

A further aspect of the invention provides a method of treatment of the human or animal body suffering from a disorder mediated by a mitogen activated protein kinase which comprises administering an effective amount of an active compound of formula (I) to the human or animal patient.

Another aspect of the present invention provides the use of an active compound of formula (I), in the preparation of a medicament for the treatment of malignant tumors, or for the treatment of alopecia induced by cancer chemotherapy or induced by radiation therapy. Alternatively, compounds of formula (I) can be used in the preparation of a medicament for the treatment of a disease mediated by a kinase selected from the group consisting of ab1, ATK, bcr-ab1, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, flt-1, Fps, Frk, Fyn, Hck, IGF-1R, INS-R, Jak, KDR, Lck, Lyn, MEK, p38, PDGFR, PIK, PKC, PYK2, ros, tie$_1$, tie$_2$, TRK, Yes, and Zap70. Additionally, compounds of formula (I) can be used in the preparation of a medicament for the treatment of organ transplant rejection, of inhibiting tumor growth, of treating chemotherapy-induced alopecia, chemotherapy-induced thrombocytopenia or chemotherapy-induced leukopenia, or of treating a disease state selected from the group consisting of mucocitis, restenosis, atherosclerosis, rheumatoid arthritis, angiogenesis, hepatic cirrhosis, glomerulonephritis, diabetic nephropathy, malignant nephrosclerosis, thrombotic microangiopathy, a glomerulopathy, psoriasis, diabetes mellitus, inflammation, a neurodegenerative disease, macular degeneration, actinic keratosis and hyperproliferative disorders.

Another aspect of the present invention provides the use of an active compound of formula (I), in coadministration with previously known anti-tumor therapies for more effective treatment of such tumors.

Another aspect of the present invention provides the use of an active compound of formula (I) in the preparation of a medicament for the treatment of viral or eukaryotic infections.

Other aspects of the present invention related to the inhibition of mitogen activated protein kinases are discussed in more detail below.

Compounds we have synthesized as part of the present invention which are currently preferred are listed in Tables 1 and 2 below. Compounds are identified by the numbers shown in the first column; variables below in the rest of the columns are with reference to the generic structure (I). Corresponding IUPAC nomenclature are disclosed in Table 2. Since all substituents at each point of substitution are capable of independent synthesis of each other, the tables are to be read as a matrix in which any combination of substituents is within the scope of the disclosure and claims of the invention.

TABLE 1

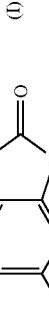

| Example | R¹ | R² | R³ | R⁴ | R⁵ | X |
|---|---|---|---|---|---|---|
| 1 | —NO$_2$ | H | H | 4'-SO$_2$NH$_2$ | H | N |
| 2 | —CONH$_2$ | H | H | 4'-SO$_2$NH$_2$ | H | N |
| 3 | —CH(CH$_3$)$_2$ | H | H | 4'-SO$_2$NH$_2$ | H | CH |
| 4 | —CH$_2$OH | H | H | 4'-SO$_2$NHCH$_3$ | H | |
| 5 | —CH$_2$CH$_2$—(4-pyridyl) | H | H | 4'-SO$_2$NH$_2$ | H | N |
| 6 | —CO$_2$CH$_2$CH$_3$ | H | H | 4'-SO$_2$NH$_2$ | H | CH |
| 7 | —CH$_2$CH(CH$_3$)$_2$ | H | H | 4'-SO$_2$NH$_2$ | H | N |
| 8 | —CH=C(CH$_3$)$_2$ | H | H | 4'-SO$_2$NH$_2$ | H | N |
| 9 | —CH=C(CH$_3$)CH$_2$CH$_3$ | H | H | 4'-SO$_2$NH$_2$ | H | N |
| 10 | and —CH$_2$C(CH$_3$)=CHCH$_3$ —CH$_2$CH(CH$_3$)CH$_2$CH$_3$ | H | H | 4'-SO$_2$NH$_2$ | H | N |
| 11 | —CH$_2$—(cyclobutyl) | H | H | 4'-SO$_2$NH$_2$ | H | N |
| 12 | =CH—(cyclobutylidene) | H | H | 4'-SO$_2$NH$_2$ | H | N |
| 13 | —CH$_2$CH$_2$—(4-hydroxyphenyl) | H | H | 4'-SO$_2$NH$_2$ | H | N |

TABLE 1-continued (I) structure with R¹, R², R³ on indolinone and R⁴, R⁵ on phenyl ring connected via X—N(H)—N group.

| Example | R¹ | R² | R³ | R⁴ | R⁵ | X |
|---|---|---|---|---|---|---|
| 15 | —CH=CH— (trans) 4-hydroxyphenyl | H | H | 4'-SO₂NH₂ | H | N |
| 16 | phenoxy (—O—C₆H₅) | H | H | 4'-SO₂NH₂ | H | N |
| 17 | OCH(CH₃)₂ | H | H | 4'-SO₂NH₂ | H | N |
| 18 | 3-methyl-1H-pyrazol-5-yl | H | H | 4'-SO₂NH₂ | H | N |
| 19 | H | 5-methyl-oxazol-2-yl | H | 4'-SO₂NH₂ | H | CH |
| 20 | H | pentafluorobenzoyloxy | H | 4'-SO₂NH₂ | H | N |
| 21 | H | —NO₂ | H | 4'-SO₂NH₂ | H | N |
| 22 | H | —OH | H | 4'-SO₂NH₂ | H | N |
| 23 | H | —CH₃ | H | 4'-SO₂NH₂ | H | N |

TABLE 1-continued

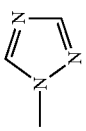

| Example | R¹ | R² | R³ | R⁴ | R⁵ | X |
|---|---|---|---|---|---|---|
| 24 | H | 1-methylimidazol-2-yl | H | 4'-SO$_2$NHCH$_3$ | H | N |
| 25 | H | —SO$_3^-$Na$^+$ | H | 4'-SO$_2$NH$_2$ | H | N |
| 26 | H | —CONH$_2$ | H | 4'-SO$_2$NHCH$_3$ | H | N |
| 27 | H | —CO$_2$CH$_3$ | H | 4'-SO$_2$NH$_2$ | H | CH |
| 28 | H | Br | H | 4'-SO$_2$CH$_3$ | H | CH |
| 29 | H | I | H | —NH—N═N— | H | CH |
| 30 | H | —SO$_2$NH$_2$ | H | 4'-SO$_2$NH$_2$ | H | N |
| 31 | H | —SO$_2$CH$_3$ | H | 4'-SO$_2$NH$_2$ | H | N |
| 32 | H | —SO$_2$NHCH$_3$ | H | 4'-SO$_2$NHCH$_3$ | H | N |
| 33 | H | —C(═NOH)CH$_3$ | H | 4'-SO$_2$NHCH$_3$ | H | N |
| 34 | H | 5-methyloxazol-2-yl | H | 4'-SO$_2$NH$_2$ | H | CCH$_3$ |
| 35 | H | 5-methyloxazol-2-yl | H | 4'-SO$_2$N(CH$_3$)$_2$ | H | CH |
| 36 | H | 5-methyloxazol-2-yl | H | 4'-SO$_2$NH$_2$ | H | N |
| 37 | H | -phenyl | H | 4'-SO$_2$NH$_2$ | H | CH |
| 38 | H | —CON(CH$_3$)$_2$ | H | 4'-SO$_2$NH$_2$ | H | N |

TABLE 1-continued
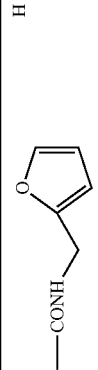
(I)
| Example | R¹ | R² | R³ | R⁴ | R⁵ | X |
|---|---|---|---|---|---|---|
| 39 | H | —CONH—CH₂—(2-furyl) | H | 4'-SO₂NH₂ | H | N |
| 40 | H | —CONH—CH₂—(2,6-dimethoxyphenyl) | H | 4'-SO₂NH₂ | H | N |
| 41 | H | —CONH—CH₂CH₂—(morpholin-4-yl) | H | 4'-SO₂NH₂ | H | N |
| 42 | H | —CONH—CH₂CH₂—(imidazol-1-yl) | H | 4'-SO₂NH₂ | H | N |
| 43 | H | —CONH—CH₂CH₂CH₂—(imidazol-1-yl) | H | 4'-SO₂NH₂ | H | N |
| 44 | H | —CONH(CH₂)₂OCH₃ | H | 4'-SO₂NH₂ | H | N |
| 45 | H | —CONH(CH₂)₂OH | H | 4'-SO₂NH₂ | H | N |
| 46 | H | —CONH(CH₂)₃OH | H | 4'-SO₂NH₂ | H | N |
| 47 | H | —CONH—CH₂—C(CH₃)₂—CH₂OH | H | 4'-SO₂NH₂ | H | N |

TABLE 1-continued

| Example | R¹ | R² | R³ | R⁴ | R⁵ | X |
|---|---|---|---|---|---|---|
| 48 | H | ![pyridine-CONH] | H | 4-SO₂NH₂ | H | N |
| 49 | H | ![pyridine-CONH] | H | 4-SO₂NH₂ | H | N |
| 50 | H | —OCH₃ | H | 4-SO₂NH₂ | H | N |
| 51 | H | —NH₃⁺Cl⁻ | H | 4-SO₂NH₂ | H | N |
| 52 | H | H | —CH₂CH₃ | 4-SO₂NH₂ | H | CH |
| 53 | H | H | H | SO₂OC₆H₅ | H | CH |
| 54 | H | H | —CH₂OH | 4-NHSO₂NH₂ | H | CH |
| 55 | H | H | Br | 4-SO₂NH₂ | H | N |
| 56 | H | H | —O—C₆H₅ | 4-SO₂NH₂ | H | N |
| 57 | H | H | —OCH₂CH₃ | 4-SO₂NH₂ | H | N |
| 58 | H | —NO₂ | H | 4-SO₂NH(CH₂)₂O(CH₂)₂OH | H | CH |
| 59 | —SCH=N— | | H | 4-SO₂NH(CH₃)₂OH | H | CH |
| 60 | —SCH=N— | | H | 4-SO₂NHCH₃ | H | N |
| 61 | —CH₃ | | H | 4-SO₂NH₂ | H | N |
| 62 | —CH—NNH | | H | 4-SO₂NH₂ | H | N |
| 63 | —NH—N=CH | | H | 4-SO₂NH₂ | H | N |
| 64 | —N=N—NH | | H | 4-SO₂NH₂ | H | N |
| 65 | —C(Cl)=NNH | | H | 4-SO₂NHCH₃ | H | N |
| 66 | —C(O)NHCH2 | | H | 4-CH₂SO₂NHCH₂C(CH₃)₂CH₂OH | H | N |
| 67 | —SCH=N— | | H | 4-CH₂SO₂NHCH₃ | H | CH |
| 68 | —CH=CHCH=N— | | H | 4-SO₂NH₂ | H | N |

TABLE 1-continued

Structure (I): indolin-2-one with R¹, R², R³ on benzene ring; =X-NH-aryl at 3-position; aryl has R⁴, R⁵.

| Example | R¹ | R² | R³ | R⁴ | R⁵ | X |
|---|---|---|---|---|---|---|
| 69 | —SCH=N— | | H | 4'-SO$_2$NH-(1H-indazol-6-yl) | H | CH |
| 70 | —SCH=N— | | H | 4'-SO$_2$NH-(thiazol-2-yl) | H | CH |
| 71 | —SCH=N— | | H | 4'-SO$_2$NH—C(=NH)NH$_2$ | H | CH |
| 72 | —SCH=N— | | H | 4'-SO$_2$NH-(pyridin-2-yl) | H | CH |
| 73 | —SCH=N— | | H | —CH$_2$SO$_2$CH$_3$ | H | CH |
| 74 | —SCH=N— | | H | 4'-CH$_2$SO$_2$NH$_2$ | H | CH |
| 75 | —SCH=N— | | H | 4'-CH$_2$SO$_2$NHCH$_2$CH=CH$_2$ | H | CH |
| 76 | —SCH=N— | | H | 4'-CH$_2$SO$_2$CH$_3$ | H | CH |
| 77 | —SCH=N— | | H | 4'-SO$_2$NHCH$_2$C(CH$_3$)$_2$CH$_2$OH | H | CH |
| 78 | —SCH=N— | | H | 4'-SO$_2$NH-(3-CF$_3$-phenyl) | H | CH |

TABLE 1-continued

| Example | R¹ | R² | R³ | R⁴ | R⁵ | X |
|---|---|---|---|---|---|---|
| 79 | —SCH=N— | | H | 4'-SO₂NH-(2-pyrimidinyl) | H | CH |
| 80 | —SCH=N— | | H | 4'-SO₂NH-(5-methyl-1,3,4-thiadiazol-2-yl) | H | CH |
| 81 | —SCH=N— | | H | 4'-SO₂NHCOCH₃ | H | CH |
| 82 | —SCH=N— | | H | 4'-SO₂NH-C(O)-phenyl | H | CH |
| 83 | —SCH=N— | H | H | 4'-SO₂NHCH₃ | H | N |
| 84 | —SCH=N— | H | H | 4'-SO₂N(CH₃)(CH₂)₂O(CH₂)₂OH | H | CH |
| 85 | —SCH=N— | —CH₃ | —CH₃ | 4'-SO₂NH[(CH₂)₂O]₄CH₃ | H | N |
| 86 | H | —NHCOCH₃ | —OH | 4'-SO₂NH₂ | H | N |
| 87 | H | —OCH₃ | Cl | 4'-CH₂SO₂NHCH₃ | H | N |
| 88 | H | —OH | —CH(CH₃)₂ | 4'-SO₂NH₂ | H | N |
| 89 | H | —N=C(CH₃)O— | H | 4'-SO₂NH₂ | H | N |
| 90 | H | —N(COCH₃)(CH₂)₂— | H | 4'-SO₂NH₂ | H | N |
| 91 | H | —OCH₂O— | H | 4'-SO₂NH₂ | H | N |
| 92 | H | —NH₃⁺(Br⁻)(CH₂)₂— | Cl | 4'-SO₂NH₂ | H | N |
| 93 | Cl | —OCH₃ | —CH₃ | 4'-CH₂SO₂NHCH₃ | H | N |
| 94 | Cl | —OH | —CH₃ | 4'-SO₂NH₂ | H | N |
| 95 | —CH₃ | —OH | H | —NHN=CH— | H | CH |
| 97 | H | H | H | —CH=NNH— | H | CH |
| 98 | H | H | H | | | CH |

TABLE 1-continued
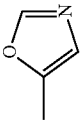
| Example | R¹ | R² | R³ | R⁴ | R⁵ | X |
|---|---|---|---|---|---|---|
| 99 | —CH₃ | —OH | —CH₃ | 4'-CH₂SO₂NHCH₃ | H | N |
| 100 | H | ![oxazole] | H | 4'-CH₂SO₂NHCH₃ | H | CH |
| 101 | —SCH=N— | —CO₂CH₂CH(CH₃)₂ | H | —N=N—NH— | H | CH |
| 102 | —CH=CHCH=N— | | H | 4'-SO₂NH₂ | H | N |
| 103 | H | | H | 4'-SO₂NH₂ | H | CH |
| 104 | —SCH=N— | | H | 4'-SO₂NHCH₂-(4-pyridyl) | H | CH |

Standard accepted nomenclature corresponding to the Examples set forth in this specification are set forth below. In some cases nomenclature is given for one or more possible isomers.

Example 1: 4-[N'-(4-Nitro-2-oxo-1,2-dihydro-indol-3-ylidene)-hydrazino]-benzenesulfonamide (Z isomer).

Example 2: 2-Oxo-3-[(4-sulfamoyl-phenyl)-hydrazono]-2,3-dihydro-1H-indole-4-carboxylic acid amide (E isomer).

Example 3: 4-[N'-(4-Isopropyl-2-oxo-1,2-dihydro-indol-3-ylidene)-hydrazino]-benzenesulfonamide (Z isomer).

Example 4: 4-[(4-Hydroxymethyl-2-oxo-1,2-dihydro-indol-3-ylidenemethyl)-amino]-N-methyl-benzenesulfonamide (Z-isomer).

Example 5: 4-{N'-[2-Oxo-4-(2-pyridin-4-yl-ethyl)-1,2-dihydro-indol-3-ylidene]-hydrazino}-benzenesulfonamide (Z isomer).

Example 6: 2-Oxo-3-(4-sulfamoyl-phenylamino-methylene)-2,3-dihydro-1H-indole-4-carboxylic acid ethyl ester (Z-isomer).

Example 7: 4-[N'-(4-Iodo-2-oxo-1,2-dihydro-indol-3-ylidene)-hydrazino]-benzenesulfonamide (Z-isomer).

Example 8: 4-[N'-(4-Isobutyl-2-oxo-1,2-dihydro-indol-3-ylidene)-hydrazino]-benzenesulfonamide (Z-isomer).

Example 9: 4-{N'-[4-(2-Methyl-propenyl)-2-oxo-1,2-dihydro-indol-3-ylidene]-hydrazino}-benzenesulfonamide (Z-isomer).

Example 10: 4-{N'-[4-(2-Methyl-1-butenyl)-2-oxo-1,2-dihydro-indol-3-ylidene]-hydrazino}-benzenesulfonamide and 4-{N'-[4-(2-methyl-2-butenyl)-2-oxo-1,2-dihydro-indol-3-ylidene]-hydrazino}-benzenesulfonamide (Z-isomer).

Example 11: 4-{N'-[4-(2-methylbutyl)-2-oxo-1,2-dihydro-indol-3-ylidene]-hydrazino}-benzenesulfonamide (Z-isomer).

Example 12: 4-[N'-(4-Cyclobutylmethyl-2-oxo-1,2-dihydro-indol-3-ylidene)-hydrazino]-benzenesulfonamide (Z isomer).

Example 13: 4-[N'-(4-Cyclobutylidenemethyl-2-oxo-1,2-dihydro-indol-3-ylidene)-hydrazino]-benzenesulfonamide (Z isomer).

Example 14: 4-(N'-{4-[2-(4-Hydroxyphenyl)-ethyl]-2-oxo-1,2-dihydro-indol-3-ylidene}-hydrazino)-benznensulfonamide (Z-isomer).

Example 15: 4-(N'-{4-[2-(4-Hydroxyphenyl)-vinyl]-2-oxo-1,2-dihydro-indol-3-ylidene}-hydrazino)-benznensulfonamide (Z-isomer).

Example 16: 4-[N'-(2-Oxo-4-phenoxy-1,2-dihydro-indol-3-ylidene)-hydrazino]-benzenesulfonamide (mixture of E and Z isomers).

Example 17: 4-[N'-(4-Isopropoxy-2-oxo-1,2-dihydro-indol-3-ylidene)-hydrazino]-benzenesulfonamide (Z-isomer).

Example 18: 4-{N'-[2-Oxo-4-(1H-pyrazol-3-yl)-1,2-dihydro-indol-3-ylidene]-hydrazino}-benzenesulfonamide (Z-isomer).

Example 19: 4-[(5-Oxazol-5-yl-2-oxo-1,2-dihydro-indol-3-ylidenemethyl)-amino]benzenesulfonamide (Z-isomer).

Example 20: 2-Oxo-3-[(4-sulfamoyl-phenyl)-hydrazone]-2,3-dihydro-1H-indole-5-carboxylic acid 2,3,4,5,6-pentafluorophenyl ester (Z-isomer).

Example 21: 4-[N'-(5-Nitro-2-oxo-1,2-dihydro-indol-3-ylidene)-hydrazino]-benzenesulfonamide (Z isomer).

Example 22: 4-[N'-(5-Hydroxy-2-oxo-1,2-dihydro-indol-3-ylidene)-hydrazino]-benzenesulfonamide (Z-isomer).

Example 23: 4-[N'-(5-Methyl-2-oxo-1,2-dihydro-indol-3-ylidene)-hydrazino]-benzenesulfonamide (E isomer).

Example 24: N-Methyl-4-[N'-(2-oxo-5-[1,2,4]triazol-1-yl-1,2-dihydro-indol-3-ylidene)-hydrazino]-benzenesulfonamide (Z isomer).

Example 25: 2-Oxo-3-[(4-sulfamoyl-phenyl)-hydrazono]-2,3-dihydro-1H-indole-5-sulfonic acid sodium salt (Z-isomer).

Example 26: 3-[(4-Methylsulfamoyl-phenyl)-hydrazono]-2-oxo-2,3-dihydro-1H-indole-5-carboxylic acid amide (Z-isomer).

Example 27: 2-Oxo-3-(4-sulfamoyl-phenylamino-methylene)-2,3-dihydro-1H-indole-5-carboxylic acid methyl ester (Z-isomer).

Example 28: 5-Bromo-3-[(4-Methylsulfonyl-phenyl)-hydrazono]-1,3-dihydro-indol-2-one (Z-isomer).

Example 29: 3-(3H-benzotriazol-5-ylamino-methylene)-5-iodo-1,3-dihydro-indol-2-one (Z-isomer).

Example 30: 2-Oxo-3-[(4-sulfamoyl-phenyl)-hydrazono]-2,3-dihydro-1H-indole-5-sulfonic acid amide (Z-isomer).

Example 31: 4-[N'-(5-Methylsulfonyl-2-oxo-1,2-dihydro-indol-3-ylidene)-hydrazino]-benzenesulfonamide (Z-isomer).

Example 32: 3-[(4-Methylsulfamoyl-phenyl)-hydrazono]-2-oxo-2,3-dihydro-1H-indole-5-sulfonic acid methylamide (Z-isomer).

Example 33: 4-{N'-[5-(1-Hydroxyimino-ethyl)-2-oxo-1,2-dihydro-indol-3-ylidene]-hydrazino}-N-methyl-benzenesulfonamide (Z-isomer).

Example 34: 4-[1-(5-Oxazol-5-yl-2-oxo-1,2-dihydro-indol-3-ylidene)-ethylamino]-benzenesulfonamide (Z-isomer).

Example 35: N,N-Dimethyl-4-[(5-oxazol-5-yl-2-oxo-1,2-dihydro-indol-3-ylidenemethyl)-amino]-benzenesulfonamide (Z-isomer).

Example 36: 4-[1-(5-Oxazol-5-yl-2-oxo-1,2-dihydro-indol-3-ylidene)-hydrazino]-benzenesulfonamide (mixture of E and Z isomers).

Example 37: 4-[(2-Oxo-5-phenyl-1,2-dihydro-indol-3-ylidenemethyl)-amino]-benzenesulfonamide (Z-isomer).

Example 38: 2-Oxo-3[(4-sulfamoyl-phenyl)-hydrazono]-2,3-dihydro-1H-indole-5-carboxylic acid dimethylamide (Z-isomer).

Example 39: 2-Oxo-3-[(4-sulfamoyl-phenyl)-hydrazono]-2,3-dihydro-1H-indol-5-carboxylic acid (furan-2-ylmethyl)-amide (Z-isomer).

Example 40: 2-Oxo-3-[(4-sulfamoyl-phenyl)-hydrazono]-2,3-dihydro-1H-indol-5-carboxylic acid-2,6-dimethoxybenzylamide (Z-isomer).

Example 41: 2-Oxo-3[(4-sulfamoyl-phenyl)-hydrazono]-2,3-dihydro-1H-indole-5-carboxylic acid(2-morpholin-4-yl-ethyl)-amide (Z-isomer).

Example 42: 2-Oxo-3-[(4-sulfamoyl-phenyl)-hydrazono]-2,3-dihydro-1H-indole-5-carboxylic acid (2-imidazol-1-yl-ethyl)-amide (Z-isomer).

Example 43: 2-Oxo-3-[(4-sulfamoyl-phenyl)-hydrazono]-2,3-dihydro-1H-indole-5-carboxylic acid (3-imidazol-1-yl-propyl)-amide (Z-isomer).

Example 44: 2-Oxo-3-[(4-sulfamoyl-phenyl)-hydrazono]-2,3-dihydro-1H-indole-5-carboxylic acid (2-methoxy-ethyl)-amide (Z-isomer).

Example 45: 2-Oxo-3-[(4-sulfamoyl-phenyl)-hydrazono]-2-3-dihydro-1H-indole-5-carboxylic acid (2-hydroxyethyl)-amide (Z-isomer).

Example 46: 2-Oxo-3-[(4-sulfamoyl-phenyl)-hydrazono]-2,3-dihydro-1H-indole-5-carboxylic acid (3-hydroxypropyl)-amide (Z-isomer).

Example 47: 2-Oxo-3-[(4-sulfamoyl-phenyl)-hydrazono]-2,3-dihydro-1H-indole-5-carboxylic acid (3-hydroxy-2,2-dimethylpropyl)-amide (Z-isomer).

Example 48: 2-Oxo-3-[(4-sulfamoyl-phenyl)-hydrazono]-2,3-dihydro-1H-indole-5-carboxylic acid (pyridin-3-ylmethyl)-amide (Z-isomer).

Example 49: 2-Oxo-3-[(4-sulfamoyl-phenyl)-hydrazono]-2,3-dihydro-1H-indole-5-carboxylic acid (pyridin-4-ylmethyl)-amide (Z-isomer).

Example 50: 4-[N'-(5-Methoxy-2-oxo-1,2-dihydro-indol-3-ylidene)-hydrazino]-benzenesulfonamide (Z-isomer).

Example 51: 4-[N'-(5-Amino-2-oxo-1,2-dihydro-indol-3-ylidene)-hydrazino]-benzenesulfonamide hydrochloride (Z-isomer).

Example 52: 4-[N'-(6-Ethyl-2-oxo-1,2-dihydro-indol-3-ylidene)-hydrazino]-benzenesulfonamide (Z isomer).

Example 53: 4-[(2-Oxo-1,2-dihydro-indol-3-ylidenemethyl)-amino]-benzensulfonic-acid-phenyl-ester (Z-isomer).

Example 54: N-{4-[(2-Oxo-1,2-dihydro-indol-3-ylidenemethyl)-amino]-phenyl}sulfamide (Z-isomer).

Example 55: 4-[(6-Hydroxymethyl-2-oxo-1,2-dihydro-indol-3-ylidenemethyl)-amino]-benzenesulfonamide (Z-isomer).

Example 56: 4-[N'-(6-Bromo-2-oxo-1,2-dihydro-indol-3-ylidene)-hydrazino]-benzenesulfonamide (Z-isomer).

Example 57: 4-[N'-(2-Oxo-6-phenoxy-1,2-dihydro-indol-3-ylidene)-hydrazino]-benzenesulfonamide (Z-isomer).

Example 58: 4-[N'-(6-Ethoxy-2-oxo-1,2-dihydro-indol-3-ylidene)-hydrazino]-benzenesulfonamide (Z-isomer).

Example 59: N-[2-(2-Hydroxyethoxy)ethyl]-4-[7-oxo-6,7-dihydro-1-thia-3,6-diaza-as-indacene-8-ylidenemethyl)-amino]benzenesulfonamide (Z-isomer).

Example 60: N-[2-(2-Hydroxyethyl]-4-[7-oxo-6,7-dihydro-1-thia-3,6-diaza-as-indacene-8-ylidenemethyl)-amino]benzenesulfonamide (Z-isomer).

Example 61: N-Methyl-4-[N'-(4-methyl-5-nitro-2-oxo-1,2-dihydro-indol-3-ylidene)-hydrazino]-benzenesulfonamide (Z-isomer).

Example 62: 4-[N'-(7-Oxo-6,7-dihydro-3H-pyrrolo[3,2-e]indazol-8-ylidene)-hydrazino]-benzenesulfonamide (Z isomer).

Example 63: 4-[N'-(7-Oxo-6,7-dihydro-i H-pyrrolo[2,3-g]indazol-8-ylidene)-hydrazino]-benzenesulfonamide (mixture of E and Z isomers).

Example 64: 4-[N'-(7-Oxo-6,7-dihydro-3H-1,2,3,6-tetraaza-as-indacen-8-ylidene)-hydrazino]-benzenesulfonamide (mixture of E and Z isomers).

Example 65: 4-[N'-(1-Chloro-7-oxo-6,7-dihydro-3H-pyrrolo[3,2-e]indazol-8-ylidene)-hydrazino]-benzenesulfonamide (Z isomer).

Example 66: 4-[N'-(1,7-Dioxo-2,3,6,7-tetrahydro-1H-2,6-diaza-as-indacen-8-ylidene)-hydrazino]-N-methyl-benzenesulfonamide (Z-isomer).

Example 67: N-(3-Hydroxy-2,2-dimethyl-propyl)-C-{4-[(7-oxo-6,7-dihydro-1-thia-3,6-diaza-as-indacen-8-ylidenemethyl)-amino]-phenyl}-methanesulfonamide (Z-isomer).

Example 68: N-Methyl-C-{4-[N'-(2-oxo-2,3-dihydro-pyrrolo[3,2-f]quinolin-1-ylidene)-hydrazino]-phenyl}-methanesulfonamide (Z-isomer).

Example 69: N-(1H-Indazol-6-yl)4-[(7-oxo-6,7-dihydro-1-thia-3,6-diaza-as-indacen-8-ylidenemethyl)-amino]-benzenesulfonamide (Z-isomer).

Example 70: 4-[(7-Oxo-6,7-dihydro-1-thia-3,6-diaza-as-indacen-8-ylidenemethyl)-amino]-N-thiazol-2-yl-benzenesulfonamide (Z-isomer).

Example 71: N-(Amino-imino-methyl)4-[(7-oxo-6,7-dihydro-1-thia-3,6-diaza-as-?indacen-8-ylidenemethyl)-amino]-benzenesulfonamide (Z-isomer).

Example 72: 4-[(7-Oxo-6,7-dihydro-1-thia-3,6-diaza-as-indacen-8-ylidenemethyl)-amino]-N-pyridin-2-yl-benzenesulfonamide (Z-isomer).

Example 73: 8-[(2,2-Dioxo-1,3-dihydro-benzo[c]thiophen-5-ylamino-methylene)-6,8-dihydro-1-thia-3,6-diaza-as-indacen-7-one (Z-isomer).

Example 74: {4-[(7-Oxo-6,7-dihydro-1-thia-3,6-diaza-as-indacen-8-ylidenemethyl)-amino]-phenyl}-methanesulfonamide (Z-isomer).

Example 75: N-Allyl-C-{4-[(7-oxo-6,7-dihydro-1-thia-3,6-diaza-as-indacen-8-ylidenemethyl)-amino]-phenyl}-methanesulfonamide (Z-isomer).

Example 76: 8-(4-Methylsulfonylmethyl-phenylamino-methylene)-6,8-dihydro-1-thia-3,6-diaza-as-indacen-7-one (Z-isomer).

Example 77: N-(3-Hydroxy-2,2-dimethyl-propyl)4-[(7-oxo-6,7-dihydro-1-thia-3,6-diaza-as-indacen-8-ylidenemethyl)-amino]-benzenesulfonamide (Z-isomer).

Example 78: 4-[(7-Oxo-6,7-dihydro-1-thia-3,6-diaza-as-indacen-8-ylidenemethyl)-amino]-N-(3-trifluoromethyl-phenyl)-benzenesulfonamide (Z-isomer).

Example 79: 4-[(7-Oxo-6,7-dihydro-1-thia-3,6-diaza-as-indacen-8-ylidenemethyl)-amino]-N-pyrimidin-2-yl-benzenesulfonamide (Z-isomer).

Example 80: N-(5-Methyl-[1,3,4]thiadiazol-2-yl)-4-(7-oxo-6,7-dihydro-1-thia-3,6-diaza-as-indacen-8-ylidenemethyl)-amino]-benzenesulfonamide (Z-isomer).

Example 81: N-Acetyl-4-[(7-oxo-6,7-dihydro-1-thia-3,6-diaza-as-indacen-8-ylidenemethyl)-amino]-benzenesulfonamide (Z-isomer).

Example 82: N-Benzoyl-4-[(7-oxo-6,7-dihydro-1-thia-3,6-diaza-as-indacen-8-ylidenemethyl)-amino]-benzenesulfonamide (Z-isomer).

Example 83: N-Methyl-4-[N'(7-oxo-6,7-dihydro-1-thia-3,6-diaza-as-indacen-8-ylidene)-hydrazino]-benzenesulfonamide (Z-isomer).

Example 84: N-[2-(2-Hydroxy-ethoxy)-ethyl]-N-methyl-4-[(7-oxo-6,7-dihydro-1-thia-3,6-diaza-as-indacen-8-ylidenemethyl)-amino]-benzenesulfonamide (Z-isomer).

Example 85: N-(2-{2-[2-(2-Methoxy-ethoxy)-ethoxy]-ethoxy}-ethyl)-4-[(7-oxo-6,7-dihydro-1-thia-3,6-diaza-as-indacen-8-ylidenemethyl)-amino]-benzenesulfonamide (Z-isomer).

Example 86: 4-[N'-(5,6-Dimethyl-2-oxo-1,2-dihydro-indol-3-ylidene)-hydrazino]-benzenesulfonamide (Z isomer).

Example 87: N-{6-Hydroxy-3-[(4-methylsulfamoylmethyl-phenyl)-hydrazono]-2-oxo-2,3-dihydro-1H-indol-5-yl}-acetamide (Z isomer).

Example 88: 4-[N'-(6-Chloro-5-methoxy-2-oxo-1,2-dihydro-indol-3-ylidene)-hydrazino]benzene-sulfonamide (Z-isomer).

Example 89: 4-[N'-(5-Hydroxy-6-isopropyl-2-oxo-1,2-dihydro-indol-3-ylidene)-hydrazino]-benzenesulfonamide (Z-isomer).

Example 90: 4-[N'-(2-Methyl-6-oxo-5,6-dihydro-3-oxa-1,5-diaza-s-indacen-7-ylidene)-hydrazino]-benzenesulfonamide (Z isomer).

Example 91: 4-[N'-(5-Acetyl-2-oxo-2,5,6,7-tetrahydro-1H-pyrrolo[2,3-f]indol-3-ylidene)-hydrazino]-benzenesulfonamide (Z-isomer).

Example 92: 4-[N'-(6-Oxo-5,6-dihydro-[1,3]-dioxolo[4,5-f]indol-7-ylidene)-hydrazino]-benzenesulfonamide (Z-isomer).

Example 93: 4-[N'-(2-Oxo-2,5,6,7-tetrahydro-1H-pyrrolo[2,3-f]indol-3-ylidene)-hydrazino]-benzenesulfonamide hydrobromide (Z-isomer).

Example 94: C-{4-[N'-(4,6-Dichloro-5-methoxy-2-oxo-1,2-dihydro-indol-3-ylidene)-hydrazino]-phenyl}-N-methyl-methanesulfonamide (Z isomer).

Example 95: 4-[N'-(4-Chloro-5-hydroxy-6-methyl-2-oxo-1,2-dihydro-indol-3-ylidene)-hydrazino]-benzenesulfonamide (Z-isomer).

Example 96: 4-[N'-(5-Hydroxy-4,6-dimethyl-2-oxo-1,2-dihydro-indol-3-ylidene)-hydrazino]-benzenesulfonamide (Z-isomer).
Example 97: 3-(1H-Indazol-5-ylamino-methylene)-1,3-dihydro-indol-2-one (Z-isomer).
Example 98: 3-[(1H-Indazol-6-yl)-hydrazone]-1,3-dihydro-indol-2-one (Z-isomer).
Example 99: 4-[N'-(5-Hydroxy-4,6-dimethyl-2-oxo-1,2-dihydro-indol-3-ylidene)-hydrazino]-phenyl}-N-methyl-methanesulfonamide (Z isomer).
Example 100: N-Methyl-4-[(5-oxazol-5-yl-2-oxo-1,2-dihydro-indol-3-ylidenemethyl)-amino]-phenylmethanesulfonamide (Z-isomer).
Example 101: 8-(3H-Benzotriazol-5-ylaminomethylene)-6,8-dihydro-1-thia-3,6-diaza-as-indacene-7-one (Z-isomer).
Example 102: 4-[N'-2-Oxo-2,3-dihydropyrrolo[3,2-f]quinolin-1-ylidene)hydrazino]-benzenesulfonamide (Z-isomer).
Example 103: 2-Oxo-3-(4-sulfamoyl-phenylamino-methylene)-2,3-dihydro-1H-indole-5-carboxylic acid isobutyl ester (Z-isomer).
Example 104: 4-[(7-Oxo-6,7-dihydro-1-thia-3,6-diaza-as-indacen-8-ylidenemethyl)amino]-N-pyridinyl-4-yl-methyl benzenesulfonamide (Z-isomer).

The invention discloses six different points of substitution on structural formula (I). Each of these points of substitution bears a substituent whose selection and synthesis as part of this invention was independent of all other points of substitution on formula (I). Thus, each point of substitution is now further described individually.

Preferred substitutions at the $R^1$ position include hydrogen, halogen, amide, nitro, lower alkyl, hydroxy, hydroxyalkyl, pyrimidineloweralkyl, loweralkoxycarbonyl, cyclic loweralkyl, hydroxyphenylloweralkyl, phenoxy, alkoxy, or pyrazole, or are fused with $R^2$ to form fused thiazole, pyrazole, triazole, halogen-substituted diazole, acyl substituted pyrrole, and pyridine, rings. Most preferred are hydrogen, methyl and fused with $R^2$ for form fused thiazole and fused pyridine. Most highly preferred are to be fused with $R^2$ to form fused thiazole.

Preferred substitutions at the $R^2$ position include hydrogen, halogen, sulfate, amine, quaternary amine, amide, ester, phenyl, alkoxy, aminosulfonyl, lower alkyl sulfonyl, furanyl lower alkyl amide, pyridinyl lower alkyl amide, alkoxy-substituted phenyl lower alkyl amide, morpholino lower alkyl amide, imidazolyl lower alkyl amide, hydroxy lower alkyl amide, alkoxy lower alkyl amide, lower alkyl amide, lower alkyl sulfonamide, lower alkyl hydroxy substituted amino, nitro, halogen-substituted phenoxycarbonyl, or triazole or oxazole rings, or are fused with $R^3$ to form a fused oxazole, pyrrole, or dioxolane ring, which fused rings can be substituted by lower alkyl, lower alkyl carbonyl, or, when said fused ring is a hetero ring having nitrogen as the heteroatom, forming a quaternary ammonium salt ionically bonded with a halogen atom. Most preferred are hydrogen, hydroxyl, oxazolyl, or fused with $R^1$ to form fused thiazolyl or fused pyridyl Most highly preferred are to be fused with $R^1$ to form fused thiazole.

Preferred substitutions at $R^3$ include hydrogen, lower alkyl, hydroxy lower alkyl, halogen, phenoxy, and alkoxy. Most preferred are hydrogen and methyl. Most highly preferred is hydrogen.

Preferred substitutions at $R^4$ include sulfonamide, sulfonamideamino, lower alkyl sulfonamide, lower alkylsulfonyl lower alkyl, alkoxysulfonamide, phenylcarbonylsulfonamide, phenoxysulfonyl, hydroxy lower alkylsulfonamide, hydroxy lower alkylsulfonamide lower alkyl, alkyl, phenylsulfonamide, optionally substituted by halogen substituted lower alkyl, aminoiminosulfonamide, alkylsulfonamidealkyl, pyridinyl lower alkyl sulfonamide, benzamideazolesulfonamide, pyridylsulfonamide, pyrimidinylsulfonamide, thiadiazolylsulfonamide optionally substituted by lower alkyl, thiazolesulfonamide, hydroxyalkoxyalkylsulfonamide, or the group 4'-$SO_2NH[(CH_2)_2O]_4CH_3$, or are fused with $R^5$ to form a fused imidazole, triazole, cyclic sulfonamide or thiaphene ring optionally disubstituted on the sulfur heteroatom by oxo. The most preferred substitutions are 2 pyridine sulfonamide, 4 pyridine sulfonamide, hydroxy n-butyl sulfonamide, methylsulfonamidemethylene, dimethylaminosulfonyl, fused 1,2,3-triazole, and sulfonamide. Most highly preferred is 2 pyridine sulfonamide, 4 pyridine sulfonamide and hydroxy n-butyl sulfonamide.

The preferred substitution at $R^5$ is hydrogen.

Preferred substitutions at X include N, CH, and CCH$_3$. Most preferred is NH.

Preferred individual compounds of the present invention include any one of the following compounds:

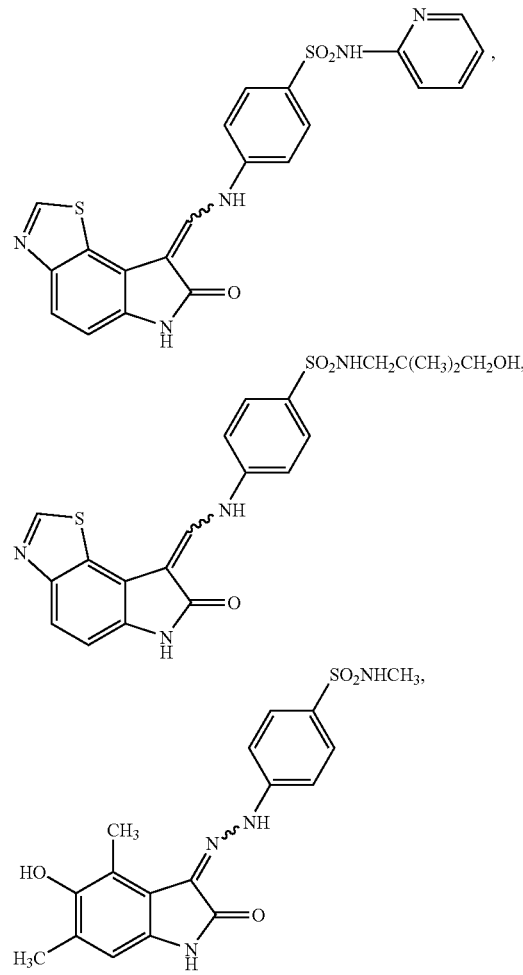

-continued

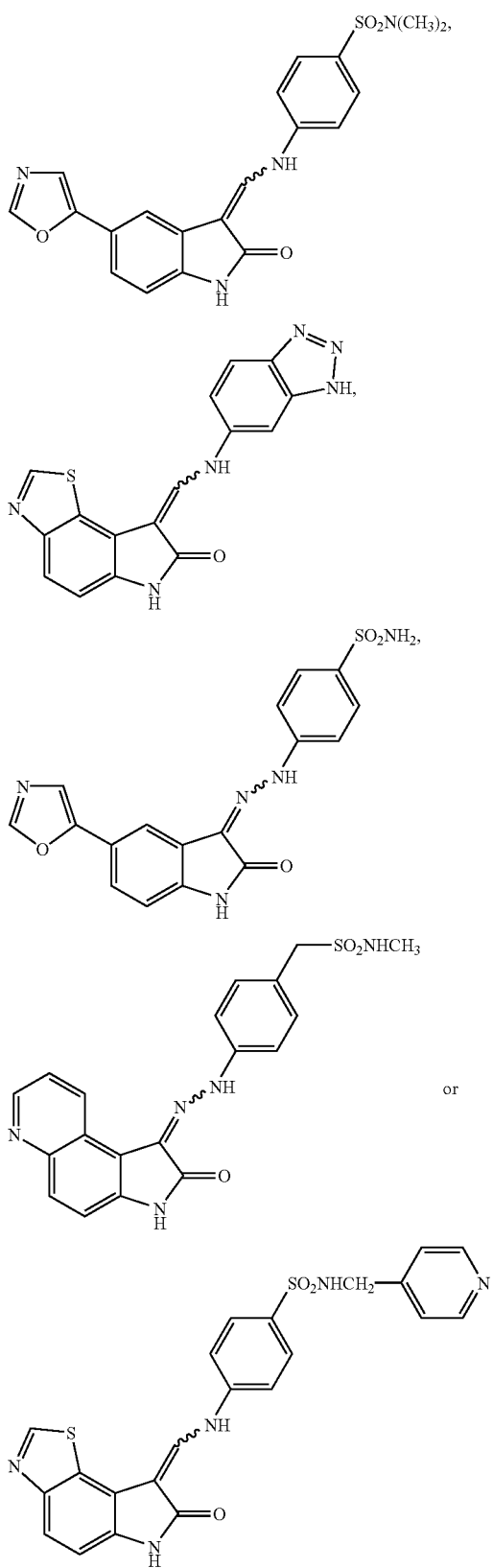

-continued
Highly preferred compounds include

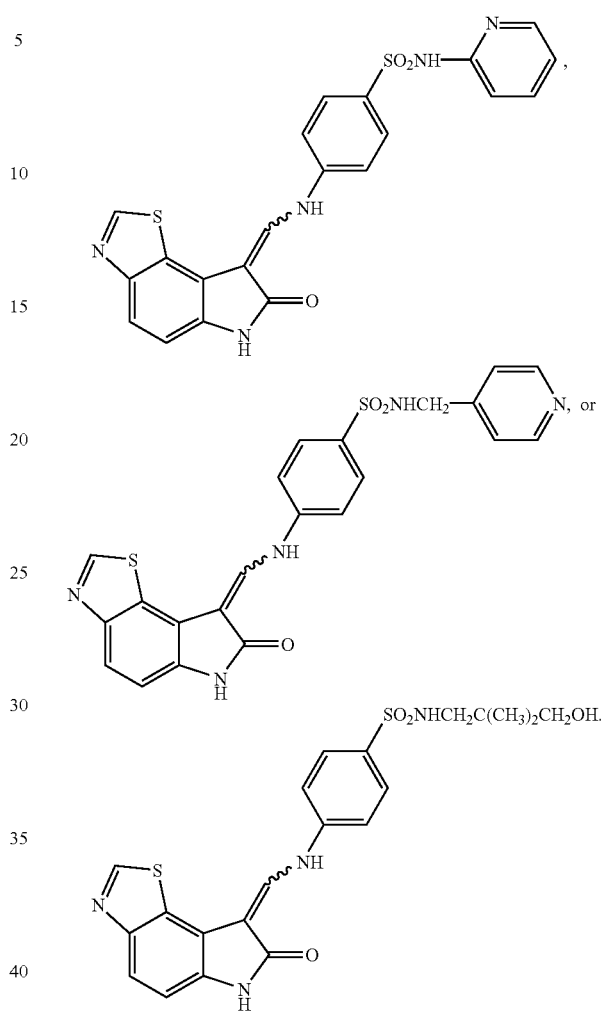

DETAILED DESCRIPTION OF THE INVENTION

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Diethanolamine, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Metaphosphoric, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teociate, Tosylate, Trifluoroacetate, Triethiodide, Trimethylammonium and Valerate.

Other salts which are not pharmaceutically acceptable may be useful in the preparation of compounds of formula (I) and these form a further aspect of the invention.

Also included within the scope of the invention are the individual isomers of the compounds represented by formula (I) above as well as any wholly or partially equilibrated mixtures thereof. The present invention also covers the individual isomers of the compounds represented by formula above as mixtures with isomers thereof in which one or more chiral asymmetric centers are inverted.

As used herein, the term "aliphatic" refers to the terms alkyl, alkylene, alkenyl, alkenylene, alkynyl, and alkynylene.

As used herein, the term "lower" refers to a group having between one and six carbons.

As used herein, the term "alkyl" refers to a straight or branched chain hydrocarbon having from one to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkyl" as used herein include, but are not limited to, n-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, aminosulfonyl optionally substituted by alkyl, nitro, cyano, halogen, or lower perfluoroalkyl, multiple degrees of substitution being allowed. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkenylene" refers to an straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, the term "cycloaliphatic" refers to the terms cycloalkyl, cycloalkylene, cycloalkenyl, cycloalkenylene, cycloalkynyl and cycloalkylnylene.

As used herein, "cycloalkyl" refers to a alicyclic hydrocarbon group with one or more degrees of unsaturation, having from three to twelve carton atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene-4-yl, and the like.

As used herein, the term "cycloalkenylene" refers to a substituted alicyclic divalent hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heteroatom ring system" refers to the terms heterocyclic, heterocyclyl, heteroaryl, and heteroarylene. Non-limiting examples of such heteroatom ring systems are recited in the Summary of the Invention, above.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to a benzene ring or to an optionally substituted benzene ring system fused to one or more optionally substituted benzene rings to form anthracene, phenanthrene, or napthalene ring systems, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of aryl include, but are not limited to, phenyl, 2-naphthyl, 1-naphthyl, biphenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms at any position, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO$, where $R_a$ is aliphatic.

As used herein, the term "alkylsulfanyl" refers to the group $R_aS$—, where $R_a$ is aliphatic.

As used herein, the term "alkylsulfenyl" refers to the group $R_aS(O)$—, where $R_a$ is aliphatic.

As used herein, the term "alkylsulfonyl" refers to the group $R_aSO_2$—, where $R_a$ is aliphatic.

As used herein, the term "acyl" refers to the group $R_aC(O)$—, where $R_a$ is aliphatic, cycloaliphatic, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is aliphatic.

As used herein, the term "acyloxy" refers to the group $R_aC(O)O$—, where $R_a$ is aliphatic, cycloaliphatic, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both conditions.

As used herein, the term "substituted" refers to substitution with the named substituent or substituents, multiple degrees of substitution being allowed.

As used herein, the terms "contain" or "containing" can refer to in-line substitutions at any position along the above-defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of formula (I)) and a solvent. Such solvents for the purpose of the invention may not interfere with the biological activity of the solute. Solvents may be, by way of example, water, ethanol, or acetic acid.

As used herein, the terms "biohydrolyzable carbonate", "biohydrolyzable ureide" and "biohydrolyzable carbamate" is a carbonate, ureide, or carbamate, respectively of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable carbamate is orally absorbed from the gut and is transformed to (I) in plasma. Many examples of such are known in the art and include by way of example lower alkyl carbamates.

As used herein, the term "biohydrolyzable ester" is an ester of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters, lower acyloxy-alkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, a-amino acid amides, alkoxyacyl amides, and alkylaminoalkylcarbonyl amides.

As used herein, the term "prodrug" includes biohydrolyzable amides, biohydrolyzable esters and biohydrolyzable carbamates and also encompasses a) compounds in which the biohydrolyzable functionality in such a prodrug is encompassed in the compound of formula (I): for example, a lactam formed by a carboxylic group in $R_1$ and an amine in $R_2$, and compounds which may be oxidized or reduced biologically at a given functional group to yield drug substances of formula (I). Examples of these functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" is a group attached to the compound of formula (I) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An example of an affinity reagent according to b) would be biotin either directly attached to (I) or linked with a spacer of one to 50 atoms selected from the group consisting of C, H, O, N, S, or P in any combination. An example of an affinity reagent according to a) above would be fluorescein, either directly attached to (I) or linked with a spacer of one to 50 atoms selected from the group consisting of C, H, O, N, S, or P in any combination.

The term "pharmacologically effective amount" shall mean that amount of a drug or pharmaceutical agent that will elicit the biological or medical response of a tissue, system, animal or human that is being sought by a researcher or clinician.

Whenever the terms "aliphatic" or "aryl" or either of their prefixes appear in a name of a substituent (e.g. arylalkoxyaryloxy) they shall be interpreted as including those limitations given above for "aliphatic" and "aryl". Aliphatic or cycloalkyl substituents shall be recognized as being term equivalents to those having one or more degrees of unsaturation. Designated numbers of carbon atoms (e.g. $C_{1-10}$) shall refer independently to the number of carbon atoms in an aliphatic or cyclic aliphatic moiety or to the aliphatic portion of a larger substituent in which the term "aliphatic" appears as a prefix (e.g. "al-").

As used herein, the term "disubstituted amine" or "disubstituted amino-" shall be interpreted to include either one or two substitutions on that particular nitrogen atom.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —S(O)$_2$—.

The compounds of formula (I) can be prepared readily according to the following reaction General Synthesis Scheme (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

General Synthesis Scheme

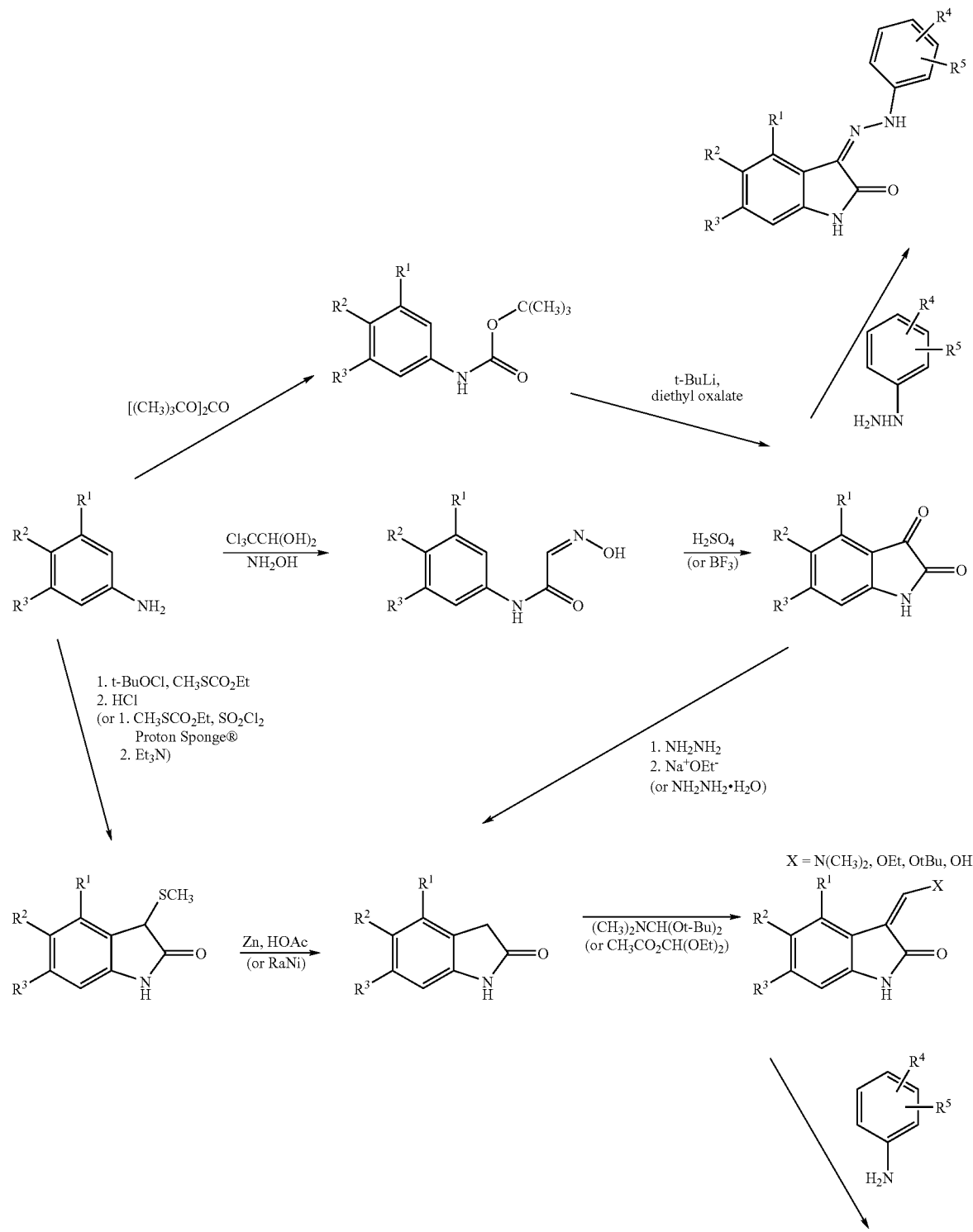

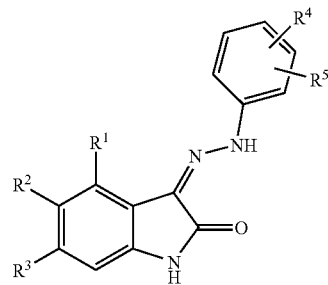

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:
g=grams
mg=milligrams
L=liters
mL=milliliters
M=molar
N=normal
mM=millimolar
i.v.=intravenous
p.o.=per oral
s.c.=subcutaneous
Hz=hertz
mol moles
mmol=millimoles
mbar=millibar
psi=pounds per square inch
rt=room temperature
min=minutes
h=hours
mp=melting point
TLC=thin layer chromatography
$R_f$=relative TLC mobility
MS=mass spectrometry
NMR=nuclear magnetic resonance spectroscopy
APCI=atmospheric pressure chemical ionization
ESI=electrospray ionization
m/z=mass to charge ratio
$t_r$=retention time
Pd/C=palladium on activated carbon
ether=diethyl ether
MeOH=methanol
EtOAc=ethyl acetate
TEA=triethylamine
DIEA=diisopropylethylamine
THF=tetrahydrofuran
DMF=N,N-dimethylformamide
DMSO=dimethylsulfoxide
DDQ=2,3-dichloro-5,6-dicyano-1,4-benzoquinone
LAH=lithium aluminum hydride
TFA=trifluoroacetic acid
LDA=lithium diisopropylamide
THP=tetrahydropyranyl
NMM=N-methylmorpholine, 4-methylmorpholine
HMPA=hexamethylphosphoric triamide
DMPU=1,3-dimethypropylene urea
d=days
ppm=parts per million
kD=kiloDalton
LPS=lipopolysaccharide
PMA=phorbol myristate acetate
SPA=scintillation proximity assay
EDTA=ethylenediamine tetraacetic acid
FBS=fetal bovine serum
PBS=phosphate buffered saline solution
BrdU=bromodeoxyuridine
BSA=bovine serum albumin
FCS=fetal calf serum
DMEM=Dulbecco's modified Eagle's medium
pfu=plaque forming units
MOI=multiplicity of infection Reagents are commercially available or are prepared according to procedures in the literature. The physical data given for the compounds exemplified is consistent with the assigned structure of those compounds. $^1$H NMR spectra were obtained on VARIAN Unity Plus NMR spectrophotometers at 300 or 400 Mhz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterisation, and to follow the progess of reactions. Unless otherwise stated, this was done using silica gel (Merck Silica Gel 60 F254). Unless otherwise stated, column chromatography for the purification of some compounds, used Merck Silica gel 60 (230400 mesh), and the stated solvent system under pressure.

Procedure A—First method for 1H-indol-2,3-dione (isatin) formation: preparation of 6-H-1-thia-3,6-diaza-as-indacen-7,8-dione.

To a 1-L flask was added a magnetic stir bar, 85 g of sodium sulfate, and 100 mL of water. The mixture was magnetically stirred until all the solids were dissolved. To the resultant aqueous solution was added a solution of 6-aminobenzothiazole (4.96 g, 33.0 mmol) in 50 mL of 1N aqueous hydrochloric acid and 10 mL of ethanol. The mixture was stirred, and chloral (6.0 g, (36 mmol) was added. To the resultant solution was added a solution of hydroxyl amine hydrochloride (7.50 g, 108 mmol) in 30 mL of water. The final mixture was heated with stirring to a gentle boil until all solids dissappeared, and heating was continued for an additional 15 min. The flask was removed from the heat, and the solution was poured onto 500 g of ice. The mixture was stirred as the product precipatated from solution. The precipatate was collected by suction filtration, washed thoroughly with water, filtered, and air dried to provide 6.9 g (94%) of N-benzothiazol-6-yl-2-hydroxy-imino-acetamide: $^1$H NMR (DMSO-$d_6$): δ 12.2 (s, 1H), 10.4 (s, 1H), 9.2 (s, 1H), 8.5 (s, 1H), 7.9 (d, 1H), 7.7 (m, 1H), 7.7 (s, 1H); APCI-MS m/z 220 (M−H)$^-$. To a 1-L 3-neck round bottom flask was placed a magnetic stir bar and 100 ml of concentrated sulfuric acid. The flask was fitted with a thermometer to monitor the temperature of the reaction. The sulfuric acid was heated to 100° C., and 10.0 g (45.2 mmol) of N-benzothiazol-6-yl-2-hydroxyimino-acetamide was added slowly. The solution was heated for 1 h, and the reaction mixture was poured into 750 g of ice and water. The residual reaction mixture in the reaction vessel was washed out with an additional 20 mL of cold water. The aqueous slurry was stirred for about 1 h and filtered. The solid was washed thoroughly with water, filtered, and air dried to yield 4.3 g (46%) of 6-H-1-thia-3,6-diaza-as-indacen-7,8-dione: $^1$H NMR (DMSO-$d_6$): δ 11.1 (s, 1H), 9.2 (s, 1H), 8.2 (d, 1H), 7.0 (d, 1H); APCI-MS m/z 203 (M−H)$^-$.

Procedure B—Second method for 1H-indol-2,3-dione (isatin) formation: preparation of 6-phenoxy-1H-indole-2,3-dione To a stirred solution of 1.0 g (6.0 mmol) of chloral hydrate in 25 mL of water was added 7.0 g (22 mmol) of sodium sulfate decahydrate, followed by a solution of 1.18 g (17.0 mmol) of hydroxylamine hydrochloride in 10 mL of water. A solution of 1.0 g (5.4 mmol) of 3-phenoxyaniline in 10 mL of 1.0 N HCl was then added with stirring. The resulting suspension was warmed, and 40 mL of 95% EtOH was added to dissolve the suspenion. The solution was refluxed for 0.75 h and then cooled to ambient temperature. The resulting solid was collected by vacuum filtration and air dried to afford 0.95 g (67%) of 2-hydroxyimino-N-(3-phenoxyphenyl)acetamide as a solid: $^1$H NMR (DMSO-$d_6$): δ 6.42 (d, J=8.4 Hz, 1H), 7.06 (d, J=7.9 Hz, 2H), 7.18 (t, J=7.3 Hz, 1H), 7.25–7.50 (m, 5H), 7.64 (s, 1H), 10.29 (s, 1H), 12.21 (s, 1H); APCI-MS: m/z 255 (M−H)$^-$. A suspension of 0.15 g (0.58 mmol) of 2-hydroxyimino-N-(3-phenoxyphenyl)acetamide in 0.4 mL of BF$_3$ etherate was heated to 85° C. for 0.75 h. The mixture was cooled to rt and 10 g of crushed ice was added. The resulting solid was collected by vacuum filtration and subjected to flash chromatography on silica gel (hexane/EtOAc 1.5:1) to afford 6-phenoxy-1H-indole-2,3-dione as a solid (0.018 g, 13%): $^1$H NMR (DMSO-$d_6$): δ 6.44 (d, J=2.0 Hz, 1H), 6.56 (dd, J=2.0, 8.4 Hz, 1H), 7.08 (d, J=8.2 Hz, 1H), 7.22–7.29 (m, 1H), 7.38–7.46 (m, 2H), 7.52 (d, J=8.4 Hz, 1H), 9.05 (s, 1H); APCI-MS: m/z 255 (M+Na)$^+$.

Procedure C—Third method for 1H-indol-2,3-dione (isatin) formation (Hewawasam and Meanwell, Tetrahedron Letters 1994, 35, 7303–6): reparation of 4-isopropoxy-1H-indol-2,3-dione and conversion to 4-[N'-(4-isopropoxy-2-oxo-1,2-dihydro-indol-3-ylidene)-hydrazino]-benzene-sulfonamide.

EXAMPLE 17

4-[N'-(4-Isopropoxy-2-oxo-1,2-dihydro-indol-3-ylidene)-hydrazino]-benzenesulfonamide A solution of 3.78 g (25.0 mmol) of 3-isopropoxy aniline and di-tert-butyl dicarbonate in 25 mL of THF was heated to reflux for 2 h. The solution was cooled to ambient temperature, and solvent was removed in vacuo. The residue was dissolved in 100 mL of EtOAc, and the solution was washed with three 50-mL portions of 0.5 M citric acid and 50 mL of brine. The solution was dried over MgSO$_4$ and removal of solvent in vacuo afforded N-(t-butyloxy-carbonyl)-3c acid and 50 mL of brine. The solution was dried over MgSO$_4$ and removal of solvent in vacuo afforded N-(t-butyloxy-carbonyl)-3-isopropoxyaniline as a white solid (5.75 g, 92%): mp 79–81° C.; $^1$H NMR (DMSO-$d_6$): δ 1.21 (d, J=6.0 Hz, 6H), 1.43 (s, 9H), 4.46 (septet, J=6 Hz, 1H), 6.47 (dd, J=2.1, 8.1 Hz, 1H), 6.94 (d, J=8.1 Hz, 1H), 7.0–7.1 (m, 2H), 9.23 (s, 1H); APCI-MS: m/z 274 (M+Na)$^+$. To a solution of 2.5 g (10 mmol) of N-(t-butyloxycarbonyl)-3-isopropoxyaniline in 15 mL of dry THF at −78° C. was added 15 mL (25 mmol) of 1.7 M t-butyllithium in hexanes. The mixture was stirred at −20° C. for 2 h. A solution of 1.84 g (12.5 mmol) of diethyl oxalate in 10 mL of dry THF was added slowly over 5 min, and the mixture was stirred at −20° C. for 2 h. The reaction mixture was then poured into 100 mL of 1.0 N HCl and extracted with two 100-mL portions of EtOAc. Solvent was removed in vacuo, and the residue was dissolved in 100 mL of a 1:1 mixture of EtOH and 6 N HCl and heated to reflux for 1 h. The mixture was cooled to ambient temperature and was extracted with four 100-mL portions of EtOAc. The combined extracts were evaporated to dryness to provide crude 4-isopropoxy-1H-indol-2,3-dione, which was dissolved in 10 mL of EtOH containing 0.50 g (2.2 mmol) of 4-sulfonamidophenylhydrazine hydrochloride. The solution was heated to 80° C. for 1 h and cooled to ambient temperature. The resulting solid was collected by vacuum filtration and purified by flash chromatography on silica gel (EtOAc/hexane 3:2) to afford the title compound as a yellow solid (0.052 g, 1.4%): mp>250° C.; $^1$H NMR (DMSO-$d_6$): δ 3.35 (d, J=6 Hz, 6H), 4.74 (septet, J=6 Hz, 1H), 6.48 (d, J=7.7 Hz, 1H), 6.69 (d, J=8 Hz, 1H), 7.14–7.2 (m, 3H), 7.47 (d, J=8.7 Hz, 2H), 7.75 (d, J=8.7 Hz, 2H), 11.01 (s, 1H), 12.79 (s, 1H); APCI-MS: m/z 373 (M−H)$^-$. Anal. Calcd for $C_{17}H_{18}N_4O_4S$: C, 54.53; H, 4.85; N, 14.96; S, 8.56. Found: C, 54.46; H, 4.84; N, 14.90; S, 8.50.

Procedure D—First method for 1,3-dihydro-indol-2-one (oxindole) formation (Gassman and van Bergen, Journal of the American Chemical Society 1974, 96, 5508–12): Preparation of 6,8-dihydro-1-thia-3,6-diaza-as-indacen-7-one.

A 2-L three-neck round bottom flask was fitted with an internal thermometer, 250-mL addition funnel, magnetic stir bar and septa. The flask was charged with nitrogen, 200 mL of dry THF, and 6-aminobenzothiazole (15.2 g, 0.100 mol). The mixture was stirred and cooled in a dry ice-acetone bath to an internal temperature of −74° C. A solution of tert-butyl hypoclorite (11.0 g, 0.103 mol) in 50 mL of dichloromethane was added over a 15 min period. The resultant solution was stirred for an additional 3 h at dry ice-acetone bath temperature. To the reaction was then added by slow, dropwise addition a solution of ethyl methylthioacetate (13.8 g, 0.103 mol) in 50 mL of dichloromethane. The resultant solution was stirred for an additional 3 h at dry ice-acetone bath temperature. A solution of triethyl amine (25.3 g, 0.250 mol) and 50 ml of dichloromethane was added at dry ice-acetone bath temperature, and the solution was stirred for 0.5 h. The cooling bath was removed, and the reaction was allowed to warm to rt. The reaction was then concentrated to a thick residue. The thick oil was resuspended in 200 mL of ether and 600 mL of 0.25 M hydrochloric acid. The mixture was allowed to stir for 24 h. The resulting solid was filtered from the mixture and triturated with water and ether. The solid was then resuspended in cold MeOH, filtered and dried under vacum for 16 h to yield 18.7 g (79%) of 8-methylsulfanyl-6,8-dihydro-1-thia-3,6-diaza-as-indacen-7-one: $^1$H NMR(DMSO-$d_6$)δ 10.8 (s, 1H), 9.2 (s, 1H), 8.0 (d, 1H), 7.1 (d, 1H), 1.8 (s, 3H); APCI-MS m/z 235 (M−H)$^-$. To a 500-mL erlenmeyer flask was added a stir bar, 8.1 g (0.034 moles) of 8-methylsulfanyl-6,8-dihydro-1-thio-3,6-diaza-as-indacen-7-one and 100 mL of glacial acetic acid. The mixture was stirred until all the starting material had dissolved. The reaction mixture was then diluted with 100 mL of THF. Zinc metal (16 g, 325 mesh) was then added. The heterogeneous mixture was then stirred and heated to 60° C. for 2.5 h. The mixture was vacuum filtered through a one half inch pad of celite. The residue on the filter pad was washed with additional THF. The filtrates were combined and concentrated to a wet solid. The solid was triturated with MeOH, filtered and air dried to yield 4.51 g (70%) of 6,8-dihydro-1-thia-3,6-diaza-as-indacen-7-one as a free-flowing solid: $^1$H NMR (DMSO-$d_6$): δ 10.5 (s, 1H), 9.1 (s, 1H), 7.9 (d, 1H), 7.0 (d, 1H), 3.6 (s, 2H); APCI-MS m/z 191 (M+H)$^+$.

Procedure E—Second method for 1,3-dihydro-indol-2-one (oxindole) formation (Johnson and Aristoff, Journal of Organic Chemistry 1990, 55, 1374–5): Preparation of 2-oxo-2,3-dihydro-1H-indole-5-carboxylic acid methyl ester and conversion to 2-oxo-3-(4-sulfamoyl-phenylamino-methylene)-2,3-dihydro-1H-indole-5-carboxylic acid methyl ester (Z-isomer).

EXAMPLE 27

2-Oxo-3-(4-sulfamoyl-phenylamino-methylene)-2,3-dihydro-1H-indole-5-carboxylic acid ethyl ester (Z-isomer)

A solution of 2.66 g (20.0 mmol) of ethyl (methylthio)acetate dissolved in 200 mL of dichloromethane was cooled with stirring to −70° C. and 2.7 g (20.0 mmol) of sulfuryl chloride was added. The reaction was stirred for 30 min. at −70° C., and a solution of 3.0 g (20 mol) of methyl 4-aminobenzoate and 4.3 g (20 mmol) of Proton Sponge® in 250 mL of dichloromethane was added dropwise over 1 h. The resulting pink slurry was treated with 2.3 g (23 mmol) of TEA in one portion, and the solution was allowed to warm to rt. The solution was washed with three 250-mL portions of water, dried over MgSO$_4$, and concentrated to give an oil. This was chromatographed on silica gel eluting with hexane:EtOAc (1:1) to yield 2.0 g (42% yield) of 3-methylthio-2-oxo-2,3-dihydro-1H-indole-5-carboxylic acid methyl ester: $^1$H NMR (DMSO-$d_6$): δ 1.97 (s, 3H), 3.35 (s, 3H), 4.67 (s, 1H), 6.97 (d, J=8.2 Hz, 1H), 7.84 (s, 1H), 7.91 (d, J=8.2 Hz, 1H), 10.97 (s, 1H). A solution of 2.0 g (8.4 mmol) of 3-methylthio-2-oxo-2,3-dihydro-1H-indole-5-carboxylic acid methyl ester in 20 mL of acetic acid was treated with 10 g of zinc powder. The reaction mixture was stirred for 2 h at rt, filtered through celite and concentrated to dryness. The residue was chromatographed on silica gel eluting with hexane:EtOAc (1:1) to yield 1.6 g (99% yield) of 2-oxo-2,3-dihydro-1H-indole-5-carboxylic acid methyl ester as a pink solid: $^1$H NMR (DMSO-$d_6$): δ 3.52 (s, 2H), 3.77 (s, 3H), 6.87 (d, J=8.2 Hz, 1H), 7.74 (s, J=1H), 7.80 (d, J=8.2 Hz, 1H), 10.72 (br s, 1H). Conversion to the 3-dimethylaminomethylene-2-oxo-2,3-dihydro-1H-indole-5-carboxylic acid methyl ester (mixture of E and Z isomers) was carried out via Procedure G in 49% yield: $^1$H NMR (DMSO-$d_6$): δ 3.29 Z (s, 6H), 3.31 E (s, 6H), 3.76 Z (s, 3H), 3.76 E (s, 3H), 6.74 Z (d, J=8.1 Hz, 1H), 6.81 E (d, J=8.2 Hz, 1H), 7.47–7.50 Z (m, 1H), 7.50–7.52 E (m, 1H), 7.57 E (dd, J=1.3, 8.2 Hz, 1H), 7.74 Z (s, 1H), 7.89 Z (s, 1H), 7.94 E (s, 1H), 10.33 Z (bs, 1H), 10.43 E (bs, 1H). The title compound was prepared in 41% yield from 3-[(dimethylamino)methylene]oxindole-5-carboxylic acid methyl ester and 4-aminobenzenesulfonamide according to Procedure J: $^1$H NMR (DMSO-$d_6$): δ 3.81 (s, 3H), 6.92 (d, J=8.2 Hz, 1H), 7.26 (s, 2H), 7.60 (d, J=8.4 Hz, 2H), 7.69 (d, J=8.2 Hz, 1H), 7.75 (d, J=8.4 Hz, 2H), 8.29 (s, 1H), 8.86 (d, J=12.4 Hz, 1H), 10.80 (d, J=12.4 Hz, 1H), 10.94 (s, 1H); APCI-MS m/z 372 (M−1)$^-$. Anal. Calcd for $C_{17}H_{15}N_3O_5S$: C, 54.68, H, 4.05; N, 11.25; S, 8.59. Found C, 54.65, H, 4.12; N, 11.17; S, 8.49.

Procedure F—Third method for 1,3-dihydro-indol-2-one (Oxindole) formation (Seibert, Chemie Berichte 1947, 80, 494–502): preparation of 3-H-pyrrolo[3,2-f]quinoline-2-one.

A solution of 2.3 g (12 mmol) of 3-H-pyrrolo[3,2-f]quinoline-1,2-dione and 2.0 ml (0.06 mol) of hydrazine in 50 ml of DMF and 50 ml of ethanol was stirred at reflux for 2 h. The resulting suspension was allowed to cool to ambient temperature and was then chilled in an ice bath and filtered. The solid was washed with a small volume of ethanol and allowed to air dry to give 1-hydrazono-1,3-dihydropyrrolo[3,2-f]quinolin-2-one as an orange solid (1.8 g, 73%): $^1$H NMR (DMSO-$d_6$): δ 7.37 (d, J=8.8 Hz, 1H), 7.47 (dd, J=8.4, 4.2 Hz, 1H), 7.81 (d, J=8.8 Hz, 1H), 8.71 (dd, J=4.2, 1.6 Hz, 1H), 8.80 (d, J=8.4 Hz, 1H), 9.90 (br d, J=14.7 Hz, 1H), 10.89 (br d, J=14.7 Hz, 1H), 10.95 (br s, 1H); ESI-MS m/z 213 (M+H)$^+$. A solution 1.8 g (8.5 mmol) of 1-hydrazono-1,3-dihydropyrrolo[3,2-f]quinolin-2-one in 50 ml of freshly prepared 0.5 M sodium ethoxide solution was stirred at reflux for 3 h. The solution was diluted with 50 ml of water, neutralized with acetic acid, and concentrated on a rotary evaporator until cloudy. The solution was stored in a refrigerator overnight. The solid was filtered off, and the filtrate was extracted with three 80-ml portions of EtOAc. A solution of the solid in MeOH/EtOAc was combined with the extracts and passed through a short pad of silica gel, eluting with EtOAc. The solution was then concentrated to a small volume on a rotary evaporator, and the resulting suspension was diluted with an equal volume of ethanol, sonicated, and filtered to give 3-H-pyrrolo[3,2-f]quinoline-2-one as a light green solid (0.52 g, 33%); $^1$H NMR (DMSO-$d_6$): δ 3.80 (s, 2H), 7.35 (d, J=8.8 Hz, 1H), 7.44 (dd, J=8.4, 4.2 Hz, 1H), 7.88 (d, J=8.8 Hz, 1H), 8.08 (d, J=8.4 Hz, 1H), 8.70 (dd, J=4.2, 1.6 Hz, 1H), 10.57 (br s, 1H); APCI-MS m/z 183 (M−H)$^-$.

Procedure G—Method for isatin hydrazone formation: preparation of C-{4-[N'-(5-hydroxy-4,6-dimethyl-2-oxo-1,2-dihydroindol(3-ylidene)hydrazino]phenyl}-N-methylmethanesulfonamide.

EXAMPLE 99

C-{4-[N'-(5-hydroxy-4,6-dimethyl-2-oxo-1,2-dihydroindol(3-ylidene)hydrazino]phenyl}-N-methylmethanesulfonamide 4,6-Dimethyl-5-hydroxy-1H-indol-2,3-dione was prepared from 3,5-dimethyl-4-hydroxyaniline according to Procedure A: $^1$H NMR (DMSO-$d_6$): δ 2.17 (s, 3H), 2.30 (s, 3H), 6.45 (s, 1H), 8.29 (s, 1H), 10.65 (s, 1H); ESI-MS m/z 190 (M−H)⁻. A mixture of 100 mg (0.52 mmol) of 4,6-dimethyl-5-hydroxy-1H-indol-2,3-dione and 144 mg (0.57 mmol) of C-(4-hydrazinophenyl)-N-methylmethanesulfonamide hydrochloride in 5 ml of EtOH was heated to 80° C. for 1 h. Upon cooling 10 ml of H$_2$O was added and the solid was collected by vacuum filtration and dried in a vacuum oven at 60° C. to afford the title compound as a yellow solid (79 mg, 79%); mp 252–255° C.; ¹H NMR (DMSO-d$_6$): δ 2.16 (s, 3H), 2.44 (s, 3H) 2.52 (d, J=4.9 Hz, 3H), 4.25 (s, 2H), 6.47 (s, 1H), 6.84 (q, J=4.9 Hz, 1H), 7.28–7.34 (m, 4H), 7.92 (s, 1H), 10.69 (s, 1H), 12.87 (s, 1H); APCI-MS m/z 411 (M+Na)⁺. Anal. Calcd for C$_{18}$H$_{20}$N$_4$O$_4$S: C, 55.66; H, 5.19; N, 14.42; S, 8.25. Found: C, 55.56; H, 5.21; N, 14.25; S, 8.08.

Procedure H—Method for dimethylaminomethinyloxindole formation: preparation of 8-dimethylamino-methylene-6,8-dihydro-1-thia-3,6-diaza-as-indacen-7-one.

To a suspension of 1.0 g (5.3 mmol) of 6,8-dihydro-1-thia-3,6-diaza-as-indacen-7-one in 7.5 mL of DMF was added 1.38 g (6.80 mmol) of N,N-dimethylformamide-di-t-butyl acetal. The mixture was stirred at ambient temperature for 1 h and diluted with 7.5 mL of Et$_2$O. The resulting precipitate was isolated filtration to afford 8-dimethylaminomethylene-6,8-dihydro-1-thia-3,6-diaza-as-indacen-7-one as a tan solid (1.0 g, 77%): ¹H NMR (DMSO-d$_6$): δ 3.33 (bs, 3H), 3.59 (bs, 3H), 6.97 (d, J=8.4, 1H), 7.33 (s, 1H), 7.62 (d, J=8.4, 1H), 9.13 (s, 1H), 10.29 (s, 1H); APCI-MS: m/z 246 (M+H)⁺.

Procedure I—Method for ethoxymethinyloxindole formation: preparation of 8-ethoxymethylene-6,8-dihydro-1-thia-3,6-diaza-as-indacen-7-one.

To a 250-ml round bottom flask was added a stir bar, 6.8-dihydro-1-thia-3,6-diaza-as-indacen-7-one (4.0 g, 0.021 mol), 40 mL of glacial acetic and diethoxymethyl acetate (17.0 g, 0.105 moles). The flask was fitted with a reflux condensor and charged with nitrogen. The reaction was heated to reflux for 8 h. The flask was cooled, the stir bar was removed and the reaction was concentrated to a wet solid. The solid was triturated with a solution of ether and ethanol. The mixture was filtered, the solid was washed with an ethanol-ether solution, and the solid was dried under vacuum to yield 8-ethoxymethylene-6,8-dihydro-1-thia-3,6-diaza-as-indacen-7-one: ¹H NMR (DMSO-d$_6$): δ 10.5 (s, 1H), 9.1 (s, 1H), 7.8 (d, 1H), 7.7 (s, 1H), 7.0 (d, 1H), 4.5 (q, 2H), 1.4 (t, 3H); APCI-MS m/z 245 (M−H)⁻.

Procedure J—Method for vinylogous urea formation: preparation of 4-[(7-oxo-6,7-dihydro-1-thia-3,6-diaza-as-indacen-8-ylidenemethyl)-amino]-N-pyridin-2-yl-benzenesulfonamide.

EXAMPLE 72

4-[(7-Oxo-6,7-dihydro-1-thia-3,6-diaz-as-indacen-8-ylidenemethyl)-amino]-N-pyridin-2-yl-benzene-sulfonamide To a 25 ml round bottom flask was added a stir bar, 246 mg (1.00 mmol) of 8-ethoxymethylene-6,8-dihydro-1-thia-3,6-diaza-as-indacen-7-one, 249 mg (1.00 mmol) of sulfapyridine and 10 ml of ethanol. The flask was fitted with a water-cooled reflux condenser, and the mixture was heated to reflux using an oil bath with stirring for 18 h. The reaction was allowed to cool and was filtered. The precipitate was washed with excess ethanol and dried under vacuum to yield 321 mg (71%) of the title compound: ¹H NMR (DMSO-d$_6$): δ 11.9 (br s, 1H), 11.2 (d, 1H), 10.9 (s, 1H), 9.3 (s, 1H), 8.1 (d, 2H), 7.9 (m, 3H), 7.8 (m, 1H), 7.6 (d, 2H), 7.2 (d, 1H), 7.2 (d, 1H), 6.9 (t, 1H); C$_{21}$H$_{15}$N$_5$O$_3$S$_2$: APCI-MS m/z 450 (M+H)⁺.

Note: One equivalent of strong acid, e.g., HCl or methanesulfonic acid, is generally required in this reaction. The acid can be supplied as the aniline salt or as a separate component. Similar conditions can be used for condensing anilines with 3-dimethylaminomethylene-, 3-t-butoxymethylene-, and 3-hydroxymethylene-substituted 2,3-dihydro-1H-indol-2-ones.

Procedure K—Method for 5-N-substituted amide formation: preparation of 2-oxo-3[(4-sulfamoyl-phenyl)-hydrazono]-2,3-dihydro-1H-indole-5-carboxylic acid dimethylamide

EXAMPLE 38

2-Oxo-3[(4-sulfamoyl-phenyl)-hydrazono]-2,3-dihydro-1H-indole-5-carboxylic acid dimethylamide To 100 mg (0.190 mmol) 2-oxo-3[(4-sulfamoyl-phenyl)-hydrazono]-2,3-dihydro-1H-indole-5-carboxylic acid pentafluorophenyl ester in 5 mL acetonitrile was added 50 μL (5.6 M in ethanol, 0.28 mmol) of a solution of dimethylamine and 20 μL (0.25 mmol) of pyridine, and the reaction was stirred overnight. The solution was concentrated, and the resulting solid was triturated with EtOAc to give the title compound as a yellow solid (39 mg, 53%): mp>230° C.; ¹H NMR (DMSO-d$_6$): δ 12.71 (s, 1H), 11.22 (s, 1H), 7.75 (d, J=8.8 Hz, 2H), 7.60 (s, 1H), 7.58 (d, J=8.8 Hz, 2H), 7.31 (dd, J=1.7, 8.1 Hz, 1H), 7.23 (s, 2H), 6.93 (d, J=8.0 Hz, 1H), 2.95 (s, 6H); APCI-MS: m/z 386 (m-H). Anal. Calcd for C$_{17}$H$_{17}$N$_5$O$_5$S-1/2H$_2$O: C, 51.51; H, 4.58; N, 17.67. Found: C, 51.69; H, 4.25; N, 17.63.

Procedure L—Method for introducing 4-substituents via palladium-catalyzed coupling: preparation of 4-(N'-{4-[2-(4-hydroxyphenyl)-vinyl]-2-oxo-1,2-dihydro-indol-3-ylidene}-hydrazino)-benzenesulfonamide (Z isomer).

EXAMPLE 15

4-(N'-{4-[2-(4-Hydroxyphenyl)-vinyl]-2-oxo-1,2-dihydro-indol-3-ylidene}-hydrazino)-benzene-sulfonamide (Z isomer)

A mixture of 1.0 g (3.6 mmol) of 4-iodo-1H-indole-2,3-dione (Snow, et al., Journal of the American Chemical Society 1977, 99, 3734–44), 0.42 g (4.2 mmol) of TEA, 0.06 g (0.27 mmol) of palladium(II) acetate, 0.16 g (0.54 mmol) of tri-o-tolylphosphine and 5.0 g (4.2 mmol) of a 10% solution of 4-vinylphenol in propylene glycol was suspended in 15 mL of dry acetonitrile in a pyrex sealed tube and heated to 100° C. for 4 h. The mixture was cooled to rt, quenched with 50 mL of 10% hydrochloric acid and extracted with two 100 mL-portions of EtOAc. The combined extracts were dried over MgSO$_4$ and concentrated to give a brown solid, which was subjected to chromatography on silica gel, eluting with hexane:EtOAc (3:1), to yield 0.125 g (13%) of trans-4-[2-(4-hydroxyphenyl)-vinyl]-1H-indole-2,3-dione as a red solid: ¹H NMR (DMSO-d$_6$): δ 6.6–7.6 (m, 8H), 7.77 (d, J=16.4 Hz, 1H), 9.85 (bs, 1H), 11.00 (bs, 1H); APCI-MS m/z 264 (M−1)⁻. Condensation of trans-4-[2-(4-hydroxyphenyl)-vinyl]-1H-indole-2,3-dione and 4-sulfonamidophenylhydrazine hydrochloride according to Procedure G gave the title compound in 27% yield as an orange solid: ¹H NMR (DMSO-d$_6$): δ 6.78 (d, J=7.8 Hz, 1H), 6.88 (d, J=8.7 Hz, 2H), 7.26 (t, J=7.8 Hz, 1H), ), 7.29

(s, 2H), 7.36 (d, J=16.5 Hz, 1H), 7.47 (d, J=7.8 Hz, 1H), 7.53 (d, J=8.7 Hz, 2H), 7.57 (d, J=8.7 Hz, 2H), 7.81 (d, J=8.7 Hz, 2H), 8.03 (d, J=16.5 Hz, 1H), 9.78 (s, 1H), 11.17 (s, 1H), 13.02 (s, 1H); APCI-MS m/z 433 (M−1)⁻.

Procedure M—Method for reducing 4-alkenyl substituents: preparation of 4-(N'-{4-[2-(4-hydroxyphenyl)-ethyl]-2-oxo-1,2-dihydro-indol-3-ylidene}-hydrazino)-benzenesulfonamide

EXAMPLE 14

4-(N'-{4-[2-(4-Hydroxyphenyl)-ethyl]-2-oxo-1,2-dihydro-indol-3-ylidene}-hydrazino)-benzenesulfonamide A mixture of 0.028 g (0.64 mmol) of 4-(N'-{4-[2-(4-hydroxyphenyl)-vinyl]-2-oxo-1,2-dihydro-indol-3-ylidene}-hydrazino)-benzenesulfonamide (Z isomer) and 0.015 g of 10% palladium on charcoal in 60 mL of MeOH:THF (4:1) was subjected to hydrogenation on a Parr apparatus at 50 psi for 1 h. The mixture was filtered through celite, and the filtrate was concentrated to give 0.026 g (93%) of the title compound as a yellow solid: $^1$H NMR (DMSO-$d_6$): δ 2.82 (t, J=8.0 Hz, 2H), 3.23 (t, J=8.0 Hz, 2H), 6.69 (d, J=8.4 Hz, 2H), 6.78 (d, J=7.7 Hz, 1H), 6.89 (d, J=7.7 Hz, 1H), 7.07 (d, J=8.4 Hz, 2H), 7.18 (t, J=7.7 Hz, 1H), 7.26 (s, 2H), 7.45 (d, J=8.8 Hz, 2H), 7.71 (d, J=8.8 Hz, 2H), 9.20 (bs, 1H), 11.12 (s, 1H), 13.02 (s, 1H); APCI-MS m/z 435 (M−1)⁻.

EXAMPLE 1

4-[N'-(4-Nitro-2-oxo-1,2-dihydro-indol-3-ylidene)-hydrazino]-benzenesulfonamide (Z isomer)

The title compound was prepared from 4-nitro-1H-indole-2,3-dione (Gassman, et al., Journal of Organic Chemistry 1977, 42,1344–8) and 4-sulfonamidophenylhydrazine hydrochloride according to Procedure G in 33% yield: $^1$H NMR (DMSO-$d_6$): δ 7.23 (d, J=7.7 Hz, 1H), 7.31 (s, 2H), 7.47 (t, J=7.9 Hz, 1H), 7.56 (d, J=7.9 Hz, 2H), 7.59 (d, J=7.2 Hz, 1H), 7.83 (d, J=7.7 Hz, 2H), 11.59 (s, 1H), 13.20 (s, 1H); APCI-MS m/z 361 (M). Anal. Calcd for $C_{14}H_{11}N_5O_5S$: C, 46.54, H, 3.07; N, 19.38; S, 8.87. Found C, 46.62, H, 3.09; N, 19.46; S, 8.81.

EXAMPLE 2

2-Oxo-3-[(4-sulfamoyl-phenyl)-hydrazono]-2,3-dihydro-1H-indole-4-carboxylic acid amide (E isomer)

1H-Indole-2,3-dione-4-carboxamide was prepared from aniline-3-carboxamide according to Procedure A in 3% yield: $^1$H NMR (DMSO-$d_6$): δ 7.17 (d, J=8.1 Hz, 1H), 7.32 (d, J=8.1 Hz, 1H), 7.56 (t, J=8.1 Hz, 1H), 8.02 (bs, 2H), 11.86 (bs, 1H); APCI+MS m/z 191 (M+1)⁻. Condensation of 1H-indole-2,3-dione-4-carboxamide with 4-sulfonamidophenylhydrazine hydrochloride according to Procedure G gave the title compound in 31% yield: $^1$H NMR (DMSO-$d_6$): δ 7.11 (d, J=8.3 Hz, 1H), 7.18 (s, 2H), 7.27 (d, J=8.8 Hz, 2H), 7.32 (d, J=7.0 Hz, 1H), 7.51 (d, J=7.4 Hz, 1H), 7.75 (d, J=8.8 Hz, 2H), 8.0 (bs, 2H), 10.40 (s, 1H), 10.80 (s, 1H); APCI-MS m/z 359 (M)⁻. Anal. Calcd for $C_{15}H_{13}N_5O_4S \cdot 0.12H_2O$: C, 49.83, H, 3.69; N, 19.37; S, 8.86. Found C, 49.71, H, 3.71; N, 19.32; S, 8.84.

EXAMPLE 3

4-[N'-(4-Isopropyl-2-oxo-1,2-dihydro-indol-3-ylidene)-hydrazino]-benzenesulfonamide (Z isomer)

The title compound was prepared from 4-isopropyl-1H-indole-2,3-dione (Krantz and Young, 1989, U.S. Pat. No. 4,873,232) and 4-sulfonamidophenylhydrazine hydrochloride according to Procedure G in 73% yield: $^1$H NMR (DMSO-$d_6$): δ 1.30 (d, J=6.7 Hz, 6H), 3.82 (septet, J=6.7 Hz, 1H), 6.76 (d, J=7.8 Hz, 1H), 7.01 (d, J=7.8 Hz, 1H), 7.23 (t, J=7.8 Hz, 1H), 7.24 (s, 2H), 7.48 (d, J=8.7 Hz, 2H), 7.79 (d, J=8.7 Hz, 2H), 11.10 (s, 1H), 13.05 (s, 1H); APCI-MS m/z 357 (M−1)⁻. Anal. Calcd for $C_{17}H_{18}N_4O_3S$: C, 56.97, H, 5.06; N, 15.63; S, 8.95. Found C, 56.88, H, 5.12; N, 15.73; S, 8.91.

EXAMPLE 4

4-[(4-Hydroxymethyl-2-oxo-1,2-dihydro-indol-3-ylidenemethyl)-amino]-N-methyl-benzenesulfonamide A mixture of 3.0 g (20 mmol) of 3-aminobenzyl alcohol, 3.36 g (22.0 mmol) of t-butyidimethylsilyl chloride and 1.52 g (22.0 mmol) of imidazole were dissolved in 20 mL of DMF. The solution was stirred at rt for 16 h and then diluted with 250 mL of hexane and 250 mL of EtOAc. The organic phase was washed twice with brine, dried over MgSO₄ and concentrated to give 4.8 g of 3-([t-butyidimethylsilyloxy]methyl-benzenamine as a clear oil. This was dissolved in 100 mL of $CH_2Cl_2$, cooled with stirring to −65° C. and 2.17 g (20.0 mmol) of t-butyl hypochlorite was added. After 10 min of stirring, a solution of 2.68 g (20.0 mmol) of ethyl methylthioaceatate in 10 mL of $CH_2Cl_2$ was added, and the solution was stirred for 1 h. TEA (2.02 g, 20.0 mmol) was added and the reaction was warmed to rt over 1 h. The solution was washed with water and concentrated to an oil. This was redissolved in 100 mL of ether, 12 mL of 2 N hydrochloric acid was added, and the mixture was stirred overnight. The ether phase was separated and concentrated to an oil. This was chromatographed on silica gel eluting with hexane:EtOAc (initially a 3:1 ratio increasing to 1:2). to yield 0.82 g (20%) of 4-hydroxymethyl-3-methylsulfanyl-1,3-dihydro-indol-2-one: $^1$H NMR (DMSO-$d_6$): δ 1.89 (s, 3H), 4.45 (s, 1H), 4.62 (m, 2H), 5.1 (bs, 1H), 6.87 (d, J=7.7 Hz, 1H), 7.02 (d, J=7.7 Hz, 1H), 7.17 (t, J=7.7 Hz, 1H), 10.44 (s, 1H). Further elution yielded 0.53 g (13%) of 6-hydroxymethyl-3-methysulfanyl-1,3-dihydro-indol-2-one: $^1$H NMR (DMSO-$d_6$): δ 1.99 (s, 3H), 4.48 (s, 2H), 4.50 (s, 1H), 5.1 (bs, 1H), 6.84 (s, 1H), 6.94 (d, J=7.6 Hz, 1H), 7.22 (d, J=7.6 Hz, 1H), 10.54 (s, 1H).

A solution of 0.82 g (3.9 mmol) of 4-hydroxymethyl-3-methylsulfanyl-1,3-dihydro-indol-2-one in DMF (20 mL) was treated with 0.65 g (4.3 mmol) of t-butyidimethylsilyl chloride and 0.3 g (4.4 mmol) of imidazole and stirred for 24 h. The solution was diluted with 75 mL of hexane and 75 mL of EtOAc. The organic phase was washed with brine, dried over MgSO₄ and concentrated to give 1.2 g (95%) of 3-methylsulfanyl-4-(t-butyldimethylsilyloxy)methyl-1,3-dihydro-indol-2-one as a clear oil which crystallised upon storage at rt: $^1$H NMR (DMSO-$d_6$): δ 0.051 (s, 3H), 0.064 (s, 3H), 0.881 (s, 9H), 1.87 (s, 3H), 4.43 (s, 1H), 4.79 (d, J=14.2 Hz, 1H), 4.88 (d, J=14.2 Hz, 1H), 6.70 (d, J=7.9 Hz, 1H), 7.00 (d, J=7.9 Hz, 1H), 7.19 (t, J=7.9 Hz, 1H), 10.48 (s, 1H); APCI-MS m/z 346 (M+23)⁺.

A solution of 1.2 g (3.7 mmol) of 3-methylsulfanyl-4-(t-butyldimethylsilyloxy)-methyl-1,3-dihydro-indol-2-one in THF (25 mL) was stirred with saturated ammonium chloride solution (20 mL), and activated zinc dust (5 g) was added. The mixture was stirred for 60 h at rt. The organic phase was separated, dried over $MgSO_4$ and concentrated to give 1.16 g of impure 4-(t-butyidimethylsilyloxy)methyl-1,3-dihydro-indol-2-one as an off-white solid: $^1H$ NMR (DMSO-$d_6$): δ 0.11 (s, 6H), 0.86 (s, 9H), 3.42 (s, 2H), 4.67 (s, 2H), 6.74 (d, J=7.7 Hz, 1H), 6.95 (d, J=7.7 Hz, 1H), 7.18 (t, J=7.7 Hz, 1H), 10.40 (s, 1H). A solution of 0.64 g (2.3 mmol) of 4-(t-butyidimethylsilyloxy)methyl-1,3-dihydro-indol-2-one in DMF dimethylacetal (5 mL) was heated to 100° C. for 1 h. The excesss DMF dimethylacetal was removed under high vacuum, and the resulting dark oil was chromatographed on silica gel, eluting with EtOAc, to give 0.34 g (44%) of 3-dimethylaminomethylene-4-(t-butyldimethyl-silyloxy)methyl-1,3-dihydro-indol-2-one as a white solid: $^1H$ NMR (DMSO-$d_6$): δ-0.03 (s, 6H), 0.81 (s, 9H), 3.29 (s, 6H), 4.64 (s, 2H), 6.66 (d, J=7.3 Hz, 1H), 6.73 (d, J=7.3 Hz, 1H), 6.79 (t, J=7.3 Hz, 1H), 7.76 (s, 1H), 9.97 (s, 1H); APCI-MS m/z 333 (M+1)$^+$. A solution of 0.115 g (0.34 mmol) of 3-dimethylaminomethylene-4-(t-butyidimethylsilyloxy)methyl-1,3-dihydro-indol-2-one in ethanol (10 mL) was treated with 0.076 g (0.34 mmol) N-methylsulfanilamide hydrochloride. The solution was refluxed for 0.5 h and cooled to rt. The resulting yellow precipitate was isolated by filtration, washed with ethanol and dried to yield 0.048 g (38%) of the title compound: $^1H$ NMR (DMSO-$d_6$): δ 2.37 (d, J=5.0 Hz, 3H), 4.67 (s, 2H), 5.3 (bs, 1H), 6.78 (d, J=7.5 Hz, 1H), 6.93 (d, J=7.5 Hz, 1H), 6.99 (t, J=7.5 Hz, 1H), 7.33 (q, J=5.0 Hz, 1H), 7.44 (d, J=8.6 Hz, 2H), 7.71 (d, J=8.6 Hz, 2H), 8.32 (d, J=12.2 Hz, 1H), 10.67 (s, 1H), 11.26 (d, J=12.2 Hz, 1H); APCI-MS m/z 358 (M−1)$^-$. Anal. Calcd for $C_{17}H_{17}N_3O_4S$: C, 56.81, H, 4.77; N, 11.69, S, 8.92. Found C, 56.89, H, 4.81; N, 11.70; S, 8.84.

EXAMPLE 5

4-{N'-[2-Oxo-4-(2-pyridin-4-ylethyl)-1,2-dihydro-indol-3-ylidene]-hydrazino}-benzenesulfonamide (Z isomer)

A mixture of 3.0 g (20 mmol) of 3-nitroiodobenzene, 3.5 mL (25 mmol) of TEA, 0.045 g (0.20 mmol) of palladium (II) acetate and 2.77 g (25.0 mmol) of 4-vinylpyridine was suspended in 4 mL of dry acetonitrile in a pyrex sealed tube and heated to 100° C. for 48 h. The mixture was cooled to rt and was quenched with 200 mL of 10% hydrochloric acid. The resulting yellow solid was isolated by filtration and partitioned between 250 mL of EtOAc and 250 mL of 1 N aqueous sodium hydroxide. The organic phase was dried over $MgSO_4$ and concentrated to give 3.0 g (66%) of 4-[2-(3-nitrophenyl)ethenyl]-pyridine as a yellow solid: $^1H$ NMR (DMSO-$d_6$): δ 3.04.6 (br s, 1H), 7.71–7.78 (m, 2H), 8.07 (d, J=15.8 Hz, 1H), 8.13–8.16 (m, 3H), 8.24 (d, J=8.0 Hz, 1H), 8.56 (s, 1H), 8,84 (d, J=5.7 Hz, 2H); ESI-MS m/z 227 (M+1)$^+$. A portion (1.3 g, 7.1 mmol) of this solid was dissolved in 100 mL of EtOAc, and 0.5 g of 10% palladium on charcoal was added. The mixture was hydrogenated on a Parr apparatus at 40 psi for 1.5 h. Another 0.5 g batch of 10% palladium on charcoal was added and the mixture was subjected to further hydrogenation for 1 h. The palladium catalyst was removed by filtration through a pad of celite, and the filtrate was concentrated to give 1.13 g (100%) of 3-(4-pyridinyl)ethylaniline: $^1H$ NMR (DMSO-$d_6$): δ 2.69 (m, 2H), 2.80 (m, 2H), 4.9 (bs, 2H), 6.33 (d, J=7.7 Hz, 2H), 6.38 (s, 1H), 6.86 (t, J=7.7 Hz, 1H), 7.20 (d, J=5.8 Hz, 2H), 8.41 (d, J=5.8 Hz, 2H). Conversion of 3-[2-(4-pyridinyl)ethyl]-aniline to 4-(2-pyridin-4-yl-ethyl)-1H-indole-2,3-dione was accomplished according to Procedure A in 24% overall yield: $^1H$ NMR (DMSO-$d_6$): δ 2.80 (m, 2H), 3.10 (m, 2H), 6.70 (d, J=8.0 Hz, 1H), 6.81 (d, J=8.0 Hz, 1H), 7.24 (m, 2H), 7.40 (t, J=8.0 Hz, 1H), 8.42 (bs, 2H), 11.00 (s, 1H). Conversion of 4-(2-pyridin-4-yl-ethyl)-1H-indole-2,3-dione to the title compound was accomplished according to Procedure G in 40% overall yield: $^1H$ NMR (DMSO-$d_6$): δ 2.98 (t, J=7.9 Hz, 2H), 3.30 (m, 2H, underneath water peak), 6.78 (d, J=7.7 Hz, 1H), 6.88 (d, J=7.6 Hz, 1H), 7.17 (t, J=7.6 Hz, 1H), 7.25 (s, 2H), 7.29 (d, J=6.0 Hz, 2H), 7.37 (d, J=8.8 Hz, 2H), 7.66 (d, J=8.8 Hz, 2H), 8.47 (d, J=6.0 Hz, 2H), 11.13 (s, 1H), 12.98 (s, 1H); APCI-MS m/z 420 (M−1)$^-$. Anal. Calcd for $C_{21}H_{19}N_5O_3S$ 0.15HCl: C, 55.93, H, 4.43; N, 15.53; S, 7.11. Found C, 56.05, H, 4.36; N, 15.38; S, 7.18.

EXAMPLE 6

2-Oxo-3-(4-sulfamoyl-phenylamino)-methylene]-2,3-dihydro-1H-indole-4-carboxylic acid ethyl ester (Z isomer)

The title compound was prepared from 2-oxo-2,3-dihydro-1H-indole-4-carboxylic acid ethyl ester (Connolly and Durst, Synlett 1996, 663–4; Kozikowski and Kuniak, Journal of Organic Chemistry 1978, 43, 2083–4) and sulfanilamide according to Procedure J in 14% overall yield: $^1H$ NMR (DMSO-$d_6$): δ 1.33 (t, J=7.1 Hz, 3H), 4.37 (q, J=7.1 Hz, 2H), 7.10 (d, J=7.6 Hz, 1H), 7.15 (t, J=7.6 Hz, 1H), 7.30 (s, 2H), 7.41 (d, J=8.6 Hz, 2H), 7.57 (d, J=7.6 Hz, 1H), 7.82 (d, J=8.6 Hz, 2H), ), 9.50 (d, J=12.6 Hz, 1H), 10.96 (s, 1H), 11.75 (d, J=12.6 Hz, 1H); APCI-MS m/z 386 (M−1)$^-$.

EXAMPLE 7

4-[N'-(4-Iodo-2-oxo-1,2-dihydro-indol-3-ylidene)-hydrazino]-benzenesulfonamide (Z isomer)

The title compound was prepared from 4-iodo-1H-indole-2,3-dione (Snow, et al., Journal of the American Chemical Society 1977, 99, 3734–44) and 4-sulfonamidophenyl-hydrazine hydrochloride according to Procedure G in 87% overall yield: $^1H$ NMR (DMSO-$d_6$): δ 6.93 (d, J=7.6 Hz, 1H), 6.99 (t, J=7.6 Hz, 1H), 7.25 (s, 2H), 7.50 (d, J=7.6 Hz, 1H), 7.66 (d, J=8.7 Hz, 2H), 7.77 (d, J=8.7 Hz, 2H), 11.17 (s, 1H), 12.94 (s, 1H); APCI-MS m/z 441 (M−1)$^-$. Anal. Calcd for $C_{14}H_{11}IN_4O_3S$: C, 38.02, H, 2.51; 1, 28.70; N, 12.67; S, 7.25. Found C, 38.05, H, 2.51; I, 28.78; N, 12.64; S, 7.19.

EXAMPLE 8

4-[N'-(4-Isobutyl-2-oxo-1,2-dihydro-indol-3-ylidene)-hydrazino]-benzenesulfonamide A mixture of 0.20 g (1.0 mmol) of 4-(2-methyl-propenyl)-1H-indole-2,3-dione and 0.05 g of 10% palladium on charcoal in 25 mL of EtOAc was subjected to hydrogenation on a Parr apparatus at 46 psi for 1 h. The mixture was filtered through celite, and the filtrate was concentrated to dryness. The solid was purified by chromatography on silica gel, eluting with hexane:EtOAc (4:1), to furnish 0.027 g (13%) of 4-isobutyl-1H-indole-2,3-dione: $^1H$ NMR (DMSO-$d_6$): δ 0.89 (d, J=6.7 Hz, 6H), 1.86 (nonet, J=6.7 Hz, 1H), 2.72 (d, J=6.7 Hz, 1H), 6.74 (d, J=7.8 Hz, 1H), 6.86 (d, J=7.8 Hz, 1H), 7.48 (t, J=7.8 Hz, 1H), 11.03 (s, 1H).

Condensation of 4-isobutyl-1H-indole-2,3-dione and 4-sulfonamidophenylhydrazine hydrochloride according to Procedure G gave the title compound in 65% yield: $^1$H NMR (DMSO-$d_6$): δ 0.96 (d, J=6.4 Hz, 6H), 2.05 (m, 1H), 2.87 (d, J=7.0 Hz, 2H), 6.79 (d, J=7.6 Hz, 1H), 6.85 (d, J=7.6 Hz, 1H), 7.20 (t, J=7.6 Hz, 1H), 7.26 (s, 2H), 7.51 (d, J=8.5 Hz, 2H), 7.81 (d, J=8.5 Hz, 2H), 11.13 (s, 1H), 13.03 (s, 1H); APCI-MS m/z 371 (M−1)$^-$.

EXAMPLE 9

4-{N'-[4-(2-Methyl-propenyl)-2-oxo-1,2-dihydro-indol-3-ylidene]-hydrazino}-benzenesulfonamide By methods described in Procedure L, 4-(2-methyl-propenyl)-1H-indole-2,3-dione was prepared from 4-iodo-1H-indole-2,3-dione and isobutylene in 34% yield: $^1$H NMR (DMSO-$d_6$): δ 1.82 (s, 3H), 1.90 (s, 3H), 6.79 (d, J=7.9 Hz, 1H), 6.94 (d, J=7.9 Hz, 1H), 7.47 (t, J=7.9 Hz, 1H), 10.97 (s, 1H); APCI-MS m/z 200 (M−1)$^-$. Condensation of 4-(2-methyl-propenyl)-1H-indole-2,3-dione and 4-sulfonamidophenylhydrazine hydrochloride according to Procedure G gave the title compound as a yellow solid (51% yield): $^1$H NMR (DMSO-$d_6$): δ 1.84 (s, 3H), 2.04 (s, 3H), 6.78 (s, 1H), 6.79 (d, J=7.8 Hz, 1H), 6.96 (d, J=7.8 Hz, 1H), 7.24 (t, J=7.8 Hz, 1H), 7.24 (s, 2H), 7.48 (d, J=8.8 Hz, 2H), 7.80 (d, J=8.8 Hz, 2H), 11.11 (s, 1H), 12.91 (s, 1H); APCI-MS m/z 369 (M−1)$^-$. Anal. Calcd for $C_{18}H_{18}N_4O_3S$: C, 58.36, H, 4.90; N, 15.12; S, 8.66. Found C, 58.41, H, 4.87; N, 15.18; S, 8.56.

EXAMPLE 10

4-{N'-[4-(2-Methyl-1-butenyl)-2-oxo-1,2-dihydro-indol-3-ylidene]-hydrazino}-benzenesulfonamide and 4-{N'-[4-(2-methyl-2-butenyl)-2-oxo-1,2-dihydro-indol-3-ylidene]-hydrazino}-benzenesulfonamide Coupling of 4-iodoisatin and 2-methyl-1-butene according to Procedure L gave a mixture of isomers [the major pair of isomers was E/Z-4-(2-methyl-1-butenyl)-1H-indole-2,3-dione and the minor pair of isomers was E/Z-4-(2-methyl-2-butenyl)-1H-indole-2,3-dione] in 21% yield.: $^1$H NMR (DMSO-$d_6$, integral ratios are normalized to the 1H singlet observed at δ 10.97): δ 1.06 (m, 2.6H), 1.47 (s, 1.05H), 1.83 (m, 1.4H), 1.88 (s, 1.1H), 2.19 (m, 1.6H), 3.50 (s, 0.26H), 5.22 (m, 0.16H), 6.60–6.72 (m, 2H), 6.76–6.82 (m, 0.23H), 6.86 (d, J=7.7 Hz, 0.35H), 7.46 (d, J=7.6 Hz, 0.42H), 7.4–7.6 (m, 1H), 10.97 (s, 1H); APCI-MS m/z 214 (M−1)$^-$. Condensation of the mixture of E/Z-4-(2-methyl-1-butenyl)-1H-indole-2,3-dione and E/Z-4-(2-methyl-2-butenyl)-1H-indole-2,3-dione and 4-sulfonamidophenyl-hydrazine hydrochloride according to Procedure G gave the title compound mixture as a yellow solid (51% yield): $^1$H NMR (DMSO-$d_6$, integral ratios are normalized to the 1H singlet observed at δ 11.11): δ 1.07 (t, J=7.5 Hz, 1.3H), 1.21 (t, J=7.5 Hz, 1.3H), 1.54 (d, J=6.5 Hz, 0.7H), 1.63 (s, 0.7H), 1.86 (s, 1.2H), 2.03 (s, 1.1H), 2.21 (q, J=7.7 Hz, 0.7H), 2.32 (q, J=7.7 Hz, 0.8H), 3.71 (s, 0.4H), 5.2 (m, 0.2H), 6.72–6.85 (m, 2.1H), 6.89 (d, J=7.9 Hz, 0.39H), 6.97 (d, J=7.9 Hz, 0.42H), 7.18–7.26 (m, 3.1H), 7.47–7.51 (m, 2.1H), 7.77–7.81 (m, 2.1H), 11.11 (s, 1H), 12.89 (s, 0.3H), 12.97 (s, 0.35H), 13.02 (s, 0.24H); APCI-MS m/z 383 (M−1)$^-$.

EXAMPLE 11

4-{N'-[4-(2-methylbutyl)-2-oxo-1,2-dihydro-indol-3-ylidene]-hydrazino}-benzenesulfonamide Reduction of the mixture of 4-{N'-[4-(2-methyl-1-butenyl)-2-oxo-1,2-dihydro-indol-3-ylidene]-hydrazino}-benzenesulfonamide and 4-{N'-[4-(2-methyl-2-butenyl)-2-oxo-1,2-dihydro-indol-3-ylidene]-hydrazino}-benzenesulfonamide according to Procedure M gave the title compound in 79% yield: $^1$H NMR (DMSO-$d_6$): δ 0.87–0.90 (m, 6H), 1.21–1.25 (m, 2H), 1.47–1.63 (m, 1H), 2.82 (dd, J=12.6, 8.1 Hz, 1H), 2.95 (dd, J=12.6, 6.6 Hz, 1H), 6.77 (d, J=7.7 Hz, 1H), 6.84 (d, J=7.7 Hz, 1H), 7.18 (t, J=7.7 Hz, 1H), 7.25 (s, 2H), 7.49 (d, J=8.6 Hz, 2H), 7.79 (d, J=8.6 Hz, 2H), 11.12 (s, 1H), 13.04 (s, 1H); APCI-MS m/z 385 (M−1)$^-$.

EXAMPLE 12

4-[N'-(4-Cyclobutylmethyl-2-oxo-1,2dihydro-indol-3-ylidene)-hydrazino]-benzenesulfonamide (Z isomer)

Reduction of 4-[N'-(4-cyclobutylidenemethyl-2-oxo-1,2-dihydro-indol-3-ylidene)-hydrazino]-benzenesulfonamide according to methods described in Procedure M gave the title compound in 94% yield: $^1$H NMR (DMSO-$d_6$): δ 1.81 (m, 4H), 1.96 (m, 2H), 2.73 (m, 1H), 3.07 (d, J=7.2 Hz, 2H), 6.76 (d, J=7.8 Hz, 1H), 6.86 (d, J=7.8 Hz, 1H), 7.17 (t, J=7.8 Hz, 1H), 7.24 (s, 2H), 7.48 (d, J=8.6 Hz, 2H), 7.79 (d, J=8.6 Hz, 2H), 11.08 (s, 1H), 12.93 (s, 1H); APCI-MS m/z 383 (M−1)$^-$.

EXAMPLE 13

4-[N'-(4-Cyclobutylidenemethyl-2-oxo-1,2-dihydro-indol-3-ylidene)-hydrazino]-benzenesulfonamide (Z isomer)

By methods described in Procedure L, 4-cyclobutylidenemethyl-1H-indole-2,3-dione was prepared from 4-iodo-1H-indole-2,3-dione and methylene cyclobutene in 25% yield: $^1$H NMR (DMSO-$d_6$): δ 2.08 (quintet, J=7.8 Hz, 2H), 2.91 (m, 2H), 3.06 (m, 2H), 6.67 (d, J=7.7 Hz, 1H), 6.94 (d, J=7.7 Hz, 1H), 6.96 (s, 1H), 7.47 (d, J=7.7 Hz, 1H), 11.00 (bs, 1H); APCI-MS m/z 211 (M−1)$^-$. Condensation of 4-(cyclobutylidenemethyl)-1H-indole-2,3-dione and 4-sulfonamidophenylhydrazine hydrochloride according to Procedure G gave the title compound in 76% yield: $^1$H NMR (DMSO-$d_6$): δ 2.11 (quintet, J=7.8 Hz, 2H), 3.00 (t, J=7.8 Hz, 2H), 3.06 (t, J=7.8 Hz, 2H), 6.74 (d, J=7.7 Hz, 1H), 6.97 (d, J=7.7 Hz, 1H), 7.07 (s, 1H), 7.21 (t, J=7.7 Hz, 1H), 7.25 (s, 2H), 7.47 (d, J=8.7 Hz, 2H), 7.81 (d, J=8.7 Hz, 2H), 11.12 (s, 1H), 13.03 (s, 1H); APCI-MS m/z 381 (M−1)$^-$.

EXAMPLE 14

See Procedure M

EXAMPLE 15

See Procedure L

EXAMPLE 16

4-[N'-(2-Oxo-4-phenoxy-1,2-dihydro-indol-3-ylidene)-hydrazino]-benzenesulfonamide (mixture of E and Z isomers)

The title compound was prepared from 3-phenoxyaniline and 4-sulfonamidophenyl-hydrazine hydrochloride according to Procedure C: mp>250° C.; $^1$H NMR (DMSO-$d_6$): δ 6.42 E (d, J=8.4 Hz, 1H), 6.70 E (d, J=7.7 Hz, 1H), 6.76 Z (d, J=8.2 Hz, 1H), 6.82 Z (d, J=7.8 Hz, 1H), 6.99 Z (d, J=8.1 Hz, 2H), 7.06 Z (d, J=8.8 Hz, 2H), 7.1–7.6 E (m, 10H), 7.1–7.6 Z (m, 6H), 7.62 Z (d, J=8.8 Hz, 2H), 7.74 E (d, J=8.7 Hz, 2H), 10.88 E (s, 1H), 11.18 E (s, 1H), 11.27 Z (s, 1H), 12.77 Z (s, 1H); APCI-MS: m/z 407 (M–H)$^-$. Anal. Calcd for $C_{20}H_{16}N_4O_4S$: C, 58.81; H, 3.95; N, 13.72; S, 7.85. Found: C, 58.53; H, 4.02; N, 13.66; S, 7.79.

EXAMPLE 17

See Procedure C

EXAMPLE 18

4-{N'-[2-Oxo-4-(1H-pyrazol-3-yl)-1,2-dihydro-indol-3-ylidene]-hydrazino}-benzenesulfonamide 4-(1H-Pyrazol-3-yl)-1H-indole-2,3-dione was prepared from 3-(1H-pyrazol-3-yl)aniline according to Procedure A. The title compound was prepared from 4-(1H-pyrazol-3-yl) isatin and 4-sulfonamidophenylhydrazine hydrochloride according to Procedure G: $^1$H NMR (DMSO-$d_6$): δ 6.72 (s, 1H), 7.22 (s, 2H), 7.39 (s, 1H), 7.48–7.60 (m, 4H), 7.76 (d, J=8.7 Hz, 2H), 7.77 (s, 1H), 11.11 (s, 1H), 12.93 (s, 1H); ESI-MS: m/z 381 (M–H)$^-$.

EXAMPLE 19

4-[(5-Oxazol-5-yl-2-oxo-1,2-dihydro-indol-3-ylidenemethyl)amino]-benzenesulfonamide (Z-isomer)

The title compound was prepared in 68% yield from ethoxymethylene-5-oxazol-5-yl-1,3-dihydro-indol-2-one and 4-aminobenzenesulfonamide hydrochloride according to Procedure J: $^1$H NMR (DMSO-$d_6$): δ 10.79 (d, 1H), 10.73 (s, 1H), 8.76 (d, 1H), 8.38 (s, 1H), 8.0 (s, 1H), 7.77 (d, 2H), 7.56 (d, 2H), 7.43 (s, 1H), 7.40 (d, 1H), 7.26 (s, 2H), 6.91 (d, 1H); APCI-MS: m/z 381 (MH)$^-$.

EXAMPLE 20

2-Oxo-3-[(4-sulfamoyl-phenyl)-hydrazono-2,3-dihydro-1H-indole-5-carboxylic acid pentafluorophenyl ester 2-Oxo-3-[(4-sulfamoyl-phenyl)-hydrazono]-2,3-dihydro-1H-indole-5-carboxylic acid was prepared from 1H-indole-2,3-dione-5-carboxylic acid and 4-sulfonamidophenyl-hydrazine hydrochloride according to Procedure G. To a suspension of 2.75 g (7.63 mmol) of the 2-oxo-3[(4-sulfamoyl-phenyl)-hydrazono]-2,3-dihydro-1H-indole-5-carboxylic acid in 20 mL DMF was added 1.38 mL (8.03 mmol) pentafluorophenyltrifluoroacetate (PFPTFA), 0.69 mL (8.53 mmol) pyridine, and the suspension was stirred under $N_2$ for 20 min. TLC (silica gel, 20% MeOH/$CH_2Cl_2$) indicated residual starting material remained, and the reaction was treated with 10 mL DMF and additional PFPTFA and pyridine (equal portions to above). The reaction was stirred overnight and then poured into 400 mL ether. The solution was washed with two 500-mL portions of water, and 300 mL of EtOAc was added to dissolve precipitate. The solution was washed with 500 mL water, dried over $Na_2SO_4$, filtered through silica gel and concentrated to remove ether. The resulting solid was collected by filtration, washed 50 mL 1:1 ethylacetate:hexanes and dried overnight in a vacuum oven at 70° C. to give the title compound as a bright yellow solid (2.30 g, 57%): mp>230° C.; $^1$H NMR (DMSO-$d_6$): δ 12.77 (s, 1H), 11.68 (s, 1H), 8.32 (d, J=1.9 Hz, 1H), 8.11 (dd, J=1.9 Hz, J=8.2 Hz, 1H), 7.79 (d, J=8.9 Hz, 2H), 7.67 (d, J=8.9 Hz, 2H), 7.28 (s, 2H), 7.16 (d, J=8.4 Hz, 1H); APCI-MS: m/z 525 (M–H)$^-$. Anal. Calcd for $C_{21}H11N_4O_5SF_5$: C, 47.92; H, 2.11; N, 10.64. Found: C, 48.00; H, 2.13; N, 10.54.

EXAMPLE 21

4-[N'-(5-Nitro-2-oxo-1,2-dihydro-indol-3-ylidene)-hydrazino]-benzenesulfonamide (Z isomer)

The title compound was prepared from 5-nitro-1H-indole-2,3-dione (Gassman, et al., Journal of Organic Chemistry 1977, 42, 1344–8) and 4-sulfonamidophenylhydrazine hydrochloride according to Procedure G in 94% yield: $^1$H NMR (DMSO-$d_6$): δ 7.14 (d, J=8.6 Hz, 1H), 7.33 (s, 2H), 7.75 (d, J=8.8 Hz, 2H), 7.84 (d, J=8.8 Hz, 2H), 8.23 (dd, J=2.2, 8.6 Hz, 1H), 8.42 (d, J=2.2 Hz, 1H), 11.76 (s, 1H), 12.78 (s, 1H). Anal. Calcd for $C_{14}H_{11}N_5O_5S$: C, 46.54, H, 3.07; N, 19.38. Found C, 46.76, H, 3.13; N, 19.23.

EXAMPLE 22

4-[N'-(5-Hydroxy-2-oxo-1,2-dihydro-indol-3-ylidene)-hydrazino]-benzenesulfonamide (Z isomer)

The title compound was prepared from 5-hydroxy-1H-indole-2,3-dione (Ijaz, et al., Indian Journal of Chemistry 1994, 33B, 288–9) and 4-sulfonamidophenylhydrazine hydrochloride according to Procedure G in 30% yield: $^1$H NMR (DMSO-$d_6$): δ 6.79 (dd, J=2.2, 8.3 Hz, 1H), 6.72 (d, J=8.3 Hz, 1H), 6.98 (d, J=2.2 Hz, 1H), 7.25 (s, 2H), 7.53 (d, J=8.7 Hz, 2H), 7.78 (d, J=8.7 Hz, 2H), 9.20 (s, 1H), 10.80 (s, 1H), 12.82 (s, 1H); APCI-MS m/z 331 (M–H)$^-$.

EXAMPLE 23

4-[N'-(5-Methyl-2-oxo-1,2-dihydro-indol-3-ylidene)-hydrazino]-benzenesulfonamide (E isomer)

The title compound was prepared from 5-methyl-1H-indole-2,3-dione (Gassman, et al., Journal of Organic Chemistry 1977, 42, 1344–8) and 4-sulfonamidophenylhydrazine hydrochloride according to Procedure G in 86% yield: $^1$H NMR (DMSO-$d_6$): δ 2.3 (s, 3H), 6.76 (d, J=7.9 Hz, 1H), 7.11 (d, J=7.9 Hz, 1H), 7.20 (s, 2H), 7.57 (d, J=8.8 Hz, 2H), 7.77 (d, J=8.8 Hz, 2H), 8.02 (s, 1H), 10.51 (s, 1H), 10.62 (s, 1H); APCI-MS m/z 329 (M–1)$^-$. Anal. Calcd for $C_{15}H_{14}N_4O_3S$: C, 54.54, H, 4.27; N, 16.96; S, 9.71. Found C, 54.54, H, 4.32; N, 16.87; S, 9.62.

EXAMPLE 24

N-Methyl-4-[N'-(2-oxo-5-[1,2,4]triazol-1-yl-1,2-dihydro-indol-3-ylidene)-hydrazino]-benzenesulfonamide (Z isomer)

5-[1,2,4]Triazol-1-yl-1H-indole-2,3-dione was prepared from 4-[1,2,4]-triazol-1-yl-phenylamine according to Procedure A in 6% yield: $^1$H NMR (DMSO-$d_6$): δ 7.04 (d, J=8.4 Hz, 1H), 7.97 (d, J=2.2 Hz, 1H), 8.01 (dd, J=2.2, 8.4 Hz, 1H), 8.20 (s, 1H), 9.26 (s, 1H), 11.19 (bs, 1H); APCI-MS m/z 215 (M+1)$^+$. Condensation of 5-[1,2,4]triazol-1-yl-1H-indole-2,3-dione with 4-hydrazino-N-methyl-phenylsulfonamide according to Procedure G gave the title compound in 86% yield: $^1$H NMR (DMSO-$d_6$): δ 2.38 (d, J=5.0 Hz, 3H), 7.05 (d, J=8.4 Hz, 1H), 7.30 (q, J=5.0 Hz, 1H), 7.65 (d, J=8.7 Hz, 2H), 7.72 (d, J=8.7 Hz, 3H), 8.01 (s, 1H), 8.20 (s, 1H), 9.23 (s, 1H), 11.27 (s, 1H), 12.80 (s, 1H); Anal. Calcd for $C_{16}H_{15}N_7O_3S \cdot 1.3H_2O$: C, 48.52, H, 4.22; N, 23.30; S, 7.62. Found C, 48.53, H, 4.25; N, 23.17; S, 7.55.

EXAMPLE 25

2-Oxo-3-[(4-sulfamoyl-phenyl)-hydrazono]-2,3-dihydro-1H-indole-5-sulfonic acid sodium salt The title compound was prepared from 1H-indole-2,3-dione-5-sulfonic acid and 4-sulfonamidophenylhydrazine according to Procedure G: $^1$H NMR (DMSO-$d_6$): δ 6.83 (d, J=8.0 Hz, 1H), 7.22 (s, 2H), 7.50 (dd, J=1.7, 8.0 Hz, 1H), 7.56 (d, J=8.7 Hz, 2H), 7.76 (d, J=8.7 Hz, 2H), 7.77 (d, J=1.7 Hz, 1H), 11.12 (s, 1H), 12.70 (s, 1H); APCI-MS: m/z 395 (M–H)$^-$. Anal. Calcd for $C_{14}H_{11}N_4O_6S_2Na \cdot 0.9H_2O \cdot 0.2 C_2H_6O$: C, 38.97; H, 3.18; N, 12.62; S, 14.45. Found: C, 38.84; H, 3.31; N, 12.63; S, 14.59.

EXAMPLE 26

3-[(4-Methylsulfamoyl-phenyl)-hydrazono]-2-oxo-2,3-dihydro-1H-indole-5-carboxylic acid amide The title compound was prepared from 1H-indole-2,3-dione-5-carboxylic acid amide and 4-N-methylsulfonamidophenylhydrazine according to Procedure G: mp>250° C.; $^1$H NMR (DMSO-$d_6$): δ 2.37 (d, J=5.0 Hz, 3H), 6.94 (d, J=8.2 Hz, 1H), 7.26 (bs, 1H), 7.30 (q, J=5.1 Hz, 1H), 7.62 (d, J=8.7 Hz, 2H), 7.72 (d, J=8.7 Hz, 2H), 7.82 (dd, $J_1$=1.5 Hz, $J_2$=8.2 Hz, 1H), 7.96 (bs, 1H), 8.12 (s, 1H), 11.30 (s, 1H), 12.73 (s, 1H); APCI-MS: m/z 372 (M–H)$^-$.

EXAMPLE 27

See Procedure E

EXAMPLE 28

5-Bromo-3-[(4-methylsulfonyl-phenyl)-hydrazono]-1,3-dihydro-indol-2-one

The title compound was prepared in 72% yield from 5-bromo-1H-indole-2,3-dione (Meth-Cohn and Goon, Tetrahedron Letters 1996, 37, 9381–4) and 4-methylsulfonylphenylhydrazine according to Procedure G: $^1$H NMR (DMSO-$d_6$): δ 12.7 (s, 1H), 11.3 (s, 1H), 7.9 (d, 2H), 7.7–7.8 (m, 3H), 7.4 (dd, 1H), 6.9 (d, 1H), 3.2 (s, 3H); ESI-MS m/z 392 (M–H)$^-$.

EXAMPLE 29

3-(3H-Benzotriazol-5-ylimino-methylene)-5-iodo-1,3-dihydro-indol-2-one

The title compound was prepared in 43% yield from 3-hydroxymethylene-1,3-dihydro-indol-2-one and 5-aminobenzotriazole according to Procedure J: $^1$H NMR (DMSO-$d_6$): δ 10.8 (d, 1H), 10.7 (s, 1H), 8.8 (d, 1H), 8.0 (s, 1H), 7.8–7.9 (br m), 7.5 (d, 1H), 7.3 (d, 1H); ESI-MS m/z 404 (M+H)$^+$.

EXAMPLE 30

2-Oxo-3-[(4-sulfamoyl-phenyl)-hydrazono]-2,3-dihydro-1H-indole-5-sulfonic acid amide The title compound was prepared from 1H-indole-2,3-dione-5-sulfonic acid amide and 4-sulfonamidophenylhydrazine hydrochloride according to Procedure G: mp>250° C.; $^1$H NMR (DMSO-$d_6$): δ 7.04 (d, J=8.4 Hz, 1H), 7.25 (s, 2H), 7.26 (s, 2H), 7.60 (d, J=8.9 Hz, 2H), 7.70 (dd, J=8.2, 1.9 Hz, 1H), 7.78 (d, J=8.7 Hz, 2H), 7.98 (d, J=1.6 Hz, 1H), 11.43 (s, 1H), 12.75 (s, 1H); APCI-MS m/z 395 (M)$^-$. Anal. Calcd for $C_{14}H_{13}N_5O_5S_2 \cdot 0.5H_2O$: C, 41.58; H, 3.49; N, 17.32; S, 15.86. Found: C, 41.67; H, 3.46; N, 17.26; S, 15.78.

EXAMPLE 31

4-[N'-(5-Methylsulfonyl-2-oxo-1,2-dihydro-indol-3-ylidene)-hydrazino]-benzenesulfonamide 5-Methylsulfonyl-1H-indole-2,3-dione was prepared from 4-methylsulfonylaniline according to Procedure A: $^1$H NMR (DMSO-$d_6$): δ 3.21 (s, 3H), 7.07 (d, J=8.3 Hz, 1H), 7.92 (d, J=1.7 Hz, 1H), 8.05 (dd, J=8.2, 2.0 Hz, 1H), 11.46 (s, 1H); APCI-MS m/z 225 (M)$^-$. The title compound was prepared from 5-methylsulfonyl-1H-indole-2,3-dione and 4-sulfonamidophenylhydrazine hydrochloride according to Procedure G: mp>250° C.; $^1$H NMR (DMSO-$d_6$): δ 3.20 (s, 3H), 7.11 (d, J=8.3 Hz, 1H), 7.26 (s, 2H), 7.65 (d, J=8.9 Hz, 2H), 7.78 (d, J=8.7 Hz, 2H), 7.79 (dd, J=8.2, 1.9 Hz, 1H), 8.06 (d, J=1.6 Hz, 1H), 11.54 (s, 1H), 12.75 (s, 1H); APCI-MS m/z 394 (M)$^-$. Anal. Calcd for $C_{15}H_{14}N_4O_5S_2 \cdot 0.9H_2O$: C, 43.87; H, 3.88; N, 13.64; S, 15.62. Found: C, 43.96; H, 3.80; N, 13.58; S, 15.67.

EXAMPLE 32

3-[(4-Methylsulfamoyl-phenyl)-hydrazono]-2-oxo-2,3-dihydro-1H-indole-5-sulfonic acid methylamide 1H-indole-2,3-dione-5-sulfonic acid methylamide was prepared from N-methylsulfonamidoaniline hydrochloride according to Procedure A: $^1$H NMR (DMSO-$d_6$): δ 2.37 (d, J=4.7 Hz, 3H), 7.04 (d, J=8.4 Hz, 1H), 7.45 (q, J=5.0 Hz, 1H), 7.73 (s, 1H), 7.91 (d, J=8.4 Hz, 1H), 11.38 (s, 1H); APCI-MS m/z 239 (M–H)$^-$. The title compound was prepared from 1H-indole-2,3-dione-5-sulfonic acid methylamide and 4-(N-methylsulfonamido)-phenylhydrazine according to Procedure G: mp>250° C.; $^1$H NMR (DMSO-$d_6$): δ 2.38 (d, J=4.9 Hz, 6H), 7.08 (d, J=8.2 Hz, 1H), 7.33 (q, J=5.2 Hz, 1H), 7.35 (q, J=4.9 Hz, 1H), 7.65 (d, J=8.7 Hz, 2H), 7.66 (dd, J=8.1, 1.8 Hz, 1H), 7.73 (d, J=8.8 Hz, 2H), 7.91 (d, J=1.5 Hz, 1H), 11.48 (s, 1H), 12.77 (s, 1H);

APCI-MS m/z 422 (M−H)⁻. Anal. Calcd for $C_{16}H_{17}N_5O_5S_2$: C, 45.38; H, 4.05; N, 16.54. Found: C, 45.46; H, 4.04; N, 16.45.

EXAMPLE 33

4-{N'-[5-(1-Hydroxyimino-ethyl)-2-oxo-1,2-dihydro-indol-3-ylidene]-hydrazino}-N-methyl-benzenesulfonamide 5-(1-Hydroxyiminoethyl)-1H-indole-2,3-dione was prepared from 4-aminoacetophenone according to Procedure A: ¹H NMR (DMSO-d₆): δ 2.00 (s, 3H), 6.83 (d, J=8.6 Hz, 1H), 7.60 (dd, J=8.5, 2.1 Hz, 1H), 7.77 (d, J=1.7 Hz, 1H), 9.99 (s, 1H), 10.91 (s, 1H); APCI-MS m/z 203 (M−H)⁻. The title compound was prepared from 5-(1-hydroxyiminoethyl)-1H-indole-2,3-dione and 4-(N-methylsulfonamido)phenylhydrazine according to Procedure G: mp>250° C.; ¹H NMR (DMSO-d₆): δ 2.00 (s, 3H), 2.37 (d, J=4.9 Hz, 3H), 6.85 (d, J=8.4 Hz, 1H), 7.31 (q, J=5.0 Hz, 1H), 7.37 (dd, J=8.4, 1.8 Hz, 1H), 7.56 (d, J=8.7 Hz, 2H), 7.74 (d, J=8.8 Hz, 2H), 7.91 (d, J=1.9 Hz, 1H), 9.88 (s, 1H), 10.99 (s, 1H), 12.79 (s, 1H); APCI-MS m/z 386 (M−H)⁻. Anal. Calcd for $C_{17}H_{17}N_5O_4S$: C, 52.70; H, 4.42; N, 18.08. Found: C, 52.80; H, 4.50; N, 17.90.

EXAMPLE 34

4-[1-(5-Oxazol-5-yl-2-oxo-1,2-dihydro-indol-3-ylidene)-ethylamino]-benzenesulfonamide 3-(1-Dimethylaminoethylidene)-5-(oxazol-5-yl)-1,3-dihydroindol-2-one was prepared from 5-(oxazol-5-yl)-1,3-dihydroindol-2-one and N,N-dimethylacetamide dimethyl acetal according to Procedure H. Condensation of 3-(1-dimethylaminoethylidene)-5-(oxazol-5-yl)-1,3-dihydroindol-2-one and sulfanilamide according to Procedure J provided the title compound: mp>250° C; ¹H NMR (DMSO-d₆): δ 2.51 (s, 0.8H, DMSO), 2.61 (s, 3H), 6.97 (d, J=8.2 Hz, 1H), 7.37 (s, 2H), 7.40 (dd, J=8.0, 1.5 Hz, 1H), 7.45 (d, J=8.8 Hz, 2H), 7.56 (s, 1H), 7.66 (d, J=1.2 Hz, 1H), 7.83 (d, J=8.5 Hz, 2H), 8.34 (s, 1H), 10.85 (s, 1H), 12.33 (s, 1H); APCI-MS m/z 395 (M−H)⁻. Anal. Calcd for $C_{19}H_{16}N_4O_4S.0.1\ C_2H_6OS.0.6H_2O$: C, 55.56; H, 4.32; N, 13.50; S, 8.50. Found: C, 55.53; H, 4.32; N, 13.27; S, 8.58.

EXAMPLE 35

N,N-Dimethyl-4-[(5-oxazol-5-yl-2-oxo-1,2-dihydro-indol-3-ylidenemethyl)-amino]-benzenesulfonamide 3-Methylsulfanyl-5-oxazol-5-yl-1,3-dihydro-indol-2-one was prepared from 4-oxazol-5-yl-aniline according to Procedure D: ¹H NMR (DMSO-d₆): δ 10.7 (s, 1H), 8.3 (s, 1H), 7.5 (s, 3H), 6.9 (d, 1H), 4.5 (s, 1H), 2.0 (s, 3H); APCI-MS m/z 247 (M+H)⁺. 5-Oxazol-5-yl-1,3-dihydro-indol-2-one was prepared from 3-methylsulfanyl-5-oxazol-5-yl-1,3-dihydro-indol-2-one according to Procedure D: ¹H NMR (DMSO-d₆): δ 10.5 (s, 1H), 8.3 (s, 1H), 7.5 (m, 3H), 6,8 (d, 1H), 3.5 (s, 2H); APCI-MS m/z 201 (M+H)⁺. 3-Ethoxymethylene-5-oxazol-5-yl-1,3-dihydro-indol-2-one was prepared from 5-oxazol-5-yl-1,3-dihydro-indol-2-one according to Procedure I: ¹H NMR (DMSO-d₆): δ 10.43 (s, 1H), 8.37 (s, 1H), 7.76 (s, 1H), 7.51 (m, 2H), 6.90, (d, 1H), 4.43 (q, 2H), 1.4 (t, 3H): APCI-MS m/z 255 (M−H)⁺. The title compound was prepared in 36% yield from 3-ethoxymethylene-5-oxazol-5-yl-1,3-dihydro-indol-2-one and N,N-dimethyl-4-aminobenzenesulfonamide according to Procedure J: ¹H NMR (DMSO-d₆): δ 10.9(d, 1H), 10.8 (s, 1H), 8.8(d, 1H), 8.4 (s, 1H), 8.0 (s, 1H), 7.7 (br d, 4H), 7.5 (m, 2H), 7.0 (d, 1H), 2.6 (s, 6H); APCI-MS m/z 409 (M−H)⁻.

EXAMPLE 36

4-[1-(5-Oxazol-5-yl-2-oxo-1,2-dihydro-indol-3-ylidene)-hydrazino]-benzenesulfonamide (5:1 E:Z isomer mixture)

The title mixture of isomers was prepared from 5-(oxazol-5-yl)-1H-indole-2,3-dione and 4-sulfonamidophenylhydrazine hydrochloride according to Procedure G: mp>250° C.; ¹H NMR (DMSO-d₆): δ (5:1 ratio of Z:E isomers), E 6.97 (d, J=8.2 Hz, 1H), Z 7.00 (d, J=8.2 Hz, 1H), E 7.23 (s, 2H), Z 7.25 (s, 2H), Z 7.61 (d, J=9.1 Hz, 2H), E 7.61 (d, J=9.1 Hz, 2H), Z 7.62 (dd, J=8.2,1.7 Hz, 1H), Z 7.65 (s, 1H), E 7.65 (s, 1H), E 7.65 (dd, J=8.2, 1.5 Hz, 1H), Z 7.78 (d, J=8.9 Hz, 2H), E 7.81 (d, J=8.9 Hz, 2H), Z 7.90 (d, J=1.7 Hz, 1H), Z 8.40 (s, 1H), E 8.43 (s, 1H), E 8.47 (d, J=1.3 Hz, 1H), E 10.83 (s, 1H), E 10.98 (s, 1H), Z 11.25 (s, 1H), Z 12.78 (s, 1H); ESI-MS m/z 382 (M−H)⁻. Anal. Calcd for $C_{17}H_{13}N_5O_4S.1.2H_2O.0.4\ C_2H_6O$: C, 50.49; H, 4.24; N, 16.54. Found: C, 50.50; H, 4.15; N, 16.56.

EXAMPLE 37

4-[(2-Oxo-5-phenyl-1,2-dihydro-indol-3-ylidenemethyl)-amino]-benzenesulfonamide (Z-isomer)

A solution of 0.62 g (3.0 mmol) of 5-phenyl-1,3-dihydro-indol-2-one (Hewawasam and Meanwell, Tetrahedron Letters 1994, 35, 7303–6) in 10 mL of DMF was treated with 0.90 g (4.5 mmol) of DMF di-tert-butyl acetal for 2 h at rt. DMF was removed under high vaccum, and the residue was subjected to chromatography on silica gel, eluting with hexane:EtOAc (1:1), to yield 0.09 g (10%) of 3-tert-butoxymethylene-5-phenyl-1,3-dihydro-indol-2-one: ¹H NMR (DMSO-d₆): δ 1.46 (s, 9H), 6.85 (d, J=8.0 Hz, 1H), 7.27 (t, J=7.3 Hz, 1H), 7.34–7.39 (m, 1H), 7.41 (d, J=7.5 Hz, 2H), 7.53 (d, J=7.5 Hz, 2H), 7.72 (s, 1H), 7.83 (s, 1H), 10.28 (s, 1H); APCI+MS m/z 316 (M+23)⁺. Further elution with EtOAc:MeOH (98:2) gave 0.11 g (14%) of 3-dimethylaminomethylene-5-phenyl-1,3-dihydro-indol-2-one.

A solution of 0.09 g (0.31 mmol) of 5-phenyl-3-tert-butoxymethylene-1,3-dihydro-indol-2-one, 0.053 g (0.31 mmol) of sulfanilamide, and 2 drops of conc. HCl in 15 mL of ethanol was refluxed for 1 h and cooled to rt. The resulting yellow solid was isolated by filtration, washed with ethanol and dried to give 0.068 g (56%) of the title compound: ¹H NMR (DMSO-d₆): δ 6.90 (d, J=8.2 Hz, 1H), 7.25 (s, 2H), 7.29 (t, J=7.5 Hz, 1H), 7.34 (dd, J=1.6, 8.2 Hz, 1H), 7.43 (d, J=7.5 Hz, 2H), 7.55 (d, J=8.8 Hz, 2H), 7.64 (d, J=7.5 Hz, 2H), 7.77 (d, J=8.8 Hz, 2H), 7.99 (d, J=1.6 Hz, 1H), 8.74 (d, J=12.5 Hz, 1H), 10.62 (s, 1H), 10.76 (d, J=12.5 Hz, 1H); APCI-MS m/z 390 (M−H)⁻.

EXAMPLE 38

See Procedure K

EXAMPLE 39

2-Oxo-3-[(4-sulfamoyl-phenyl)-hydrazono]-2,3-dihydro-1H-indol-5-carboxylic acid (furan-2-ylmethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2-aminomethylfuran according to Procedure K: mp>250° C.; $^1$H NMR (DMSO-$d_6$): δ 4.51 (d, J=5.5 Hz, 2H), 6.31 (d, J=3 Hz, 1H), 6.44 (d, J=3 Hz), 7.02 ( d, J=8.3, 1H), 7.30 (s, 2H), 7.66 (m, 3H), 7.88 (m, 3H), 8.18 (s, 1H), 9.02 (br t, J=5.5 Hz, 1H), 11.4 (s, 1H), 12.8 (s, 1H); APCI-MS m/z 438 (M–H)$^-$; Anal. Calcd for $C_{20}H_{17}N_5O_5S.\frac{1}{2}H_2O$: C, 53.57; H, 4.05; N, 15.62; S, 7.15. Found: C, 53.91; H, 4.01; N, 15.13; S, 6.78.

EXAMPLE 40

2-Oxo-3-[(4-sulfamoyl-phenyl)-hydrazono]-2,3-dihydro-1H-indol-5-carboxylic acid-2,6-dimethoxybenzylamide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2,6-dimethoxybenzylamine according to Procedure K: mp>250° C.; $^1$H NMR (DMSO-$d_6$): δ 3.76 (s, 6H), 4.43 (d, J=4.2 Hz, 2H), 6.65 (d, J=8.4 Hz, 2H), 6.91 (d, J=8.2 Hz, 1H), 7.23 (s, 2H), 7.25 (d, J=8.2 Hz, 1H), 7.56 (d, J=8.6 Hz, 2H), 7.79 (m, 3H), 8.07 (s, 1H), 8.13 (br s, 1H), 11.27 (s, 1H), 12.76 (s, 1H); APCI-MS m/z 532 (M+Na)$^+$; Anal. Calcd for $C_{24}H_{23}N_5O_6S.\frac{1}{2}H_2O$: C, 55.59; H, 4.67; N, 13.51; S, 6.18. Found: C, 55.69; H, 4.64; N, 13.61; S, 6.09.

EXAMPLE 41

2-Oxo-3[(4-sulfamoyl-phenyl)-hydrazono]-2,3-dihydro-1H-indole-5-carboxylic acid (2-morpholin-4yl-ethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2-(N-morpholino)ethylamine according to Procedure K: mp 210–212° C.; Anal. Calcd for $C_{21}H_{24}N_6O_5S.\frac{1}{4}H_2O$: C, 52.88; H, 5.18; N, 17.62. Found: C, 52.91; H, 5.24; N, 17.35.

EXAMPLE 42

2-Oxo-3-[(4-sulfamoyl-phenyl)-hydrazono]-2,3-dihydro-1H-indole-5-carboxylic acid (2-imidazol-1-yl-ethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2-(N-imidazolo)ethylamine according to Procedure K: mp>230° C.; Anal. Calcd for $C_{20}H_{18}N_7O_4S$: C, 53.09; H, 4.01; N, 21.67. Found: C, 52.83; H, 4.24; N, 21.55.

EXAMPLE 43

2-Oxo-3-[(4-sulfamoyl-phenyl)-hydrazono]-2,3-dihydro-1H-indole-5-carboxylic acid (3-imidazol-1-yl-propyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 3-(N-morpholino)propylamine according to Procedure K: mp>230° C.; Anal. Calcd for $C_{21}H_{21}N_7O_4S.\frac{1}{2}H_2O$: C, 52.93; H, 4.65; N, 20.58. Found: C, 52.93; H, 4.40; N, 20.17.

EXAMPLE 44

2-Oxo-3-[(4-sulfamoyl-phenyl)-hydrazono]-2,3-dihydro-1H-indole-5-carboxylic acid (2-methoxyethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2-methoxyethylamine according to Procedure K: mp>230° C.; Anal. Calcd for $C_{18}H_{19}N_5O_5S$: C, 51.79; H, 4.59; N, 16.78. Found: C, 51.69; H, 4.54; N, 16.72.

EXAMPLE 45

2-Oxo-3-[(4-sulfamoyl-phenyl)-hydrazono]-2,3-dihydro-1H-indole-5-carboxylic acid (2-hydroxyethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2-hydroxyethylamine according to Procedure K: mp>230° C.; Anal. Calcd for $C_{17}H_{17}N_5O_5S$: C, 50.61; H, 4.25; N, 17.36. Found: C, 50.53; H, 4.28; N, 17.27.

EXAMPLE 46

2-Oxo-3-[(4-sulfamoyl-phenyl)-hydrazono]-2,3-dihydro-1H-indole-5-carboxylic acid (3-hydroxypropyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2-hydroxypropylamine according to Procedure K: mp>230° C.; Anal. Calcd for $C_{18}H_{19}N_5O_5S.\frac{1}{3}H_2O$: C, 51.06; H, 4.68; N, 16.54. Found: C, 51.07; H, 4.45; N, 16.45.

EXAMPLE 47

2-Oxo-3-[(4-sulfamoyl-phenyl)-hydrazono]-2,3-dihydro-1H-indole-5-carboxylic acid (3-hydroxy-2,2-dimethylpropyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 3-hydroxy-2,2-dimethylpropylamine according to Procedure K: mp>230° C.; Anal. Calcd for $C_{20}H_{23}N_5O_5S$: C, 53.92; H, 5.20; N, 15.72. Found: C, 54.04; H, 5.17; N, 15.77.

EXAMPLE 48

2-Oxo-3-[(4-sulfamoyl-phenyl)-hydrazono]-2,3-dihydro-1H-indole-5-carboxylic acid (pyridin-3-ylmethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and (3-pyridyl)methylamine according to Procedure K: mp 211–215° C.; Anal. Calcd for $C_{21}H_{18}N_6O_4S.H_2O$: C, 53.84; H, 4.30; N, 17.94. Found: C, 54.29; H, 4.03; N, 17.82.

EXAMPLE 49

2-Oxo-3-[(4-sulfamoyl-phenyl)-hydrazono]-2,3-dihydro-1H-indole-5-carboxylic acid (pyridin-4-ylmethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and (4-pyridyl)methylamine according to Procedure K: mp 211–215° C.; Anal. Calcd for $C_{21}H_{18}N_6O_4S \cdot \frac{3}{4}H_2O$: C, 54.36; H, 4.24; N, 18.11. Found: C, 54.41; H, 4.20; N, 18.12.

EXAMPLE 50

4-[N'-(5-Methoxy-2-oxo-1,2-dihydro-indol-3-ylidene)-hydrazino]-benzenesulfonamide (Z-isomer)

The title compound was prepared from 5-methoxy-1H-indole-2,3-dione (Gassman, et al., Journal of Organic Chemistry 1977, 42, 1344–8) and 4-hydrazinobenzenesulfonamide hydrochloride according to Procedure G: mp>250° C.; $^1$H NMR (DMSO-$d_6$): δ 3.80 (s, 3H), 6.87 (s, 2H), 7.20 (s, 1H), 7.28 (s, 2H), 7.60 (d, J=8.8 Hz, 2H), 7.81 (d, J=8.8 Hz, 2H), 10.93 (s, 1H), 12.85 (s, 1H); APCI-MS m/z 344.9 (M–H)$^-$.

EXAMPLE 51

4-[N'-(5-Amino-2-oxo-1,2-dihydro-indol-3-ylidene)-hydrazino]-benzenesulfonamide hydrochloride (Z-isomer)

The title compound was prepared from 5-amino-1H-indole-2,3-dione and 4-hydrazinobenzenesulfonamide hydrochloride according to Procedure G: $^1$H NMR (DMSO-$d_6$): δ 6.95 (d, J=8 Hz, 1H), 7.2 (d, J=8 Hz, 1H), 7.26 (s, 2H), 7.46 (s, 1H), 7.5 (d, J=8 Hz, 2H), 7.8 (d, J=8 Hz, 2H), 9.7 (br s, 3H), 11.2 (s, 1H), 12.8 (s, 1H); APCI-MS m/z 330.2 (M–H)$^-$.

EXAMPLE 52

4-[N'-(6-Ethyl-2-oxo-1,2-dihydro-indol-3-ylidene)-hydrazino]-benzenesulfonamide (Z isomer)

The title compound was prepared from 6-ethyl-1H-indole-2,3-dione (Krantz and Young, 1989, U.S. Pat. No. 4,873,232) and 4-sulfonamidophenylhydrazine hydrochloride according to Procedure G in 79% yield: $^1$H NMR (DMSO-$d_6$): δ 1.16 (t, J=7.5 Hz, 3H), 2.60 (q, J=7.5 Hz, 2H), 6.74 (s, 1H), 6.89 (d, J=7.5 Hz, 1H), 7.22 (s, 2H), 7.46 (d, J=7.5 Hz, 1H), 7.50 (d, J=8.7 Hz, 1H), 7.75 (d, J=8.7 Hz, 2H), 11.02 (s, 1H), 12.70 (s, 1H); APCI-MS m/z 343 (M–H)$^-$. Anal. Calcd for $C_{16}H_{16}N_4O_3S \cdot 0.32H_2O$: C, 54.88, H, 4.79; N, 16.00; S, 9.16. Found C, 54.81, H, 4.59; N, 16.06; S, 9.04.

EXAMPLE 53

4-[(2-Oxo-1,2-dihydro-indol-3-ylidenemethyl)-amino]-benzensulfonic acid phenyl ester (Z-isomer)

The title compound was prepared in 23% yield from 3-hydroxymethylene-1,3-dihydro-indol-2-one and phenyl 4-aminobenzenesulfonate according to Procedure J: $^1$H NMR (DMSO-$d_6$): δ 10.8 (d, 1H), 10.5 (s, 1H), 8.6 (d, 1H), 7.7 (d, 2H), 7.6 (m, 3H), 7.4 (m, 2H), 7.3 (m, 1H), 7.0 (m., 3H), 6.9 (t, 1H), 6.8 (d, 1H); APCI-MS m/z 391 (M–H)$^-$.

EXAMPLE 54

N-{4-[(2-Oxo-1,2-dihydro-indol-3-ylidenemethyl)-amino]-phenyl}sulfamide (Z-isomer)

The title compound was prepared from 3-hydroxymethylene-1,3-dihydro-indol-2-one and 4-aminophenylsulfamide according to Procedure J in 52% yield: $^1$H NMR (DMSO-$d_6$): δ 6.85 (d, J=7.5 Hz, 1H), 6.93 (t, J=7.5 Hz, 1H), 7.01 (t, J=7.5 Hz, 1H), 7.08 (s, 2H), 7.21 (d, J=8.8 Hz, 2H), 7.36 (d, J=8.8 Hz, 2H), 7.57 (d, J=7.5 Hz, 1H), 8.53 (d, J=12.7 Hz, 1H), 9.38 (s, 1H), 10.48 (s, 1H), 10.70 (d, J=12.7 Hz, 1H): APCI-MS m/z 329 (M–H)$^-$. Anal. Calcd for $C_{15}H_{14}N_4O_3S$: C, 54.54, H, 4.27; N, 16.96; S, 9.71. Found C, 54.48, H, 4.30; N, 16.90; S, 9.63.

EXAMPLE 55

4-[(6-Hydroxymethyl-2-oxo-1,2-dihydro-indol-3-ylidenemethyl)-amino]-benzenesulfonamide (Z-isomer)

A solution of 0.42 g (2.0 mmol) of 6-hydroxymethyl-3-methylsulfanyl-1,3-dihydro-indol-2-one in DMF (10 mL) was treated with 0.32 g (2.1 mmol) of t-butyldimethylsilyl chloride and 0.15 g (2.2 mmol) of imidazole and stirred for 16 h. The solution was diluted with 50 mL of hexane and 50 mL of EtOAc, washed with brine, dried over MgSO$_4$ and concentrated to give 0.28 g (43%) of 3-methylsulfanyl-6-(t-butyldimethylsilyloxy)methyl-1,3-dihydro-indol-2-one as a clear oil which crystallised upon storage at rt: $^1$H NMR (DMSO-$d_6$): δ 0.01 (s, 6H), 0.97 (s, 9H), 2.00 (s, 3H), 4.52 (s, 1H), 4.72 (s, 2H), 6.85 (s, 1H), 6.96 (d, J=7.7 Hz, 1H), 7.25 (d, J=7.7 Hz, 1H), 10.54 (s, 1H). A solution of 0.28 g (0.86 mmol) of 3-methylsulfanyl-4-(t-butyldimethylsilyloxy)methyl-1,3-dihydro-indol-2-one in THF (10 mL) was stirred with saturated ammonium chloride solution (10 mL), and activated zinc dust (2 g) was added. The mixture was stirred 16 h at rt. The organic phase was separated, dried over MgSO$_4$ and concentrated to give 0.32 g of impure 4-(t-butyldimethylsilyloxy)methyl-1,3-dihydro-indol-2-one as a gummy white solid: $^1$H NMR (DMSO-$d_6$): δ 0.04 (s, 6H), 0.87 (s, 9H), 3.39 (s, 2H), 4.62 (s, 2H), 6.75 (s, 1H), 6.81 (d, J=7.5 Hz, 1H), 7.10 (d, J=7.5 Hz, 1H), 10.30 (bs, 1H). A solution of 0.32 g (1.2 mmol) of 4-(t-butyidimethylsilyloxy)methyl-1,3-dihydro-indol-2-one in DMF dimethylacetal (3 mL) was heated to 100° C. for 0.75 h. The excess DMF dimethylacetal was removed under high vacuum, and the resulting dark oil was chromatographed on silica gel, eluting with EtOAc/MeOH (98:2), to give 0.16 g (41%) of 3-dimethylaminomethylene-6-(t-butyldimethylsilyloxy)methyl-1,3-dihydro-indol-2-one (11:9 mixture of E and Z isomers) as a yellow solid: $^1$H NMR (DMSO-$d_6$, peak areas normalized using the combined peak areas for δ 9.88 and 9.66 as 1H): δ 0.21 (s, 2.70H), 0.34 (s, 3.3H), 0.85 (s, 4.05H), 0.86 (s, 4.95H), 3.25 (s, 2.70H), 3.30 (s, 3.30H), 4.58 (s, 0.9H), 4.59 (s, 1.1H), 6.64–6.71 (m, 2H), 7.16 (d, J=7.7 Hz, 0.45H), 7.29 (d, J=8.3 Hz, 0.55H), 7.33 (s, 0.55H), 7.47 (s, 0.45H), 9.88 (s, 0.55H) 9.96 (s, 0.45H); APCI-MS m/z 331 (M+1)$^+$. A solution of 0.334 g (1.00 mmol) of 3-dimethylamino-methylene-6-(t-butyldimethylsilyloxy) methyl-1,3-dihydro-indol-2-one in 2-methylpropanol (3 mL) was treated with 0.174 g (1.00 mmol) of sulfanilamide and 0.25 g (4.0 mmol) of acetic acid. The solution was refluxed for 3 h and cooled to rt. The resulting yellow precipitate was isolated by filtration, washed with ethanol and dried to yield 0.134 g (29%) of 6-([t-butyldimethyl-silyloxy]methyl-2-oxo-1,2-dihydro-indol-3-ylidenemethyl)-amino]-benzenesulfonamide (Z isomer).: $^1$H NMR (DMSO-$d_6$): δ 0.05 (s, 6H), 0.87 (s, 9H), 4.65 (s, 2H), 6.81 (s, 1H), 6.85 (d, J=8.0 Hz, 1H), 7.23 (s, 2H), 7.49–7.51 (m, 3H), 7.75 (d, J=8.4 Hz, 2H), 8.56 (d, J=12.3 Hz, 1H), 10.52 (s, 1H), 10.76 (d, J=12.3 Hz, 1H); APCI-MS m/z 458 (M–H)$^-$. To a solution of 0.125 g (2.80 mmol) of 6-([t-butyidimethylsilyloxy]methyl-2-oxo-1,2-dihydro-indol-3-ylidenemethyl)-amino]-benzenesulfonamide in THF (5 mL) was added 0.27 mL of a 1 M solution of t-butylammonium fluoride in THF, and the mixture was stirred at rt for 1 h. The resulting yellow precipitate was isolated by filtration, washed with THF and dried. Chromatographic purification of the solid on silica gel, eluting with a hexane to EtOAc gradient, gave 0.053 g (55%) of the title compound: 1K NMR (DMSO-$d_6$): δ 4.43 (d, J=5.8 Hz, 2H), 5.08 (t, J=5.8 Hz, 1H), 6.82 (s, 1H), 6.85 (d, J=8.2 Hz, 1H), 7.23 (s, 2H), 7.50 (d, J=7.5 Hz, 2H), 7.74 (d, J=8.7 Hz, 3H), 8.56 (d, J=12.2 Hz, 1H), 10.54 (s, 1H), 10.75 (d, J=12.1 Hz, 1H); APCI-MS m/z 345 (M–H)$^-$. Anal. Calcd for $C_{16}H_{15}N_3O_4S.0.5H_2O$: C, 54.43, H, 4.55; N, 11.86, S, 9.05. Found C, 54.47, H, 4.63; N, 11.66; S, 8.86.

EXAMPLE 56

4-[N'-(6-Bromo-2-oxo-1,2-dihydro-indol-3-ylidene)-hydrazino]-benzenesulfonamide (Z-isomer)

The title compound was prepared from 6-bromo-1H-indole-2,3-dione (Meth-Cohn and Goon, Tetrahedron Letters 1996, 37, 9381–4) and 4-hydrazinobenzenesulfonamide hydrochloride according to Procedure G: mp>250° C.; $^1$H NMR (DMSO-$d_6$): δ 7.05 (s, 1H), 7.23 (d, J=8.1 Hz, 1H), 7.50 (d, J=8.1 Hz, 1H), 7.56 (d, J=8.7 Hz, 2H), 7.75 (d, J=8.7 Hz, 2H), 11.2 (s, 1H), 12.7 (s, 1H); APCI-MS m/z 395 (M–H)$^-$.

EXAMPLE 57

4-[N'-(2-Oxo-6-phenoxy-1,2-dihydro-indol-3-ylidene)-hydrazino]-benzenesulfonamide (Z-isomer)

The title compound was prepared from 6-phenoxy-1H-indole-2,3-dione and 4-sulfonamidophenylhydrazine according to Procedure G in 87% yield: mp>250° C.; $^1$H NMR (DMSO-$d_6$): δ 6.42 (d, J=2.2 Hz, 1H), 6.73 (dd, $J_1$=2.2 Hz, $J_2$=8.5 Hz, 1H), 7.17 (d, J=8 Hz, 2H), 7.25 (s, 1H), 7.28 (d, J=7.4 Hz, 2H), 7.49 (t, J=7.9 Hz, 2H), 7.73 (d, J=8.8 Hz, 2H), 7.82 (d, J=8.8 Hz, 2H), 8.25 (d, J=8.5 Hz, 2H), 10.61 (s, 1H), 10.65 (s, 1H); APCI-MS: m/z 431 (M+Na)$^+$. Anal. Calcd for $C_{20}H_{16}N_4O_4S.0.25H_2O$: C, 58.17; H, 4.03; N, 13.57; S, 7.76. Found: C, 58.45; H, 4.39; N, 13.40; S, 7.63.

EXAMPLE 58

4-[N'-(4-Ethoxy-2-oxo-1,2-dihydro-indol-3-ylidene)-hydrazino]-benzenesulfonamide (Z-isomer)

The title compound was prepared from 3-ethoxyaniline and 4-hydrazinobenzene sulfonamide hydrochloride according to Procedure C: mp>250° C.; $^1$H NMR (DMSO-$d_6$): δ 1.43 (t, J=7.0 Hz, 3H), 4.13 (q, J=7.0 Hz, 2H), 6.50 (d, J=7.6 Hz, 1H), 6.68 (d, J=8.4 Hz, 1H), 7.15–7.21 (m, 3H), 7.46 (d, J=8.8 Hz, 2H), 7.74 (d, J=8.8 Hz, 2H), 11.03 (s, 1H), 12.78 (s, 1H); APCI-MS: m/z 359 (M–H)$^-$. Anal. Calcd for $C_{16}H_{16}N_4O_4S$: C, 53.32; H, 4.47; N, 15.55; S, 8.90. Found: C, 53.21; H, 4.50; N, 15.66; S, 8.85.

EXAMPLE 59

N-[2-(2-Hydroxyethoxy)ethyl]-4-[7-oxo-6,7-dihydro-1-thia-3,6-diaza-as-indacene-8-ylidenemethyl)-amino]benzenesulfonamide (Z-isomer)

The title compound was prepared from 4-amino-N-(2-(2-hydroxyethoxy)ethyl)-benzenesulfonamide (see Example 84) and 8-ethoxymethylene-6,8-dihydro-1-thia-3,6-diaza-as-indacen-7-one according to Procedure J: $^1$H NMR (DMSO-$d_6$): δ 2.88 (q, J=6.0 Hz, 2H), 3.31 (t, J=5.0 Hz, 2H), 3.36 (t, J=5.8 Hz, 2H), 3.42 (t, J=5.1 Hz, 2 Hz), 4.5 (br s, 1H), 7.10 (d, J=8.4 Hz, 1H), 7.59 (d, J=8.8 Hz, 2H), 7.60 (t, J=6.0 Hz, 1H), 7.77 (d, J=8.7 Hz, 2H), 7.81 (d, J=8.6 Hz, 1H), 8.07 (d, J=12.2 Hz, 1H), 9.25 (s, 1H), 10.91 (s, 1H), 11.16 (d, J=12.2 Hz, 1H); APCI-MS m/z 459 (M–H)$^-$. Anal. Calcd for $C_{20}H_{20}N_4O_5S_2.H_2O$: C, 50.20; H, 4.63; N, 11.71. Found: C, 50.06; H, 4.59; N, 11.68.

EXAMPLE 60

N-[2-(2-Hydroxyethyl]-4-[7-oxo-6,7-dihydro-1-thia-3,6-diaza-as-indacene-8-ylidenemethyl)-amino]benzenesulfonamide (Z-isomer)

The title compound was prepared in 51% yield from N-(2-hydroxyethyl)-4-aminobenzene sulfonamide and 8-ethoxymethylene-6,8-dihydro-1-thia-3,6-diaza-as-indacen-7-one according to Procedure J: $^1$H NMR (DMSO-$d_6$): δ 11.18 (d, 1H), 10.9 (s, 1H), 9.25 (s, 1H), 8.06 (d, 1H), 7.8 (d, 1H), 7.76 (d, 2H), 7.58 (d, 2H), 7.52 (t, 1H), 7.1 (d, 1H), 4.66 (t, 1H), 3.35 (q, 2H), 2.76 (q, 2H); APCI-MS m/z 415 (MH)$^-$.

EXAMPLE 61

N-Methyl-4-[N'-(4-methyl-5-nitro-2-oxo-1,2-dihydro-indol-3-ylidene)-hydrazino]-benzenesulfonamide (Z-isomer)

4-Methyl-5-nitro-1H-indole-2,3-dione was prepared from 3-methyl-4-nitroaniline according to Procedure A: $^1$H NMR (DMSO-$d_6$): δ 11.5 (s, 1H), 8.2 (d, 1H), 6.8 (d, 1H), 2.7 (s, 3H); APCI-MS m/z 205 (M–H)$^-$. The title compound was prepared in 84% yield from 4-methyl-5-nitro-1H-indole-2,3-dione and 4-sulfonamidophenylhydrazine hydrochloride according to Procedure G: $^1$H NMR (DMSO-$d_6$): δ 13.0 (s, 1H), 11.6 (s, 1H), 7.9 (d, 1H), 7.7 (d, 2H), 7.6 (d, 2H), 7.3 (q, 1H), 6.9 (d, 1H), 2.8 (s, 3H), 2.4 (d, 3H); APCI-MS m/z 388 (M–H)$^-$.

EXAMPLE 62

4-[N'-(7-Oxo-6,7-dihydro-3H-pyrrolo[3,2-e]indazol-8-ylidene)-hydrazino]-benzenesulfonamide (Z isomer)

The title compound was prepared from 3,6-dihydro-pyrrolo[3,2-e]indazole-7,8-dione (Cuny, et al., Chemie Berichte 1981, 114,1624–35) and 4-sulfonamidophenylhydrazine hydrochloride according to Procedure G in 8% yield: $^1$H NMR (DMSO-$d_6$): δ 7.02 (d, J=8.7 Hz, 1H), 7.28 Z (s, 2H), 7.51 (d, J=8.6 Hz, 2H), 7.68 (d, J=8.8 Hz, 1H), 7.82 (d, J=8.7 Hz, 2H), 8.34 (s, 1H), 10.98 (s, 1H), 12.90 (s, 1H), 13.20 (s, 1H); APCI-MS m/z 356 (M)$^-$. Anal. Calcd for $C_{15}H_{12}N_6O_3S \cdot 1.46H_2O \cdot 0.2$ EtOAc: C, 47.41, H, 4.16; N, 20.99; S, 8.01. Found C, 47.40, H, 3.70; N, 21.00; S, 7.85.

EXAMPLE 63

4-[N'-(7-Oxo-6,7-dihydro-1H-pyrrolo[2,3-g]indazol-8-ylidene)-hydrazino]-benzenesulfonamide (mixture of E and Z isomers)

The title compound was prepared from isatin 1,6-dihydropyrrolo[2,3-g]indazole-7,8-dione (Lichtenthaler and Cuny, Heterocycles 1981, 15, 1053–9) and 4-sulfonamidophenyl-hydrazine hydrochloride according to Procedure G in 76% yield: $^1$H NMR (DMSO-d$_6$): δ 6.82 Z (d, J=8.3 Hz, 1H), 6.87 E (d, J=8.5 Hz, 1H), 7.24 E (s, 2H), 7.27 Z (s, 2H), 7.43 E (d, J=8.6 Hz, 2H), 7.73 Z (d, J=8.3 Hz, 1H), 7.78 Z (d, J=8.8 Hz, 2H), 7.85 E (d, J=8.8 Hz, 2H), 7.89 E (d, J=8.5 Hz, 1H), 7.89 Z (d, J=8.5 Hz, 2H), 8.12 Z (s, 1H), 8.56 E (s, 1H), 10.67 E (s, 1H), 11.20 Z (s, 1H), 12.86 Z (s, 1H), 13.27 E (s, 1H), 13.27 Z (s, 1H), 14.27 E (s, 1H); APCI-MS m/z 355 (M–H)$^-$. Anal. Calcd for $C_{15}H_{12}N_6O_3S$: C, 50.56, H, 3.39; N, 23.58; S, 9.00. Found C, 50.65, H, 3.40; N, 23.59; S, 8.97.

EXAMPLE 64

4-[N'-(7-Oxo-6,7-dihydro-3H-1,2,3,6-tetraaza-as-indacen-8-ylidene)-hydrazino]-benzenesulfonamide (mixture of E and Z isomers)

1,6-Dihydro-1,2,3,6-tetraaza-as-indacene-7,8-dione was prepared according to Procedure A in 56% yield: $^1$H NMR (DMSO-d$_6$): δ 6.93 (d, J=8.6 Hz, 1H), 8.32 (d, J=8.6 Hz, 1H), 11.14 (s, 1H); APCI-MS m/z 189 (M+1)$^+$. Condensation of 1,6-dihydro-1,2,3,6-tetraaza-as-indacene-7,8-dione with 4-sulfonamidophenylhydrazine hydrochloride according to Procedure G gave the title compound in 15% yield: $^1$H NMR (DMSO-d$_6$): δ 7.06 Z (d, J=8.4 Hz, 1H), 7.24 E (d, J=8.4 Hz, 1H), 7.30 Z (s, 2H), 7.30 E (s, 2H), 7.55 E (d, J=8.5 Hz, 2H), 7.82 Z (d, J=8.5 Hz, 2H), 7.82 E (d, J=8.5 Hz, 1H), 7.90 E (d, J=8.7 Hz, 2H), 7.90 Z (d, J=8.8 Hz, 2H), 7.98 Z (d, J=8.4 Hz, 1H), 10.86 E (s, 1H), 11.35 Z (s, 1H), 12.87 Z (s, 1H), 12.95 E (s, 1H), 16.00 Z (s, 1H), 16.25 E (s, 1H); APCI-MS m/z 356 (M–H)$^-$. Anal. Calcd for $C_{14}H_{11}N_7O_3S \cdot H_2O$: C, 44.80, H, 3.49; N, 26.12; S, 8.54. Found C, 44.72, H, 3.46; N, 26.05; S, 8.48.

EXAMPLE 65

4-[N'-(1-Chloro-7-oxo-6,7-dihydro-3H-pyrrolo[3,2-e]indazol-8-ylidene)-hydrazino]-benzenesulfonamide (Z-isomer)

1-Chloro-3,6-dihydro-pyrrolo[3,2-e]indazole-7,8-dione was prepared from 5-amino-3-chloroindazole according to Procedure A in 38% yield: $^1$H NMR (DMSO-d$_6$): δ 7.08 (d, J=7.9 Hz, 1H), 7.92 (d, J=7.9 Hz, 1H), 10.95 (s, 1H), 13.70 (s, 1H). Condensation of 1-chloro-3,6-dihydro-pyrrolo[3,2-e]indazole-7,8-dione and 4-sulfonamidophenylhydrazine hydrochloride according to Procedure G gave the title compound in 45% yield: $^1$H NMR (DMSO-d$_6$): δ 7.11 (d, J=8.8 Hz, 1H), 7.26 (s, 2H), 7.51 (d, J=8.8 Hz, 1H), 7.64 (d, J=8.8 Hz, 2H), 7.82 (d, J=8.8 Hz, 2H), 11.17 (s, 1H), 13.25 (s, 1H), 13.41 (s, 1H): APCI-MS m/z 389/391 (M–H)$^-$. Anal. Calcd for $C_{15}H_{11}ClN_6O_3S$: C, 44.86, H, 3.06; N, 20.93; S, 7.98. Found C, 45.02, H, 3.31; N, 20.92; S, 7.77.

EXAMPLE 66

4-[N'-(1,7-Dioxo-2,3,6,7-tetrahydro-1H-2,6-diaza-as-indacen-8-ylidene)-hydrazino]-N-methyl-benzenesulfonamide (Z-isomer)

A solution of 16.2 g (100 mmol) of 6-aminophthalimide, 9.6 g (100 mmol) of methanesulfonic acid, and 4.0 g of 10% Pd/C in 140 mL of TFA was hydrogenated overnight at 50 psi. The catalyst was filtered off and and the filtrate concentrated on a rotary evaporator. The residue was diluted with 70 mL of ice water, adjusted to pH 8 with $K_2CO_3$, and chilled in an ice bath. The resulting solid was filtered to give 6.7 g of a 5:4 ratio of 5-amino:6-amino lactam isomers. Recrystallization from hot ethanol/water afforded 1.45 g of undesired isomer. The filtrate was preabsorbed onto silica gel and chromatographed with TEA:MeOH:methylene chloride (1:2:47). The resulting solid was slurried in methylene chloride/MeOH and filtered to afford a low yield of 5-amino-2,3-dihydro-isoindol-1-one: $^1$H NMR (DMSO-d$_6$): δ 4.13 (s, 2H), 5.67 (s, 2H), 6.55 (dd, J=8.7, 1.9 Hz, 1H), 6.55 (d, J=1.9 Hz, 1H), 7.25 (d, J=8.7 Hz, 1H), 7.83 (s, 1H); APCI-MS m/z 149 (M+H)$^+$.

2,6-Dihydro-1H-2,6-diaza-as-indacene-3,7,8-trione was prepared from 5-amino-2,3-dihydro-isoindol-1-one according to Procedure X: $^1$H NMR (DMSO-d$_6$): δ 4.46 (s, 2H), 6.94 (d, J=8.1 Hz, 1H), 7.80 (d, J=8.0 Hz, 1H), 8.51 (s, 1H), 11.28 (s, 1H); APCI-MS m/z 201 (M–H)$^-$. The title compound was prepared from 2,6-dihydro-1H-2,6-diaza-as-indacene-3,7,8-trione and 4-(N-methylsulfonamido)phenylhydrazine according to Procedure G: mp>250° C.; $^1$H NMR (DMSO-d$_6$): δ 2.37 (d, J=4.9 Hz, 3H), 4.56 (s, 2H), 6.99 (d, J=7.9 Hz, 1H), 7.31 (q, J=5.2 Hz, 1H), 7.55 (d, J=8.1 Hz, 1H), 7.60 (d, J=8.8 Hz, 2H), 7.72 (d, J=8.7 Hz, 2H), 8.50 (s, 1H), 11.35 (s, 1H), 12.70 (s, 1H); APCI-MS m/z 384 (M–H)$^-$. Anal. Calcd for $C_{17}H_{15}N_5O_4S \cdot 0.75H_2O$: C, 51.19; H, 4.17; N, 17.56. Found: C, 51.29; H, 4.15; N, 17.47.

EXAMPLE 67

N-(3-Hydroxy-2,2-dimethyl-propyl)-C-{4-[(7-oxo-6,7-dihydro-1-thia-3,6-diaza-as-indacen-8-ylidenemethyl)-amino]-phenyl}-methanesulfonamide (Z-isomer)

A solution of 3.16 g (30.6 mmol) of 3-amino-2,2-dimethylpropanol in 10 mL of $CH_2Cl_2$ was added at once to a solution of 2.40 g (10.2 mmol) of 4-nitrophenylmethanesulphonyl chloride (Lee, et al., Journal of the American Chemical Society 1987, 109, 7472–7; Macor, et al., Tetrahedron Letters 1992, 33, 8011–4) in 40 mL of $CH_2Cl_2$. The mixture was stirred at rt for 15 min, the solvent was removed in vacuo and the residue was redissolved in 50 mL of EtOAc. The solution was washed with three 50-mL portions of 1.0 N HCl and concentrated in vacuo. Purification of the residue by flash chromatography on silica gel (hexane/EtOAc 1:1) afforded N-(3-hydroxy-2,2-dimethyl-propyl)-(4-nitrophenyl)-methanesulfonamide as a white solid (0.84 g, 27%): $^1$H NMR (DMSO-d$_6$): δ 0.74 (s, 6H), 2.78 (d, J=6.4 Hz, 2H), 3.11 (d, J=5.3 Hz, 2H), 4.47 (t, J=5.3 Hz, 1H), 4.52 (s, 2H), 7.02 (t, J=6.4 Hz, 1H), 7.65 (d, J=8.8 Hz, 2H), 8.25 (d, J=8.8 Hz, 2H); APCI-MS: m/z 301 (M–H)$^-$. A mixture of 0.66 g (2.2 mmol) of N-(3-hydroxy-2,2-dimethyl-propyl)-(4-nitro-phenyl)-methanesulfonamide and ~0.06 g Pd/C 10% in 50 mL of MeOH was shaken on a Parr hydrogenator for 3.5 h. The catalyst was removed via filtration, and 0.273 mL (3.28 mmol) of conc. HCl was added. The solvent was removed in vacuo, and the solid residue was redissolved in 20 mL of EtOH and added to 0.486 g (1.98 mmol) of 8-dimethylaminomethylene-6,8-dihydro-1-thia-3,6-diaza-as-indacen-7-one. The mixture was heated to reflux for 4.5 h and cooled to ambient tempurature. The solid was collected by vacuum filtration, washed with water, and dried in a vacuum oven at 70° C. to afford the title compound as a yellow solid (0.66 g, 70%): mp 229–230° C. (dec); $^1$H NMR (DMSO-$d_6$): δ 0.74 (s, 6H), 2.73 (d, J=6.4 Hz, 2H), 3.08 (d, J=5.3 Hz, 2H), 4.27 (s, 2H), 4.43 (t, J=5.3 Hz, 1H), 6.84 (t, J=6.4 Hz, 1H), 7.09 (d, J=8.3 Hz, 1H), 7.37 (d, J=8.5 Hz, 2H), 7.42 (d, J=8.5 Hz, 2H), 7.77 (d, J=8.3 Hz, 1H), 8.03 (d, J=12.3 Hz, 1H), 9.24 (s, 1H), 10.84 (s, 1H), 11.04 (d, J=12.3 Hz, 1H); ESI-MS: m/z 471 (M−H)$^-$. Anal. Calcd for $C_{22}H_{24}N_4O_4S_2 \cdot 0.5H_2O$: C, 54.87; H, 5.23; N, 11.63; S, 13.32. Found: C, 54.90; H, 5.26; N, 11.68; S, 13.25.

EXAMPLE 68

N-Methyl-C-{4-[N'-(2-oxo-2,3-dihydro-pyrrolo[3,2f-]quinolin-1-ylidene)-hydrazino]-phenyl}-methanesulfonamide (Z-isomer)

2-Hydroxyimino-N-quinolin-6-yl-acetamide was prepared in 61% yield from 6-aminoquinoline according to Procedure A: $^1$H NMR (DMSO-$d_6$): δ 12.4 (s, 1H), 10.8 (s, 1H), 9.0 (d, 1H), 8.8 (d, 1H), 8.7 (s, 1H), 8.2 (s, 2H), 7.81 (m, 1H), 7.78 (s, 1H); $C_{11}H_9N_3O_2$: APCI-MS m/z 216 (M+H)$^+$. To a 1-L 3-neck round bottom flask was placed a magnetic stir bar and 110 mL of concentrated sulfuric acid. The flask was fitted with a thermometer to monitor the temperature of the reaction. The sulfuric acid was heated to 100° C. followed by slow addition of 2-hydroxyimino-N-quinolin-6-yl-acetamide (26.0 g, 0.121 mol). Heat to the reaction was maintained for approximately 1 h. The flask was removed from the heat source, and the reaction was poured slowly and carefully onto a mixture of 1 Kg of ice and 200 g of sodium carbonate. The residual reaction mixture in the reaction vessel was washed out with an additional 40 mL of cold water. The resulting aqueous slurry was stirred for about 1 h and filtered. The solid was washed thoroughly with water, filtered, and air dried to yield 7.31 g (31%) of 3-H-pyrrolo[3,2-f]quinoline-1,2-dione: $^1$H NMR (DMSO-$d_6$): δ 11.1 (s, 1H), 8.8 (d, 1H), 8.7 (d, 1H), 8.2 (d, 1H), 7.6 (m, 1H), 7.4 (d, 1H); APCI-MS m/z 197 (M−H)$^-$. The title compound was prepared in 77% yield from 3-H-pyrrolo[3,2-f]quinoline-1,2-dione and 4-hydrazinophenylmethane sulfonamide according to Procedure G: $^1$H NMR (DMSO-$d_6$): δ 13.1 (s, 1H), 11.5 (s, 1H), 9.3 (d, 1H), 8.9 (d, 1H), 8.0 (d, 1H), 7.9 (m, 1H), 7.6 (d, 1H), 7.6(d, 2H), 7.4 (d, 2H), 6.9(d, 1H), 4.3 (s, 2H), 2.55 (d, 3H); APCI-MS m/z 396 (M+H)$^+$.

EXAMPLE 69

N-(1H-Indazol-6-yl)-4-[(7-oxo-6,7-dihydro-1-thia-3,6-diaza-as-indacen-8-ylidenemethyl)-amino]-benzenesulfonamide (Z-isomer)

The title compound was prepared in 16% yield from 8-ethoxymethylene-6,8-dihydro-1-thia-3,6-diaza-as-indacen-7-one and 4-amino-N-(1H-indazol-6-yl)-benzenesulfonamide according to Procedure J: $^1$H NMR (DMSO-$d_6$): δ 12.9 (s, 1H), 11.1 (d, 1H), 10.9 (s, 1H), 10.4 (s, 1H), 9.3 (s, 1H), 8.1 (d, 1H), 8.0 (s, 1H), 7.8 (d, 1H), 7.8 (d, 2H), 7.7 (d, 1H), 7.6 (d, 2H), 7.3 (s, 1H), 7.1 (d, 1H), 6.9 (d, 1H); APCI-MS m/z 487 (M−H)$^-$.

EXAMPLE 70

4-[(7-Oxo-6,7-dihydro-1-thia-3,6-diaza-as-indacen-8-ylidenmethyl)-amino]-N-thiazol-2-yl-benzenesulfonamide (Z-isomer)

The title compound was prepared in 33% yield from 8-ethoxymethylene-6,8-dihydro-1-thia-3,6-diaza-as-indacen-7-one and 4-amino-N-(thiazol-2-yl)-benzenesulfonamide according to Procedure J: $^1$H NMR (DMSO-$d_6$): δ 12.7 (s, 1H), 11.2 (d, 1H), 10.9 (s, 1H), 9.3 (s, 1H), 8.1 (d, 1H), 7.8 (t, 3H), 7.6 (d, 2H), 7.3 (d, 1H), 7.2 (d, 1H), 6.8 (d, 1H); APCI-MS m/z 456 (M+H)$^+$ and 454 (M−H)$^-$.

EXAMPLE 71

N-(Amino-imino-methyl)-4-[(7-oxo-6,7-dihydro-1-thia-3,6-diaza-as-indacen-8-ylidenemethyl)-amino]-benzenesulfonamide (Z-isomer)

The title compound was prepared in 26% yield from 8-ethoxymethylene-6,8-dihydro-1-thia-3,6-diaza-as-indacen-7-one and 4-amino-N-(amino-imino-methyl)-benzenesulfonamide according to Procedure J: $^1$H NMR (DMSO-$d_6$): δ 11.2 (d, 1H), 10.9 (s, 1H), 9.3 (s, 1H), 8.1 (d, 1H), 7.85 (d, 1H), 7.8 (d, 2H), 7.5 (d, 2H), 7.4 (d, 1H), 7.3 (d, 1H), 6.5 (d, 1H), 5.7 (s, 1H); $C_{17}H_{14}N_6O_3S_2$: APCI-MS m/z 415 (M+H)$^+$.

EXAMPLE 72

See Procedure J

EXAMPLE 73

8-(2,2-Dioxo-1,3-dihydro-benzo[c]thiophene-5-ylamino-methylene)-6,8-dihydro-1-thia-3,6-diaza-as-indacen-7-one (Z-isomer)

The title compound was prepared in 37% yield from 8-ethoxymethylene-6,8-dihydro-1-thia-3,6-diaza-as-indacen-7-one and 2,2-dioxo-1,3-dihydrobenzo[c]thiophene-5-ylamine according to Procedure J: $^1$H NMR (DMSO-$d_6$): δ 11.11 (d, 1H), 10.89 (s, 1H), 9.27 (s, 1H), 8.06 (d, 1H), 7.82 (d, 1H), 7.47 (m, 2H), 7.13 (d, 1H), 6.98 (d, 1H), 6.5 (m, 2H); APCI-MS m/z 384 (M+H)$^+$.

EXAMPLE 74

{4-[-(7-Oxo-6,7-dihydro-1-thia-3,6-diaza-as-indacent-ylidenemethyl)-amino]-phenyl}-methanesulfonamide (Z-isomer)

The title compound was prepared in 25% yield from 8-ethoxymethylene-6,8-dihydro-1-thia-3,6-diaza-as-indacen-7-one and 4-aminophenylmethane sulfonamide according to Procedure J: $^1$H NMR (DMSO-$d_6$): δ 11.1 (d, 1H), 10.9 (s, 1H), 9.3 (s, 1H), 8.1 (d, 1H), 7.8 (d, 1H), 7.5 (q, 4H), 7.2 (d, 1H), 6.9 (s, 2H), 4.2 (s, 2H); APCI-MS m/z 387 (M+H)$^+$.

EXAMPLE 75

N-Allyl-C-{4-[(7-oxo-6,7-dihydro-1-thia-3,6-diaza-as-indacen-8-ylidenemethyl)-amino]-phenyl}-methansulfonamide (Z-isomer)

The title compound was prepared in 26% yield from 8-ethoxymethylene-6,8-dihydro-1-thia-3,6-diaza-as-indacen-7-one and N-allyl-4-aminophenylmethane sulfonamide according to Procedure J: $^1$H NMR (DMSO-$d_6$): δ 11.1 (d, 1H), 10.9 (s, 1H), 9.3 (s, 1H), 8.1 (d, 1H), 7.8 (d, 1H), 7.5 (q, 4H), 7.3 (t, 1H), 7.1 (d, 1H), 5.8 (m, 1H), 5.2 (d, 1H), 5.1 (d, 1H), 4.4 (s, 2H), 3.6 (t, 2H); APCI-MS m/z 427 (M+H)$^+$.

EXAMPLE 76

8-(4-Methylsulfonylmethyl-phenylamino-methylene)-6,8-dihydro-1-thia-3,6-diaza-as-indacen-7-one (Z-isomer)

The title compound was prepared in 66% yield from 8-ethoxymethylene-6,8-dihydro-1-thia-3,6-diaza-as-indacen-7-one and 4-methylsulfonylmethylaniline according to Procedure J: $^1$H NMR (DMSO-$d_6$): δ 11.1 (d, 1H), 11.0 (s, 1H), 9.3 (s, 1H), 8.1 (d, 1H), 7.8 (d, 1H), 7.5 (q, 4H), 7.1 (d, 1H), 4.45 (s, 2H), 2.9 (s, 3H); APCI-MS m/z 384 (M–H)$^-$.

EXAMPLE 77

N-(3-Hydroxy-2,2-dimethyl-propyl)-4-[(7-oxo-6,7-dihydro-1-thia-3,6-diaza-as-indacen-8-ylidenemethyl)-amino]-benzenesulfonamide (Z-isomer)

The title compound was prepared from 8-ethoxymethylene-6,8-dihydro-1-thia-3,6-diaza-as-indacen-7-one and 4-amino-N-(3-hydroxy-2,2-dimethyl-propyl)benzenesulfonamide according to Procedure J: mp>250° C.; $^1$H NMR (DMSO-$d_6$): δ 0.74 (s, 6H), 2.52 (d, J=6.7 Hz, 2H), 3.06 (bs, 2H), 4.43 (bs, 1H), 7.10 (d, J=8.3 Hz, 1H), 7.32 (t, J=6.7 Hz, 1H), 7.58 (d, J=8.8 Hz, 2H), 7.77 (d, J=8.8 Hz, 2H), 7.81 (d, J=8.3 Hz, 1H), 8.07 (d, J=12.2 Hz, 1H), 9.26 (s, 1H), 10.91 (s, 1H), 11.16 (d, J=12.3 Hz, 1H); APCI-MS: m/z 457 (M–H)$^-$. Anal. Calcd for $C_{21}H_{22}N_4O_4S_2$: C, 55.01; H, 4.84; N, 12.22; S, 13.98. Found: C, 54.90; H, 4.86; N, 12.25; S, 13.94.

EXAMPLE 78

4-[(7-Oxo-6,7-dihydro-1-thia-3,6-diaza-as-indacen-8-ylidenemethyl)-amino]-N-(3-trifluoromethyl-phenyl)-benzenesulfonamide (Z-isomer)

The title compound was prepared in 29% yield from 8-ethoxymethylene-6,8-dihydro-1-thia-3,6-diaza-as-indacen-7-one and N-(3-trifluoromethylphenyl)-4-aminobenzenesulfonamide according to Procedure J: $^1$H NMR (DMSO-$d_6$): δ 11.2 (d, 1H), 10.9 (s, 1H), 10.7 (s, 1H), 9.3 (s, 1H), 8.1 (d, 1H), 7.8 (m, 3H), 7.5 (m, 4H), 7.1 (d, 1H); APCI-MS m/z 515 (M–H)$^-$.

EXAMPLE 79

4-[(7-Oxo-6,7-dihydro-1-thia-3,6-diaza-as-indacen-8-ylidenemethyl)-amino]-N-pyrimidin-2-yl-benzenesulfonamide (Z-isomer)

The title compound was prepared in 29% yield from 8-ethoxymethylene-6,8-dihydro-1-thia-3,6-diaza-as-indacen-7-one and 4-amino-N-pyrimidin-2-yl-benzenesulfonamide according to Procedure J: $^1$H NMR (DMSO-$d_6$): δ 11.18 (d, 1H), 10.94 (s, 1H), 9.28 (s, 1H), 8.52 (d, 1H) 8.08 (d, 1H), 7.99 (d, 1H), 7.84 (d, 1H), 7.6 (d, 1H), 7.13 (d, 1H), 7.06 (m, 1H), 7.01 (m, 1H),; APCI-MS m/z 449 (M–H)$^-$.

EXAMPLE 80

N-(5-Methyl-[1,3,4]thiadiazol-2-yl)-4-[(7-oxo-6,7-dihydro-1-thia-3,6-diaza-as-indacen-8-ylidenemethyl)-amino]-benzenesulfonamide (Z-isomer)

The title compound was prepared in 36% yield from 8-ethoxymethylene-6,8-dihydro-1-thia-3,6-diaza-as-indacen-7-one and 4-amino-N-(5-methyl[1,3,4]thiadiazol-2-yl)-benzenesulfonamide according to Procedure J: $^1$H NMR (DMSO-$d_6$): δ 11.2 (d, 1H), 10.9 (s, 1H), 9.3 (s, 1H), 8.1 (d, 1H), 7.8 (m, 3H), 7.6 (d, 2H), 7.1 (d, 1H); ESI-MS m/z 469 (M–H)$^-$.

EXAMPLE 81

N-Acetyl-4-[(7-oxo-6,7-dihydro-1-thia-3,6-diaza-as-indacen-8-ylidenemethyl)-amino]-benzenesulfonamide (Z-isomer)

The title compound was prepared in 26% yield from 8-ethoxymethylene-6,8-dihydro-1-thia-3,6-diaza-as-indacen-7-one and N-acetyl-4-aminobenzenesulfonamide according to Procedure J: $^1$H NMR (DMSO-$d_6$): δ 12.0 (s, 1H), 11.2 (d, 1H), 10.9 (s, 1H), 8.1 (d, 1H), 7.9 (m, 3H), 7.6 (d, 2H), 7.1 (d, 1H), 2.0 (s, 3H); ESI-MS m/z 413 (M–H)$^-$.

EXAMPLE 82

N-Benzoyl-4-[(7-oxo-6,7-dihydro-1-thia-3,6-diaza-as-indacen-8-ylidenemethyl)-amino]-benzenesulfonamide (Z-isomer)

The title compound was prepared in 25% yield from 8-ethoxymethylene-6,8-dihydro-1-thia-3,6-diaza-as-indacen-7-one and N-benzoyl-4-aminobenzenesulfonamide according to Procedure J: $^1$H NMR (DMSO-$d_6$): δ 12.5 (br s, 1H), 11.2 (d, 1H), 10.9 (s, 1H), 9.3 (s, 1H), 8.1 (d, 1H), 8.0 (d, 2H), 7.9 (t, 3H), 7.65 (t, 3H), 7.5 (t, 2H), 7.2 (d, 1H); ESI-MS m/z 475 (M–H)$^-$.

EXAMPLE 83

N-Methyl-4-[N'-(7-oxo-6,7-dihydro-1-thia-3,6-diaza-as-indacen-8-ylidene)-hydrazino]-benzenesulfonamide (Z-isomer)

6H-1-Thia-3,6-diaza-as-indacene-7,8-dione was prepared from 6-aminobenzothiazole according to Procedure A: $^1$H NMR (DMSO-$d_6$): δ 7.10 (d, J=8.4 Hz, 1H), 8.31 (d, J=8.5 Hz, 1H), 9.35 (s, 1H), 11.19 (s, 1H); ESI-MS m/z 204 (M)$^-$. The title compound was prepared from 6H-1-thia-3,6-diazaas-indacene-7,8-dione and 4-sulfonamidophenylhydrazine hydrochloride according to Procedure G: mp>260° C.; $^1$H NMR (DMSO-d$_6$): δ 2.39 (d, J=5.1 Hz, 3H), 7.12 (d, J=8.4 Hz, 1H), 7.32 (q, J=5.1 Hz, 1H), 7.63 (d, J=8.8 Hz, 2H), 7.76 (d, J=8.7 Hz, 2H), 7.99 (d, J=8.6 Hz, 1H), 9.30 (s, 1H), 11.26 (s, 1H), 12.69 (s, 1H); APCI-MS m/z 387 (M)$^-$. Anal. Calcd for C$_{16}$H$_{13}$N$_5$O$_3$S$_2$.0.33H$_2$O: C, 48.85; H, 3.50; N, 17.80; S, 16.30. Found: C, 48.89; H, 3.40; N, 17.67; S, 16.23.

EXAMPLE 84

N-[2-(2-Hydroxy-ethoxy)-ethyl]-N-methyl-4-[(7-oxo-6,7-dihydro-1-thia-3,6-diaza-as-indacen-8-ylidenemethyl)-amino]-benzenesulfonamide (Z-isomer)

To a solution of 3.3 g (31 mmol) of 2-(2-aminoethoxy) ethanol in 30 mL of MeOH was added 7.0 g (30 mmol) of N-acetylsulfanilyl chloride, followed by 3.3 g (33 mmol) of TEA. The reaction mixture was stirred for 30 min at rt and then acidified with 5 mL (60 mmol) of concentrated HCl and stirred at reflux for 75 min. After cooling, the mixture was diluted with 40 mL of water and made basic with solid NaHCO$_3$. MeOH was removed on a rotary evaporator, and the residual aqueous solution was extracted with four 50-mL portions of EtOAc. The combined extracts were dried over Na$_2$CO$_3$, and the solvent was removed on a rotary evaporator to give 4-amino-N-(2-(2-hydroxyethoxy)ethyl)-benzenesulfonamide as a viscous oil (7.5 g, 96%): $^1$H NMR (DMSO-d$_6$): δ 2.77 (q, J=6.0 Hz, 2H), 3.30 (t, J=4.9 Hz, 2H), 3.31 (t, J=6.5 Hz, 2H), 3.41 (q, J=5.2 Hz, 2H), 4.54 (t, J=5.5 Hz, 1H), 5.89 (s, 2H), 6.57 (d, J=8.7 Hz, 2H), 7.10 (t, J=7.37 (d, J=8.6 Hz, 2H); ESI-MS m/s 259 (M–H)$^-$. To a solution of 0.63 g (2.4 mmol) of 4-amino-N-(2-(2-hydroxyethoxy)ethyl)-benzenesulfonamide in 10 mL of THF was added 0.10 g (2.5 mmol) of 60% sodium hydride. The mixture was stirred for 1 h at rt, 1 mL of DMSO and ~0.2 mL (~3 mmol) of methyl iodide were added to the resulting suspension. The reaction mixture was stirred 2 h at rt and then poured into 15 mL of half saturated NaCl solution and extracted with 30 mL of EtOAc. The organic solution was dried with MgSO$_4$ and concentrated on a rotary evaporator. The residue was chromatographed on silica gel with EtOAc to give 4-amino-N-(2-(2-hydroxyethoxy)ethyl)-N-methyl-benzenesulfonamide as an oil (0.43 g, 65%): $^1$H NMR (DMSO-d$_6$): δ 2.59 (s, 3H), 2.96 (t, J=5.9 Hz, 2H), 3.36 (t, J=5.2 Hz, 2H), 3.43 (t, J=5.2 Hz, 2H), 3.47 (t, J=5.9 Hz, 2H), 4.55 (t, J=5.4 Hz, 1H), 5.99 (s, 2H), 6.59 (d, J=8.7 Hz, 2H), 7.34 (d, 8.8 Hz, 2H); APCI-MS m/z 297 (M+Na)$^+$. The title compound was prepared from 4-amino-N-(2-(2-hydroxyethoxy)ethyl)-N-methyl-benzenesulfonamide and 8-ethoxymethylene-6,8-dihydro-1-thia-3,6-diaza-as-indacen-7-one according to Procedure J: mp 165° C.; $^1$H NMR (DMSO-d$_6$): δ 2.71 (s, 3H), 3.11 (t, J=5.6 Hz, 2H), 3.37 (t, J=5.0 Hz, 2H), 3.44 (dt, J=5.1, 5.0 Hz, 2H), 3.52 (t, J=5.6 Hz, 2H), 4.56 (br t, J=5.2 Hz, 1H), 7.10 (d, J=8.4 Hz, 1H), 7.61 (d, J=8.7 Hz, 2H), 7.75 (d, J=8.7 Hz, 2H), 7.81 (d, J=8.5 Hz, 1H), 8.06 (d, J=12.0 Hz, 1H), 9.25 (s, 1H), 10.91 (s, 1H), 11.16 (d, J=12.0 Hz, 1H); APCI-MS m/z 474 M$^-$. Anal. Calcd for C$_{21}$H$_{22}$N$_4$O$_5$S$_2$.H$_2$O: C, 51.21; H, 4.91; N, 11.37. Found: C, 51.18; H, 4.88; N, 11.33.

EXAMPLE 85

N-(2-{2-[2-(2-Methoxy-ethoxy)-ethoxy]ethoxy}-ethyl)-4-[(7-oxo-6,7-dihydro-1-thia-3,6-diaza-as-indacen-8-ylidenemethyl)-amino]-benzenesulfonamide (Z-isomer)

A solution of 2.3 g (6.3 mmol) of toluene-4-sulfonic acid 2-{2-[2-(2-methoxy-ethoxy)-ethoxy]-ethoxy}-ethyl ester and ~4 mL (~60 mmol) of ammonium hydroxide in 10 mL of ethanol was stirred overnight at ~60° C. The solvent was removed on a rotary evaporator, and the residue was sequentially redissolved in ethanol and concentrated several times. The residue was then dissolved in ethanol, treated with ~1.5 mL of TEA and concentrated on a rotary evaporator. This residue was dissolved in 10 mL of THF, and 1.4 g (6.0 mmol) of 4-N-acetylsulfanilyl chloride and 1 mL (7 mmol) of TEA were added. The reaction mixture was stirred 1.5 h at rt and then 30 min at reflux. The solution was concentrated onto silica gel and chromatographed with an EtOAc to 5% MeOH/EtOAc gradient to give 4-N-(2-{2-[2-(2-methoxy-ethoxy)-ethoxy]-ethoxy}-ethyl)sulfonamidophenyl]acetamide as an oil (1.92 g, 79%): $^1$H NMR (DMSO-d$_6$): δ 2.05 (s, 3H), 2.83 (q, J=5.9 Hz, 2H), 3.19 (s, 3H), 3.30–3.48 (m, 14H), 7.52 (t, J=5.8 Hz, 1H), 7.68 (d, J=9.0 Hz, 2H), 7.72 (d, J=8.8 Hz, 2H), 10.27 (s, 1H); APCI-MS m/z 403 (M–H)$^-$. A solution of 1.9 g (4.7 mmol) of N-[4-(2-{2-[2-(2-methoxy-ethoxy)-ethoxy]-ethoxy}-ethylsulfamoyl)-phenyl]-acetamide and 0.45 g (4.7 mmol) of methanesulfonic acid in 15 mL of ethanol was stirred at ~70° C. for 1 d. Excess TEA was added and the solvent was removed on a rotary evaporator. The residue was applied to a short column of silica gel and eluted with EtOAc to give 4-(N-(2-{2-[2-(2-methoxyethoxy)-ethoxy]ethoxy}ethyl)-sulfonamidoaniline as an oil (1.2 g, 70%): $^1$H NMR (DMSO-d$_6$): δ 2.76 (q, J=6.0 Hz, 2H), 3.20 (s, 3H), 3.32 (t, J=6.2 Hz, 2H), 3.37–3.48 (m, 12H), 5.88 (s, 2H), 6.56 (d, J=8.6 Hz, 2H), 7.11 (t, J=6.0 Hz, 1H), 7.37 (d, J=8.7 Hz, 2H); APCI-MS m/z 361 (M–H)$^-$. The title compound was prepared from 4-(N-(2-{2-[2-(2-methoxyethoxy)-ethoxy]ethoxy}ethyl)sulfonamidoaniline and 8-ethoxymethylene-6,8-dihydro-1-thia-3,6-diaza-as-indacen-7-one according to Procedure J: mp 158–159° C.; $^1$H NMR (DMSO-d$_6$): δ 2.87 (dt, J=5.6, 5.6 Hz, 2H), 3.17 (s, 3H), 3.33–3.38 (m, 4H), 3.38–3.47 (m, 10H), 7.10 (d, J=8.3 Hz, 1H), 7.58 (d, J=8.7 Hz, 2H), 7.63 (t, J=5.7 Hz, 1H), 7.77 (d, J=8.7 Hz, 2H), 7.81 (d, J=8.5 Hz, 1H), 8.06 (br d, J=8.9 Hz, 1H), 9.25 (s, 1H), 10.91 (s, 1H), 11.16 (br d, J=10.8 Hz, 1H); APCI-MS m/z 561 (M–H)$^-$. Anal. Calcd for C$_{25}$H$_{30}$N$_4$O$_7$S$_2$.0.33H$_2$O: C, 52.81; H, 5.43; N, 9.85. Found: C, 52.81; H, 5.29; N, 9.82.

EXAMPLE 86

4-[N'-(5,6-Dimethyl-2-oxo-1,2dihydro-indol-3-ylidene)-hydrazino]-benzenesulfonamide (Z isomer)

The title compound was prepared from 5,6-dimethyl-1H-indole-2,3-dione and 4-sulfonamidophenylhydrazine hydrochloride according to Procedure G in 32% yield: $^1$H NMR (DMSO-d$_6$): δ 2.22 (s, 3H), 2.24 (s, 3H), 6.72 (s, 1H), 7.23 (s, 2H), 7.36 (s, 1H), 7.52 (d, J=8.8 Hz, 2H), 7.77 (d, J=8.8 Hz, 2H), 10.93 (s, 1H), 12.71 (s, 1H). APCI-MS m/z 343 (M–H)$^-$. Anal. Calcd for C$_{16}$H$_{16}$N$_4$O$_3$S: C, 55.80, H, 4.68; N, 16.27; S, 9.31. Found C, 55.78, H, 4.74; N, 16.37; S, 9.22.

EXAMPLE 87

N-{6-Hydroxy-3-[(4-methylsulfamoylmethyl-phenyl)-hydrazono]-2-oxo-2,3-dihydro-1H-indol-5-yl}-acetamide (Z isomer)

Condensation of N-(6-hydroxy-2,3-dioxo-2,3-dihydro-1H-indol-4-yl)acetamide and 4-hydrazino-N-methyl-benzylsulfonamide hydrochloride according to Procedure G gave the title compound in 4% yield: $^1$H NMR (DMSO-d$_6$): δ 2.04 (s, 3H), 2.51 (d, J=4.8 Hz, 3H), 4.24 (s, 2H), 6.45 (s, 1H), 6.84 (t, J=4.8 Hz, 1H), 7.30 (s, 4H), 7.82 (s, 1H), 9.12 (s, 1H), 10.20 (s, 1H), 10.77 (s, 1H), 12.50 (s, 1H); APCI-MS m/z 416 (M−H)$^−$.

EXAMPLE 88

4-[N'-(6-Chloro-5-methoxy-2-oxo-1,2-dihydro-indol-3-ylidene)-hydrazino]benzene-sulfonamide (Z-isomer)

The title compound was prepared from 6-chloro-5-methoxy-1H-indole-2,3-dione (Pajouhesh et al., Journal of Pharmaceutical Sciences 1983, 72, 318–21) and 4-sulfonamidophenylhydrazine hydrochloride according to Procedure G: mp>250° C.; $^1$H NMR (DMSO-d$_6$): δ 3.88 (s, 3H), 6.93 (s, 1H), 7.25 (s, 2H), 7.35 (s, 1H), 7.59 (d, J=8.8 Hz, 2H), 7.76 (d, J=8.8 Hz, 2H), 10.97 (s, 1H), 12.78 (s, 1H); APCI-MS: m/z 379 (M−H)$^−$. Anal. Calcd for $C_{15}H_{13}N_4O_4ClS$: C, 47.31; H, 3.44; N, 14.71; Cl, 9.31 S$_8$.8.42. Found: C, 47.57; H, 3.71; N, 14.93; Cl, 9.11 S, 8.17.

EXAMPLE 89

4-[N'-(5-Hydroxy-6-isopropyl-2-oxo-1,2-dihydro-indol-3-ylidene)-hydrazino]-benzenesulfonamide (Z-isomer)

5-Hydroxy-6-isopropyl-1H-indole-2,3-dione was prepared from 3-isopropyl-4-hydroxyaniline according to Procedure A: $^1$H NMR (DMSO-d$_6$): δ 1.12 (d, J=6.8 Hz, 6H), 3.21 (septet, J=6.9 Hz, 1H), 6.62 (s, 1H), 6.82 (s, 1H), 9.51 (s, 1H), 10.61 (s, 1H); ESI-MS m/z 204 (M−H)$^−$. The title compound was prepared from 5-hydroxy-6-isopropyl-1H-indole-2,3-dione and 4-sulfonamidophenylhydrazine hydrochloride according to Procedure G: mp>250° C.; $^1$H NMR (DMSO-d$_6$): δ 1.12 (d, J=7.0 Hz, 6H), 3.21 (septet, J=6.8 Hz, 1H), 6.62(s, 1H), 6.97 (s, 1H), 7.21 (s, 2H), 7.45 (d, J=8.9 Hz, 2H), 7.75 (d, J=8.7 Hz, 2H), 9.11 (s, 1H), 10.70 (s, 1H), 12.74 (s, 1H); ESI-MS m/z 373 (M−H)$^−$. Anal. Calcd for $C_{17}H_{18}N_4O_4S$: C, 54.53; H, 4.85; N, 14.96; S, 8.56. Found: C, 54.37; H, 4.95; N, 14.84; S, 8.48.

EXAMPLE 90

4-[N'-(2-Methyl-6-oxo-5,6-dihydro-3-oxa-1,5diaza-s-indacen-7-ylidene)-hydrazino]-benzenesulfonamide (Z isomer)

N-(6-Hydroxy-2,3-dioxo-2,3-dihydro-1H-indol-4-yl)acetamide was prepared from 6-amino-2-methylbenzoxazole (Heleyova, et al., Collection of Czechoslovakian Chemical Communications 1996, 61, 371–80) according to Procedure A in 12% overall yield. Condensation of N-(6-hydroxy-2,3-dioxo-2,3-dihydro-1H-indol-4-yl)acetamide and 4-sulfonamidophenylhydrazine hydrochloride according to Procedure G gave the title compound in 6% yield: $^1$H NMR (DMSO-d$_6$): δ 2.55 (s, 3H), 7.13 (s, 1H), 7.23 (s, 2H), 7.57 (d, J=8.8 Hz, 2H), 7.76 (d, J=8.8 Hz, 2H), 7.78 (s, 1H), 11.12 (s, 1H), 12.67 (s, 1H); APCI-MS m/z 370 (M−H)$^−$. Anal. Calcd for $C_{16}H_{15}N_5O_4S$: C, 51.75, H, 3.53; N, 18.86; S, 8.86. Found C, 51.50, H, 3.61; N, 18.69; S, 8.49.

EXAMPLE 91

4-[N'-(5-Acetyl-2-oxo-2,5,6,7-tetrahydro-1H-pyrrolo[2,3-f]indol-3-ylidene)-hydrazino]-benzenesulfonamide (Z-isomer)

5-Acetyl-1,5,6,7-tetrahydro-pyrrolo[2,3-f]indole-2,3-dione was prepared from 1-acetyl-5-aminoindoline according to Procedure A in 90% yield: mp>250° C.; $^1$H NMR (DMSO-d$_6$): δ 2.11 (s, 3H), 3.16 (t, J=8.4 Hz, 2H), 4.06 (t, J=8.4 Hz, 2H), 6.78 (s, 1H), 8.02 (s, 1H), 10.87 (s, 1H); APCI-MS: m/z 229 (M−H)$^−$. Anal. Calcd for $C_{12}H_{10}N_2O_3 \cdot 0.3H_2O$: C, 61.17; H, 4.53; N, 11.89. Found: C, 60.91; H, 4.62; N, 12.10. The title compound was prepared from 5-acetyl-1,5,6,7-tetrahydro-pyrrolo[2,3-f]indole-2,3-dione and 4-sulfonamidophenylhydrazine hydrochloride according to Procedure G in 53% yield: mp>250° C.; $^1$H NMR (DMSO-d$_6$): d2.13 (s, 3H), 3.13 (t, J=8.4 Hz, 2H), 4.06 (t, J=8.4 Hz, 2H), 6.79 (s, 1H), 7.22 (s, 2H), 7.48 (d, J=8.7 Hz, 2H), 7.76 (d, J=8.7 Hz, 2H), 8.24 (s, 1H), 10.96 (s, 1H), 12.78 (s, 1H); APCI-MS: m/z 422 (M+Na)$^+$. Anal. Calcd for $C_{18}H_{17}N_5O_4S$: C, 54.13; H, 4.29; N, 17.53; S, 8.03. Found: C, 53.85; H, 4.23; N, 17.28; S, 7.89.

EXAMPLE 92

4-[N'-(6-Oxo-5,6-dihydro-[1,3]-dioxolo[4,5-f]indol-7-ylidene)-hydrazino]-benzenesulfonamide (Z-isomer)

The title compound was prepared from 5H-[1,3]dioxolo[4,5-f]indole-6,7-dione (Lackey and Sternbach, Synthesis 1993, 993–7) and 4-sulfonamidophenylhydrazine hydrochloride in 55% yield as an orange crystalline solid following Procedure G: mp>220° C.; $^1$H NMR (DMSO-d$_6$): δ 12.63 (s, 1H), 10.89 (s, 1H), 7.73 (d, J=7 Hz, 2H), 7.50 (d, J=7 Hz, 2H), 7.22 (s, 2H), 7.13 (s, 1H), 6.56 (s, 1H), 6.00 (s, 2H). Anal. Calcd for $C_{15}H_{12}N_4OsS$: C, 50.00; H, 3.36; N, 15.55. Found: C, 50.08; H, 3.35; N, 15.49.

EXAMPLE 93

4-[N'-(2-Oxo-2,5,6,7-tetrahydro-1H-pyrrolo[2,3-f]indol-3-ylidene)-hydrazino]-benzenesulfonamide hydrobromide (Z-isomer)

A solution of 0.10 g (0.44 mmol) of 5-acetyl-1,5,6,7-tetrahydro-pyrrolo[2,3-f]indole-2,3-dione in 3 mL of conc. HBr was heated to 100° C. for 18 h. The mixture was cooled to ambient temperature, diluted with 10 mL of water and filtered. The filtrate was concentrated in vacuo and added to a solution of 0.05 g (0.2 mmol) 4-sulfonamidophenylhydrazine hydrochloride in 5 mL of EtOH. The mixture was heated to 80° C. for 1 h and cooled to ambient tempurature. The resulting solid was collected by vacuum filtration, washed with water and dried in a vacuum oven at 70° C. to afford the title compound as a tan solid (0.026 g, 17%): mp>250° C.; $^1$H NMR (DMSO-d$_6$): δ 3.17 (t, J=7.8 Hz, 2H), 3.69 (t, J=7.8 Hz, 2H), 6.96 (s, 1H), 7.25 (s, 2H), 7.52 (s, 1H), 7.57 (d, J=8.8 Hz, 2H), 7.77 (d, J=8.8 Hz, 2H), 10.65 (bs, 2H), 11.24 (s, 1H), 12.73 (s, 1H); APCI-MS: m/z 356

(M–H)⁻. Anal. Calcd for $C_{16}H_{15}N_5O_3S \cdot 0.9$ HBr $\cdot 0.5$ H$_2$O: C, 43.75; H, 3.88; N, 15.94; S, 7.30. Found: C, 44.01; H, 4.14; N, 15.70; S, 7.12.

EXAMPLE 94

C-{4-[N'-(4,6-Dichloro-5-methoxy-2-oxo-1,2-dihydro-indol-3-ylidene)-hydrazino]-phenyl}-N-methyl-benzenesulfonamide (Z-isomer)

4,6-Dichloro-5-methoxy-1H-indole-2,3-dione was prepared from 3,5-dichloro-4-hydroxyaniline according to Procedure A in 91% yield: $^1$H NMR (DMSO-d$_6$): δ 3.81 (s, 3H), 6.98 (s, 1H), 11.26 (s, 1H); APCI-MS m/z 244/246/248 (M–H)⁻. Condensation of 4,6-dichloro-5-methoxy-1H-indole-2,3-dione with 4-hydrazino-N-methyl-benzylsulfonamide according to Procedure G gave the title compound in 59% yield: $^1$H NMR (DMSO-d$_6$): δ 2.58 (d, J=4.7 Hz, 3H), 3.84 (s, 3H), 4.33 (s, 2H), 6.93 (q, J=4.7 Hz, 1H), 6.99 (s, 1H), 7.41 (d, J=8.5 Hz, 2H), 7.51 (d, J=8.5 Hz, 2H), 11.31 (s, 1H), 12.99 (s, 1H); APCI-MS m/z 441/443 (M–H)⁻. Anal. Calcd for $C_{17}H_{16}Cl_2N_4O_4S$: C, 46.06, H, 3.64; Cl, 15.99; N, 12.64; S, 7.23. Found C, 45.80, H, 3.55; Cl, 16.20; N, 12.57; S, 7.11.

EXAMPLE 95

4-[N'-(4-Chloro-5-hydroxy-6-methyl-2-oxo-1,2-dihydro-indol-3-ylidene)-hydrazino]-benzenesulfonamide (Z-isomer)

4-Chloro-5-hydroxy-6-methyl-1H-indole-2,3-dione was prepared from 3-chloro-4-hydroxy-5-methyl aniline according to Procedure A and employing flash chromatography (hexanes:EtOAc 1:1) to isolate the desired isomer: $^1$H NMR (DMSO-d$_6$): δ 2.35 (s, 3H), 6.67 (s, 1H), 9.17 (s, 1H), 10.81 (s, 1H); APCI-MS: m/z 210 (M–H)⁻. Anal. Calcd for $C_9H_6NO_3Cl$: C, 51.08; H, 2.85; N, 6.62; Cl, 16.75. Found: C, 51.20; H, 2.90; N, 6.67; Cl, 16.85. The title compound was prepared from 4-chloro-5-hydroxy-6-methyl-1H-indole-2,3-dione and 4-sulfonamidophenylhydrazine hydrochloride according to Procedure G in 95% yield: mp>250° C.; $^1$H NMR (DMSO-d$_6$): δ 2.26 (s, 3H), 6.69 (s, 1H), 7.28 (s, 1H), 7.57 (d, J=8.8 Hz, 2H), 7.82 (d, J=8.8 Hz, 2H), 8.84 (s, 1H), 11.02 (s, 1H), 13.00 (s, 1H); APCI-MS: m/z 379 (M–H)⁻. Anal. Calcd for $C_{15}H_{13}N_4O_4ClS$: C, 47.31; H, 3.44; N, 14.71; Cl, 9.31; S, 8.42. Found: C, 47.20; H, 3.47; N, 14.64; Cl, 9.41; S, 8.32.

EXAMPLE 96

4-[N'-(5-Hydroxy-4,6-dimethyl-2-oxo-1,2-dihydro-indol-3-ylidene)-hydrazino]-benzenesulfonamide (Z-isomer)

5-Hydroxy-4,6-dimethyl-1H-indole-2,3-dione was prepared from 4-hydroxy-3,5-dimethylaniline according to Procedure A. The title compound was prepared from 5-hydroxy-4,6-dimethyl-1H-indole-2,3-dione and 4-sulfonamidophenylhydrazine hydrochloride according to Procedure G: mp>250° C.; $^1$H NMR (DMSO-d$_6$): δ 2.18 (s, 3H), 2.47 (s, 3H), 6.50 (s, 1H), 7.22 (s, 2H), 7.44 (d, J=8.7 Hz, 2H), 7.77 (d, J=8.7 Hz, 2H), 7.99 (s, 1H), 10.78 (s, 1H), 12.98 (s, 1H); APCI-MS: m/z 359 (M–H)⁻. Anal. Calcd for $C_{16}H_{16}N_4O_4S \cdot 0.25H_2O$: C, 52.67; H, 4.56; N, 15.35; S, 8.79. Found: C, 52.69; H, 4.47; N, 15.33; S, 8.87.

EXAMPLE 97

3-(1H-Indazol-5-yl-amino-methylene)-1,3-dihydro-indol-2-one (Z-isomer)

The title compound was prepared in 68% yield from 3-hydroxymethylene-1,3-dihydro-indol-2-one and 5-aminoindazole according to Procedure J: $^1$H NMR (DMSO-d$_6$): δ 13.1 (s, 1H), 10.8 (d, 1H), 10.4 (s, 1H), 8.6 (d, 1H), 8.0 (s, 1H), 7.8 (s, 1H), 7.6 (m, 2H), 7.4 (m, 1H), 7.0 (m, 2H), 6.8 (d, 1H); $C_{16}H_{12}N_4O_2$: ESI-MS m/z 275 (M–H)⁻.

EXAMPLE 98

3-(1H-Indazol-6-ylimino-methylene)-1,3-dihydro-indol-2-one (Z-isomer)

The title compound was prepared in 79% yield from 3-hydroxymethylene-1,3-dihydro-indol-2-one and 6-aminoindazole according to Procedure J: $^1$H NMR (DMSO-d$_6$): δ 13.02 (s, 1H), 10.86 (d, 1H), 10.51 (s, 1H), 8.7 (d, 1H), 8.0 (s, 1H), 7.74 (d, 1H), 7.63 (d, 1H), 7.51 (s, 1H), 7.15 (dd, 1H), 7.02 (m, 1H), 6.94 (m, 1H), 6.85 (d, 1H); ESI-MS m/z 275 (M–H)⁻.

EXAMPLE 99

See Procedure G

EXAMPLE 100

N-Methyl-4-[(5-oxazol-5-yl-2-oxo-1,2-dihydro-indol-3-ylidenemethyl)-amino]-phenylmethanesulfonamide (Z-isomer)

The title compound was prepared in 56% yield from ethoxymethylene-5-oxazol-5-yl-1,3-dihydro-indol-2-one and N-methyl-4-aminophenylmethanesulfonamide hydrochloride according to Procedure J: $^1$H NMR (DMSO-d$_6$): δ 10.72 (d, 1H), 10.67 (s, 1H), 8.71 (d, 1H), 8.37 (s, 1H), 7.43–7.34 (m, 7H), 6.89 (m, 2H), 4.28 (s, 2H), 2.54 (d, 3H); APCI-MS m/z 409 (MH)⁻.

EXAMPLE 101

8-(3H-Benzotriazol-5-ylaminomethylene)-6,8-dihydro-1-thia-3,6-diaza-as-indacene-7-one (Z-isomer)

The title compound was prepared in 54% yield from 8-ethoxymethylene-6,8-dihydro-1-thia-3,6-diaza-as-indacen-7-one and 5-aminobenzotriazole according to Procedure J: $^1$H NMR (DMSO-d$_6$): δ 11.18 (d, 1H), 10.9 (s, 1H), 9.23 (s, 1H), 8.12 (d, 1H), 7.96 (s, 1H), 7.78 (d, 1H), 7.48 (s, 1H), 7.1 (d, 1H); APCI-MS m/z 333 (M–H)⁻.

EXAMPLE 102

4-[N'-2-Oxo-2,3-dihydropyrrolo[3,2-f]quinolin-1-ylidene)hydrazino]-benzenesulfonamide (Z-isomer)

The title compound was prepared in 24% yield from 3-H-pyrrolo[3,2-f]quinoline-1,2-dione and 4-hydrazinobenzene sulfonamide hydrochloride according to Procedure G: $^1$H NMR (DMSO-d$_6$) δ 13.12 (s, 1H), 11.64 (s, 1H), 9.32 (d, 1H), 9.01 (d, 1H), 8.13 (d, 1H), 7.9 (m, 1H), 7.83 (d, 2H), 7.69 (d, 2H), 7.62 (s, 1H), 7.33 (s, 2H). APCI-MS m/z 368 (MH)⁺.

EXAMPLE 103

2-Oxo-3-(4-sulfamoyl-phenylamino-methylene)-2,3dihydro-1H-indole-5-carboxylic acid isobutyl ester (Z-isomer)

3-Methylthio-2-oxo-2,3-dihydro-1H-indole-5-carboxylic acid isobutyl ester was prepared in 59% yield from isobutyl 4-aminobenzoate according to Procedure D: $^1$H NMR (DMSO-$d_6$): δ 0.93 (d, J=6.6 Hz, 6H), 1.93 (s, 3H), 1.98 (septet, J=6.6 Hz, 1H), 4.02 (m, 2H), 4.62 (s, 1H), 6.92 (d, J=8.2 Hz, 1H), 7.79 (s, J=1H), 7.86 (d, J=8.2 Hz, 1H), 10.91 (s, 1H); ESI-MS m/z 302 (M+23)$^-$. Zinc reduction of 3-methylthio-2-oxo-2,3-dihydro-1H-indole-5-carboxylic acid isobutyl ester according to Procedure δ provided 2-oxo-2,3-dihydro-1H-indole-5-carboxylic acid isobutyl ester in 99% yield: $^1$H NMR (DMSO-$d_6$): δ 0.93 (d, J=6.6 Hz, 6H), 1.97 (septet, J=6.6 Hz, 1H), 3.53 (s, 2H), 3.99 (d, J=6.6 Hz, 2H), 6.88 (d, J=8.2 Hz, 1H), 7.75 (s, J=1H), 7.82 (d, J=8.2 Hz, 1H), 10.72 (s, 1H); ESI-MS m/z 256 (M+23)$^+$. Conversion of 2-oxo-2,3-dihydro-1H-indole-5-carboxylic acid isobutyl ester to 3-[(dimethylamino)methylene]-2-oxo-2,3-dihydro-1H-indole-5-carboxylic acid isobutyl ester (mixture of E and Z isomers) was accomplished in 75% yield according to Procedure G: $^1$H NMR (DMSO-$d_6$): δ 0.94 Z (d, J=8.8 Hz, 6H), 0.94 E (d, J=8.8 Hz, 6H), 1.94–2.01 Z and E (m, 2H), 3.30 Z (s, 6H), 3.32 E (s, 6H), 3.97–3.99 Z and E (m, 4H), 6.75 Z (d, J=8.2 Hz, 1H), 6.83 E (d, J=8.2 Hz, 1H), 7.47 E (s, 1H), 7.53 Z (d, J=0.8.2 Hz, 1H), 7.59 E (d, J=8.2 Hz, 1H), 7.73 Z (s, 1H), 7.88 Z (s, 1H), 7.98 E (s, 1H), 10.34 Z (bs, 1H), 10.44 E (bs, 1H); ESI-MS m/z 289 (M+1)$^+$. The title compound was prepared in 66% yield from 3-[(dimethylamino)methylene]-2-oxo-2,3-dihydro-1H-indole-5-carboxylic acid isobutyl ester and 4-aminobenzenesulfonamide hydrochloride according to Procedure J: $^1$H NMR (DMSO-$d_6$): δ 0.96 (d, J=6.6 Hz, 6H), 2.01 (septet, J=6.6 Hz, 1H), 4.04 (d, J=6.6 Hz, 2H), 6.93 (d, J=8.2 Hz, 1H), 7.26 (s, 2H), 7.60 (d, J=8.7 Hz, 2H), 7.71 (dd, J=1.6, 8.2 Hz, 1H), 7.76 (d, J=8.7 Hz, 2H), 8.27 (s, 1H), 8.86 (d, J=12.5 Hz, 1H), 10.83 (d, J=12.5 Hz, 1H), 10.95 (s, 1H); APCI-MS m/z 414 (M–H)$^-$. Anal. Calcd for $C_2H_{21}N_3O_5S$: C, 57.82, H, 5.09; N, 10.11; S, 7.72. Found C, 57.91, H, 5.16; N, 10.02; S, 7.65.

EXAMPLE 104

4-[(7-Oxo-6,7-dihydro-1-thia-3,6-diaza-as-indacen-8-ylidenemethyl)amino]-N-pyridinyl-4-yl-methyl benzenesulfonamide (Z-isomer)

To a 250 ml round bottom flask was added 50 ml of dry pyridine, 4-(aminomethyl) pyridine (10.4 g, 50.0 mmol) and a magnetic stir bar. The mixture was stirred and cooled to $^0$° C. under nitrogen followed by the addition of N-acetylsulfanilyl chloride (12.8 g, 55.0 mmol). The resultant mixture was stirred at 0° C. under nitrogen for 5 min, and the reaction was allowed to warm to rt and stirred for 16 h. The reaction mixture was concentrated to a thick residue and poured onto about 500 g of ice and water. The residue in the flask was rinsed into the ice and water with 25 ml of MeOH to precipitate the N-acetyl sulfanilamide. The resultant precipitate was filtered, washed with excess water and dried under vacuum at 50° C. The solid was suspended in 75 ml of 1 N hydrochloric acid and heated to 100° C. until all starting material had been consumed. The reaction mixture was cooled and neutralized with ammonium hydroxide. The precipatate was filtered and dried under vacuum at 50° C. to yield 5.78 g, 43.9% of 4-amino-N-(4-aminomethylpyridinyl)-benzenesulfonamide: $^1$H NMR (DMSO-$d_6$): δ 8.42 (d, 2H), 7.76 (t, 1H), 7.39 (d, 2H), 7.22 (d, 2H), 6.56 (d, 2H), 5.91 (s, 2H), 3.89 (d, 2H); APCI-MS m/z 264 (MH)$^+$. The title compound was prepared in 33% yield from 8-ethoxymethylene-6,8-dihydro-1-thia-3,6-diaza-as-indacen-7-one and 4-amino-N-(4-aminomethylpyridinyl)-benzenesulfonamide according to Procedure J: $^1$H NMR (DMSO-$d_6$): δ 11.15 (d, 1H), 10.9 (s, 1H), 9.24 (s, 1H), 8.44 (d, 2H), 8.24 (m, 1H), 8.05 (d, 1H), 7.81 (d, 1H), 7.76 (m, 2H), 7.56 (d, 2H), 7.24 (d, 2H), 7.1 (d, 1H), 4.01 (d, 2H); APCI-MS m/z 464 (MH)$^+$.

Pharmaceutical Formulation and Doses

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1 to 100 mg/kg of body weight per day, and particularly 1 to 10 mg/kg of body weight per day. Oral dosage units will generally be administered in the range of from 1 to about 250 mg and more preferably from about 25 to 250 mg. The daily dosage for a 70 kg mammal will generally be in the range of about 70 mg to 7 grams of a compound of formula I or II.

While the dosage to be administered is based on the usual conditions such as the physical condition of the patient, age, body weight, past medical history, route of administrations, severity of the conditions and the like, it is generally preferred for oral administration to administer to a human. In some cases, a lower dose is sufficient and, in some cases, a higher dose or more doses may be necessary. Topical application similarly may be once or more than once per day depending upon the usual medical considerations. Advantageously, compounds of the present invention may be administered in a single daily dose, or the total daily dosage may be administered in divided doses of two, three or four times daily. The compounds of the invention can be prepared in a range of concentrations for topical use of 0.5 to 5 mg/ml of suitable solvent. A preferred volume for application to the scalp is 2 ml, resulting in an effective dosage delivered to the patient of 1 to 10 mg. For treatment of chemotherapy-induced alopecia, administration 1 to 2 times prior to chemotherapy administration would be preferred, with additional applications administered as needed. A similar regimen can be pursued for treatment of alopecia induced by radiation therapy. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidyicholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.01 to 99.5%, more particularly, 0.5 to 90% of a compound of the formula (II) in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

Biological Data

The compounds of the present invention have valuable pharmacologic properties. Different compounds from this class are particularly effective at inhibiting the CDK1 and CDK2 enzymes at concentrations which range from 0.0001 to 1 μM and additionally show specificity relative to other kinases. Substrate phosphorylation assays were carried out as follows:

CDK1 and CDK2

Cyclin dependent protein kinase assays utilized the peptides Biotin-aminohexyl-AAKAKKTPKKAKK and Biotin-aminohexyl-ARRPMSPKKKA-NH$_2$ as phosphoryl group acceptors. CDK1 and CDK2 were both expressed utilizing a baculovirus expression system and were partially purified to comprise 20–80% of total protein, with no detectable competing reactions present. Typically, assays were performed by incubating either enzyme (0.2–10 nM), with and without inhibitor, one of the two peptide substrates (1–10 nM), [γ-$^{32}$P]ATP (1–20 nM), and 10–20 mM Mg$^{2+}$ for periods of time generally within the range 10–120 min. Reactions were terminated with 0.2–2 volumes of either 20% acetic acid or 50–100 mM EDTA buffered to pH 7 (substrate consumption <20%). The buffer employed in enzyme assays was either 30 mM HEPES 7.4 containing 0.15 M NaCl and 5% DMSO, the buffer 50 mM MOPS 7.0 containing 0.15 M NaCl and 5% DMSO, or the buffer 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM=$V_{max}$*(1−([I]/(K+[I])))+nsb, or pIC50s were determined by a fit to the equation CPM=nsb+($V_{max}$−nsb)/(1+(x/1+(x/10$^x$−pIC50)), where nsb are the background counts.

UL97

UL97 was produced as a GST fusion protein from a baculovirus vector expressed in sf9 cells as described by He (He, et al., Journal of Virology 1997, 71, 405–11). UL97 was assayed as a protein kinase using $^{32}$P transfer from ATP to histone H2B with detection of radiolabeled histone bound to phosphocellulose. Assay mixes for testing inhibitors of UL97 activity contained 2 mM [γ$^{32}$P]-ATP, 15 mM histone H2B, 50 mM sodiumCHES, pH 9.5, 1 M NaCl, 2 mM dithiothreitol and 10 mM MgCl$_2$. Inhibitors were dissolved in diluted DMSO to give a final DMSO concentration in the reaction of 1% DMSO. After incubation at 20° C., the reactions were terminated by addition of 10 volumes of 75 mM phosphoric acid, 30 mM ATP, 1 mM EDTA, then were spotted onto phosphocellulose filters and washed four times with 75 mM phosphoric acid. Radioactivity was determined by liquid scintillation counting.

Src/Lck

The peptide substrates used in Src and Lck assays were biotin-aminohexyl-EEIYGEF-NH$_2$ (Src) and biotin-aminohexyl-EAIYGVLFAKKK-NH$_2$ (Lck). The src and lck proteins were purified to homogeneity from a baculovirus expression system and preactivated before adding to assay mixtures. The maximum activation was achieved by incubating concentrated enzyme (10–30 mM) on ice for 40 min in the presence of 1 mM ATP and 10 mM MgCl$_2$ in 100 mM HEPES, pH 7.5. The activated enzyme was diluted to 2 nM into a 50-mL reaction mixture containing 100 mM HEPES, pH 7.5, 5 mM ATP, 10 mM MgCl$_2$, 2 mM peptide, 0.05 mg/mL BSA, and an inhibitor at varying concentrations and with or without 8 mCi/mL [γ-$^{33}$P]ATP dependent upon the method of analysis for the extent of reaction. The controls were reactions in the presence (negative controls) or absence (positive controls) of 50 mM EDTA. Reactions were allowed to proceed for 30 min at room temperature and quenched with addition of EDTA to 50 mM in 220 mL. The extent of reactions was analyzed in one of the two ways: an Elisa-based and a radioactive isotope-based. The quenched samples (200 mL) were transferred to a neutravidin coated plate (Perice) and incubated at room temperature for 40 min to allow biotinylated peptide to bind to neutravidin. The unbound peptide and the rest of the solution was washed away using a plate washer. In the Elisa format, a 200 mL HRP-PY20 anti phosphotyrosine antibody conjugate solution was added. After incubation for about 30 min, the plated was washed to remove unbound antibody-HRP conjugate. An Elisa substrate, K-blue (Neogen), was added and the Elisa reaction quenched with Red-stop (Neogen) after 15 min. The plate was read at $A_{625}$ in a plate reader. In the isotope-based format, the reactions had been performed in the presence of [γ-$^{33}$P]ATP. 200 mL Scintiverce DB was added to each well of the plate with bound biotin-peptide. The plate was sealed and counted in a micro-b-counter (Wallac). IC$_{50}$ values were obtained by fitting raw data to $A_{625}$ (cpm)=$V_{max}$*(1−([I]/(IC$_{50}$+[I])))+b, where b is background.

VEGFR-2

The peptide substrate used in the VEGFR-2 assay was biotin-aminohexyl-EEEEYFELVAKKKK-NH$_2$. The kinase domain of the enzyme was purified to homogeneity from a baculovirus expression system. The enzyme was preactivated on ice for 15 min in the presence of 100 μM ATP and 20 mM MgCl$_2$, and stored at −80° C. until needed for assay. The activated enzyme was diluted to 0.4 nM into a 60 μl reaction containing 100 mM HEPES, pH 7.5, 5 μM ATP, 10 mM MgCl$_2$, 5 μM peptide, 0.1 mM DTT, 0.05 mg/ml BSA, and an inhibitor at varying concentrations. The controls were reactions in the presence (negative controls) or absence (positive controls) of 50 mM EDTA. Reactions were incubated for 30 min at room temperature, and then quenched by the addition of EDTA to 60 mM in 210 µl. The quenched samples (190 µl) were transferred to a neutravidin-coated plate (Pierce) and incubated at room temperature for 40 min to allow biotinylated peptide to bind to the neutravidin. The unbound components of the reaction were removed by washing with a plate washer, then 200 µl HRP-PY20 anti-phosphotyrosine antibody conjugate was added to each well. After incubation for 40 min, the plate was washed to remove any unbound anitbody. A HRP substrate, K-blue (Neogen) was added and the reaction was quenched with Red Stop (Neogen) after 20 min. The absorbance of the wells was read at $A_{650}$ in a plate reader. $IC_{50}$ values were obtained by fitting raw data to $A_{650} = V_{MAX} * (1-[I]/IC_{50}+[I]))) + b$, where b is background.

The results shown in Table 2 summarise representative data: Table 2 illustrates the inhibitory activity of compounds of the present invention against several different kinases (CDK2, CDK1, cSrc, Lck, UL97, and VEGFR2).

TABLE 2

Kinase inhibition data of representative compounds

| Compound | CDK2 | CDK1 | cSrc | Lck | UL97 | VEGFR2 |
|---|---|---|---|---|---|---|
| Example 72 | +++ | ++ | + | + | +++ | ++ |
| Example 99 | ++ | + | + | + | ++++ | + |
| Example 68 | ++++ | ++ |  | + | +++ |  |
| Example 77 | ++++ | ++++ |  |  | ++++ |  |
| Example 36 | ++++ | ++++ | + | + | +++ | + |
| Example 101 | +++ | ++ |  |  |  |  |
| Example 35 | ++++ | +++ |  |  |  |  |
| Example 27 | ++++ | +++ |  |  |  |  |
| Example 11 | ++++ | +++ |  |  |  |  |
| Example 103 | ++++ | +++ |  |  |  |  |
| Example 76 | +++ | + | + | + |  | + |
| Example 104 | ++++ | +++ |  |  |  |  |

Key ($IC_{50}$, nM)
1–10: ++++
11–50: +++
51–100: ++
>100: +

As may be expected in light of the specific inhibitory activity of these compounds against several kinases involved in growth regulation, the compounds of this invention have antiproliferative properties which can be directly demonstrated in several cell proliferation assays. The results shown in Table 3 summarise some of these data for three different cell proliferation assays: MTT, FACS and G1-S progression. These assays are described below.

MTT Assay

Compounds are tested for their ability to inhibit cell proliferation and cell viability. The metabolic conversion of 3-(4,5-dimethylthiazol-2-yl)-2,5-diphenyltetrazolium bromide (MTT, Sigma #M2128) to a reduced form is a commonly used measure of cellular viability. Following is the procedure:

Cells are maintained in 75 cm² tissue culture flasks until ready for use. The cells are grown and plated for the assay in Dulbecco's modified Eagle's media (DMEM) containing 10% fetal bovine serum. For example, the following cell lines can be used: a) human foreskin fibroblasts (HFF); b) HT29 (human colon carcinoma cell line); c) MDA-MB468 (human breast carcinoma cell line); d) RKO (human colon adenocarcinoma cell line); e) SW620 (human colon carcinoma cell line); f $A_{549}$ (human lung carcinoma cell line); and g) MIA PACA (human pancreatic carcinoma cell line). Cells are maintained at 37° C. in 10% $CO_2$, 90% humidified air. Cells are plated in 96-well tissue culture plates at the densities listed below. 100 µL of cell suspension is added to each well of the 96-well plate except the top row of the plate which contains no cells and serves as a reference for the spectrophotometer.

| cell line | density |
|---|---|
| HFF | 2500 cells/well |
| HT29 cell lines | 2500 cells/well |
| MDA-MB-468 cell line | 5000 cells/well |
| RKO cell line | 4000 cells/well |
| SW620 | 4000 cells/well |
| A549 | 5,500 cells/well |
| MIA PACA | 3000 cells/well |

Cells are incubated overnight in DMEM containing 10% fetal bovine serum at 37° C. in 10% $CO_2$, 90% humidified air prior to dosing. Cells are dosed in 10 sequential 3-fold dilutions starting at 30 µM depending upon the solubility of the compound. Compounds with solubilities of less than 30 µM are dosed at the highest soluble concentration. Stock solutions of compounds are made in 100% dimethyl sulfoxide (DMSO). Stock solutions are diluted in DMEM containing 100 µg/ml gentamicin and 0.3 to 0.6% DMSO at the twice the highest concentration to be placed on the cells. If compounds have been dissolved in DMSO the final concentration of DMSO on the cells is kept below 0.3%. Three-fold serial dilutions are performed on each compound to prepare 10 concentrations of the compound for dosing. 100 µl of diluted compound is added to the 100 µl of media currently on the dish. For each concentration of compound, 2–4 replicate wells are prepared.

Cells are returned to incubator and allowed to proliferate in the presence of compound for 72 h before addition of MTT. MTT is prepared in phosphate buffered saline (Irvine Scientific #9240) at a concentration of 2 mg/ml. 50 µl per well of MTT solution is added to the 200 µl of media to yield a final concentration of 0.4 mg/ml and plates are returned to the incubator for 4 h. After 4 h incubation the media, compound and MTT mixture is aspirated from the plates and 100 µl of 100% DMSO is added to each well in addition to 25 µl of Sorenson's Buffer (0.1M glycine, 0.1M NaCl, pH 10.5). Quantitation of metabolic reduction of MTT in each plate is performed by reading optical density at 570 nm wavelength on a Molecular Devices UVmax microplate reader. Growth inhibition curves and 50% inhibitory concentrations are determined using Microsoft Excel.

FACS Assay

The antiproliferative activity of the compounds of the present invention against a variety of normal or tumour cell lines can also be demonstrated by flow cytometry. These assays allow determination of both cell death and changes in cell cycle profile in cells following treatment of the compound. The assay is performend as follows:

1. Cells are incubated in DMEM to which 10% FCS has been added in a humidified incubator at 37° C. and 5% by volume of $CO_2$ in air. The cells are innoculated in 6-well plates at a density of 0.5–5×10⁵ cells per well.
2. The test compound is added in serial dilutions 24–36 h after plating in 0.5% DMSO. The plates are then incubated a further 72 h in the presence of the compound. During this time, cells in control cultures undergo at least three cell divisions.

3. After incubation, the media is collected and cells are harvested by trypsinization. The cells and media are pooled and pelleted by centrifugation.
4. The cell pellet is fixed in a final volume of 3 mL of 50% ice cold MeOH and incubated for a minimum of 30 min at −20° C.
5. The cells are pelleted by centrifugation and resuspended in 0.5 mL PBS containing 1%FCS, 10 mg/mL Propidium Iodide (PI) and 5 mg/mL RNase A and incubated 30 min at 37° C. in the dark.
6. The samples are analysed by flow cytometry using the relative incorporation of PI as a measure of DNA content of each cell. The % Dead cells is recorded as % of events with less than 2N DNA. The $IC_{50}$ values for the compound are determined as the concentration of compound which results in 50% cell death relative to the control cultures. The compounds of the present invention give $IC_{50}$ values from 0.1 to >25 mmol/L. The compounds of the present invention additionally display $IC_{50}$ values for cell killing of 5- to 30-fold lower in several tumour cell lines, including the RKO and SW620 colon tumours, MDA MB468 breast tumour, H460 lung tumour and MES/.SA ovarian tumour cell lines, as compared to normal epithelial or fibroblast cell lines and therefore discriminate between normal cell lines and tumour derived cell lines for toxicity.

G1-S Progression Assay

This assay is designed to determine the ability of compounds to inhibit progression of cells from G1 into S-phase. CDK2 has been shown to be required for progression into S-phase in normal fibroblastic cells and therefore inhibition of this activity will prevent progression from G1-S. This assay therefore provides a rapid assessment of activity consistent with the inhibition of CDK2 in a cell-based format. The protocol is as follows:

(1) Grow human diploid fibroblasts (HDF-3) in 100 mm tissue culture dish to confluency. (2) Plate $6–7 \times 10^3$ cells/well in a 96 well plate in 100 µl of DMEM. (3) After 16–17 h add various dilutions of test compounds (0.045–100 µM). Dilute compound in DMEM containing DMSO and add 100 µl to each well so that the DMSO conc. is 0.6–0.8% in 200 µl final volume. (4) Two h after addition of compound, add 20 µl of 100 µM Br dU (final conc. 10 µM) Make 100 µM solution in DMEM from 10 mM stock solution. (5) After 4 h, add 200 µl PBS to each well and remove the contents of the wells by inverting the plate and soaking on to the paper towel. Repeat the washing step three times, with 400 ul PBS each time. (6) Fix the cells and denature the DNA by adding 200 µl fixation/denaturation solution to each well for 30–40 min. (7) Remove the fixation/denaturation solution by tapping the plate on the paper towel and add 75 µl of anti BrdU peroxidase antibody to each well. (dilute the antibody to 0.1 U/mL from 15 U/mL stock in PBS containing 1% BSA, Fraction V). Incubate the plate O/N at 4° C. (8) Remove the antibody solution and wash wells four times with 400 µl of PBS. Let the wash solution stay for 3–4 min during each wash. (9) Drain the wells and add 100 µl of chemiluminiscence Elisa reagent (Prepare the reagent 15–20 min before use to bring it to rt by mixing 100 parts of reagent A with 1 part of reagent B). (10) Read the plate in a luminometer. Take 2–3 readings within 6–7 min. Perform the following controls:

| Well contents | Blank | Background control |
|---|---|---|
| culture media | 200 µl | 100 µl |
| cells | — | 100 µl |
| BrdU | 20 µl | — |
| AntiBrdU-POD | 75 µl | 75 µl |

Reagents:

Deoxybromouridine (BrdU), anti BrdU peroxidase antibodies, fixation/denaturation solution, chemiluminiscence reagent and BSA Fraction V, were obtained from Boehringer Mannheim. The 96-well white plate with clear bottom were purchased from Corning Costar Corporation. Dulbecco's Modified Eagle Medium containing high glucose, L-glutamine and pyridoxine HCl was obtained from GIBCO BRL.

The compounds of the present invention prevent progression of normal fibroblasts into S-phase with $IC_{50}$ values ranging from 0.05–10 µM. This inhibition of G1-S progression is consistent with these compounds acting as inhibitors of CDK2.

Results of these cell-based assays with representitive compounds are summarized in Table 3. HDF are normal diploid fibroblast cells. RKO are colon adenocarcinoma cells and MES/SA are ovarian carcinoma cells.

TABLE 3

Cell-based activities of representative compounds

| | | FACS | | | MTT | | |
|---|---|---|---|---|---|---|---|
| Compound | G1/S Chkpt | HDF | RKO | MES/SA | HDF | RKO | MDA MB468 |
| Example 72 | ++ | + | ++ | + | + | ++ | + |
| Example 99 | ++ | + | ++++ | + | +++ | ++++ | ++++ |
| Example 68 | ++ | + | ++ | | + | + | + |
| Example 77 | ++ | + | ++ | +++ | + | ++ | + |
| Example 36 | +++ | + | +++ | ++++ | ++ | +++ | +++ |
| Example 101 | + | + | + | | + | | ++ |
| Example 35 | + | | ++ | + | + | ++ | + |
| Example 27 | ++ | + | ++ | | ++ | ++ | ++ |
| Example 11 | ++ | + | ++ | | | | |
| Example 103 | ++ | | | | ++ | ++ | ++ |
| Example 76 | ++ | + | ++ | ++ | + | + | + |
| Example 104 | ++ | | | | ++ | ++ | ++ |

Key ($IC_{50}$, µM) 0.1–0.5: ++++
0.6–1.0: +++
1.1–5.0: ++
>5.0: +

Utility of Invention

Inhibitors of members of the CDK family of kinases find utility as agents in the treatment of a wide variety of disorders which have a proliferative component or which involve regulation of cyclin dependent kinase function. These include cancers, restenosis, psoriasis, and actinic keratosis.

The tumour inhibitory activity of the compounds of the present invention can be demonstrated in vivo. The tumour inhibiting activity is determined using Swiss Nu/Nu female mice in which the human RKO colon adenocarcinoma has been implanted subcutaneously. In this assay, the compounds induce a marked reduction in the average tumour volume compared to vehicle treated controls.

The present invention demonstrates methodologies by which the onset of cell death in normal proliferating cells induced by chemotherapeutic drugs may be prevented by the prior treatment with inhibitors of cyclin dependent kinases. This may be useful to decrease the severity of chemotherapy-induced side effects due to killing of normal cells. These side effects may include, but are not limited to alopecia, mucocitis (nausea and vomiting, diahrea, oral lesions), neutropenia and thrombocytopenia. Inhibitors of cyclin dependent kinases CDK2 and CDK4 prevent the progression of normal cells into both S-phase (DNA synthesis) or M-phase (mitosis), reducing their susceptibility to incur damage by certain chemotherapeutic drugs which act in those phases of the cell cycle.

When the compounds of the present invention are used in conjunction with chemotherapeutic agents, they reduce the severity of chemotherapy-induced side effects. The protective effects of these compounds can be demonstrated in tissue culture using normal diploid fibroblasts. Cells are plated 36 h prior to the administration of the compounds of the present invention, which are dosed at or above the $IC_{50}$ concentrations determined by the G1 checkpoint assay. Cells are then treated with cytotoxic compounds anywhere from 0 to 24 h after treatment with the compounds of the present invention. Cells are incubated with the combination of the cytotoxic and the compound of the present invention from 3 to 72 h. Cytotoxic drugs include, but are not limited to taxanes, vinca alkyloids, anthracyclins, etoposide, mitoxantrone, topoisomerase I inhibitors, and Ara C. Cell death may be recorded by morphological observation, or by assessment by MTT or FACS analysis. The compounds of the present invention reduce the amount of cell death when used in combination with cytotoxics, as compared to the cytotoxic alone.

The chemoprotective activity of these agents has additionally been demonstrated in vivo. Protection from chemotherapy-induced alopecia is determined in 7 day old Sprague-Dawley rat pups. The treatment is carried out by administering the compounds topically to the head of the animal in doses from 0.01 to 10 mg/kg 2 h before and 2 h after the administration of a single dose of 6 mg/kg etoposide intraperitoneally. Six days after dosing, animals are scored visually for hair loss using a grading scale from 1 (complete hair loss) to 4 (no apparent hair loss). In this assay, the prior treatment of the animal with the compound of this invention results in a marked reduction in the severity of alopecia compared to vehicle treated controls. Under the above described conditions of treatment, the compounds of the present invention also protect against other toxicities of etoposide. Animals treated with etoposide alone show a dramatic lack of weight gain compared to untreated animals. Animals treated with the compounds of the present invention in combination with etoposide, in the schedule indicated above, gain weight normally and even exceed the body weight of control, untreated animals.

The compounds of the present invention additionally show an additive or synergistic effect on cell kill when dosed in combination with cytotoxic drugs in tumour cells (but not normal cells). This can be demonstrated by pretreating normal fibroblasts or RKO colon carcinoma cells with the compounds of the present invention (at concentrations that equals the $IC_{50}$ in the G1 checkpoint assay) for 4 h prior to the administration of cytotoxic drug. Cytotoxic drugs include, but are not limited to taxanes, vinca alkyloids, anthracyclins, etoposide, mitoxantrone, topoisomerase I inhibitors, and Ara C. This synergistic effect may also be shown in vivo. Neonatal Sprague-Dawley rats bearing WARD syngeneic tumours are dosed with a combination of etoposide with the compound of the present invention as described above for the protection experiments. Animals dosed in such a manner show an increased antitumour effect as compared to animals dosed with etoposide alone. The compounds of the present invention may therefore be administered systemically to animals in combination with cell-cycle specific cytotoxic drugs to both increase the antitumour effect of the cytotoxic as well as reduce the severtiy of side effects of the cytotoxic drug. This will allow the dose of cytotoxic to be escalated to further improve antitumor activity without increasing the host toxicity of the cytotoxic.

The compounds of the present invention may also be used in combination with radiation treatment to show similar protection of normal cells from the effects of radiation and may be used as radiosensitizers to increase the tumour killing by radiation therapy.

The compounds of the present invention which are inhibitory for CDK4 or CDK6 activity will selectively inhibit cell cycle progression in cells which retain a functional retinoblastoma protein. Thus, it will be expected that inhibition of CDK4 will systemically protect normal dividing cells, including the G1 and oral mucosa, hematopoietic cells and cells in the hair follicle, but be unable to protect tumour cells with loss of RB function, either by deletion or mutation. This implies that compounds which inhibit CDK4 will be useful as systemically administered cytoprotectant drugs in patients with tumours which have lost Rb, with no protective effect on the tumour itself. Such compounds could be expected to allow for increased dosing frequency and dose escalation of the cytotoxic regimens in these patients, improving the outcome of the patient.

The compounds from the present invention will also have utility in the treatment of viral infections. The antiviral activity of these compounds can be demonstrated in cytomegalovirus (CMV) and human papillomavirus (HPV) replication assays. The $IC_{50}$ for inhibition of CMV replication ranges from 0.05 to 5 µM.

The assay for CMV replication is performed as follows:

1. Growth of Human Fibroblast Cells:

MRC-5 human lung fibroblasts (passage #27–30)were were cultured in minimal essential medium with added 8% v/v fetal calf serum, 2 mM L-glutamine, 100 units/mL penicillin G, and 100 µg/mL streptomycin sulfate, (MEM 8-1-1). Incubation was at 37° C. in air plus 5% $CO_2$. Cells were inoculated into 96-well plates at ~$7 \times 10^3$ cells/well and incubated a further 3 days to confluence (~$2 \times 10^4$ cells/well).

2. Infection of cells:

Medium is removed from each well down to 20 µl and 150 pfu of HCMV (Strain AD169) suspended in 25 µl of medium MEM 2-1-1 (same as MEM 8-1-1 above, but with 2% v/v fetal calf serum) is added. (MOI ≈0.013). Plates are centrifuged at 1500 rpm for 10 min at 25° C. and incubated 90 min at 37° C. 180 µl of medium MEM 2-1-1 containing compounds is added to give a range of final concentrationsfrom 0.01 to 100 mM. Multiple plates are set up for each combination with one mock-infected plate for estimation of cytotoxicity. Plates are then incubated at 37° C. in air plus 5% $CO_2$ for six days (two rounds of viral replication). Cytotoxicity is estimated microscopically on the mock-infected plates, and the infected plates were harvested by decanting the medium from the wells.

3. Preparation, Blotting and Quantitative Hybridization of DNA:

Cells are lysed by adding 50 µl of 0.1 M Tris Cl (pH 8), 50 mM EDTA, 0.2% SDS, and 0.1 mg/mL proteinase K to each well and incubating 1 h at 55° C. The lysates were diluted with 150 µl of water and extracted by mixing with 65 µl phenol saturated with 0.01 M Tris Cl (pH 8) and 1 mM EDTA. The plates were centrifuged at 2200 rpm for 15 min. Next, 50 µl of the aqueous layer was transferred to a new 96-well plate and mixed with 50 µl of 0.5 N NaOH. After incubation at 95° C. for 15 min, the samples were made to 1.5 M Ammonium acetate, 0.15 M Ammonium $H_2$ phosphate, 5 mM EDTA, pH 6.5 (APE buffer), and blotted onto BRL Supported Nitrocellulose (cat # 1465MH) membranes under vacuum Each well was washed with 200 µl APE buffer. The samples were crosslinked to the membrane with UV light.

4. Quantitative DNA-DNA Hybridization:

The hybridization probe was prepared from cosmids pC7S31 & pCS37 (Sullivan, et al., Antimicrobial Agents & Chemotherapy 1993, 37,19–25). These contain the HCMV AD169 sequences from nucleotides 102,000 to 143,300 and 51,600 to 92,900, respectively. The probe is a 1:1 mixture of the two cosmids labeled with $\alpha$-[$^{32}$P]-dCTP Prehybridization of the membranes is carried out in 6× SSPE, 1% Ficoll, 1% polyvinylpyrrolidine, 1% BSA, 0.5% SDS, and 50 µg/mL salmon sperm DNA at 45° C. for 2 to 12 h. The prehybridization solution was replaced with hybridization solution (6× SSPE, 0.5% SDS, 50 µg/mL salmon sperm DNA) containing $1 \times 10^6$ cpm/mL of each heat-denatured probe. Hybridization was for 16 h at 65° C. The membranes were then washed as follows: 6× SSPE with 0.5% SDS, room temperature, 2× for 2 min; 1× SSPE with 0.5% SDS, 65° C., 2× for 15 min; 0.1× SSPE with 0.5% SDS, 65° C., once for 1 h. The membranes were blotted dry and wrapped in Saran wrap for quantitation by PhosphorImager. The counts of the drug dilution wells were compared to the counts of untreated control wells to produce a response curve and were used to calculate the $IC_{50}$ values. These $IC_{50}$ values were calculated by weighted linear regression according to the Hill equation.

The compounds of the present invention may also be used for the treament of other conditions mentioned in connection with modulators of CDK activity. In particular for the treatment of diseases that respond to inhibition of CDK activity, including protection of cells from infection by other viruses and treatment of Alzheimers. Furthermore, these compounds will have utility in the specific inhibition of non-human CDK activities, such as the *Aspergillus fumigatus* cdc2 homologue and will therefore be useful in the treatment of fungal or other eukaryotic infections.

The compounds of the present invention also inhibit other kinases. In particular, these compounds show affinity for the Src tyrosine kinase. The Src tyrosine kinase participates in a variety of fundamental processes within the cell, including signal transduction from cell-surface receptors, apoptosis and cell division. Compounds which are able to inhibit the src TK find utility as tumour inhibitory and antiinflammatory agents. These compounds are also useful for the prevention of osteoporosis and bone building by inhibition of src in osteoclasts (Tanaka, et al., Nature 1996, 383, 528–31). In addition, the compounds of this invention are suitable for other utilities mentioned in connection with Src modulators, and they can be used in particular for the treatment of diseases that respond to the inhibition of the Src tyrosine kinase.

Part II, The Additional Disclosure Added by Continuation in Part

The present invention relates generally to cyclin-dependent kinase II inhibitor compounds having utility as pharmacological agents for preventing/reducing the severity of epithelial cytotoxicity side effects of chemotherapy and/or radiation therapy, including alopecia, plantar-palmar syndrome and/or mucositis. The invention also relates to a corresponding method of preventing/reducing the severity of such side effects, by administration of such a pharmacological agent to a patient subjected to chemotherapy and/or radiation therapy treatment.

BACKGROUND OF THE INVENTION

Protein kinases play a critical role in the control of cell growth and differentiation and are key mediators of cellular signals leading to the production of growth factors and cytokines. See, for example, Schlessinger and Ullrich, *Neuron* 1992, 9, 383. . A partial non-limiting list of such kinases includes abl, ARaf, ATK, ATM, bcr-abl, Blk, BRaf, Brk, Btk, CDK1, CDK2, CDK3, CDK4, CDK5, CDK6, CDK7, CDK8, CDK9, cfms, c-fms, c-kit, c-met, cRaf1, CSF1 R, CSK, c-src, EGFR, ErbB2, ErbB3, ErbB4, ERK, ERK1, ERK2, Fak, fes, FGFR1, FGFR2, FGFR3, FGFR4, FGFR5, Fgr, FLK4, Fps, Frk, Fyn, GSK, gsk3a, gsk3b, Hck, IGF-1R, IKK, IKK1, IKK2, IKK3, INS-R, Integrin-linkedkinase, Jak, JAK1, JAK2, JAK3, JNK, JNK, Lck, Lyn, MEK, MEK1, MEK2, p38, PDGFR, PIK, PKB1, PKB2, PKB3, PKC, PKC$\alpha$, PKC$\beta$, PKC$\delta$, PKC$\epsilon$, PKC$\gamma$, PKC$\lambda$, PKC$\mu$, PKC$\zeta$, PLK1, Polo-like kinase, PYK2, tie$_1$, tie$_2$, TrkA, TrkB, TrkC, UL13, UL97, VEGF-R1, VEGF-R2, Yes and Zap70. Protein kinases have been implicated as targets in central nervous system disorders such as Alzheimer's (Mandelkow, E. M. et al. *FEBS Lett.* 1992, 314, 315. Sengupta, A. et al. *Mol. Cell. Biochem.* 1997, 167,99), pain sensation (Yashpal, K. *J. Neurosci.* 1995, 15, 3263–72), inflammatory disorders such as arthritis (Badger, *J. Pharm. Exp. Ther.* 1996, 279, 1453), psoriasis (Dvir, et al, *J. Cell Biol.* 1991, 113, 857), and chronic obstructive pulmononary disease, bone diseases such as osteoporosis (Tanaka et al, *Nature,* 1996, 383, 528), cancer (Hunter and Pines, *Cell* 1994, 79, 573), atherosclerosis (Hajjar and Pomerantz, *FASEB J.* 1992, 6, 2933), thrombosis (Salari, *FEBS* 1990, 263, 104), metabolic disorders such as diabetes (Borthwick, A. C. et al. *Biochem. Biophys. Res. Commun.* 1995, 210, 738), blood vessel proliferative disorders such as angiogenesis (Strawn et al *Cancer Res.* 1996, 56, 3540; Jackson et al *J. Pharm. Exp. Ther.* 1998, 284, 687), restenosis (Buchdunger et al, *Proc, Nat. Acad. Sci USA* 1991, 92, 2258), autoimmune diseases and transplant rejection (Bolen and Brugge, *Ann. Rev. Immunol.* 1997, 15, 371) and infectious diseases such as viral (Liftler, E. *Nature* 1992, 358,160), and fungal infections (Lum, R. T. PCT Int.Appl., WO9805335 A1 980212).

Chemotherapeutic techniques and radiation therapy techniques are well-established in the treatment of neoplastic conditions of various types. As concomitant side-effects to the administration of chemotherapy and/or radiation therapy, patients commonly experience severe host epithelial cell toxicity. The consequences of damage to the proliferating epithelium induced by chemotherapy frequently include hair loss (alopecia), plantar-palmar syndrome and mucositis; such side effects, especially mucositis, are also known to occur as a result of radiation therapy. These side-effects may be of varying severity, depending on the type, dosages and dosing schedule of the respective chemotherapy and/or radiation therapy involved.

SUMMARY OF THE INVENTION

The present invention provides a novel approach to preventing/reducing the severity of epithelial cytotoxicity side effects such as alopecia, plantar-palmar syndrome and/or mucositis in a subject receiving chemotherapy and/or radiation therapy, by administering to such subject an effective amount of a cyclin-dependent kinase II inhibitor.

A wide variety of particular cyclin-dependent kinase II inhibitor species useful in the broad practice of the present invention are hereinafter more fully described.

The cyclin-dependent kinase inhibitor is non-systemically administered to the subject, preferably topically.

The cyclin-dependent kinase II inhibitor may be administered topically to prevent/reduce the severity of alopecia incident to chemotherapy and/or radiation therapy, by application of the inhibitor compound, or a formulation containing same, to a corporeal locus susceptible to alopecia. For example, a topical formulation may be made up with the cyclin-dependent kinase II inhibitor present in an effective amount and such topical formulation may then be administered to the subject's scalp and/or facial areas, to combat alopecia incident to chemotherapy and/or radiation therapy treatment.

For preventing/reducing the severity of plantar-palmar syndrome incident to chemotherapy and/or radiation therapy, the cyclin-dependent kinase II inhibitor may be topically administered to the plantar and/or palmar regions that are susceptible to lesioning as a concomitant condition of such therapeutic treatment.

In preventing/reducing the severity of mucositis as a side effect incident to chemotherapeutic and/or radiation therapy treatment, the cyclin-dependent kinase II inhibitor is preferably administered topically to mouth and throat mucosa of the oral cavity.

In a combination therapeutic approach according to one embodiment of the invention, the patient receiving chemotherapy and/or radiation therapy may be contemporaneously administered the cyclin-dependent kinase II inhibitor in accordance with a selected dosage regimen that is effective to prevent/reduce the severity of two or more of the aforementioned side effects. Such administration is desirably of a non-systemic character, being topically applied to head regions susceptible to occurrence or progression of alopecia, being topically applied to plantar and/or palmar regions susceptible to the occurance or progression of plantar-palmar lesions, and/or being topically administered to oral cavity mucosa in the mouth and throat areas susceptible to occurrence or progression of mucositis.

The invention in another aspect relates to a cytoprotective composition for preventing/reducing the severity of epithelial cytotoxicity side effects incident to the administration of chemotherapy and/or radiation therapy, e.g., alopecia, plantar-palmar syndrome and/or mucositis. Such composition is suitably formulated to comprise an effective amount of a cyclin-dependent kinase II inhibitor for the prevention or reduction in the severity of the epithelial cytotoxicity side effects of the chemotherapy and/or radiation therapy. The composition may be formulated for such purpose with one or more pharmaceutically acceptable carriers, excipients or diluents.

Other aspects and features of the invention will be more fully apparent from the ensuing disclosure and appended claims.

DETAILED DESCRIPTION OF THE INVENTION, AND PREFERRED EMBODIMENTS THEREOF

The present invention provides a method and composition for preventing/reducing the severity of epithelial cytotoxicity side effects, e.g., alopecia, plantar-palmar syndrome and/or mucositis, in a subject receiving chemotherapy and/or radiation therapy, involving administration to the subject of an effective amount of a cyclin-dependent kinase II inhibitor.

Cyclin-dependent kinase II (sometimes hereinafter referred to as "CDK2") is a protein serine/threonine kinase that is required for progression of cells through the G1 and S phases of the cell cycle. Inhibition of CDK2 in normal cells results in a reversible cell cycle arrest and can therefore protect cells from antineoplastic agents with cytotoxic activity dependent on progression through the cell cycle. The present invention exploits this characteristic.

In one preferred aspect of the present invention, an inhibitor of CDK2 is topically applied to the scalp and optionally other hirsute areas to prevent alopecia, one of the most common and distressing side effects of chemotherapy and/or radiation therapy. By direct delivery of the CDK2 inhibitor agent to the follicular target, systemic exposure of the compound is minimized, without compromising the antineoplastic efficacy of the chemotherapeutic agent.

In other aspects of the invention, the CDK2 inhibitor is topically applied to the hands and/or feet of a patient, to prevent or reduce the severity of plantar-palmar syndrome, and/or is topically applied to the mouth and throat mucosa of the oral cavity to prevent or reduce the severity of mucositis incident to chemotherapy and/or radiation therapy treatment.

The cyclin-dependent kinase II inhibitor of the invention may comprise any suitable compound having inhibitory action on cyclin-dependent kinase II activity, i.e., a compound that is effective to suppress or ameliorate cyclin-dependent kinase II activity so as to prevent/reduce the severity of epithelial cytotoxicity side effects such as alopecia, plantar-palmar syndrome and/or mucositis incident to the administration of chemotherapy and/or radiation therapy.

Illustrative cyclin-dependent kinase II inhibitors that may be employed in the broad practice of the invention to prevent/reduce the severity of epithelial cytotoxicity side effects of chemotherapy and/or radiation therapy, such as alopecia, plantar-palmar syndrome and/or mucositis, include the cyclin-dependent kinase II inhibitor compounds described in the following references, as well as in the references identified in the Bibliography set forth hereinafter, the disclosures of all of which are hereby incorporated herein by reference in their respective entireties:

substituted oxindole derivatives described in International Patent Application No. PCT/EP98/05559 filed Sep. 3, 1998 for "Substituted Oxindole Derivatives,"

purine derivatives described in International Publication WO97/20842 of CNRS Center Natural Research;

pyridylpyrimidinamine derivatives described in International Publication WO95/09852 of Ciba-Geigy (Novartis);

2,6,9-trisubstituted compounds described in International Publication WO98/05335 of CV Therapeutics;

4H-1-benzopyran-4-one derivatives described in German Patent 3836676 of Hoechst AG;

2-thiol and 2-oxo-flavopiridol analogues described in U.S. Pat. Nos. 5,705,350, and in U.S. Pat. No. 5,849,733;

pyrido [2,3-D] pyrimidines and 4-aminopyrimidines described in International Publication WO98/33798 of Warner Lambert Company as well as in U.S. Pat. Nos. 5,776,942; 5,733,913; 5,223,503; 4,628,089; 4,536,575; 4,431,805; and 4,252,946;

antiviral CDK2 inhibitor compounds described in International Publication WO98/39007 of the University of Texas; chimeric CDK2 inhibitors described in International Publication WO97/27297 of Mitotix Inc.;

the 2,6,9-trisubstituted purines described in Imbach, P., et al., 2,6,9-Trisubstituted Purines: Optimization Towards Highly Potent and Selective CDK1 Inhibitors, Bioorganic and Medicinal Chemistry Letters, 9 (1999), 91–96.

the peptide inhibitors described in U.S. Pat. No. 5,625,031 issued Apr. 29, 1997 to K. R. Webster, et al.

CDK2 inhibitor antisense sequences described in U.S. Pat. No. 5,821,234 issued Oct. 13, 1998 to Viktor J. Dzau;

the C2 alkynylated purines described in Legraverend, M., et al., Synthesis of C2 Alkynylated Purines, a New Family of Potent Inhibitors of Cyclin-Dependent Kinases, Bioorganic & Medicinal Chemistry Letters 8 (1998) 793–798; and the tyrphostins described in Kleinberger-Doron, N., et al., Inhibition of Cdk2 Activation by Selected Tyrphostins Causes Cell Cycle Arrest at Late G1 and S Phase, Experimental Cell Research 241, 340–351 (1998).

The therapeutic compositions of the present invention may include one or more than one cyclin-dependent kinase II inhibitor agent, as suitable to achieve the desired efficacy in a given end use application of the invention.

One class of compounds that may be usefully employed in the practice of the invention is described in International Patent Application PCT/EP98/05559, the entire disclosure of which is incorporated herein by reference. Such class comprises compounds of the Formula (A):

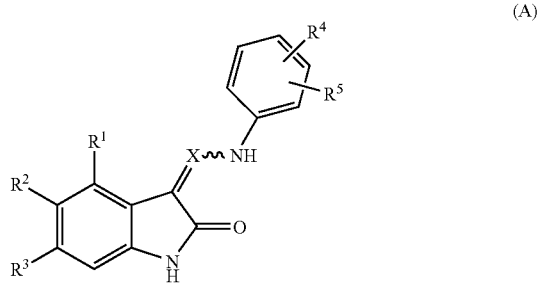

(A)

wherein:

X is N, CH, CCF$_3$, or C(C$_{1-12}$ aliphatic);

R$^1$ is selected from the group consisting of: hydrogen, C$_{1-12}$ aliphatic, thiol, hydroxy, hydroxy-C$_{1-12}$ aliphatic, Aryl, Aryl-C$_{1-12}$ aliphatic, R$^6$-Aryl-C$_{1-12}$ aliphatic, Cyc, Cyc-C$_{1-6}$ aliphatic, Het, Het-C$_{1-12}$ aliphatic, C$_{1-12}$ alkoxy, Aryloxy, amino, C$_{1-12}$ aliphatic amino, di-C$_{1-12}$ aliphatic amino, di-C$_{1-12}$ aliphatic aminocarbonyl, di-C$_{1-12}$ aliphatic aminosulfonyl, C$_{1-12}$ alkoxycarbonyl, halogen (e.g., fluoro, bromo, iodo), cyano, sulfonamide, or nitro, where R$^6$, Aryl, Cyc and Het are as defined below;

R$^2$ is selected from the group consisting of: hydrogen, C$_{1-12}$ aliphatic, N-hydroxyimino-C$_{12}$ aliphatic, C$_{1-12}$ alkoxy, hydroxy-C$_{1-12}$ aliphatic, C$_{12}$ alkoxycarbonyl, carboxyl C$_{1-12}$ aliphatic, Aryl, R$^5$-Aryl-oxycarbonyl, R$^6$-oxycarbonyl-Aryl, Het, aminocarbonyl, C$_{1-12}$ aliphatic-aminocarbonyl, Aryl-C$_{1-12}$ aliphatic-aminocarbonyl, R$^6$-Aryl-C$_{1-12}$ aliphatic-aminocarbonyl, Het-C$_{1-12}$ aliphatic-aminocarbonyl, hydroxy-C$_{1-12}$ aliphatic-aminocarbonyl, C$_{1-12}$-alkoxy-C$_{1-12}$ aliphatic-aminocarbonyl, C$_{1-12}$ alkoxy-C$_{1-12}$ aliphatic-amino, di-C$_{1-12}$ aliphatic amino, di-C$_{1-12}$ aliphatic aminocarbonyl, di-C$_{1-12}$ aliphatic aminosulfonyl, halogen, hydroxy, nitro, C$_{1-12}$ aliphatic-sulfonyl, aminosulfonyl, and C$_{1-12}$ aliphatic-aminosulfonyl, where Aryl and Het are as defined below;

further wherein R$^1$ and R$^2$ are optionally joined to form a fused ring selected from the group as defined for Het below, and said fused ring is optionally substituted by C$_{1-12}$ aliphatic, halogen, nitro, cyano, C$_{1-12}$ alkoxy, amino, hydroxyl, carbo-C$_{1-12}$ alkoxy, or oxo;

R$^3$ is selected from the group consisting of: hydrogen, C$_{1-12}$ aliphatic, hydroxy, hydroxy C$_{1-12}$ aliphatic, di-C$_{1-12}$ aliphatic amino, di-C$_{1-12}$ aliphatic aminocarbonyl, di-C$_{1-12}$ aliphatic aminosulfonyl, C$_{1-12}$alkoxy, Aryl, Aryloxy, hydroxy-Aryl, Het, hydroxy-Het, Het-oxy, or halogen, where Aryl and Het are as defined below;

further wherein R$^2$ and R$^3$ are optionally joined to form a fused ring selected from the group as defined for Het below, and said fused ring is optionally substituted by C$_{1-6}$ aliphatic or C$_{1-6}$ aliphatic-carbonyl;

with the proviso that R$^1$, R$^2$ and R$^3$ cannot simultaneously be hydrogen;

R$^4$ is selected from the group consisting of: sulfonic acid, C$_{1-12}$ aliphatic-sulfonyl, sulfonyl-C$_{1-12}$ aliphatic, C$_{1-6}$ aliphatic-amino, R$^7$-sulfonyl, R$^7$-sulfonyl-C$_{1-12}$ aliphatic, R$^7$-aminosulfonyl, R$^7$-sulfonylamino-C$_{1-2}$ aliphatic, aminosulfonylamino, di-C$_{1-12}$ aliphatic amino, di-C$_{1-12}$aliphatic aminocarbonyl, di-C$_{1-12}$ aliphatic aminosulfonyl, di-C$_{1-12}$ aliphatic amino, di-C$_{1-12}$ aliphatic aminocarbonyl, di-C$_{1-12}$ aliphatic aminosulfonyl-C$_{1-12}$ aliphatic, (R$^8$)$_{1-3}$-Arylamino, (R$^8$)$_{1-3}$-Arylsulfonyl, (R$^3$)$_{1-3}$-Arylaminosulfonyl, (R$^3$)$_{1-3}$-Arylsulfonylamino, Het-amino, Het-sulfonyl, Het-aminosulfonyl, aminoiminoamino, or aminoiminoaminosulfonyl, where R$^7$, R$^8$, Aryl and Het are as defined below;

R$^5$ is hydrogen;

and further wherein R$^4$ and R$^5$ are optionally joined to form a fused ring, said ring being selected from the group as defined for Het below, or any of said fused rings optionally substituted by C$_{1-12}$aliphatic, oxo or dioxo;

R$^6$ is selected from the group consisting of C$_{1-12}$aliphatic, hydroxy, C$_{1-12}$alkoxy, or halogen;

R$^7$ is selected from the group consisting of: hydrogen, C$_{1-12}$ aliphatic, C$_{1-12}$ alkoxy, hydroxy-C$_{1-12}$ alkoxy, hydroxy-C$_{1-12}$ aliphatic, carboxylic acid, C$_{1-12}$ aliphatic-carbonyl, Het, Het-C$_{1-12}$ aliphatic, Het-C$_{1-12}$ alkoxy, di-Het-C$_{1-12}$ alkoxy Aryl, Aryl-C$_{1-12}$ aliphatic, Aryl-C$_{1-12}$ alkoxy, Aryl-carbonyl, C$_{1-18}$ alkoxyalkoxyalkoxyalkoxyaliphatic, or hydroxyl where Het and Aryl are as defined below;

R$^8$ is selected from the group consisting of: hydrogen, nitro, cyano, C$_{1-12}$ alkoxy, halo, carbo-C$_{1-12}$ alkoxy and halo-C$_{1-12}$ aliphatic;

Aryl is selected from the group consisting of: phenyl, naphthyl, phenanthryl or anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole;

and the pharmaceutically acceptable salts, esters, amides, carbamates, solvates, hydrates, affinity reagents and prodrugs thereof in either crystalline or amorphous form. The esters, amides and carbamates, are preferably hydrolyzable and more preferably are biohydrolyzable.

Preferred species of cyclin-dependent kinase II inhibitors that may be usefully employed in the practice of the present invention include the following compounds within the foregoing formula (A):

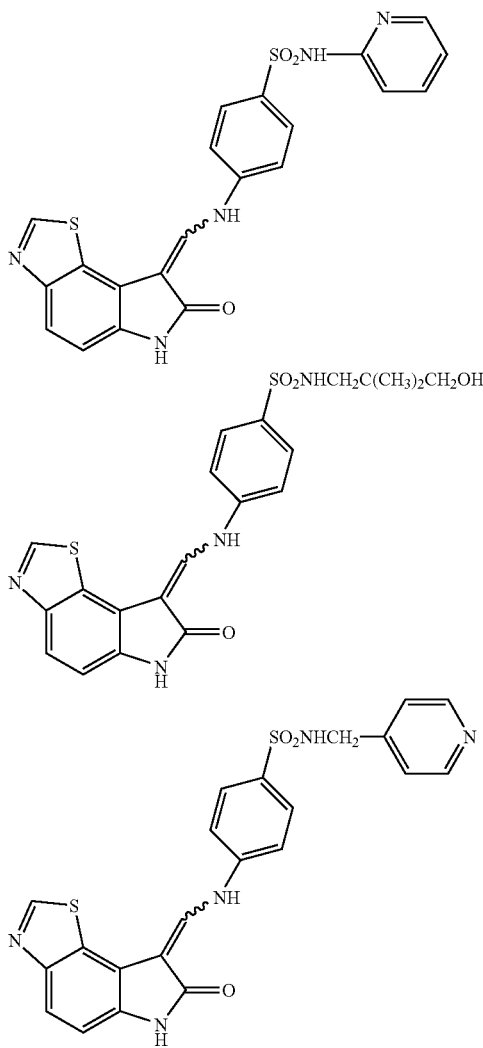

with the last such species being most preferred.

The CDk2 inhibitor compound that is selected for use in a given application of the methodology of the present invention may then be formulated as the active ingredient in a pharmaceutically acceptable composition, for topical or otherwise non-systemic administration to a subject (e.g., a mammalian subject such as a human subject), to prevent/reduce the severity of epithelia[cytotoxicity side effects (e.g., alopecia, plantar-palmar syndrome, and/or mucocitis) induced by chemotherapy and/or radiation therapy contemporaneously being administered to the subject.

To prevent/reduce the severity of alopecia induced by chemotherapy and/or radiation therapy in a subject receiving such therapy, the CDK2 inhibitor compound is preferably administered topically to the corporeal locus that is susceptible to alopecia, such as the head (e.g., the scalp, eyebrow regions, beard and mustache areas, etc.).

For such topical application, the cyclin dependant kinase II inhibitor compound may be formulated in a topical administration formulation, by combination of the compound with a selected pharmaceutically acceptable vehicle (carrier, diluent or excipient), so that the amount of the compound in the formulation is sufficient to achieve the prevention or reduction in severity of the alopecia side effect, when administered in accordance with an appropriately designed treatment protocol. The formulation can be in any useful dosage unit form for corresponding administration.

Formulations of the thiazole-oxindole compound may be constituted and administered in any suitable manner, such as in a liquid formulation for aerosolized spray administration to the head region of a subject susceptible to chemotherapy-induced alopecia, or by a dermal patch or dressing containing the CDK2 inhibitor formulation in a releasable form, for positioning on the head in contact with the area of susceptibility.

The formulation may alternatively be prepared as a lotion, salve, gel, foam, paste, oil, creme, or other suitable form, for administration to the appropriate corporeal locus, e.g., to the scalp or other area of the head for preventing/reducing the severity of alopecia, with initial administration being followed by massage, brushing, or toweling to distribute the formulation on the scalp evenly for uniformity of therapeutic effect.

As one example of compositions that may be used for topical adminstration of the CDK2 inhibitor agents of the invention to the corporeal locus of a subject receiving chemotherapy and/or radiation therapy, a formulation of the type described in Tata, S., et al., Relative Influence of Ethanol and Propylene Glycol Cosolvents on Deposition of Minoxidil into the Skin, Journal of Pharmaceutical Sciences, Vol. 83, No. 10, October 1994, pp. 1508–1510, may be employed. Such a formulation may comprise a 2% solution of the active ingredient in 60% ethanol, 20% propylene glycol and 20% water, for topical administration of the solution to the scalp.

Still other formulations that may be usefully employed for topical administration of the CDK2 inhibitor agents of the invention, include the formulations identified in U.S. Pat. Nos. 5,849,733; 5,807,698; 5,625,031; and 5,486,509, the disclosures of which are incorporated herein by reference in their entireties.

Additional illustrative examples of formulations that may be usefully employed for the topical administration of the CDK2 inhibitor agent of the invention include: the lipid based formulations described in Hoffman, R. M., et al., Liposomes Can Specifically Target Entrapped Melanin To Hair Follicles in Histocultured Skin, In Vivo Cell. Dev. Biol., Vol. 29A: 192–194, March 1993, and in Niemiec, S. M., et al., Influence of Nonionic Liposomal Composition on Topical Delivery of Peptide Drugs into Pilosebaceous Units: An in Vivo Study Using the Hamster Ear Model, Pharmaceutical Research, Vol.12, No. 8, 1995, pp. 1184–1188; and the polymeric microsphere formulations described in Rolland, A., et al., Site-Specific Drug Delivery to Pilosebaceous Structures Using Polymeric Microspheres, Pharmaceutical Research, Vol. 10, No.12, 1993, pp. 1738–1744.

The formulation may be constituted to provide an appropriate dose for a desired dosing schedule. The dosage and dosage schedule may be readily determined for a given subject, within the skill of the art, based on the character of the chemotherapy and/or radiation therapy being employed.

Analogous considerations apply to the formulation and administration of the CDK2 inhibitor for preventing/reducing the severity of plantar-palmar syndrome, involving topical administration to the areas of the hands and feet susceptible to the syndrome as a side-effect of chemotherapy and/or radiation therapy.

For preventing/reducing the severity of mucositis, the cyclin-dependent kinase II inhibitor may be formulated in a suitable topical formulation for application to the oral cavity mucosa. Illustrative delivery systems for the cyclin-dependent kinase II inhibitor of the invention, as used to combat mucositis, include the formulations and delivery techniques described in Cullinan U.S. Pat. No. 5,496,828 issued Mar. 5, 1996 for "Methods of Inhibiting Ulcerative Mucositis." Useful formulations may include the active ingredient and excipients, diluents, or carriers, formed into tablets, capsules, sprays, mouthwashes, lozenges, troches, pastilles, lollipops, suspensions, powders and the like, for application to the mucosa of the oral cavity.

Acceptable daily dosages of the CDK2 inhibitor for preventing/reducing the severity of epithtelial cytotoxicity side effects induced by chemotherapy and/or radiation therapy, may be from about 0.1 to about 1000 mg/day, and preferably from about 0.2 to about 100 mg/day.

The cyclin-dependent kinase II inhibitor in the preferred practice of the invention is administered contemporaneously with the chemotherapy and/or radiation therapy treatment (i.e., simultaneously with, or sufficiently near in time to, the chemotherapy and/or radiation therapy, so as to achieve a preventative or ameliorative effect on the epithelial cytotoxicity side effect that would otherwise be presented in the absence of the CDK2 inhibitor). The chemotherapy and/or radiation therapy may be of any appropriate type for the neoplastic condition, or other disease state or condition, of the patient being treated. As an illustrative example, the chemotherapy may comprise administration of chemotherapeutic agents, including cycle-specific agents (such as cytosine arabinoside (ARA-C)) and non-cycle-specific agents (such as Cytoxan), individually or in combination with one another.

The cyclin-dependent kinase II inhibitor in one embodiment of the invention is administered 1–4 times in a chemotherapeutic cycle, as a cytoprotective composition for preventing/reducing the severity of epithelial cytotoxicity side effects such as alopecia, plantar-palmar syndrome and/or mucositis, in a subject receiving chemotherapy and/or radiation therapy.

In the specific application of preventing/reducing the severity of chemotherapy-induced alopecia, the cyclin-dependent kinase II inhibitor effects a desired temporary arrest of the hair follicle cell cycle by inhibition of cyclin-dependent kinase II activity. For such purpose, the inhibitor agent, formulated in a suitable topically administerable formulation, may be applied 1–2 times per chemotherapeutic cycle prior to and during the time of administration of chemotherapy, in one specific preferred illustrative embodiment.

In one preferred aspect of the invention, cyclin-dependent kinase II inhibitor agents that are topically administerable to prevent/reduce the severity of chemotherapy-induced alopecia, are assessed for efficacy and selected for use based on the following characteristics:

(1) an $IC_{50}$ value of less than 2.5 nanoMolar and preferably less than 20 nanoMolar against CDK2;

(2) an $IC_{50}$ value of less than 1.5 microMolar and preferably less than 5 microMolar in a G1 checkpoint assay;

(3) exhibition of reproducible protection in a baby rat alopecia model using at least 2 different cytotoxic regimens one of which includes an alkylating agent (e.g., a regimen involving doxorubicin/cyclophosphamide (anthracyclin/alkylating agent), etoposide (topoisomerase II inhibitor), taxol, etc.);

(4) a topical dose of 10 mg/kg of body weight of the subject yielding a plasma concentration of less than 15 nanoMolar, and preferably a systemic exposure to less than 0.01 of the $IC_{50}$ concentration for protection of the HT29 tumour cell line;

(5) an acceptable dermal irritation profile; and (6) suitability for the particular topical formulation to be employed (in terms of compatibility, bioavailability, etc.).

The compound of the invention may be formulated for topical administration in any suitable manner to prevent/reduce the severity of plantar/palmar syndrome, involving a suitable dosing and treatment regimen for the patient receiving chemotherapy and/or radiation therapy.

For the prevention/reduction of severity of mucositis in a patient receiving chemotherapy and/or radiation therapy, the compound of the invention in an appropriate form is most preferably formulated for topical administration to the oral cavity mucosa, in a mouthwash, lozenge or lollipop.

The invention may be practiced with a wide variety of CDK2 inhibitor compounds, some of which are described more fully below.

One class of compounds that may be usefully employed in the practice of the invention includes C2 alkynylated purines, including CDK2 inhibitor compounds of formula (B) below:

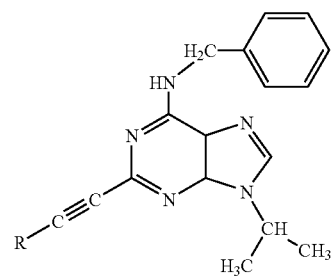

Formula 10 and their further saturated derivatives, wherein R may comprise a substituent such as:

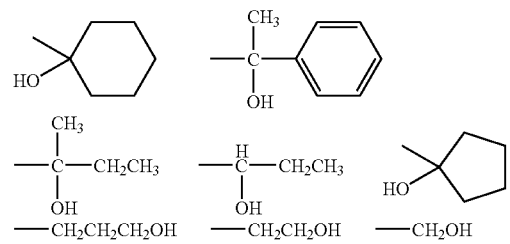

as more fully described in Legraverend, M., et al., Synthesis of C2 Alkynylated Purines, a New Family of Potent Inhibitors of Gyclin-Dependent Kinases, Bioorganic & Medicinal Chemistry Letters 8 (1998) 793–798.

Other purine compounds that may be usefully employed in the broad practice of the invention include those disclosed in International Publication WO 97/20842 published 12 June 1997 and entitled, "NOVEL PURINE DERIVATIVES HAVING, IN PARTICULAR, ANTIPROLIFERATIVE PROPERTIES, AND BIOLOGICAL USES THEREOF" (CENTRE NATIONAL DE LA RECHERCHE SCIENTIFIQUE (C.N.R.S.), which describes 2-, 6- and 9-substituted purine derivatives, such as 2-(1-R hydroxymethylpropylamino)-6-benzylamino-9-isopropyl-purine, having antiproliferative properties, and including roscovitine and olomoucine, whose formulae are set out below:

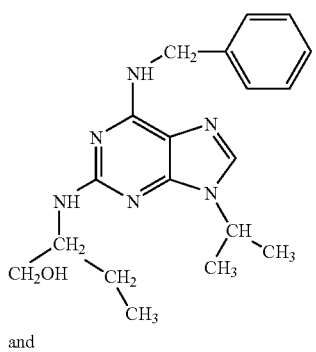

and

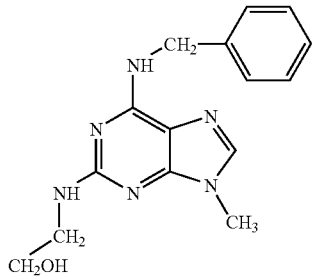

Another class of CDK2 inhibitor compounds that may be usefully employed in the practice of the invention includes 2-thio or 2-oxo flavopiridol analogs, as for example the compounds of the formula:

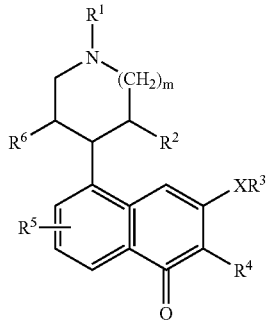

wherein:

X is oxygen or sulfur;

$R^1$ is hydrogen, alkyl, aryl, arylalkyl, cycloalkyl, —$(CH_2)_q$—$NR^7R^8$, alkylcarbonyl, arylcarbonyl, arylalkylcarbonyl, alkoxycarbonyl, arylalkyloxycarbonyl or aryloxycarbonyl;

$R^2$ is hydrogen, alkyl, aryl, arylalkyl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, aryloxycarbonyl, amino, —$NR^7R^8$, thiol, alkylthio, arylalkylthio, or arylthio;

$R^3$ is alkyl, cycloalkyl, aryl, arylaklyl, heterocycle, or heterocycloalkyl;

$R^4$ is hydrogen, alkyl, aryl, arylalkyl, nitro, amino, —$(CH_2)_p$—$NR^7R^8$, halogen, hydroxy, alkoxy, carboxy, heterocycle or alkyloxycarbonyl;

$R^5$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, cyano, nitro, —$NR^7R^8$, halogen, alkylhalo, —CHO, alkylS(O)$_m$- or —OC(O)$NR^7R^8$;

$R^6$ is hydrogen, alkyl, arylalkyl, aryl, cycloalkyl, hydroxy, alkoxy, arylalkoxy, aryloxy, alkylcarbonyloxy, arylalkylcarbonyloxy, arylcarbonyloxy, carboxy, alkyloxycarbonyl, arylalkoxycarbonyl, amino, cyano, nitro, —$NR^7R^8$, halogen, alkylhalo, —CHO, alkylS(O)$_m$— or —OC(O)$NR^7R^8$, $NR^7R^8$, thiol, alkylthio, arylalkylthio or arylthio;

$R^7$ and $R^8$ are independently hydrogen, alkyl, aryl, arylalkyl, cycloalkyl, heterocycle or alkylcarbonyl; or $R^7$ and $R^8$ together with a nitrogen atom to which they are bonded can form a heterocycle;

m is an integer of 0 to 2;

n is an integer of 0 to 3;

p is an integer of 1 to 3; and q is an integer of 2 to 5.

Such flavopiridol derivatives are more fully described in U.S. Pat. No. 5,849,733 and in International Publication WO 97/42949 published Nov. 20, 1997, "2-THIO OR 2-OXO FLAVOPIRIDOL ANALOGS," (BRISTOL-MYERS SQUIBB COMPANY).

Another illustrative class of CDK2 inhibitor compounds usefully employed in the practice of the invention includes the compounds of the formula:

wherein

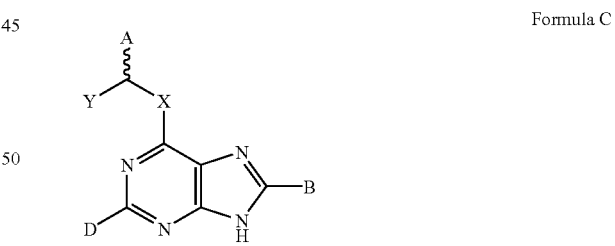

Formula C

X is O, S or CHR$_x$ where R$_x$ is H or C$_{1-6}$ alkyl; D is H, halo or NZ$_1$Z$_2$ where Z$_1$ and Z$_2$ are each independently H or C$_{1-4}$ alkyl or C$_{1-4}$ hydroxyalkyl; A is selected from H, C$_{1-4}$alkyl, C$_{1-4}$alkoxy, hydroxy, CH$_2$(CH$_2$)n OH (n=1–4), and NR$_{a1}$R$_{a2}$ where R$_{a1}$ and R$_{a2}$ are each independently H or C$_{1-6}$ alkyl; B is selected from H, C$_{1-6}$ alkyl, C$_{1-6}$ alkoxy, CF$_3$, an optionally substituted aryl (e.g. phenyl) or an optionally substituted aralkyl (e.g. benzyl), and an hydroxy group that provides a C=O tautomer; and Y is or includes an optionally substituted 4- to 8-membered carbocyclic or heterocyclic ring; or comprises an optionally substituted linear or branched hydrocarbon chain.

Such purine derivatives are more fully described in International Publication WO 99/02162 published 21 Jan. 1999 entitled, "CYCLIN DEPENDENT KINASE INHIBITING PURINE DERIVATIVES" (NEWCASTLE UNIVERSITY VENTURES LIMITED).

A further class of CDK2 inhibitor compounds useful in preventing epithelial cytotoxicity incident to chemotherapy and/or radiation therapy in accordance with the present invention include the compounds described in International Publication WO 98/33798 published Aug. 6, 1998 and entitled, "PYRIDO [2,3-D] PYRIMIDINES AND 4-AMINOPYRIMIDINES AS INHIBITORS OF CELLULAR PROLIFERATION" (WARNER LAMBERT COMPANY), which discloses 7,8-dihydro-2-(amino and thio)pyrido[2,3-d]pyrimidines and 2,4-diaminopyrimidines that are potent inhibitors of cyclin-dependent kinases (cdks) and growth factor-mediated kinases, and are described as being useful for treating cell proliferatives disorders, such as cancer and restenosis. Such compounds are of Formula D1 and Formula D2 below:

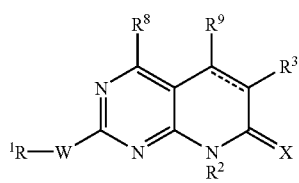

Formul

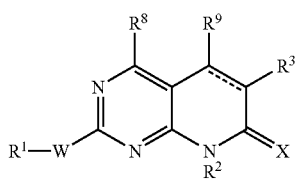

(I)

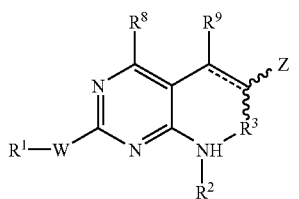

(II)

Formula D2

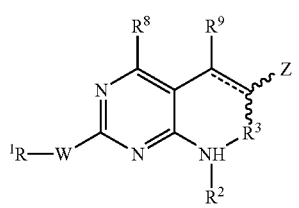

wherein W is NH, S, SO, or $SO_2$, $R_1$ includes phenyl and substituted phenyl, $R_2$ includes alkyl and cycloalkyl, $R_3$ includes alkyl and hydrogen, $R_8$ and $R_9$ include hydrogen and alkyl, and Z is carboxy.

Another category of compounds that may be usefully employed in the practice of the invention includes the 4H-1-benzopyran-4-one derivatives described in German Patent DE 3836676 (Hoechst AG).

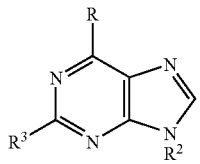

A further class of CDK2 inhibitors includes tyrphostins, such as for example tyrphostins from the AG555/AG494 family as described in N. Kleinberger-Doron, et al., Inhibition of Cdk2 Activation by Selected Tyrphostins Causes Cell Cycle Arrest at Late G1 and S Phases, Experimental Cell Research 241, 340–351 (1998).

Still other CDK2 inhibitors that may be usefully employed in the practice of the invention include the 2,6,9-trisubstituted purine compounds described in International Publication WO 98/05335 published Feb. 12, 1998, "PURINE INHIBITORS OF CYCLIN DEPENDENT KINASE 2 AND I" (CV THERAPEUTICS, INC.) of the formulae:

wherein R is halogen, $XR_1$; X=NH, O, S, $SO_2$; $R_1$=alkyl, cycloalkyl, heterocyclyl, aryl, heteroalkyl; $R_2$=H, alkyl, cycloalkyl, aryl, heteroalkyl; $R_3$=halogen, OH, SH, alkoxy, alkylthio, amino, N-bonded heterocyclyl.

Another class of compounds including CDK2 inhibitor species that may be usefully employed in the practice of the present invention include

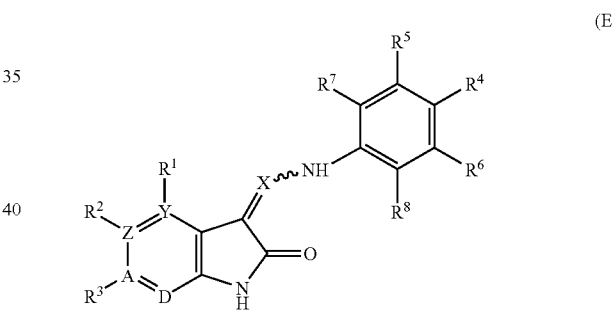

(E compounds of the formula (E1):

wherein

Y, Z, A, and D are independently selected from the group consisting of: carbon and nitrogen, with the provisos that: (1) Z and D may be nitrogen, but otherwise no more than one of Y, Z, A, and D may be nitrogen, and (2) when Y, Z, or A are nitrogen, substituent $R^1$, $R^2$, or $R^3$ designated for the respective nitrogen atom is non-existent;

X is selected from the group consisting of: N, CH, $CCF_3$, and $C(C_{1-12}$ aliphatic);

$R^1$ is selected from the group consisting of: hydrogen, $C_{1-12}$ aliphatic, thiol, hydroxy, hydroxy-$C_{1-12}$ aliphatic, Aryl, Aryl-$C_{1-12}$aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, fluoro, bromo, iodo, cyano, sulfonamide, or nitro, where $R^9$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-C$_{1-6}$ aliphatic, C$_{1-12}$ alkoxycarbonyl, carboxyl C$_{1-12}$ aliphatic, Aryl, R$^9$-Aryl-oxycarbonyl, R$^9$-oxycarbonyl-Aryl, Het, aminocarbonyl, C$_{1-12}$ aliphatic-aminocarbonyl, Aryl-C$_{1-12}$ aliphatic-aminocarbonyl, R$^9$-Aryl-C$_{1-12}$ aliphatic-aminocarbonyl, Het-C$_{1-12}$ aliphatic-aminocarbonyl, hydroxy-C$_{1-12}$ aliphatic-aminocarbonyl, C$_{1-12}$ alkoxy-C$_{1-12}$ aliphatic-aminocarbonyl, C$_{1-12}$ alkoxy-C$_{1-12}$ aliphatic-amino, di-C$_{1-12}$ aliphatic amino, di-C$_{1-12}$ aliphatic aminocarbonyl, di-C$_{1-12}$ aliphatic aminosulfonyl, halogen, hydroxy, C$_{1-12}$ aliphatic-sulfonyl, aminosulfonyl, and C$_{1-12}$ aliphatic-aminosulfonyl, where R$^9$, Aryl and Het are as defined below, with the proviso that where X is nitrogen, R$^2$ is not chloro or 3,6-dihydro-6-methyl-2-oxo-2H-1,3,4-thiadiazin-5-yl;

R$^1$ and R$^2$ are optionally joined to form a fused ring selected from the group as defined for Het below, and said fused ring is optionally substituted by a substituent selected from the group consisting of: C$_{1-12}$ aliphatic, halogen, nitro, cyano, C$_{1-12}$ alkoxy, amino, hydroxyl, (R$^{10}$, R$^{11}$)-amino, and oxo;

R$^3$ is selected from the group consisting of: hydrogen, C$_{1-12}$ aliphatic, hydroxy, hydroxy C$_{1-12}$ aliphatic, di-C$_{1-12}$ aliphatic amino, di-C$_{1-12}$ aliphatic aminocarbonyl, di-C$_{1-12}$ aliphatic aminosulfonyl, C$_{1-12}$ alkoxy, Aryl, Aryloxy, hydroxy-Aryl, Het, hydroxy-Het, Het-oxy, or halogen, where Aryl and Het are as defined below, with the proviso that where X is nitrogen R$^3$ is not fluoro;

R$^2$ and R$^3$ are optionally joined to form a fused ring selected from the group as defined for Het below, and said fused ring is optionally substituted by C$_{1-6}$ aliphatic or C$_{1-6}$ aliphatic-carbonyl;

with the proviso that R$^1$, R$^2$, and R$^3$ cannot simultaneously be hydrogen;

R$^4$, R$^5$ and R$^6$ may be the same or different and are independently selected from the group consisting of: hydrogen, C$_{1-12}$ aliphatic, thiol, C$_{1-6}$aliphatic-thio, di(trifluoromethyl)hydroxymethyl, carboxamide, mono-C$_{1-12}$ aliphatic aminocarbonyl, hydroxy, hydroxy-C$_{1-12}$ aliphatic, Aryl, Aryl-C$_{1-12}$aliphatic, R$^9$-Aryl-C$_{1-12}$ aliphatic, Cyc, Cyc-C$_{1-6}$ aliphatic, Het, Het-C$_{1-12}$ aliphatic, C$_{1-12}$ alkoxy, Aryloxy, Het-oxy, amino, (R$^{10}$,R$^{11}$)-amino-C$_{1-12}$ aliphatic aminocarbonyl, (R$^{10}$,R$^{11}$)-amino-C$_{1-12}$ aliphatic alkoxycarbonyl, (R$^{10}$,R$^{11}$)-amino-C$_{1-12}$ aliphatic aminocarbonylamino, (R$^{10}$,R$^{11}$)-amino-C$_{1-6}$ aliphatic alkoxycarbonylamino, (R$^{10}$,R$^{11}$)-amino-C$_{1-6}$ aliphaticsulfonyl, Het-C$_{1-6}$ aliphatic aminocarbonyl, Het-C$_{1-6}$ aliphatic aminocarbonylamino, Het-C$_{1-6}$ alkoxycarbonylamino, Het-C$_{1-6}$ aliphatic carbonyl, Het-C$_{1-6}$ alkoxycarbonyl, C$_{1-6}$ aliphaticsulfonyl-C$_{1-6}$ aliphatic aminoalkyl, C$_{1-6}$ aliphaticsulfonyl-C$_{1-6}$ aliphatic aminoalkyl-Het-, C$_{1-6}$ alkoxycarbonyl, C$_{1-6}$ aliphatic carbonylamino, (C$_{1-6}$ aliphatic carbonyl)(C$_{1-6}$ aliphatic)amino, (R$^{10}$,R$^{11}$)-amino-C$_{1-6}$ aliphatic carbonylamino, [(R$^{10}$,R$^{11}$)-amino-C$_{1-6}$ aliphatic carbonyl][C$_{1-6}$ aliphatic]amino, (R$^{10}$,R$^{11}$)-amino-C$_{1-6}$ aliphatic sulfonylamino, [(R$^{10}$,R$^{11}$)-amino-C$_{1-6}$ aliphaticsulfonyl][C$_{1-6}$ aliphatic]amino, halogen, cyano, diethoxyphosphorylmethyl, nitro, trifluromethyl, and trifluoromethoxy, where R$^9$, R$^{10}$, R$^{11}$, Aryl, Cyc and Het are as defined below, with the proviso that where X is nitrogen, R$^4$, R$^5$ and R$^3$ is not nitro;

R$^7$ and R$^3$ may be the same or different and are independently selected from the group consisting of: hydrogen, halogen, C$_{12}$ alkoxy, hydroxy, C$_{1-3}$-aliphatic, and C$_{1-3}$ aliphatic;

with the proviso that R$^4$, R$^5$, R$^6$, R$^7$, and R$^8$ cannot simultaneously be hydrogen;

R$^9$ is selected from the group consisting of: C$_{1-12}$ aliphatic, hydroxy, C$_{1-12}$ alkoxy and halogen;

R$^{10}$ and R$^{11}$ may be the same or different and are independently selected from the group consisting of: hydrogen, C$_{1-6}$ aliphatic and Het;

Aryl is selected from the group consisting of: phenyl, naphthyl, phenanthryl and anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole, where any of said heterocyclic rings may be optionally substituted by a substituent selected from the group consisting of: C$_{1-12}$ aliphatic, hydroxy, C$_{1-12}$ alkoxy, (R$^{10}$, R$^{11}$)-amino, (R$^{10}$,R$^{11}$)-amino-C$_{1-12}$ aliphatic, (R$^{10}$, R$^{11}$)-amino-C$_{1-12}$ aliphatic amino, oxo and dioxo;

and the pharmaceutically acceptable salts, esters, amides, carbamates, solvates, hydrates, affinity reagents and prodrugs thereof in either crystalline or amorphous form. The esters, amides and carbamates, are preferably hydrolyzable and more preferably are biohydrolyzable.

Another preferred genus of compounds including CDK2 inhibitor species that may be usefully employed in the practice of the present invention include compounds of the formula (E2), defined as follows:

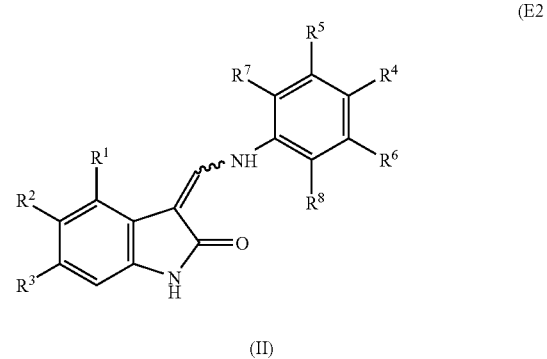

(E2)

(II)

wherein

R$^1$ is selected from the group consisting of: hydrogen, C$_{1-12}$ aliphatic, thiol, hydroxy, hydroxy-C$_{1-12}$ aliphatic, Aryl, Aryl-C$_{1-12}$ aliphatic, R$^9$-Aryl-C$_{1-12}$ aliphatic, Cyc, Cyc-C$_{1-6}$ aliphatic, Het, Het-C$_{1-12}$ aliphatic, C$_{1-12}$ alkoxy, Aryloxy, amino, C$_{1-12}$ aliphatic amino, di-C$_{1-12}$ aliphatic amino, di-C$_{1-12}$ aliphatic aminocarbonyl, di-C$_{1-12}$ aliphatic aminosulfonyl, C$_{1-12}$ alkoxycarbonyl, fluoro, bromo, iodo, cyano, sulfonamide, or nitro, where R$^9$, Aryl, Cyc and Het are as defined below;

R$^2$ is selected from the group consisting of: hydrogen, C$_{1-12}$ aliphatic, N-hydroxyimino-C$_{1-12}$ aliphatic, C$_{1-12}$ alkoxy, hydroxy-C$_{1-12}$ aliphatic, C$_{1-12}$ alkoxycarbonyl, carboxyl C$_{1-12}$ aliphatic, Aryl, R$^9$-Aryl-oxycarbonyl, R$^9$-oxycarbonyl-Aryl, Het, aminocarbonyl, $C_{1-12}$ aliphatic-aminocarbonyl, Aryl-$C_{1-2}$ aliphatic-aminocarbonyl, $R^9$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, $C_{1-12}$ aliphatic-sulfonyl, aminosulfonyl, or one or more substituents selected from the group consisting of: $C_{1-12}$ aliphatic-aminosulfonyl, where $R^9$, Aryl and Het are as defined below;

$R^1$ and $R^2$ are optionally joined to form a fused ring selected from the group as defined for Het below, and said fused ring is optionally substituted by $C_{1-12}$ aliphatic, halogen, nitro, cyano, $C_{1-12}$ alkoxy, amino, hydroxyl, $(R^{10}, R^{11})$-amino, or oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

$R^2$ and $R^3$ are optionally joined to form a fused ring selected from the group as defined for Het below, and said fused ring is optionally substituted by $C_{1-6}$ aliphatic or $C_{1-6}$ aliphatic-carbonyl;

with the proviso that $R^1$, $R^2$ and $R^3$ cannot simultaneously be hydrogen;

$R^4$, $R^5$ and $R^6$ may be the same or different and are independently selected from the group consisting of: hydrogen, $C_{1-12}$ aliphatic, thiol, $C_{1-6}$aliphatic-thio, di(trifluoromethyl)hydroxymethyl, carboxamide, mono-$C_{1-12}$ aliphatic aminocarbonyl, hydroxy, hydroxy-$C_{1-12}$ aliphatic, Aryl, Aryl-$C_{1-12}$aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, Het-oxy, amino, $(R^{1''},R^{11})$-amino-$C_{1-12}$ aliphatic aminocarbonyl, $(R^{10},R^{11})$-amino-$C_{1-12}$ aliphatic alkoxycarbonyl, $(R^{10},R^{11})$-amino-$C_{1-12}$ aliphatic aminocarbonylamino, $(R^{10},R^{11})$-amino-$C_{1-6}$ aliphatic alkoxycarbonylamino, $(R^{10},R^{11})$-amino-$C_{1-6}$ aliphaticsulfonyl, Het-$C_{1-6}$ aliphatic aminocarbonyl, Het-$C_{1-6}$ aliphatic aminocarbonylamino, Het-$C_{1-6}$ alkoxycarbonylamino, Het-$C_{1-6}$ aliphatic carbonyl, Het-$C_{1-6}$ alkoxycarbonyl, $C_{1-6}$ aliphaticsulfonyl-$C_{1-6}$ aliphatic aminoalkyl, $C_{1-6}$ aliphaticsulfonyl-$C_{1-6}$ aliphatic aminoalkyl-Het-, $C_{1-6}$ alkoxycarbonyl, $C_{1-6}$ aliphatic carbonylamino, ($C_{1-6}$ aliphatic carbonyl)($C_{1-6}$ aliphatic)amino, $R^{10},R^{11})$-amino-$C_{1-6}$ aliphatic carbonylamino, $[(R^{10},R^{11})$-amino-$C_{1-6}$ aliphatic carbonyl][$C_{1-6}$ aliphatic]amino, $(R^{10},R^{11})$-amino-$C_{1-6}$ aliphatic sulfonylamino, $[(R^{10},R^{11})$-amino-$C_{1-6}$ aliphaticsulfonyl][$C_{1-6}$ aliphatic]amino, halogen, cyano, diethoxyphosphorylmethyl, nitro, trifluromethyl, or trifluoromethoxy, where $R^9$, $R^{10}$, $R^{11}$, Aryl, Cyc and Het are as defined below;

$R^7$ and $R^8$ may be the same or different and are independently selected from the group consisting of; hydrogen, halogen, $C_{1-2}$ alkoxy, hydroxy, $C_{1-3}$-aliphatic and $C_{1-3}$ aliphatic;

with the proviso that $R^4$, $R^5$, $R^6$, $R^7$ and $R^8$ cannot simultaneously be hydrogen;

$R^9$ is selected from the group consisting of: $C_{1-12}$ aliphatic, hydroxy, $C_{1-12}$ alkoxy, or halogen;

$R^{10}$ and $R^{11}$ may be the same or different and are independently selected from the group consisting of: hydrogen, $C_{1-6}$ aliphatic and Het;

Aryl is selected from the group consisting of: phenyl, naphthyl, phenanthryl or anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole, where any of said heterocyclic rings may be optionally substituted by a substituent selected from the group consisting of: $C_{1-12}$ aliphatic, hydroxy, $C_{1-12}$ alkoxy, $(R^{10}, R^{11})$-amino, $(R^{10},R^{11})$-amino-$C_{1-12}$ aliphatic, $(R^{10},R^{11})$-amino-$C_{1-12}$ aliphatic amino, oxo or dioxo;

and the pharmaceutically acceptable salts, esters, amides, carbamates, solvates, hydrates, affinity reagents and prodrugs thereof in either crystalline or amorphous form. The esters, amides and carbamates, are preferably hydrolyzable and more preferably are biohydrolyzable.

Another preferred genus of compounds including CDK2 inhibitor species that may be usefully employed in the practice of the present invention include compounds of the formula (E3), defined as follows:

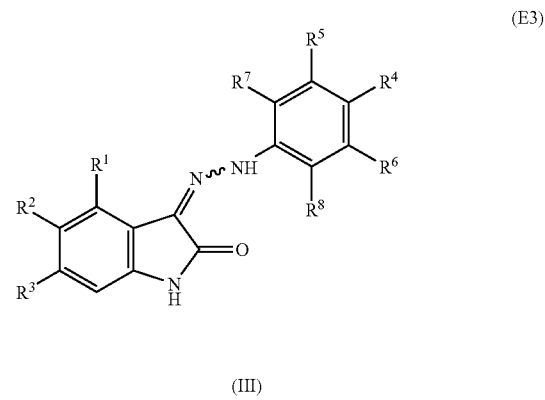

(E3)

(III)

wherein $R^1$ is selected from the group consisting of: hydrogen, $C_{1-12}$ aliphatic, thiol, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, fluoro, bromo, iodo, cyano, sulfonamide, or nitro, where $R^9$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^9$-Aryl-oxycarbonyl, $R^9$-oxycarbonyl-Aryl, Het, aminocarbonyl, $C_{1-12}$ aliphatic-aminocarbonyl, Aryl-$C_{1-12}$ aliphatic-aminocarbonyl, $R^9$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, $C_{1-12}$ aliphatic-sulfonyl, aminosulfonyl, or one or more substituents selected from the group consisting of: $C_{1-12}$ aliphatic-aminosulfonyl, where $R^9$, Aryl and Het are as defined below, with the proviso that $R^2$ is not chloro or 3,6-dihydro-6-methyl-2-oxo-2H-1,3,4-thiadiazin-5-yl;

$R^1$ and $R^2$ are optionally joined to form a fused ring selected from the group as defined for Het below, and said fused ring is optionally substituted by $C_{1-12}$ aliphatic, halogen, nitro, cyano, $C_{1-12}$ alkoxy, amino, hydroxyl, $(R^{10}, R^{11})$-amino, or oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below, with the proviso $R^3$ is not fluoro;

$R^2$ and $R^3$ are optionally joined to form a fused ring selected from the group as defined for Het below, and said fused ring is optionally substituted by $C_{1-4}$ aliphatic or $C_{1-6}$ aliphatic-carbonyl;

with the proviso that $R^1$, $R^2$ and $R^3$ cannot simultaneously be hydrogen;

$R^4$, $R^5$ and $R^6$ may be the same or different and are independently selected from the group consisting of: hydrogen, $C_{1-12}$ aliphatic, thiol, $C_{1-6}$aliphatic-thio, di(trifluoromethyl)hydroxymethyl, carboxamide, mono-$C_{1-12}$ aliphatic aminocarbonyl, hydroxy, hydroxy-$C_{1-12}$ aliphatic, Aryl, Aryl-$C_{1-12}$ aliphatic, R-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, Het-oxy, amino, $(R^{10},R^{11})$-amino-$C_{1-12}$ aliphatic aminocarbonyl, $(R^{10},R^{11})$-amino-$C_{1-12}$ aliphatic alkoxycarbonyl, $(R^{10},R^{11})$-amino-$C_{1-12}$ aliphatic aminocarbonylamino, $(R^{10},R^{11})$-amino-$C_{1-6}$ aliphatic alkoxycarbonylamino, $(R^{10},R^{11})$-amino-$C_{1-6}$ aliphaticsulfonyl, Het-$C_{1-6}$ aliphatic aminocarbonyl, Het-$C_{1-6}$ aliphatic aminocarbonylamino, Het-$C_{1-6}$ alkoxycarbonylamino, Het-$C_{1-6}$ aliphatic carbonyl, Het-$C_{1-6}$ alkoxycarbonyl, $C_{1-6}$ aliphaticsulfonyl-$C_{1-6}$ aliphatic aminoalkyl, $C_{1-6}$ aliphaticsulfonyl-$C_{1-6}$ aliphatic aminoalkyl-Het-, $C_{1-6}$ alkoxycarbonyl, $C_{1-6}$ aliphatic carbonylamino, ($C_{1-6}$ aliphatic carbonyl)($C_{1-6}$ aliphatic)amino, $(R^{10},R^{11})$-amino-$C_{1-6}$ aliphatic carbonylamino, $[(R^{10},R^{11})$-amino-$C_{1-6}$ aliphatic carbonyl][$C_{1-6}$ aliphatic]amino, $(R^{10},R^{11})$-amino-$C_{1-6}$ aliphatic sulfonylamino, $[(R^{10},R^{11})$-amino-$C_{1-6}$ aliphaticsulfonyl][$C_{1-6}$ aliphatic]amino, halogen, cyano, diethoxyphosphorylmethyl, nitro, trifluromethyl, or trifluoromethoxy, where $R^9$, $R^{10}$, $R^{11}$, Aryl, Cyc and Het are as defined below, with the proviso that $R^4$, $R^5$ and $R^6$ is not nitro;

$R^7$ and $R^8$ may be the same or different and are independently selected from the group consisting of: hydrogen, halogen, $C_{1-12}$ alkoxy, hydroxy, $C_{1-3}$-aliphatic and $C_{1-3}$ aliphatic;

with the proviso that $R^4$, $R^5$, $R^6$, $R^7$ and $R^8$ cannot simultaneously be hydrogen;

$R^9$ is selected from the group consisting of: $C_{1-12}$ aliphatic, hydroxy, $C_{1-12}$ alkoxy, or halogen;

$R^{10}$ and $R^{11}$ may be the same or different and are independently selected from the group consisting of: hydrogen, $C_{1-6}$ aliphatic and Het;

Aryl is selected from the group consisting of: phenyl, naphthyl, phenanthryl or anthracenyl;

Cyc is selected from the group consisting of: cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole, where any of said heterocyclic rings may be optionally substituted by a substituent selected from the group consisting of: $C_{1-12}$ aliphatic, hydroxy, $C_{1-12}$ alkoxy, $(R^{10}, R^{11})$-amino, $(R^{10},R^{11})$-amino-$C_{1-12}$ aliphatic, $(R^{10},R^{11})$-amino-$C_{1-12}$ aliphatic amino, oxo or dioxo;

and the pharmaceutically acceptable salts, esters, amides, carbamates, solvates, hydrates, affinity reagents and prodrugs thereof in either crystalline or amorphous form. The esters, amides and carbamates, are preferably hydrolyzable and more preferably are biohydrolyzable.

Another preferred genus of compounds including CDK2 inhibitor species that may be usefully employed in the practice of the present invention include compounds of the formula (E4), defined as follows:

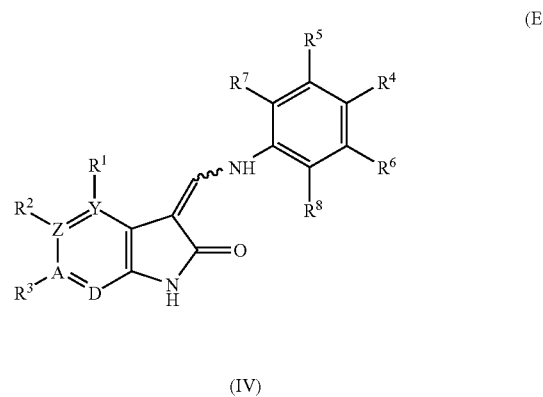

(IV)

wherein

Y, Z, A, and D are independently selected from the group consisting of: carbon and nitrogen, with the provisos that: (1) Z and D may be nitrogen, but otherwise no more than one of Y, Z, A, and D may be nitrogen, and (2) when Y, Z, or A are nitrogen, substituent $R^1$, $R^2$, or $R^3$ designated for the respective nitrogen atom is non-existent;

$R^1$ is selected from the group consisting of: hydrogen, $C_{1-12}$ aliphatic, thiol, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, fluoro, bromo, iodo, cyano, sulfonamide, or nitro, where $R^9$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^9$-Aryl-oxycarbonyl, $R^9$-oxycarbonyl-Aryl, Het, aminocarbonyl, $C_{1-12}$ aliphatic-aminocarbonyl, Aryl-$C_{1-12}$ aliphatic-aminocarbonyl, $R^9$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ aliphatic-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, $C_{1-12}$ aliphatic-sulfonyl, aminosulfonyl, or one or more substituents selected from the group consisting of: $C_{1-12}$ aliphatic-aminosulfonyl, where $R^9$, Aryl and Het are as defined below;

$R^1$ and $R^2$ are optionally joined to form a fused ring selected from the group as defined for Het below, and said fused ring is optionally substituted by $C_{1-12}$ aliphatic, halogen, nitro, cyano, $C_{1-12}$ alkoxy, amino, hydroxyl, $(R^{10}, R^{11})$-amino, or oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

$R^2$ and $R^3$ are optionally joined to form a fused ring selected from the group as defined for Het below, and said fused ring is optionally substituted by $C_{1-6}$ aliphatic or $C_{1-6}$ aliphatic-carbonyl;

with the proviso that $R^1$, $R^2$ and $R^3$ cannot simultaneously be hydrogen;

$R^4$, $R^5$ and $R^6$ may be the same or different and are independently selected from the group consisting of: hydrogen, $C_{1-12}$ aliphatic, thiol, $C_{1-6}$aliphatic-thio, di(trifluoromethyl)hydroxymethyl, carboxamide, mono-$C_{1-12}$ aliphatic aminocarbonyl, hydroxy, hydroxy-$C_{1-12}$ aliphatic, Aryl, Aryl-$C_{1-12}$ aliphatic, $R^9$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, Het-oxy, amino, $(R^{10},R^{11})$-amino-$C_{1-12}$ aliphatic aminocarbonyl, $(R^{10},R^{11})$-amino-$C_{1-12}$ aliphatic alkoxycarbonyl, $(R^{10},R^{11})$-amino-$C_{1-12}$ aliphatic aminocarbonylamino, $(R^{10},R^{11})$-amino-$C_{1-6}$ aliphatic alkoxycarbonylamino, $(R^{10},R^{11})$-amino-$C_{1-6}$ aliphaticsulfonyl, Het-$C_{1-6}$ aliphatic aminocarbonyl, Het-$C_{1-6}$ aliphatic aminocarbonylamino, Het-$C_{1-6}$ alkoxycarbonylamino, Het-$C_{1-6}$ aliphatic carbonyl, Het-$C_{1-6}$ alkoxycarbonyl, $C_{1-6}$ aliphaticsulfonyl-$C_{1-6}$ aliphatic aminoalkyl, $C_{1-6}$ aliphaticsulfonyl-$C_{1-6}$ aliphatic aminoalkyl-Het-, $C_{1-6}$ alkoxycarbonyl, $C_{1-6}$ aliphatic carbonylamino, ($C_{1-6}$ aliphatic carbonyl)($C_{1-6}$ aliphatic)amino, $(R^{10},R^{11})$-amino-$C_{1-6}$ aliphatic carbonylamino, $[(R^{10},R^{11})$-amino-$C_{1-6}$ aliphatic carbonyl][$C_{1-6}$ aliphatic]amino, $(R^{10},R^{11})$-amino-$C_{1-6}$ aliphatic sulfonylamino, $[(R^{10},R^{11})$-amino-$C_{1-6}$ aliphaticsulfonyl][$C_{1-6}$ aliphatic]amino, halogen, cyano, diethoxyphosphorylmethyl, nitro, trifluromethyl, or trifluoromethoxy, where $R^9$, $R^{10}$, $R^{11}$, Aryl, Cyc and Het are as defined below;

$R^7$ and $R^8$ may be the same or different and are independently selected from the group consisting of: hydrogen, halogen, $C_{1-2}$ alkoxy, hydroxy, $C_{1-3}$-aliphatic and $C_{1-3}$ aliphatic;

with the proviso that $R^4$, $R^5$, $R^6$, $R^7$ and $R^8$ cannot simultaneously be hydrogen;

$R^9$ is selected from the group consisting of: $C_{1-12}$aliphatic, hydroxy, $C_{1-12}$ alkoxy, or halogen;

$R^{10}$ and $R^{11}$ may be the same or different and are independently selected from the group consisting of: hydrogen, $C_{1-6}$ aliphatic and Het;

Aryl is selected from the group consisting of: phenyl, naphthyl, phenanthryl or anthracenyl;

Cyc is selected from the group consisting of: cyclopropyl, cyclobutyl, cyclopentyl, cyclohexyl, cycloheptyl or cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperidine, pyran, pyrazine, pyrazole, pyridine, pyrimidine, pyrrole, pyrrolidine, quinoline, tetrahydrofuran, tetrazine, thiadiazine, thiadiazole, thiatriazole, thiazine, thiazole, thiomorpholine, thiophene, thiopyran, triazine and triazole, where any of said heterocyclic rings may be optionally substituted by a substituent selected from the group consisting of: $C_{1-12}$ aliphatic, hydroxy, $C_{1-12}$ alkoxy, $(R^{10}, R^{11})$-amino, $(R^{10},R^{11})$-amino-$C_{1-12}$ aliphatic, $(R^{10},R^{11})$-amino-$C_{1-12}$ aliphatic amino, oxo or dioxo;

and the pharmaceutically acceptable salts, esters, amides, carbamates, solvates, hydrates, affinity reagents and prodrugs thereof in either crystalline or amorphous form. The esters, amides and carbamates, are preferably hydrolyzable and more preferably are biohydrolyzable.

While the ensuing discussion refers to the compound of formula (E1), it will be understood that the compounds of formula (E1) includes the compounds of formulas (E2), (E3) and (E4); accordingly, references hereafter to formula (E1) should hereafter be understood to includes the compounds of formulas (E2), (E3) and (E4) as well as the compounds of formula (E1). Furthermore, references in the ensuing discussion to the formula (E1) should also be understood as referring to the compounds of Examples 163–212 of Table 5 below which, while not included within the general formula (E1) of compound have been found by the inventors to have kinase inhibiting properties.

Due to the presence of an oxindole exocyclic double bond, the compounds of the invention include their respective pure E and Z geometric isomers, as well as mixtures of E and Z isomers.

Likewise, it is understood that compounds of formula (E1) as used herein includes all tautomeric forms other than the specific tautomer represented by the particular formula set forth herein.

Certain of the compounds as described contain one or more chiral, or asymmetric, centers and are therefore capable of existing as optical isomers that are either dextrorotatory or levorotatory. Also included in the compounds of formula (E1) are the respective dextrorotatory or levorotatory pure preparations, and mixtures thereof.

Certain compounds of formula (E1) above are optionally provided in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (E1) are optionally provided in various tautomeric forms within the scope of the present invention.

Another aspect of the present invention relates to the use of a CDK2 inhibitor species, in coadministration or alternating administration with previously known anti-alopecia and/or anti-mucositis therapies for more effective treatment of the patient undergoing chemotherapy.

By way of specific example, the CDK2 inhibitor agent may be administered to a patient undergoing chemotherapy, concurrently with administration to the patient of an anti-mucositis agent, such as the mucositis-preventing/reducing the severity of compounds of the formula:

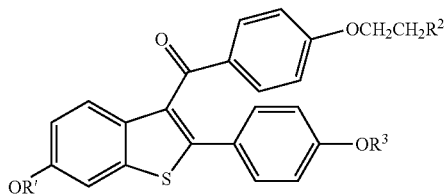

wherein $R_1$ and $R^3$ are independently hydrogen, —$CH_3$, —C(O)—($C_{1-6}$ alkyl), or
—C(O)—Ar, wherein Ar is optionally substituted phenyl;
$R^2$ is selected from the group consisting of pyrrolidine, hexamethyleneamino, and piperidino; and
pharmaceutically acceptable salts and solvates thereof, as more fully described in U.S. Pat. No. 5,496,828.

Various other co-administered active agents may be employed in combination with the CDK2 inhibitor agent(s) in a course or regimen of therapy, for enhanced therapeutic effect.

Considering now the compounds of the above-described formulae (E1)–(E4), illustrative compounds of formula (E1) are listed in Tables 1–3 below. Compounds are identified by the numbers shown in the first column; variables below in the rest of the columns are with reference to the general structure. Corresponding IUPAC nomenclature are listed in Table 4. Since all substituents at each point of substitution are capable of independent synthesis of each other, the tables are to be read as a matrix in which any combination of substituents is within the scope of the composition.

TABLE 1

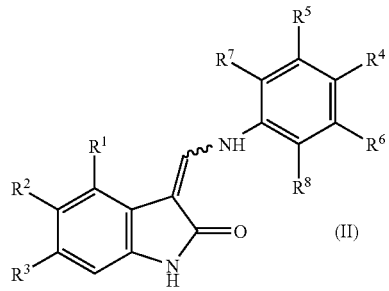

| Example | $R^1$ | $R^2$ | R3 | R4 | $R^5$ | $R^6$ | $R^7$ | $R^8$ |
|---|---|---|---|---|---|---|---|---|
| 1 | H | H | Br | 4-morpholino | H | H | H | H |
| 2 | H | H | Br | 4-pyridylmethyl | H | H | H | H |
| 3 |  | —NH—C=N— | H | $CH_3$ | H | H | H | H |
| 4 |  | —NH—N=N— | H | $NO_2$ | $CH_3$ | H | H | H |
| 5 |  | —NH—N=N— | H | $NO_2$ | $CF_3$ | H | H | H |
| 6 |  | —NH—N=N— | H | $NO_2$ | Cl | H | H | H |
| 7 |  | —NH—N=N— | H | $NO_2$ | $CH_3$ | $CH_3$ | H | H |
| 8 |  | —NH—N=N— | H | —C(OH)($CF_3$)$_2$ | H | H | H | H |
| 9 |  | —NH—N=N— | H | —$CH_2CH_2OH$ | H | H | H | H |
| 10 |  | —S—CH=N— | H | SMe | H | H | H | H |
| 11 |  | —S—CH=N— | H | H | OMe | OMe | H | H |
| 12 |  | —S—CH=N— | H | OH | H | H | H | H |
| 13 | CH=N— | —CH=CH— | H | H | OMe | H | H | H |
| 14 | CH=N— | —CH=CH— | H | H | CN | OMe | H | H |
| 15 | CH=N— | —CH=CH— | H | $CH_3$ | H | H | H | H |
| 16 | CH=N— | —CH=CH— | H | OMe | H | H | H | H |
| 17 |  | —NH—N=N— | H | H | CN | H | H | H |
| 18 |  | —NH—N=N— | H | $CH_3$ | H | H | H | H |
| 19 |  | —NH—N=N— | H | OMe | H | H | H | H |
| 20 |  | —S—CH=N— | H | 4-morpholino | H | H | H | H |
| 21 |  | —S—CH=N— | H | NHAc | H | H | H | H |
| 22 |  | —S—CH=N— | H | —$CH_2CH_2OH$ | H | H | H | H |
| 23 |  | —S—CH=N— | H | 4-pyridylmethyl | H | H | H | H |
| 24 |  | —S—CH=N— | H | $CONH_2$ | H | H | H | H |
| 25 | H | H | Br | 4-morpholino | H | H | H | H |
| 26 | H | H | Br | $CONH_2$ | H | H | H | H |
| 27 | H | H | Br | NHAc | H | H | H | H |
| 28 | H | H | Br | —$CH_2CH_2OH$ | H | H | H | H |
| 29 | CH=N— | —CH=CH— | H | 4-morpholino | H | H | H | H |
| 30 | CH=N— | —CH=CH— | H | 4-pyridylmethyl | H | H | H | H |
| 31 | CH=N— | —CH=CH— | H | NHAc | H | H | H | H |
| 32 | CH=N— | —CH=CH— | H | —$CH_2CH_2OH$ | H | H | H | H |
| 33 | CH=N— | —CH=CH— | H | $CONH_2$ | H | H | H | H |
| 34 | CH=N— | —CH=CH— | H | OH | H | H | H | H |
| 35 | H | H | 2-furanyl | 4-morpholino | H | H | H | H |
| 36 | H | H | 2-furanyl | NHAc | H | H | H | H |
| 37 | H | H | 2-furanyl | —$CH_2CH_2OH$ | H | H | H | H |
| 38 | H | H | —CH=$CH_2$ | 4-morpholino | H | H | H | H |

TABLE 1-continued

| Example | R¹ | R² | R3 | R4 | R⁵ | R⁶ | R⁷ | R⁸ |
|---|---|---|---|---|---|---|---|---|
| 39 | H | H | —CH=CH₂ | 4-pyridylmethyl | H | H | H | H |
| 40 | H | H | —CH=CH₂ | NHAc | H | H | H | H |
| 41 | H | H | —CH=CH₂ | —CH₂CH₂OH | H | H | H | H |
| 42 | H | H | 2-furanyl | 4-pyridylmethyl | H | H | H | H |
| 43 | H | H | 2-furanyl | OH | H | H | H | H |
| 44 | H | H | 2-thienyl | 4-morpholino | H | H | H | H |
| 45 | H | H | 2-thienyl | NHAc | H | H | H | H |
| 46 | H | H | Br | H | —CH₂OH | H | H | H |
| 47 | H | H | Br | 5-methyl-3-pyrazolon-1-yl | H | H | H | H |
| 48 | —S—CH=N— | | H | 3-ethyl-piperidine-2,6-dion-3-yl | H | H | H | H |
| 49 | —S—CH=N— | | H | OPh | H | H | H | H |
| 50 | —S—CH=N— | | H | OCH₂Ph | H | H | H | H |
| 51 | —S—CH=N— | | H | 4-(methoxycarbonyl)phenoxy | H | H | H | H |
| 52 | —S—CH=N— | | H | 3-(methoxycarbonyl)phenoxy | H | H | H | H |
| 53 | —S—CH=N— | | H | H | —CH₂OH | H | H | H |
| 54 | —S—CH=N— | | H | H | CONH₂ | H | H | H |
| 55 | —S—CH=N— | | H | 5-methyl-3-pyrazolon-1-yl | H | H | H | H |
| 56 | —S—CH=N— | | H | CO₂Me | H | H | H | H |
| 57 | —S—CH=N— | | H | CN | H | H | H | H |
| 58 | —S—CH=N— | | H | NMeAc | H | H | H | H |
| 59 | CH=N— | —CH=CH— | H | OPh | H | H | H | H |
| 60 | CH=N— | —CH=CH— | H | OCH₂Ph | H | H | H | H |
| 61 | CH=N— | —CH=CH— | H | 4-(methoxycarbonyl)phenoxy | H | H | H | H |
| 62 | CH=N— | —CH=CH— | H | 3-(methoxycarbonyl)phenoxy | H | H | H | H |
| 63 | CH=N— | —CH=CH— | H | 3-ethyl-piperidine-2,6-dion-3-yl | H | H | H | H |
| 64 | CH=N— | —CH=CH— | H | benzoyl | H | H | H | H |
| 65 | CH=N— | —CH=CH— | H | H | —CH₂OH | H | H | H |
| 66 | CH=N— | —CH=CH— | H | 5-methyl-3-pyrazolon-1yl | H | H | H | H |
| 67 | CH=N— | —CH=CH— | H | 2-(4-hydroxyphenyl)ethenyl | H | H | H | H |
| 68 | CH=N— | —CH=CH— | H | H | CONH₂ | H | H | H |
| 69 | CH=N— | —CH=CH— | H | CN | H | H | H | H |
| 70 | CH=N— | —CH=CH— | H | CO₂Me | H | H | H | H |
| 71 | | —S—CH=N— | H | SO₂CH₂CH₂NEt₂ | H | H | H | H |
| 72 | CH=N— | —CH=CH— | H | SO₂CH₂CH₂NEt₂ | H | H | H | H |
| 73 | H | H | Ph | H | CONH₂ | H | H | H |
| 74 | H | H | Ph | —CH₂PO(OEt)₂ | H | H | H | H |
| 75 | H | H | Ph | H | CN | H | H | H |
| 76 | H | H | Ph | H | H | H | —CH₂CH₂OH | H |
| 77 | H | H | Ph | H | —CH₂OH | H | H | H |
| 78 | H | H | Ph | H | H | H | OMe | H |
| 79 | H | H | Ph | 5-methyl-3-pyrazolon-1-yl | H | H | H | H |
| 80 | H | H | Ph | I | H | H | H | H |
| 81 | H | H | 2-furanyl | H | CONH₂ | H | H | H |
| 82 | H | H | 2-furanyl | —CH₂PO(OEt)₂ | H | H | H | H |
| 83 | H | H | 2-furanyl | H | CN | H | H | H |
| 84 | H | H | 2-furanyl | H | H | H | —CH₂CH₂OH | H |

TABLE 1-continued

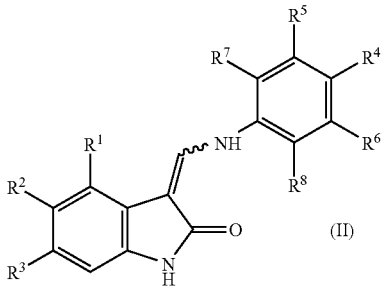

| Example | R¹ | R² | R3 | R4 | R⁵ | R⁶ | R⁷ | R⁸ |
|---|---|---|---|---|---|---|---|---|
| 85 | H | H | 2-furanyl | H | —CH₂OH | H | H | H |
| 86 | H | H | 2-furanyl | H | H | H | OMe | H |
| 87 | H | H | 2-furanyl | 5-methyl-3-pyrazolon-1-yl | H | H | H | H |
| 88 | H | H | 2-furanyl | I | H | H | H | H |

TABLE 2

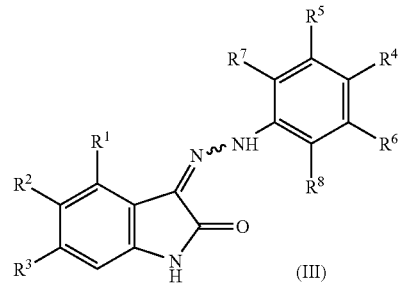

| Example | R¹ | R² | R³ | R4 | R⁵ | R⁶ | R⁷ | R⁸ |
|---|---|---|---|---|---|---|---|---|
| 89 | | —NH—N=N— | H | OMe | H | H | H | H |
| 90 | | —NH—N=N— | H | 5-oxazolyl | H | H | H | H |
| 91 | | —NH—N=N— | H | CH₃ | H | H | H | H |
| 92 | | —NH—N=N— | H | 2-(2-pyridyl)ethenyl | H | H | H | H |
| 93 | | —S—CH=N— | H | H | OMe | H | H | H |
| 94 | CH₃ | OH | CH₃ | CH₃ | H | H | H | H |
| 95 | | —NH—N=N— | H | CF₃ | H | H | H | H |
| 96 | | —S—CH=N— | H | H | F | H | H | H |
| 97 | | —S—CH=N— | H | F | H | H | H | H |
| 98 | | —S—CH=N— | H | Br | H | H | H | H |

TABLE 3

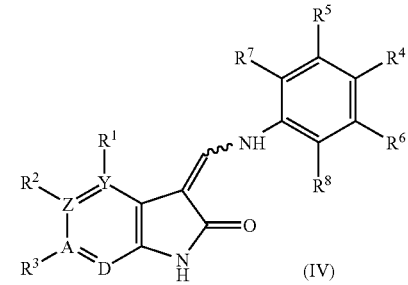

| Example | Z | A | R | R² | R³ | R4 | | R⁵ | R⁶ | R⁷ | R⁸ |
|---|---|---|---|---|---|---|---|---|---|---|---|
| 99 | C | C | C | H | Ph | H | H | CONH₂ | H | H | H |
| 100 | C | C | C | H | Ph | H | —CH₂PO(OEt)₂ | H | H | H | H |
| 101 | C | C | C | H | Ph | H | H | CN | H | H | H |

TABLE 3-continued

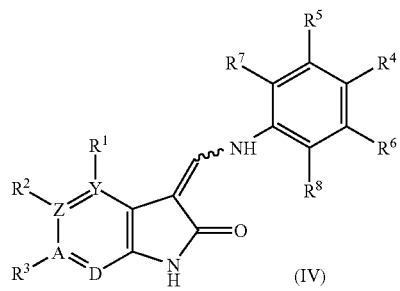

(IV)

| Example | Z | A | R | R² | R³ | R4 | R⁵ | R⁶ | R⁷ | R⁸ |
|---|---|---|---|---|---|---|---|---|---|---|
| 102 | C | C | C | H | Ph | H | H | H | H | —CH₂CH₂OH | H |
| 103 | C | C | C | H | Ph | H | H | —CH₂O | H | H | H |
| 104 | C | C | C | H | Ph | H | H | H | H | OMe | H |
| 105 | C | C | C | H | Ph | H | 5-methyl-3-pyrazolon-1-yl | H | H | H | H |
| 106 | C | C | C | H | Ph | H | I | H | H | H | H |
| 107 | C | C | C | H | 2-furanyl | H | H | CONH₂ | H | H | H |
| 108 | C | C | C | H | 2-furanyl | H | —CH₂PO(OEt)₂ | H | H | H | H |
| 109 | C | C | C | H | 2-furanyl | H | H | CN | H | H | H |
| 110 | C | C | C | H | 2-furanyl | H | H | H | H | —CH₂CH₂OH | H |
| 111 | C | C | C | H | 2-furanyl | H | H | —CH₂OH | H | H | H |
| 112 | C | C | C | H | 2-furanyl | H | H | H | H | OMe | H |
| 113 | C | C | C | H | 2-furanyl | H | 5-methyl-3-pyrazolon-1-yl | H | H | H | H |
| 114 | C | C | C | H | 2-furanyl | H | I | H | H | H | H |
| 115 | C | C | C | H | 3-thienyl | H | H | CONH₂ | H | H | H |
| 116 | C | C | C | H | 3-thienyl | H | —CH₂PO(OEt)₂ | H | H | H | H |
| 117 | C | C | C | H | 3-thienyl | H | H | CN | H | H | H |
| 118 | C | C | C | H | 3-thienyl | H | H | H | H | —CH₂CH₂OH | H |
| 119 | C | C | C | H | 3-thienyl | H | H | —CH₂OH | H | H | H |
| 120 | C | C | C | H | 3-thienyl | H | H | H | H | OMe | H |
| 121 | C | C | C | H | 3-thienyl | H | 5-methyl-3-pyrazolon-1-yl | H | H | H | H |
| 122 | C | C | C | H | 3-thienyl | H | I | H | H | H | H |
| 123 | C | C | C | H | Br | H | H | CONH₂ | H | H | H |
| 124 | C | C | C | H | Br | H | —CH₂PO(OEt)₂ | H | H | H | H |
| 125 | C | C | C | H | Br | H | H | CN | H | H | H |
| 126 | C | C | C | H | Br | H | H | H | H | —CH₂CH₂OH | H |
| 127 | C | C | C | H | Br | H | H | —CH₂O | H | H | H |
| 128 | C | C | C | H | Br | H | H | H | H | OMe | H |
| 129 | C | C | C | H | Br | H | 5-methyl-3-pyrazolon-1-yl | H | H | H | H |
| 130 | C | C | C | H | Br | H | I | H | H | H | H |
| 131 | C | C | C | H | H | Cl | H | CONH₂ | H | H | H |
| 132 | C | C | C | H | H | Cl | —CH₂PO(OEt)₂ | H | H | H | H |
| 133 | C | C | C | H | H | Cl | H | CN | H | H | H |
| 134 | C | C | C | H | H | Cl | H | H | H | —CH₂CH₂OH | H |
| 135 | C | C | C | H | H | Cl | H | —CH₂OH | H | H | H |
| 136 | C | C | C | H | H | Cl | H | H | H | OMe | H |
| 137 | C | C | C | H | H | Cl | 5-methyl-3-pyrazolon-1-yl | H | H | H | H |
| 138 | C | C | C | H | H | Cl | I | H | H | H | H |
| 139 | C | C | C | H | CO₂Et | H | H | CONH₂ | H | H | H |
| 140 | C | C | C | H | CO₂Et | H | —CH₂PO(OEt)₂ | H | H | H | H |
| 141 | C | C | C | H | CO₂Et | H | H | CN | H | H | H |
| 142 | C | C | C | H | CO₂Et | H | H | H | H | —CH₂CH₂OH | H |
| 143 | C | C | C | H | CO₂Et | H | H | —CH₂O | H | H | H |
| 144 | C | C | C | H | CO₂Et | H | H | H | H | OMe | H |
| 145 | C | C | C | H | CO₂Et | H | 5-methyl-3-pyrazolon-1-yl | H | H | H | H |
| 146 | C | C | C | H | CO₂Et | H | I | H | H | H | H |
| 147 | C | C | C | H | H | H | H | CONH₂ | H | H | H |
| 148 | C | C | C | H | H | H | —CH₂PO(OEt)₂ | H | H | H | H |
| 149 | C | C | C | H | H | H | H | CN | H | H | H |
| 150 | C | C | C | H | H | H | H | H | H | —CH₂CH₂OH | H |
| 151 | C | C | C | H | H | H | H | —CH₂OH | H | H | H |
| 152 | C | C | C | H | H | H | H | H | H | OMe | H |
| 153 | C | C | C | H | H | H | 5-methyl-3-pyrazolon-1-yl | H | H | H | H |
| 154 | C | C | C | H | H | H | I | H | H | H | H |
| 155 | N | C | C | — | H | H | H | CONH₂ | H | H | H |
| 156 | N | C | C | — | H | H | —CH₂PO(OEt)₂ | H | H | H | H |

TABLE 3-continued

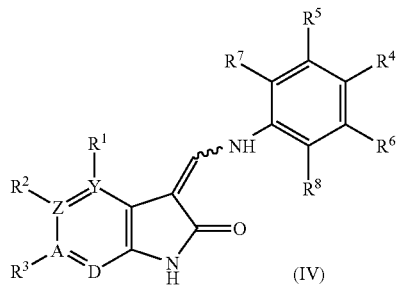

(IV)

| Example | Z | A | R | $R^2$ | $R^3$ | R4 | | $R^5$ | $R^6$ | $R^7$ | $R^8$ |
|---|---|---|---|---|---|---|---|---|---|---|---|
| 157 | N | C | C | — | H | H | H | CN | H | H | H |
| 158 | N | C | C | — | H | H | H | H | H | —$CH_2CH_2OH$ | H |
| 159 | N | C | C | — | H | H | H | —$CH_2OH$ | H | H | H |
| 160 | N | C | C | — | H | H | H | H | H | OMe | H |
| 161 | N | C | C | — | H | H | 5-methyl-3-pyrazolon-1-yl | H | H | H | H |
| 162 | N | C | C | — | H | H | I | H | H | H | H |

Standard nomenclature corresponding to the Examples set forth in this specification is set forth below. In some cases nomenclature is given for one or more possible isomers.

TABLE 4

| Example | |
|---|---|
| Example 1 | 6-Bromo-3-{(Z and E)-[4-(4-morpholinyl)anilino]methylidene}-1,3-dihydro-2H-indol-2-one; |
| Example 2 | 6-Bromo-3-{(Z and E)-[4-(4-pyridinylmethyl)anilino]methylidene}-1,3-dihydro-2H-indol-2-one; |
| Example 3 | 8-[(Z and E)-4-Toluidinomethylidene-6,8-dihydroimidazo[4,5-e]indol-7(3H)-one; |
| Example 4 | 8-[(Z and E)-(3-Methyl-4-nitroanilino)methylidene]-3,6-dihydro[1,2,3]triazolo[4,5-e]indol-7-one; |
| Example 5 | 8-{(Z and E)-[4-Nitro-3-(trifluoromethyl)anilino]methylidene}-3,6-dihydro[1,2,3]triazolo[4,5-e]indol-7-one; |
| Example 6 | 8-[(Z and E)-(3-Chloro-4-nitroanilino)methylidene]-1,6-dihydro[1,2,3]triazolo[4,5-e]indol-7-one; |
| Example 7 | 8-[(Z and E)-(3,5-Dimethyl-4-nitroanilino)methylidene]-1,6-dihydro[1,2,3]triazolo[4,5-e]indol-7-one; |
| Example 8 | 8-((Z and E)-{4-[2,2,2-Trifluoro-1-hydroxy-1-(trifluoromethyl)ethyl]anilino}methylidene)-1,6-dihydro[1,2,3]triazolo[4,5-e]indol-7-one; |
| Example 9 | 8-{(Z and E)-[4-(2-Hydroxyethyl)anilino]methylidene}-1,6-dihydro[1,2,3]triazolo[4,5-e]indol-7-one; |
| Example 10 | 8-{(Z)-[4-(Methylsulfanyl)anilino]methylidene}-6H-[1,3]thiazolo[5,4-e]indol-7-one; |
| Example 11 | 8-[(Z)-(3,5-Dimethoxyanilino)methylidene]-6H-[1,3]thiazolo[5,4-e]indol-7-one; |
| Example 12 | 8-[(Z)-(4-Hydroxyanilino)methylidene]-6H-[1,3]thiazolo[5,4-e]indol-7-one; |
| Example 13 | 1-[(Z)-(3-Methoxyanilino)methylidene]-1,3-dihydro-2H-pyrrolo[3,2-f]quinolin-2-one; |
| Example 14 | 3-{[[(Z)-(2-Oxo-2,3-dihydro-1H-pyrrolo[3,2-f]quinolin-1-ylidene)methyl]amino}benzonitrile; |
| Example 15 | 1-[(Z)-4-Toluidinomethylidene]-1,3-dihydro-2H-pyrrolo[3,2-f]quinolin-2-one; |
| Example 16 | 1-[(Z)-(4-Methoxyanilino)methylidene]-1,3-dihydro-2H-pyrrolo[3,2-f]quinolin-2-one; |
| Example 17 | 3-({[(Z and E)-7-Oxo-6,7-dihydro[1,2,3]triazolo[4,5-e]indol-8(1H)-ylidene]methyl}amino)benzonitrile; |
| Example 18 | 8-[(Z and E)-4-Toluidinomethylidene]-1,6-dihydro[1,2,3]triazolo[4,5-e]indol-7-one; |
| Example 19 | 8-[(Z and E)-(4-Methoxyanilino)methylidene]-1,6-dihydro[1,2,3]triazolo[4,5-e]indol-7-one; |
| Example 20 | 8-{(Z)-[4-(4-Morpholinyl)anilino]methylidene}-6H-[1,3]thiazolo[5,4-e]indol-7-one; |
| Example 21 | N-(4-{[(Z)-(7-Oxo-6,7-dihydro-8H-[1,3]thiazolo[5,4-e]indol-8-ylidene)methyl]amino}phenyl)acetamide; |

TABLE 4-continued

| Example | |
|---|---|
| Example 22 | 8-{(Z)-[4-(2-Hydroxyethyl)anilino]methylidene}-6H-[1,3]thiazolo[5,4-e]indol-7-one; |
| Example 23 | 8-{(Z)-[4-(4-Pyridinylmethyl)anilino]methylidene}-6H-[1,3]thiazolo[5,4-e]indol-7-one; |
| Example 24 | 4-{[(Z)-(7-Oxo-6,7-dihydro-8H-[1,3]thiazolo[5,4-e]indol-8-ylidene)methyl]amino}benzamide; |
| Example 25 | 6-Bromo-3-{(Z and E)-[4-(4-morpholinyl)anilino]methylidene}-1,3-dihydro-2H-indol-2-one; |
| Example 26 | 4-{[(Z and E)-(6-Bromo-2-oxo-1,2-dihydro-3H-indol-3-ylidene)methyl]amino}benzamide; |
| Example 27 | N-(4-{[(Z and E)-(6-Bromo-2-oxo-1,2-dihydro-3H-indol-3-ylidene)methyl]amino}phenyl)acetamide; |
| Example 28 | 6-Bromo-3-{(Z and E)-[4-(2-hydroxyethyl)anilino]methylidene}-1,3-dihydro-2H-indol-2-one; |
| Example 29 | 1-{(Z)-[4-(4-Morpholinyl)anilino]methylidene}-1,3-dihydro-2H-pyrrolo[3,2-f]quinolin-2-one; |
| Example 30 | 1-{(Z)-[4-(4-Pyridinylmethyl)anilino]methylidene}-1,3-dihydro-2H-pyrrolo[3,2-f]quinolin-2-one; |
| Example 31 | N-(4-{[(Z)-(2-Oxo-2,3-dihydro-1H-pyrrolo[3,2-f]quinolin-1-ylidene)methyl]amino}phenyl)acetamide; |
| Example 32 | 1-{(Z)-[4-(2-Hydroxyethyl)anilino]methylidene}-1,3-dihydro-2H-pyrrolo[3,2-f]quinolin-2-one; |
| Example 33 | 4-{[(Z)-(2-Oxo-2,3-dihydro-1H-pyrrolo[3,2-f]quinolin-1-ylidene)methyl]amino}benzamide; |
| Example 34 | 1-[(Z)-(4-Hydroxyanilino)methylidene]-1,3-dihydro-2H-pyrrolo[3,2-f]quinolin-2-one; |
| Example 35 | 6-(2-Furyl)-3-{(Z and E)-[4-(4-morpholinyl)anilino]methylidene}-1,3-dihydro-2H-indol-2-one; |
| Example 36 | N-[4-({(Z and E)-[6-(2-Furyl)-2-oxo-1,2-dihydro-3H-indol-3-ylidene]methyl}amino)phenyl]acetamide; |
| Example 37 | 6-(2-Furyl)-3-{(Z and E)-[4-(2-hydroxyethyl)anilino]methylidene}-1,3-dihydro-2H-indol-2-one; |
| Example 38 | 3-{(Z and E)-[4-(4-Morpholinyl)anilino]methylidene}-6-vinyl-1,3-dihydro-2H-indol-2-one; |
| Example 39 | 3-{(Z and E)-[4-(4-Pyridinylmethyl)anilino]methylidene}-6-vinyl-1,3-dihydro-2H-indol-2-one; |
| Example 40 | N-(4-{(Z and E)-[(2-Oxo-6-vinyl-1,2-dihydro-3H-indol-3-ylidene)methyl]amino}phenyl)acetamide; |
| Example 41 | 3-{(Z and E)-[4-(2-Hydroxyethyl)anilino]methylidene}-6-vinyl-1,3-dihydro-2H-indol-2-one; |
| Example 42 | 6-(2-Furyl)-3-{(Z and E)-[4-(4-pyridinylmethyl)anilino]methylidene}-1,3-dihydro-2H-indol-2-one; |
| Example 43 | 6-(2-Furyl)-3-[(Z and E)-(4-hydroxyanilino)methylidene]-1,3-dihydro-2H-indol-2-one; |
| Example 44 | 3-{(Z and E)-[4-(4-Morpholinyl)anilino]methylidene}-6-(2-thienyl)-1,3-dihydro-2H-indol-2-one; |
| Example 45 | N-[4-({(Z and E)-[2-Oxo-6-(2-thienyl)-1,2-dihydro-3H-indol-3-ylidene]methyl}amino)phenyl]acetamide; |
| Example 46 | 6-Bromo-3-{(Z and E)-[3-(hydroxymethyl)anilino]methylidene}-1,3-dihydro-2H-indol-2-one; |
| Example 47 | 6-Bromo-3-{(Z and E)-[4-(5-methyl-3-oxo-2,3-dihydro-1H-pyrazol-1-yl)anilino]methylidene}-1,3-dihydro-2H-indol-2-one; |
| Example 48 | 3-Ethyl-3-(4-{(Z and E)-[(7-oxo-6,7-dihydro-8H-[1,3]thiazolo[5,4-e]indol-8-ylidene)methyl]amino}phenyl)-2,6-piperidinedione; |
| Example 49 | 8-[(Z)-(4-Phenoxyanilino)methylidene]-6H-[1,3]thiazolo[5,4-e]indol-7-one; |
| Example 50 | 8-{(Z)-[4-(Benzyloxy)anilino]methylidene}-6H-[1,3]thiazolo[5,4-e]indol-7-one; |
| Example 51 | Methyl 4-(4-{[((Z)-7-oxo-6,7-dihydro-8H-[1,3]thiazolo[5,4-e]indol-8-ylidene)methyl]amino}phenoxy)benzoate; |
| Example 52 | Methyl 3-(4-{(Z)-[(7-oxo-6,7-dihydro-8H-[1,3]thiazolo[5,4-e]indol-8-ylidene)methyl]amino}phenoxy)benzoate; |
| Example 53 | 8-{(Z)-[3-(Hydroxymethyl)anilino]methylidene}-6H-[1,3]thiazolol[5,4-e]indol-7-one; |
| Example 54 | 3-{(Z)-[(7-Oxo-6,7-dihydro-8H-[1,3]thiazolo[5,4-e]indol-8-ylidene)methyl]amino}benzamide; |
| Example 55 | 8-{(Z)-[4-(5-Methyl-3-oxo-2,3-dihydro-1H-pyrazol-1-yl)anilino]methylidene}-6H-[1,3]thiazolo[5,4-e]indol-7-one; |
| Example 56 | Methyl 4-{(Z)-[(7-Oxo-6,7-dihydro-8H-[1,3]thiazolo[5,4-e]indol-8-ylidene)methyl]amino}benzoate; |
| Example 57 | 4-{(Z)-[(7-Oxo-6,7-dihydro-8H-[1,3]thiazolol[5,4-e]indol-8-ylidene)methyl]amino}benzonitrile; |
| Example 58 | N-Methyl-N-(4-{(Z)-[(7-oxo-6,7-dihydro-8H-[1,3]thiazolo[5,4-e]indol-8-ylidene)methyl]amino}phenyl)acetamide; |
| Example 59 | 1-[(Z)-(4-Phenoxyanilino)methylidene]-1,3-dihydro-2H-pyrrolo[3,2-f]quinolin-2-one; |
| Example 60 | 1-{(Z)-[4-(Benzyloxy)anilino]methylidene}-1,3-dihydro-2H-pyrrolo[3,2-f]quinolin-2-one; |

TABLE 4-continued

| | |
|---|---|
| Example 61 | Methyl 4-(4-{(Z)-[(2-Oxo-2,3-dihydro-1H-pyrrolo[3,2-f]quinolin-1-ylidene)methyl]amino}phenoxy)benzoate; |
| Example 62 | Methyl 3-(4-{(Z)-[(2-Oxo-2,3-dihydro-1H-pyrrolo[3,2-f]quinolin-1-ylidene)methyl]amino}phenoxy)benzoate; |
| Example 63 | 3-Ethyl-3-(4-{(Z)-[(2-oxo-2,3-dihydro-1H-pyrrolo[3,2-f]quinolin-1-ylidene)methyl]amino}phenyl)-2,6-piperidinedione; |
| Example 64 | 1-[(Z)-(4-Benzoylanilino)methylidene]-1,3-dihydro-2H-pyrrolo[3,2-f]quinolin-2-one; |
| Example 65 | 1-{(Z)-[3-(Hydroxymethyl)anilino]methylidene}-1,3-dihydro-2H-pyrrolo[3,2-f]quinolin-2-one; |
| Example 66 | 1-{(Z)-[4-(5-Methyl-3-oxo-2,3-dihydro-1H-pyrazol-1-yl)anilino]methylidene}-1H-pyrrolo[3,2-f]quinolin-2(3H)-one |
| Example 67 | 1-((E)-{4-[(E)-2-(4-Hydroxyphenyl)ethenyl]anilino}methylidene)-1,3-dihydro-2H-pyrrolo[3,2-f]quinolin-2-one; |
| Example 68 | 3-{(Z)-[(2-Oxo-2,3-dihydro-1H-pyrrolo[3,2-f]quinolin-1-ylidene)methyl]amino}benzamide; |
| Example 69 | 4-{(Z)-[(2-Oxo-2,3-dihydro-1H-pyrrolo[3,2-f]quinolin-1-ylidene)methyl]amino}benzonitrile; |
| Example 70 | Methyl 4-{(Z)-[(2-oxo-2,3-dihydro-1H-pyrrolo[3,2-f]quinolin-1-ylidene)methyl]amino}benzoate; |
| Example 71 | 8-[(Z)-(4-{[2-(Diethylamino)ethyl]sulfonyl}amino)methylidene]-6H-[1,3]thiazolo[5,4-e]indol-7-one; |
| Example 72 | 1-[(Z)-(4-{[2-(Diethylamino)ethyl]sulfonyl}anilino)methylidene]-1H-pyrrolo[3,2-f]quinolin-2(3H)-one; |
| Example 73 | 3-{[(Z and E)-(2-Oxo-6-phenyl-1,2-dihydro-3H-indol-3-ylidene)methyl]amino}benzamide; |
| Example 74 | Diethyl 4-{[(Z and E)-(2-oxo-6-phenyl-1,2-dihydro-3H-indol-3-ylidene)methyl]amino}benzylphosphonate; |
| Example 75 | 3-{[(Z and E)-(2-Oxo-6-phenyl-1,2-dihydro-3H-indol-3-ylidene)methyl]amino}benzonitrile; |
| Example 76 | 3-{(Z and E)-[2-(2-Hydroxyethyl)anilino]methylidene}-6-phenyl-1,3-dihydro-2H-indol-2-one; |
| Example 77 | 3-{(Z and E)-[3-(Hydroxymethyl)anilino]methylidene}-6-phenyl-1,3-dihydro-2H-indol-2-one; |
| Example 78 | 3-[(Z and E)-(2-Methoxyanilino)methylidene]-6-phenyl-1,3-dihydro-2H-indol-2-one; |
| Example 79 | 3-{(Z and E)-[4-(5-Methyl-3-oxo-2,3-dihydro-1H-pyrazol-1-yl)anilino]methylidene}-6-phenyl-1H-indol-2-one; |
| Example 80 | 3-[(Z and E)-(4-Iodoanilino)methylidene]-6-phenyl-1H-indol-2-one; |
| Example 81 | 3-({(Z and E)-[6-(2-Furyl)-2-oxo-1,2-dihydro-3H-indol-3-ylidene]methyl}amino)benzamide; |
| Example 82 | Diethyl 4-({(Z and E)-[6-(2-furyl)-2-oxo-1,2-dihydro-3H-indol-3-ylidene]methyl}amino)benzylphosphonate; |
| Example 83 | 3-({(Z and E)-[6-(2-Furyl)-2-oxo-1,2-dihydro-3H-indol-3-ylidene]methyl}amino)benzonitrile; |
| Example 84 | 6-(2-Furyl)-3-{(Z and E)-[2-(2-hydroxyethyl)anilino]methylidene}-1,3-dihydro-2H-indol-2-one; |
| Example 85 | 6-(2-Furyl)-3-{(Z and E)-[3-(hydroxymethyl)anilino]methylidene}-1,3-dihydro-2H-indol-2-one; |
| Example 86 | 6-(2-Furyl)-3-[(Z and E)-(2-methoxyanilino)methylidene]-1,3-dihydro-2H-indol-2-one; |
| Example 87 | 6-(2-Furyl)-3-{(Z and E)-[4-(5-methyl-3-oxo-2,3-dihydro-1H-pyrazol-1-yl)anilino]methylidene}-1H-indol-2-one; |
| Example 88 | 6-(2-Furyl)-3-[(Z and E)-(4-iodoanilino)methylidene]-1H-indol-2-one; |
| Example 89 | 3,6-Dihydro[1,2,3]triazolo[4,5-e]indole-7,8-dione8-[N-(4-methoxyphenyl)hydrazone]; |
| Example 90 | 3,6-Dihydro[1,2,3]triazolo[4,5-e]indole-7,8-dione8-{N-[4-(1,3-oxazol-5-yl)phenyl]hydrazone}; |
| Example 91 | 3,6-Dihydro[1,2,3]triazolo[4,5-e]indole-7,8-dione8-[N-(4-methylphenyl)hydrazone]; |
| Example 92 | 3,6-Dihydro[1,2,3]triazolo[4,5-e]indole-7,8-dione8-(N-{4-[(E)-2-(2-pyridinyl)ethenyl]phenyl}hydrazone); |
| Example 93 | 6H-[1,3]Thiazolo[5,4-e]indole-7,8-dione8-[N-(3-methoxyphenyl)hydrazone]; |
| Example 94 | 5-Hydroxy-4,6-dimethyl-1H-indole-2,3-dione3-[N-(4-methylphenyl)hydrazone]; |
| Example 95 | 3,6-Dihydro[1,2,3]triazolo[4,5-e]indole-7,8-dione8-{N-[4-(trifluoromethyl)phenyl]hydrazone}; |
| Example 96 | 6H-[1,3]Thiazolo[5,4-e]indole-7,8-dione8-[N-(3-fluorophenyl)hydrazone]; |
| Example 97 | 6H-[1,3]Thiazolo[5,4-e]indole-7,8-dione8-[N-(4-fluorophenyl)hydrazone]; |
| Example 98 | 6H-[1,3]Thiazolo[5,4-e]indole-7,8-dione8-[N-(4-bromophenyl)hydrazone]; |
| Example 99 | 3-{[(2-Oxo-5-phenyl-1,2-dihydro-3H-pyrrolo[2,3-b]pyridin-3-ylidene)methyl]amino}benzamide; |

TABLE 4-continued

| | |
|---|---|
| Example 100 | Diethyl 4-{[(2-oxo-5-phenyl-1,2-dihydro-3H-pyrrolo[2,3-b]pyridin-3-ylidene)methyl]amino}benzylphosphonate; |
| Example 101 | 3-{[(2-Oxo-5-phenyl-1,2-dihydro-3H-pyrrolo[2,3-b]pyridin-3-ylidene)methyl]amino}benzonitrile; |
| Example 102 | 3-{[2-(2-Hydroxyethyl)anilino]methylidene}-5-phenyl-1,3-dihydro-2H-pyrrolo[2,3-b]pyridin-2-one; |
| Example 103 | 3-{[3-(Hydroxymethyl)anilino]methylidene}-5-phenyl-1,3-dihydro-2H-pyrrolo[2,3-b]pyridin-2-one; |
| Example 104 | 3-[(2-Methoxyanilino)methylidene]-5-phenyl-1,3-dihydro-2H-pyrrolo[2,3-b]pyridin-2-one; |
| Example 105 | 3-{[4-(5-Methyl-3-oxo-2,3-dihydro-1H-pyrazol-1-yl)anilino]methylidene}-5-phenyl-1H-pyrrolo[2,3-b]pyridin-2-one; |
| Example 106 | 3-[(4-Iodoanilino)methylidene]-5-phenyl-1H-pyrrolo[2,3-b]pyridin-2-one; |
| Example 107 | 3-({[5-(2-Furyl)-2-oxo-1,2-dihydro-3H-pyrrolo[2,3-b]pyridin-3-ylidene]methyl}amino)benzamide; |
| Example 108 | Diethyl 4-({[5-(2-furyl)-2-oxo-1,2-dihydro-3H-pyrrolo[2,3-b]pyridin-3-ylidene]methyl}amino)benzylphosphonate; |
| Example 109 | 3-({[5-(2-Furyl)-2-oxo-1,2-dihydro-3H-pyrrolo[2,3-b]pyridin-3-ylidene]methyl}amino)benzonitrile; |
| Example 110 | 5-(2-Furyl)-3-{[2-(2-hydroxyethyl)anilino]methylidene}-1,3-dihydro-2H-pyrrolo[2,3-b]pyridin-2-one; |
| Example 111 | 5-(2-Furyl)-3-{[3-(hydroxymethyl)anilino]methylidene}-1,3-dihydro-2H-pyrrolo[2,3-b]pyridin-2-one; |
| Example 112 | 5-(2-Furyl)-3-[(2-methoxyanilino)methylidene]-1,3-dihydro-2H-pyrrolo[2,3-b]pyridin-2-one; |
| Example 113 | 5-(2-Furyl)-3-{[4-(5-methyl-3-oxo-2,3-dihydro-1H-pyrazol-1-yl)anilino]methylidene}-1H-pyrrolo[2,3-b]pyridin-2-one; |
| Example 114 | 5-(2-Furyl)-3-[(4-iodoanilino)methylidene]-1H-pyrrolo[2,3-b]pyridin-2-one; |
| Example 115 | 3-({[2-Oxo-5-(3-thienyl)-1,2-dihydro-3H-pyrrolo[2,3-b]pyridin-3-ylidene]methyl}amino)benzamide; |
| Example 116 | Diethyl 4-({[2-oxo-5-(3-thienyl)-1,2-dihydro-3H-pyrrolo[2,3-b]pyridin-3-ylidene]methyl}amino)benzylphosphonate; |
| Example 117 | 3-({[2-Oxo-5-(3-thienyl)-1,2-dihydro-3H-pyrrolo[2,3-b]pyridin-3-ylidene]methyl}amino)benzonitrile; |
| Example 118 | 3-{[2-(2-Hydroxyethyl)anilino]methylidene}-5-(3-thienyl)-1,3-dihydro-2H-pyrrolo[2,3-b]pyridin-2-one; |
| Example 119 | 3-{[3-(Hydroxymethyl)anilino]methylidene}-5-(3-thienyl)-1,3-dihydro-2H-pyrrolo[2,3-b]pyridin-2-one; |
| Example 120 | 3-[(2-Methoxyanilino)methylidene]-5-(3-thienyl)-1,3-dihydro-2H-pyrrolo[2,3-b]pyridin-2-one; |
| Example 121 | 3-{[4-(5-Methyl-3-oxo-2,3-dihydro-1H-pyrazol-1-yl)anilino]methylidene}-5-(3-thienyl)-1,3-dihydro-2H-pyrrolo[2,3-b]pyridin-2-one; |
| Example 122 | 3-[(4-Iodoanilino)methylidene]-5-(3-thienyl)-1H-pyrrolo[2,3-b]pyridin-2-one; |
| Example 123 | 3-{[(5-Bromo-2-oxo-1,2-dihydro-3H-pyrrolo[2,3-b]pyridin-3-ylidene)methyl]amino}benzamide; |
| Example 124 | Diethyl 4-{[(5-Bromo-2-oxo-1,2-dihydro-3H-pyrrolo[2,3-b]pyridin-3-ylidene)methyl]amino}benzylphosphonate; |
| Example 125 | 3-{[(5-Bromo-2-oxo-1,2-dihydro-3H-pyrrolo[2,3-b]pyridin-3-ylidene)methyl]amino}benzonitrile; |
| Example 126 | 5-Bromo-3-{[2-(2-hydroxyethyl)anilino]methylidene}-1,3-dihydro-2H-pyrrolo[2,3-b]pyridin-2-one; |
| Example 127 | 5-Bromo-3-{[3-(hydroxymethyl)anilino]methylidene}-1,3-dihydro-2H-pyrrolo[2,3-b]pyridin-2-one; |
| Example 128 | 5-Bromo-3-[(2-methoxyanilino)methylidene]-1,3-dihydro-2H-pyrrolo[2,3-b]pyridin-2-one; |
| Example 129 | 5-Bromo-3-{[4-(5-methyl-3-oxo-2,3-dihydro-1H-pyrazol-1-yl)anilino]methylidene}-1,3-dihydro-2H-pyrrolo[2,3-b]pyridin-2-one; |
| Example 130 | 5-Bromo-3-[(4-iodoanilino)methylidene]-1H-pyrrolo[2,3-b]pyridin-2-one; |
| Example 131 | 3-{[(6-Chloro-2-oxo-1,2-dihydro-3H-pyrrolo[2,3-b]pyridin-3-ylidene)methyl]amino}benzamide; |
| Example 132 | Diethyl 4-{[(6-chloro-2-oxo-1,2-dihydro-3H-pyrrolo[2,3-b]pyridin-3-ylidene)methyl]amino}benzylphosphonate; |
| Example 133 | 3-{[(6-Chloro-2-oxo-1,2-dihydro-3H-pyrrolo[2,3-b]pyridin-3-ylidene)methyl]amino}benzonitrile; |
| Example 134 | 6-Chloro-3-{[2-(2-hydroxyethyl)anilino]methylidene}-1,3-dihydro-2H-pyrrolo[2,3-b]pyridin-2-one; |
| Example 135 | 6-Chloro-3-{[3-(hydroxymethyl)anilino]methylidene}-1,3-dihydro-2H-pyrrolo[2,3-b]pyridin-2-one; |
| Example 136 | 6-Chloro-3-[(2-methoxyanilino)methylidene]-1,3-dihydro-2H-pyrrolo[2,3-b]pyridin-2-one; |
| Example 137 | 6-Chloro-3-{[4-(5-methyl-3-oxo-2,3-dihydro-1H-pyrazol-1-yl)anilino]methylidene}-1,3-dihydro-2H-pyrrolo[2,3-b]pyridin-2- |

TABLE 4-continued

| | |
|---|---|
| | one; |
| Example 138 | 6-Chloro-3-[(4-iodoanilino)methylidene]-1H-pyrrolo[2,3-b]pyridin-2-one; |
| Example 139 | Ethyl 3-{[3-(aminocarbonyl)anilino]methylidene}-2-oxo-2,3-dihydro-1H-pyrrolo[2,3-b]pyridine-5-carboxylate; |
| Example 140 | Ethyl 3-({4-[(diethoxyphosphoryl)methyl]anilino}methylidene)-2-oxo-1,2-dihydro-3H-pyrrolo[2,3-b]pyridine-5-carboxylate; |
| Example 141 | Ethyl 3-[(3-cyanoanilino)methylidene]-2-oxo-2,3-dihydro-1H-pyrrolo[2,3-b]pyridine-5-carboxylate; |
| Example 142 | Ethyl 3-{[2-(2-hydroxyethyl)anilino]methylidene}-2-oxo-2,3-dihydro-1H-pyrrolo[2,3-b]pyridine-5-carboxylate; |
| Example 143 | Ethyl 3-{[3-(hydroxymethyl)anilino]methylidene}-2-oxo-2,3-dihydro-1H-pyrrolo[2,3-b]pyridine-5-carboxylate; |
| Example 144 | Ethyl 3-[(2-methoxyanilino)methylidene]-2-oxo-2,3-dihydro-1H-pyrrolo[2,3-b]pyridine-5-carboxylate; |
| Example 145 | Ethyl 3-{[4-(5-methyl-3-oxo-2,3-dihydro-1H-pyrazol-1-yl)anilino]methylidene}-2-oxo-1,2-dihydro-3H-pyrrolo[2,3-b]pyridine-5-carboxylate; |
| Example 144 | Ethyl 3-[(4-iodoanilino)methylidene]-2-oxo-1,2-dihydro-3H-pyrrolo[2,3-b]pyridine-5-carboxylate; |
| Example 147 | 3-{[(2-Oxo-1,2-dihydro-3H-pyrrolo[2,3-b]pyridin-3-ylidene)methyl]amino}benzamide; |
| Example 148 | Diethyl 4-{[(2-oxo-1,2-dihydro-3H-pyrrolo[2,3-b]pyridin-3-ylidene)methyl]amino}benzylphosphonate; |
| Example 149 | 3-{[(2-Oxo-1,2-dihydro-3H-pyrrolo[2,3-b]pyridin-3-ylidene)methyl]amino}benzonitrile; |
| Example 150 | 3-{[2-(2-Hydroxyethyl)anilino]methylidene}-1,3-dihydro-2H-pyrrolo[2,3-b]pyridin-2-one; |
| Example 151 | 3-{[3-(Hydroxymethyl)anilino]methylidene}-1,3-dihydro-2H-pyrrolo[2,3-b]pyridin-2-one; |
| Example 152 | 3-[(2-Methoxyanilino)methylidene]-1,3-dihydro-2H-pyrrolo[2,3-b]pyridin-2-one; |
| Example 153 | 3-{[4-(5-Methyl-3-oxo-2,3-dihydro-1H-pyrazol-1-yl)anilino]methylidene}-1H-pyrrolo[2,3-b]pyridin-2-one; |
| Example 154 | 3-[(4-Iodoanilino)methylidene]-1H-pyrrolo[2,3-b]pyridin-2-one; |
| Example 155 | 3-{[(2-Oxo-1,2-dihydro-3H-pyrrolo[3,2-b]pyridin-3-ylidene)methyl]amino}benzamide; |
| Example 156 | Diethyl 4-{[(2-oxo-1,2-dihydro-3H-pyrrolo[3,2-b]pyridin-3-ylidene)methyl]amino}benzylphosphonate; |
| Example 157 | 3-{[(2-Oxo-1,2-dihydro-3H-pyrrolo[3,2-b]pyridin-3-ylidene)methyl]amino}benzonitrile; |
| Example 158 | 3-{[2-(2-Hydroxyethyl)anilino]methylidene}-1,3-dihydro-2H-pyrrolo[3,2-b]pyridin-2-one; |
| Example 159 | 3-{[3-(Hydroxymethyl)anilino]methylidene}-1,3-dihydro-2H-pyrrolo[3,2-b]pyridin-2-one; |
| Example 160 | 3-[(2-Methoxyanilino)methylidene]-1,3-dihydro-2H-pyrrolo[3,2-b]pyridin-2-one; |
| Example 161 | 3-{[4-(5-Methyl-3-oxo-2,3-dihydro-1H-pyrazol-1-yl)anilino]methylidene}-1H-pyrrolo[3,2-b]pyridin-2-one; and |
| Example 162 | 3-[(4-Iodoanilino)methylidene]-1H-pyrrolo[3,2-b]pyridin-2-one. |

Other compounds of the invention, not included in Formula (E1), are enumerated in Table 5.

TABLE 5

| | |
|---|---|
| Example 163 | 3-{(Z and E)-[(1-methyl-3-phenyl-1H-pyrazol-5-yl)amino]methylidene}-5-phenyl-1,3-dihydro-2H-pyrrolo[2,3-b]pyridin-2-one; |
| Example 164 | 3-{(Z and E)-[(4-Hydroxy-1-naphthyl)amino]methylidene}-5-phenyl-1,3-dihydro-2H-pyrrolo[2,3-b]pyridin-2-one; |
| Example 165 | 3-{(Z and E)-[(1-Ethyl-1H-pyrazol-5-yl)amino]methylidene}-5-phenyl-1,3-dihydro-2H-pyrrolo[2,3-b]pyridin-2-one; |
| Example 166 | 3-[(Z and E)-(1H-Benzimidazol-2-ylamino)methylidene]-5-phenyl-1H-pyrrolo[2,3-b]pyridin-2-one; |
| Example 167 | 3-((Z and E)-{[6-(4-Morpholinyl)-3-pyridinyl]amino}methylidene)-5-phenyl-1,3-dihydro-2H-pyrrolo[2,3-b]pyridin-2-one; |
| Example 168 | 5-(2-Furyl)-3-{(Z and E)-[(1-methyl-3-phenyl-1H-pyrazol-5-yl)amino]methylidene}-1,3-dihydro-2H-pyrrolo[2,3-b]pyridin-2-one; |
| Example 169 | 5-(2-Furyl)-3-{(Z and E)-[(4-hydroxy-1-naphthyl)amino]methylidene}-1,3-dihydro-2H-pyrrolo[2,3-b]pyridin-2-one; |

TABLE 5-continued

| Example 170 | 3-{(Z and E)-[(1-Ethyl-1H-pyrazol-5-yl)amino]methylidene}-5-(2-furyl)-1,3-dihydro-2H-pyrrolo[2,3-b]pyridin-2-one; |
| --- | --- |
| Example 171 | 3-[(Z and E)-(1H-Benzimidazol-2-ylamino)methylidene]-5-(2-furyl)-1H-pyrrolo[2,3-b]pyridin-2-one; |
| Example 172 | 5-(2-Furyl)-3-((Z and E)-{[6-(4-morpholinyl)-3-pyridinyl]amino}methylidene)-1,3-dihydro-2H-pyrrolo[2,3-b]pyridin-2-one; |
| Example 173 | 3-{(Z and E)-[(1-Methyl-3-phenyl-1H-pyrazol-5-yl)amino]methylidene}-5-(3-thienyl)-1,3-dihydro-2H-pyrrolo[2,3-b]pyridin-2-one; |
| Example 174 | 3-{(Z and E)-[(4-Hydroxy-1-naphthyl)amino]methylidene}-5-(3-thienyl)-1,3-dihydro-2H-pyrrolo[2,3-b]pyridin-2-one; |
| Example 175 | 3-{(Z and E)-[(1-Ethyl-1H-pyrazol-5-yl)amino]methylidene}-5-(3-thienyl)-1,3-dihydro-2H-pyrrolo[2,3-b]pyridin-2-one; |
| Example 176 | 3-[(Z and E)-(1H-Benzimidazol-2-ylamino)methylidene]-5-(3-thienyl)-1,3-dihydro-2H-pyrrolo[2,3-b]pyridin-2-one; |
| Example 177 | 3-((Z and E)-{[6-(4-Morpholinyl)-3-pyridinyl]amino}methylidene)-5-(3-thienyl)-1,3-dihydro-2H-pyrrolo[2,3-b]pyridin-2-one; |
| Example 178 | 5-Bromo-3-{(Z and E)-[(1-methyl-3-phenyl-1H-pyrazol-5-yl)amino]methylidene}-1,3-dihydro-2H-pyrrolo[2,3-b]pyridin-2-one; |
| Example 179 | 5-Bromo-3-{(Z and E)-[(4-hydroxy-1-naphthyl)amino]methylidene}-1,3-dihydro-2H-pyrrolo[2,3-b]pyridin-2-one; |
| Example 180 | 5-Bromo-3-{(Z and E)-[(1-ethyl-1H-pyrazol-5-yl)amino]methylidene}-1,3-dihydro-2H-pyrrolo[2,3-b]pyridin-2-one; |
| Example 181 | 3-[(Z and E)-(1H-Benzimidazol-2-ylamino)methylidene]-5-bromo-1,3-dihydro-2H-pyrrolo[2,3-b]pyridin-2-one; |
| Example 182 | 5-Bromo-3-((Z and E)-{[6-(4-morpholinyl)-3-pyridinyl]amino}methylidene)-1,3-dihydro-2H-pyrrolo[2,3-b]pyridin-2-one; |
| Example 183 | 6-Chloro-3-{(Z and E)-[(1-methyl-3-phenyl-1H-pyrazol-5-yl)amino]methylidene}-1,3-dihydro-2H-pyrrolo[2,3-b]pyridin-2-one; |
| Example 184 | 6-Chloro-3-{(Z and E)-[(4-hydroxy-1-naphthyl)amino]methylidene}-1,3-dihydro-2H-pyrrolo[2,3-b]pyridin-2-one; |
| Example 185 | 6-Chloro-3-{(Z and E)-[(1-ethyl-1H-pyrazol-5-yl)amino]methylidene}-1,3-dihydro-2H-pyrrolo[2,3-b]pyridin-2-one; |
| Example 186 | 3-[(Z and E)-(1H-Benzimidazol-2-ylamino)methylidene]-6-chloro-1,3-dihydro-2H-pyrrolo[2,3-b]pyridin-2-one; |
| Example 187 | 6-Chloro-3-((Z and E)-{[6-(4-morpholinyl)-3-pyridinyl]amino}methylidene)-1,3-dihydro-2H-pyrrolo[2,3-b]pyridin-2-one; |
| Example 188 | Ethyl 3-{(Z and E)-[(1-methyl-3-phenyl-1H-pyrazol-5-yl)amino]methylidene}-2-oxo-2,3-dihydro-1H-pyrrolo[2,3-b]pyridine-5-carboxylate; |
| Example 189 | Ethyl 3-{(Z and E)-[(4-hydroxy-1-naphthyl)amino]methylidene}-2-oxo-2,3-dihydro-1H-pyrrolo[2,3-b]pyridine-5-carboxylate; |
| Example 190 | Ethyl 3-{(Z and E)-[(1-ethyl-1H-pyrazol-5-yl)amino]methylidene}-2-oxo-2,3-dihydro-1H-pyrrolo[2,3-b]pyridine-5-carboxylate; |
| Example 191 | Ethyl 3-[(Z and E)-(1H-benzimidazol-2-ylamino)methylidene]-2-oxo-1,2-dihydro-3H-pyrrolo[2,3-b]pyridine-5-carboxylate; |
| Example 192 | Ethyl 3-((Z and E)-{[6-(4-morpholinyl)-3-pyridinyl]amino}methylidene)-2-oxo-2,3-dihydro-1H-pyrrolo[2,3-b]pyridine-5-carboxylate; |
| Example 193 | 3-{(Z and E)-[(1-Methyl-3-phenyl-1H-pyrazol-5-yl)amino]methylidene}-6-phenyl-1,3-dihydro-2H-indol-2-one; |
| Example 194 | 3-{(Z and E)-[(4-Hydroxy-1-naphthyl)amino]methylidene}-6-phenyl-1,3-dihydro-2H-indol-2-one; |
| Example 195 | 3-{(Z and E)-[(1-Ethyl-1H-pyrazol-5-yl)amino]methylidene}-6-phenyl-1,3-dihydro-2H-indol-2-one; |
| Example 196 | 3-[(Z and E)-(1H-Benzimidazol-2-ylamino)methylidene]-6-phenyl-1H-indol-2-one; |
| Example 197 | 3-((Z and E)-{[6-(4-Morpholinyl)-3-pyridinyl]amino}methylidene)-6-phenyl-1,3-dihydro-2H-indol-2-one; |
| Example 198 | 6-(2-Furyl)-3-{(Z and E)-[(1-methyl-3-phenyl-1H-pyrazol-5-yl)amino]methylidene}-1,3-dihydro-2H-indol-2-one; |
| Example 199 | 6-(2-Furyl)-3-{(Z and E)-[(4-hydroxy-1-naphthyl)amino]methylidene}-1,3-dihydro-2H-indol-2-one; |
| Example 200 | 3-{(Z and E)-[(1-Ethyl-1H-pyrazol-5-yl)amino]methylidene}-6-(2-furyl)-1,3-dihydro-2H-indol-2-one; |
| Example 201 | 3-[(Z and E)-(1H-Benzimidazol-2-ylamino)methylidene]-6-(2-furyl)-1H-indol-2-one; |
| Example 202 | 6-(2-Furyl)-3-((Z and E)-{[6-(4-morpholinyl)-3-pyridinyl]amino}methylidene)-1,3-dihydro-2H-indol-2-one; |

TABLE 5-continued

| | |
|---|---|
| Example 203 | 3-{(Z and E)-[(1-Methyl-3-phenyl-1H-pyrazol-5-yl)amino]methylidene}-1,3-dihydro-2H-pyrrolo[2,3-b]pyridin-2-one; |
| Example 204 | 3-{(Z and E)-[(4-Hydroxy-1-naphthyl)amino]methylidene}-1,3-dihydro-2H-pyrrolo[2,3-b]pyridin-2-one; |
| Example 205 | 3-{(Z and E)-[(1-Ethyl-1H-pyrazol-5-yl)amino]methylidene}-1,3-dihydro-2H-pyrrolo[2,3-b]pyridin-2-one; |
| Example 206 | 3-[(Z and E)-(1H-Benzimidazol-2-ylamino)methylidene]-1H-pyrrolo[2,3-b]pyridin-2-one; |
| Example 207 | 3-((Z and E)-{[6-(4-Morpholinyl)-3-pyridinyl]amino}methylidene)-1,3-dihydro-2H-pyrrolo[2,3-b]pyridin-2-one; |
| Example 208 | 3-{(Z and E)-[(1-Methyl-3-phenyl-1H-pyrazol-5-yl)amino]methylidene}-1,3-dihydro-2H-pyrrolo[3,2-b]pyridin-2-one; |
| Example 209 | 3-{(Z and E)-[(4-Hydroxy-1-naphthyl)amino]methylidene}-1,3-dihydro-2H-pyrrolo[3,2-b]pyridin-2-one; |
| Example 210 | 3-{(Z and E)-[(1-Ethyl-1H-pyrazol-5-yl)amino]methylidene}-1,3-dihydro-2H-pyrrolo[3,2-b]pyridin-2-one; |
| Example 211 | 3-[(Z and E)-(1H-Benzimidazol-2-ylamino)methylidene]-1H-pyrrolo[3,2-b]pyridin-2-one; and |
| Example 212 | 3-((Z and E)-{[6-(4-Morpholinyl)-3-pyridinyl]amino}methylidene)-1,3-dihydro-2H-pyrrolo[3,2-b]pyridin-2-one. |

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Diethanolamine, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Metaphosphoric, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Trifluoroacetate, Triethiodide, Trimethylammonium and Valerate.

Other salts which are not pharmaceutically acceptable may be useful in the preparation of compounds of formula (E1).

Also included are the individual isomers of the compounds represented by formula (E1) above as well as any wholly or partially equilibrated mixtures thereof. The present invention also covers the individual isomers of the compounds represented by formula above as mixtures with isomers thereof in which one or more chiral asymmetric centers are inverted.

As used herein, the term "aliphatic" refers to the terms alkyl, alkylene, alkenyl, alkenylene, alkynyl and alkynylene.

As used herein, the term "lower" refers to a group having between one and six carbons.

As used herein, the term "alkyl" refers to a straight or branched chain hydrocarbon having from one to twelve carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by a substituent selected from the group iniuding alkyl, nitro, cyano, halogen and lower perfluoroalkyl, multiple degrees of substitution being allowed. Examples of "alkyl" as used herein include, but are not limited to, n-butyl, n-pentyl, isobutyl, isopropyl, and the like.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed.

As used herein, the term "alkenylene" refers to an straight or branched chain divalent hydrocarbon radical having from two to ten carbon atoms and one or more carbon-carbon double bonds, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkynylene" as used herein include, but are not limited to, ethyne-1,2-diyl, propyne-1,3-diyl, and the like.

As used herein, the term "cycloaliphatic" includes the terms cycloalkyl, cycloalkylene, cycloalkenyl, cycloalkenylene, cycloalkynyl and cycloalkylnylene.

As used herein, "cycloalkyl" refers to a alicyclic hydrocarbon group with one or more degrees of unsaturation, having from three to twelve carton atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. "Cycloalkyl" includes by way of example cyclopropyl, cyclobutyl, cyclopentyl, cyclohexyl, cycloheptyl, cyclooctyl, and the like.

As used herein, the term "cycloalkylene" refers to a non-aromatic alicyclic divalent hydrocarbon radical having from three to twelve carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon-carbon double bond in the ring system, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene-4-yl, and the like.

As used herein, the term "cycloalkenylene" refers to a substituted alicyclic divalent hydrocarbon radical having from three to twelve carbon atoms and at least one carbon-carbon double bond in the ring system, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heteroatom ring system" refers to the terms heterocyclic, heterocyclyl, heteroaryl and heteroarylene.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O, or N, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, $SO_2$, O, or N, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to a benzene ring or to an optionally substituted benzene ring system fused to one or more optionally substituted benzene rings to form ring systems such as anthracene, phenanthrene and napthalene, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. Examples of aryl include, but are not limited to, phenyl, 2-naphthyl, 1-naphthyl, biphenyl, and the like.

As used herein, the term "arylene" refers to a benzene ring diradical or to a benzene ring system diradical fused to one or more optionally substituted benzene rings, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms at any position, where N-oxides and sulfur monoxides and sulfur dioxides are permissible heteroaromatic substitutions, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO$—, where $R_a$ is aliphatic.

As used herein, the term "alkylsulfanyl" refers to the group $R_aS$—, where $R_a$ is aliphatic.

As used herein, the term "alkylsulfenyl" refers to the group $R_aS(O)$—, where $R_a$ is aliphatic.

As used herein, the term "alkylsulfonyl" refers to the group $R_aSO_2$—, where $R_a$ is aliphatic.

As used herein, the term "acyl" refers to the group $R_aC(O)$—, where $R_a$ is aliphatic, cycloaliphatic, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is aliphatic.

As used herein, the term "acyloxy" refers to the group $R_aC(O)O$—, where $R_a$ is aliphatic, cycloaliphatic, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" is inclusive of circumstances in which described condition is present and circumstances in which the described condition is not present, for example, where the term is used with reference to a chemical substituent, it indicates the inclusion of embodiments in which the specified substituent is present as well as embodiments in which the specified substutient is not present.

As used herein, the term "substituted" indicates the presence of the named substituent or substituents, and includes multiple degrees of substitution.

As used herein, the terms "contain" or "containing" with reference to alkyl, alkenyl, alkynyl or cycloalkyl substituents indicates in-line substitution(s) with one or more substituents at any position along the alkyl, alkenyl, alkynyl or cycloalkyl substituents, such as one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of formula (E1)) and a solvent. Such solvents for the purpose of the invention may not interfere with the biological activity of the solute. Solvents may be, by way of example, water, ethanol, or acetic acid.

The compounds of the formula (E1) have the ability to crystallize in more than one form, a characteristic which is known as polymorphism, and such polymorphic forms ("polymorphs") are within the scope of the present invention. Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the terms "biohydrolyzable carbonate", "biohydrolyzable ureide" and "biohydrolyzable carbamate" include carbonates, ureides, and carbamates, respectively, of a compound of the general formula (E1) which carbonates, ureides, and carbamates, do not completely diminish the biological activity of the parent substance. Such carbonates, ureides, and carbamates may confer on the parent compound of the general formula (E1) advantageous properties in vivo, such as improved duration of action, onset of action, and the like. Also included are compounds which are relatively biologically inactive but which are converted in vivo by the subject to the biologically active principle. An advantage of such biohydrolyzable forms is that, for example, they facilitate improved oral administration because the carbonates, ureides, and carbamates are more readily absorbed from the gut and are then transformed to a compound of formula (E1)

in plasma. Many examples of such biohydrolyzable compounds are known in the art and include, by way of example, lower alkyl carbamates.

As used herein, the term "biohydrolyzable ester" is an ester of a compound of general formula which does not completely diminish the biological activity of the parent substance. Such esters may confer on the parent compound of the general formula (E1) advantageous properties in vivo, such as improved duration of action, onset of action, and the like. Also included are esters which are relatively biologically inactive but which are converted in vivo by the subject to the biologically active principle. An advantage of such biohydrolyzable forms is that, for example, they facilitate improved oral administration because they are more readily absorbed from the gut and are then transformed to a compound of formula (E1) in plasma. Many examples of such biohydrolyzable esters are known in the art and include, by way of example, lower alkyl esters, lower acyloxy-alkyl esters, lower alkoxyacyloxyalkyl esters, alkoxyacyloxy esters, alkyl acylamino alkyl esters and choline esters.

As used herein, the term "biohydrolyzable amide" is an amide of a compound of general formula which does not completely diminish the biological activity of the parent substance. Such amides may confer on the parent compound of the general formula (E1) advantageous properties in vivo, such as improved duration of action, onset of action, and the like. Also included are amides which are relatively biologically inactive but which are converted in vivo by the subject to the biologically active principle. An advantage of such biohydrolyzable forms is that, for example, they facilitate improved oral administration because they are more readily absorbed from the gut and are then transformed to a compound of formula (E1) in plasma. Many examples of such biohydrolyzable are known in the art and include, by way of example, lower alkyl amides, a-amino acid amides, alkoxyacyl amides and alkylaminoalkylcarbonyl amides.

As used herein, the term "prodrug" includes compounds which are hydrolyzable in vivo to yield an active compound of formula (E1), including for example, biohydrolyzable amides, biohydrolyzable esters and biohydrolyzable carbamates. The term "prodrug" also includes compounds in which the biohydrolyzable functionality is encompassed in the compound of formula (E1): for example, a lactam formed by a carboxylic group in $R_1$ and an amine in $R_2$, and compounds which may be oxidized or reduced biologically at a given functional group to yield drug substances of formula (E1). Examples of such functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" means a group attached to the compound of formula (E1) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An example of an affinity reagent according to b) would be biotin either directly attached to (E1) or linked with a spacer of one to 50 atoms selected from the group consisting of: C, H, O, N, S, or P in any combination. An Example of an affinity reagent according to a) above would be fluorescein, either directly attached to (E1) or linked with a spacer of one to 50 atoms selected from the group consisting of: C, H, O, N, S, or P in any combination.

The term "effective amount" means that amount of a drug or pharmaceutical agent that will elicit the biological or medical response of a tissue, system, animal or human that is being sought by a researcher or clinician. The term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

Whenever the terms "aliphatic" or "aryl" or either of their prefixes appear in a name of a substituent (e.g. arylalkoxyaryloxy) they include those characteristics given above for "aliphatic" and "aryl". Aliphatic or cycloalkyl substituents are term equivalents to those having one or more degrees of unsaturation. Designated numbers of carbon atoms (e.g. $C_{1-10}$) refer independently to the number of carbon atoms in an aliphatic or cyclic aliphatic moiety or to the aliphatic portion of a larger substituent in which the term "aliphatic" appears as a prefix (e.g. "al-").

As used herein, the term "disubstituted amine" or "disubstituted amino-" includes either one or two substitutions on that particular nitrogen atom.

As used herein, the term "oxo" refers to the substituent =O.

As used herein, the term "halogen" or "halo" shall include iodine, bromine, chlorine and fluorine.

As used herein, the term "mercapto" refers to the substituent —SH.

As used herein, the term "carboxy" refers to the substituent —COOH.

As used herein, the term "cyano" refers to the substituent —CN.

As used herein, the term "aminosulfonyl" refer to the substituent —SO$_2$NH$_2$

As used herein, the term "carbamoyl" refers to the substituent —C(O)NH$_2$.

As used herein, the term "sulfanyl" refers to the substituent —S—.

As used herein, the term "sulfenyl" refers to the substituent —S(O)—.

As used herein, the term "sulfonyl" refers to the substituent —S(O)$_2$—.

The compounds of formula (E1) can be prepared readily according to the following reaction General Synthesis Schemes (in which all variables are as defined before) and examples or modifications thereof using readily available starting materials, reagents and conventional synthesis procedures. In these reactions, it is also possible to make use of variants which are themselves known to those of ordinary skill in this art, but are not mentioned in greater detail.

General Synthesis Schemes for compounds of formulae E1, E2, E3 and E4
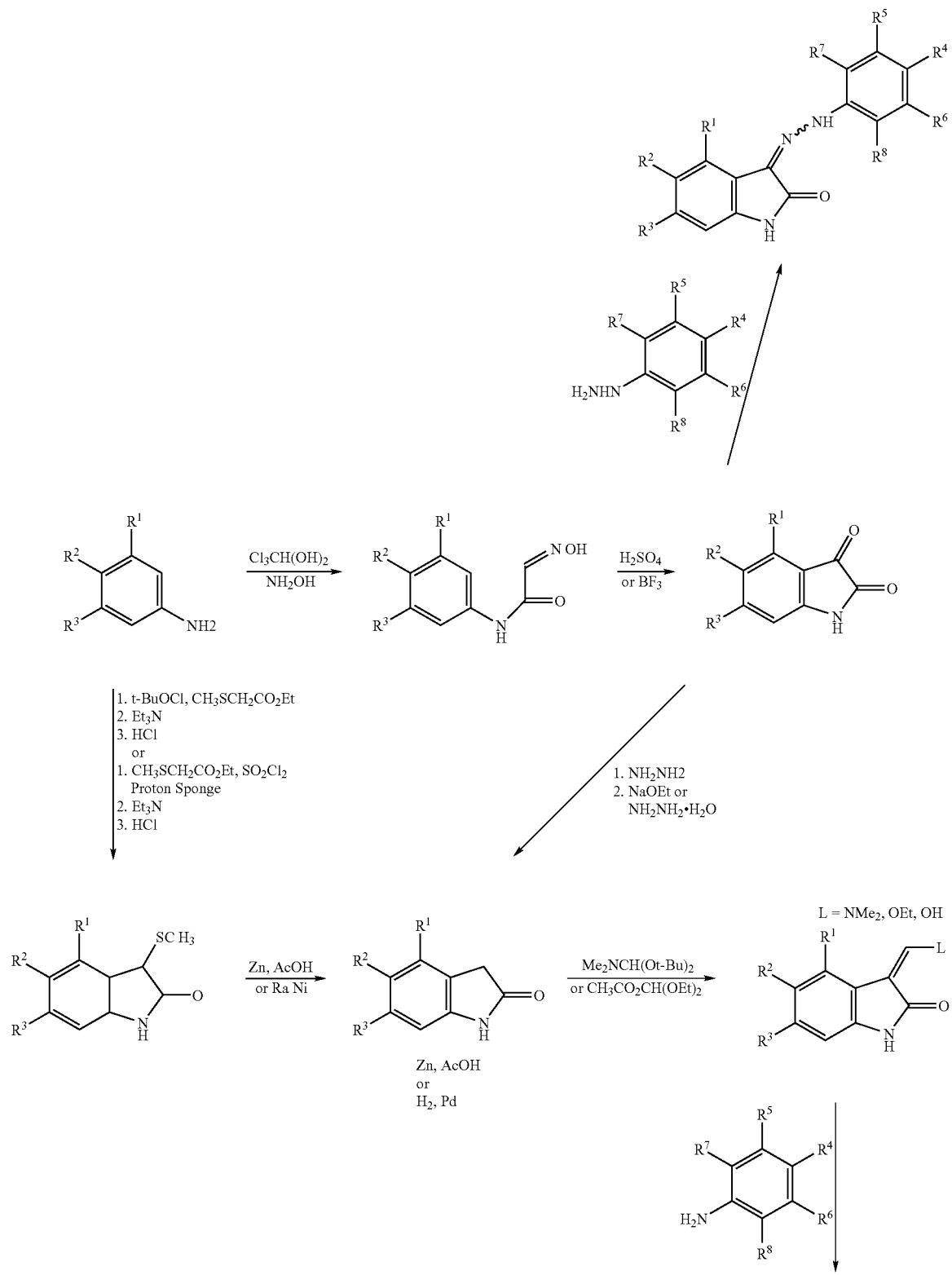

-continued

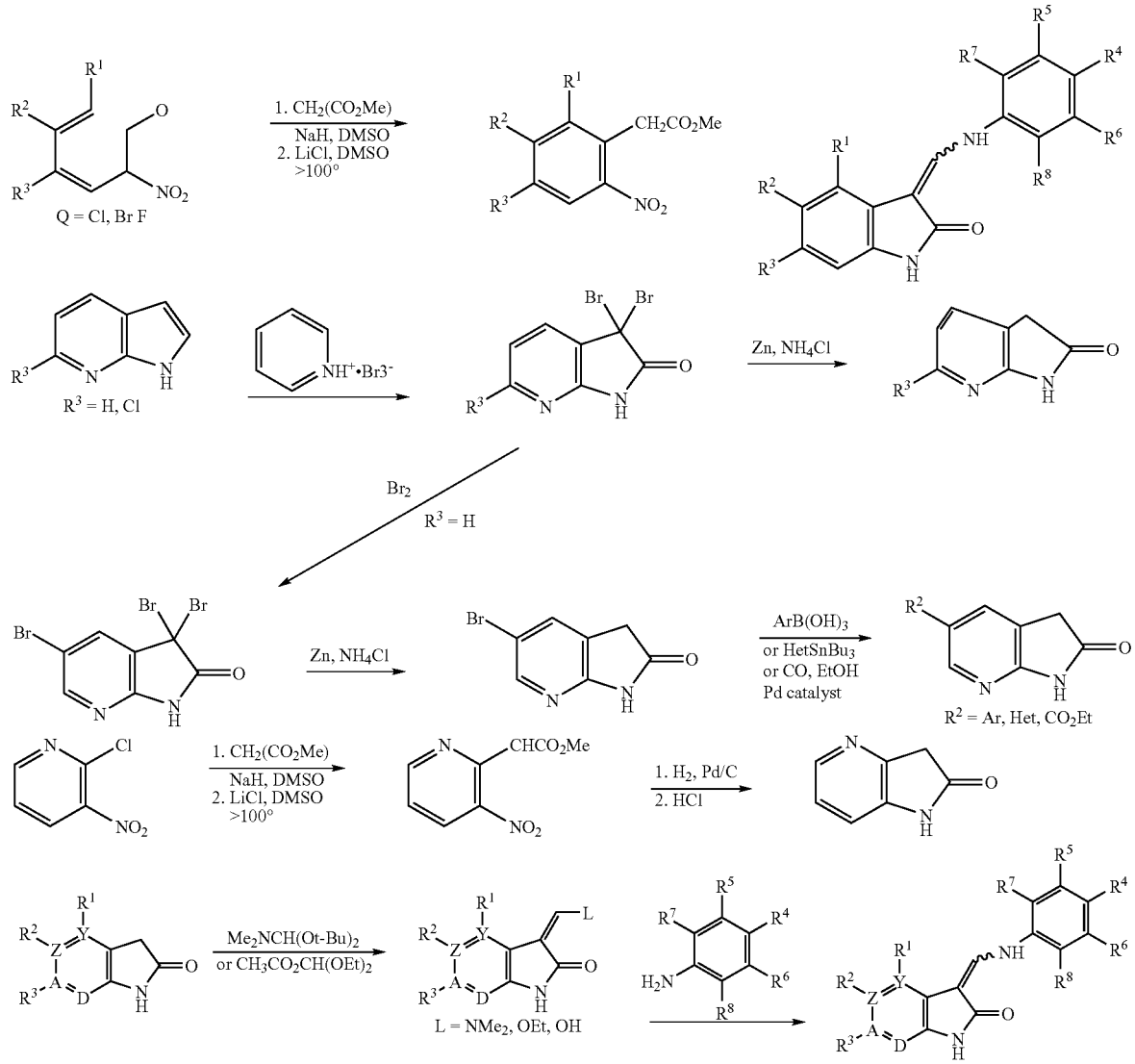

The following examples further illustrate details for the preparation of the compounds of formula (E1). Those skilled in the art will readily understand that known variations of the conditions and processes of the following preparative procedures can be used to prepare these compounds. All temperatures are degrees Celsius unless noted otherwise.

Abbreviations used in the Examples are as follows:
g=grams
mg=milligrams
L=liters
mL=milliliters
M=molar
N=normal
mM=millimolar
i.v.=intravenous
p.o.=per oral
S.C.=subcutaneous
Hz=hertz
mol=moles
mmol=millimoles
mbar=millibar
psi=pounds per square inch
rt=room temperature
min=minutes
h=hours
mp=melting point
TLC=thin layer chromatography
$R_f$=relative TLC mobility
MS=mass spectrometry
NMR=nuclear magnetic resonance spectroscopy
APCI=atmospheric pressure chemical ionization
ESI=electrospray ionization
m/z=mass to charge ratio
$t_r$=retention time
Pd/C=palladium on activated carbon
ether=diethyl ether
MeOH=methanol
EtOAc=ethyl acetate
TEA=triethylamine
DIEA=diisopropylethylamine
THF=tetrahydrofuran DMF=N,N-dimethylformamide
DMSO=dimethylsulfoxide
DDQ=2,3-dichloro-5,6-dicyano-1,4-benzoquinone
LAH=lithium aluminum hydride
TFA=trifluoroacetic acid
LDA=lithium diisopropylamide
THP=tetrahydropyranyl
NMM=N-methylmorpholine, 4-methylmorpholine
HMPA=hexamethylphosphoric triamide
DMPU=1,3-dimethypropylene urea
d=days
ppm=parts per million
kD=kiloDalton
LPS=lipopolysaccharide
PMA=phorbol myristate acetate
SPA=scintillation proximity assay
EDTA=ethylenediamine tetraacetic acid
FBS=fetal bovine serum
PBS=phosphate buffered saline solution
BrdU=bromodeoxyuridine
BSA=bovine serum albumin
FCS=fetal calf serum
DMEM=Dulbeccols modified Eaglels medium
pfu=plaque forming units
MOI=multiplicity of infection Reagents are commercially available or are prepared according to procedures in the literature. The physical data given for the compounds exemplified is consistent with the assigned structure of those compounds. $^1$H NMR spectra were obtained on VARIAN Unity Plus NMR spectrophotometers at 300 or 400 Mhz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterisation, and to follow the progess of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure.

Procedure A—First method for 1H-indol-2,3-dione (isatin) formation: preparation of 6-H-1-thia-3,6-diaza-as-indacen-7,8-dione.

To a 1-L flask was added a magnetic stir bar, 85 g of sodium sulfate, and 100 mL of water. The mixture was magnetically stirred until all the solids were dissolved. To the resultant aqueous solution was added a solution of 6-aminobenzothiazole (4.96 g, 33.0 mmol) in 50 mL of 1N aqueous hydrochloric acid and 10 mL of ethanol. The mixture was stirred, and chloral (6.0 g, (36 mmol) was added. To the resultant solution was added a solution of hydroxyl amine hydrochloride (7.50 g, 108 mmol) in 30 mL of water. The final mixture was heated with stirring to a gentle boil until all solids dissappeared, and heating was continued for an additional 15 min. The flask was removed from the heat, and the solution was poured onto 500 g of ice. The mixture was stirred as the product precipatated from solution. The precipatate was collected by suction filtration, washed thoroughly with water, filtered, and air dried to provide 6.9 g (94%) of N-benzothiazol-6-yl-2-hydroxy-imino-acetamide: $^1$H NMR (DMSO-d$_6$): δ 12.2 (s, 1H), 10.4 (s, 1H), 9.2 (s, 1H), 8.5 (s, 1H), 7.9 (d, 1H), 7.7 (m, 1H), 7.7 (s, 1H); APCI-MS m/z 220 (M−H)$^-$. To a 1-L 3-neck round bottom flask was placed a magnetic stir bar and 100 ml of concentrated sulfuric acid. The flask was fitted with a thermometer to monitor the temperature of the reaction. The sulfuric acid was heated to 100° C., and 10.0 g (45.2 mmol) of N-benzothiazol-6-yl-2-hydroxyimino-acetamide was added slowly. The solution was heated for ~1 hour, and the reaction mixture was poured into 750 g of ice and water. The residual reaction mixture in the reaction vessel was washed out with an additional 20 mL of cold water. The aqueous slurry was stirred for about 1 hour and filtered. The solid was washed thoroughly with water, filtered, and air dried to yield 4.3 g (46%) of 6-H-1-thia-3,6-diaza-as-indacen-7,8-dione: $^1$H NMR (DMSO-d$_6$): δ 11.1 (s, 1H), 9.2 (s, 1H), 8.2 (d, 1H), 7.0 (d, 1H); APCI-MS m/z 203 (M−H)$^-$.

Procedure B—First method for 1,3-dihydro-indol-2-one (oxindole) formation (Gassman and van Bergen, Journal of the American Chemical Society 1974, 96, 5508–12): preparation of 6.8-dihydro-1-thia-3,6-diaza-as-indacen-7-one.

A 2-L three-neck round bottom flask was fitted with an internal thermometer, 250-mL addition funnel, magnetic stir bar and septa. The flask was charged with nitrogen, 200 mL of dry THF, and 6-aminobenzothiazole (15.2 g, 0.100 mol). The mixture was stirred and cooled in a dry ice-acetone bath to an internal temperature of −74° C. A solution of tert-butyl hypoclorite (11.0 g, 0.103 mol) in 50 mL of dichloromethane was added over a 15 min period. The resultant solution was stirred for an additional 3 hours at dry ice-acetone bath temperature. To the reaction was then added by slow, dropwise addition a solution of ethyl methylthioacetate (13.8 g, 0.103 mol) in 50 mL of dichloromethane. The resultant solution was stirred for an additional 3 hours at dry ice-acetone bath temperature. A solution of triethyl amine (25.3 g, 0.250 mol) and 50 ml of dichloromethane was added at dry ice-acetone bath temperature, and the solution was stirred for 0.5 hours. The cooling bath was removed, and the reaction was allowed to warm to rt. The reaction was then concentrated to a thick residue. The thick oil was resuspended in 200 mL of ether and 600 mL of 0.25 M hydrochloric acid. The mixture was allowed to stir for 24 hours. The resulting solid was filtered from the mixture and triturated with water and ether. The solid was then resuspended in cold MeOH, filtered and dried under vacum for 16 hours to yield 18.7 g (79%) of 8-methylsulfanyl-6,8-dihydro-1-thia-3,6-diaza-as-indacen-7-one: $_1$H NMR (DMSO-d6) δ 10.8 (s, 1H), 9.2 (s, 1H), 8.0 (d, 1H), 7.1 (d, 1H), 1.8 (s, 3H); APCI-MS m/z 235 (M−H)$^-$. To a 500-mL erlenmeyer flask was added a stir bar, 8.1 g (0.034 moles) of 8-methylsulfanyl-6,8-dihydro-1-thio-3,6-diaza-as-indacen-7-one and 100 mL of glacial acetic acid. The mixture was stirred until all the starting material had dissolved. The reaction mixture was then diluted with 100 mL of THF. Zinc metal (16 g, 325 mesh) was then added. The heterogeneous mixture was then stirred and heated to 60° C. for 2.5 hours. The mixture was vacuum filtered through a one half inch pad of celite. The residue on the filter pad was washed with additional THF. The filtrates were combined and concentrated to a wet solid. The solid was triturated with MeOH, filtered and air dried to yield 4.51 g (70%) of 6.8-dihydro-1-thia-3,6-diaza-as-indacen-7-one as a free-flowing solid: $_1$H NMR (DMSO-d6): δ 10.5 (s, 1H), 9.1 (s, 1H), 7.9 (d, 1H), 7.0 (d, 1H), 3.6 (s, 2H); APCI-MS m/z 191 (M+H)$_+$.

Procedure C—Second method for 1,3-dihydro-indol-2-one (oxindole) formation (Seibert, Chemie Berichte 1947, 80, 494–502): preparation of 3-H-pyrrolo[3,2-f]quinoline-2-one via Wolff-Kishner reduction.

A solution of 2.3 g (12 mmol) of 3-H-pyrrolo[3,2-f]quinoline-1,2-dione (prepared from 6-aminoquinoline according to Procedure A) and 2.0 ml (0.06 mol) of hydrazine in 50 ml of DMF and 50 ml of ethanol was stirred at reflux for 2 hours. The resulting suspension was allowed to cool to ambient temperature and was then chilled in an ice bath and filtered. The solid was washed with a small volume of ethanol and allowed to air dry to give 1-hydrazono-1,3-dihydropyrrolo[3,2-f]quinolin-2-one as an orange solid (1.8 g, 73%): $^1$H NMR (DMSO-$d_6$): δ 7.37 (d, J=8.8 Hz, 1H), 7.47 (dd, J=8.4, 4.2 Hz, 1H), 7.81 (d, J=8.8 Hz, 1H), 8.71 (dd, J=4.2, 1.6 Hz, 1H), 8.80 (d, J=8.4 Hz, 1H), 9.90 (br d, J=14.7 Hz, 1H), 10.89 (br d, J=14.7 Hz, 1H), 10.95 (br s, 1H); ESI-MS m/z 213 (M+H)$^+$. A solution 1.8 g (8.5 mmol) of 1-hydrazono-1,3-dihydropyrrolo[3,2-f]quinolin-2-one in 50 ml of freshly prepared 0.5 M sodium ethoxide solution was stirred at reflux for 3 hours. The solution was diluted with 50 ml of water, neutralized with acetic acid, and concentrated on a rotary evaporator until cloudy. The solution was stored in a refrigerator overnight. The solid was filtered off, and the filtrate was extracted with three 80-ml portions of EtOAc. A solution of the solid in MeOH/EtOAc was combined with the extracts and passed through a short pad of silica gel, eluting with EtOAc. The solution was then concentrated to a small volume on a rotary evaporator, and the resulting suspension was diluted with an equal volume of ethanol, sonicated, and filtered to give 3-H-pyrrolo[3,2-f]quinoline-2-one as a light green solid (0.52 g, 33%); $^1$H NMR (DMSO-$d_6$): δ 3.80 (s, 2H), 7.35 (d, J=8.8 Hz, 1H), 7.44 (dd, J=8.4, 4.2 Hz, 1H), 7.88 (d, J=8.8 Hz, 1H), 8.08 (d, J=8.4 Hz, 1H), 8.70 (dd, J=4.2, 1.6 Hz, 1H), 10.57 (br s, 1H); APCI-MS m/z 183 (M−H)$^-$.

Procedure D—Third method for 1,3-dihydro-indol-2-one (oxindole) formation (Quallich and Morrissey, Synthesis, 1993, 51–53): preparation of 6-bromooxindole Sodium hydride (60% oil dispersion, 4.00 g, 100 mmol) was added to a dry 500 ml flask under nitrogen and washed with three 25 ml portions of hexanes. Anhydrous DMSO (100 ml) was added, followed by dimethyl malonate (11.4 ml, 100 mmol). The reaction was heated briefly to 100° C. with stirring, then cooled to room temperature. 2,5-Dibromonitrobenzene (12.9 g, 46.0 mmol) was added and the reaction was heated at 110° C. for 2 hrs. After cooling to room temperature, the solution was added in portions to 300 ml of saturated aqueous ammonium chloride with 150 ml of 1:1 hexanes/ethyl acetate. The organic layer was washed with 300 ml of saturated aqueous ammonium chloride, four 200 ml portions of water, and 200 ml of saturated aqueous sodium chloride. The organic layer was dried over magnesium sulfate and the solvent was evaporated to give 13.6 g of crude dimethyl 2-(4-bromo-2-nitrophenyl)malonate as a brown oil. This material (30–40 mmol) was heated to 110° C. in 250 ml DMSO with 3.6 g (84 mmol) of lithium chloride and 750 mg (42 mmol) of water for 4.5 hrs. The reaction was cooled to room temperature and added to 300 ml of ethyl acetate with 300 ml of saturated aqueous sodium chloride. The organic layer was washed with a second portion of 300 ml saturated aqueous sodium chloride, dried over magnesium sulfate, and the solvent was removed to give 11.1 g brown oil. This material was adsorbed on 40 g of silica gel and applied to a column containing another 80 g of silica gel. Elution with 0–10% ethyl acetate in hexanes gave 3.53 g (28% from 2,5-dibromonitrobenzene) of methyl (4-bromo-2-nitrophenyl) acetate as a yellow solid.

This material (3.53 g, 12.8 mmol) was dissolved in ethanol (80 ml) with 50 ml of 50% sulfuric acid and heated to reflux with stirring. Zinc powder (3.40 g, 52 mmol) was added in portions over 1 hr. Heating was continued for another 2 hrs and the reflux condenser was removed to allow ethanol to evaporate from the hot reaction under a stream of nitrogen. The reaction mixture was filtered through celite, washing with 100 ml of ethyl acetate. The water layer was separated from the filtrate and extracted with 100 ml of ethyl acetate. Combined ethyl acetate layers were washed with 30 ml of saturated aqueous sodium bicarbonate and 30 ml of saturated aqueous sodium chloride and dried over magnesium sulfate. Evaporation of solvent gave 1.6 g of crude product which was purified by chromatography on 25 g of silica gel with 10–40% ethyl acetate/hexanes to give 0.85 g (31%) of 6-bromooxindole as an off-white solid.

Procedure E—Method for dimethylaminomethinyloxindole formation: preparation of 8-dimethylamino-methylene-6,8-dihydro-1-thia-3,6-diaza-as-indacen-7-one.

To a suspension of 1.0 g (5.3 mmol) of 6,8-dihydro-1-thia-3,6-diaza-as-indacen-7-one (Procedure B) in 7.5 mL of DMF was added 1.38 g (6.80 mmol) of N,N-dimethylformamide-di-t-butyl acetal. The mixture was stirred at ambient temperature for 1 hours and diluted with 7.5 mL of Et$_2$O. The resulting precipitate was isolated filtration to afford 8-dimethylamino-methylene-6,8-dihydro-1-thia-3,6-diaza-as-indacen-7-one as a tan solid (1.0 g, 77%): $^1$H NMR (DMSO-$d_6$): δ 3.33 (bs, 3H), 3.59 (bs, 3H), 6.97 (d, J=8.4, 1H), 7.33 (s, 1H), 7.62 (d, J=8.4,1H), 9.13 (s, 1H), 10.29 (s, 1H); APCI-MS: m/z 246 (M+H)$^+$.

Procedure F—Method for ethoxymethinyloxindole formation: preparation of 8-ethoxymethylene-6,8-dihydro-1-thia-3,6-diaza-as-indacen-7-one.

To a 250-ml round bottom flask was added a stir bar, 6,8-dihydro-1-thia-3,6-diaza-as-indacen-7-one (Procedure B, 4.0 g, 0.021 mol), 40 mL of glacial acetic and diethoxymethyl acetate (17.0 g, 0.105 moles). The flask was fitted with a reflux condensor and charged with nitrogen. The reaction was heated to reflux for 8 hours. The flask was cooled, the stir bar was removed and the reaction was concentrated to a wet solid. The solid was triturated with a solution of ether and ethanol. The mixture was filtered, the solid was washed with an ethanol-ether solution, and the solid was dried under vacuum to yield 8-ethoxymethylene-6,8-dihydro-1-thia-3,6-diaza-as-indacen-7-one: $^1$H NMR (DMSO-$d_6$): δ 10.5 (s, 1H), 9.1 (s, 1H), 7.8 (d, 1H), 7.7 (s, 1H), 7.0 (d, 1H), 4.5 (q, 2H), 1.4 (t, 3H); APCI-MS m/z 245 (M−H)$^-$.

Procedure G—Method for vinylogous urea formation: preparation of N-methyl-N-(4-{(Z)-[(7-oxo-6,7-dihydro-8H-[1,3]thiazolo[5,4-e]indol-8-ylidene)methyl]amino}phenyl) acetamide (Example 58).

A mixture of 8-dimethylamino-methylene-6,8-dihydro-1-thia-3,6-diaza-as-indacen-7-one (Procedure E, 0.040 g, 0.163 mmol) or 8-ethoxymethylene-6,8-dihydro-1-thia-3,6-diaza-as-indacen-7-one (Procedure F, 0.163 mmol), 4-amino-N-methylacetanilide (0.040 g, 0.244 mmol) in absolute ethanol (5 ml) was heated with stirring at 90° C. for 16 h. The reaction was diluted with ethanol and diethyl ether and the product collected by filtration to yield 0.038 g (64%) of the title compound. $^1$H NMR (DMSO-$d_6$): δ 11.03 (d, 1H, J=12.3 Hz), 10.84 (s, 1H), 9.23 (s, 1H), 8.02 (d, 1H, J=12.3 Hz), 7.78 (d, 1H, J=8.4 Hz), 7.48 (d, 2H, J=8.2 Hz), 7.35 (d, 2H, J=8.2 Hz), 7.09 (d, 1H, J=8.4 Hz), 3.11 (s, 3H), 1.76 (s, 3H); ES-MS m/z 363 (M−H).

Procedure H—Method for condensation of a phenylhydrazine with an isatin to form hydrazones: preparation of 3,6-dihydro[1,2,3]triazolo[4,5-e]indole-7,8-dione 8-[N-(4-methoxyphenyl)hydrazone] (Example 89).

3,6-Dihydro[1,2,3]triazolo[4,5-e]indole-7,8-dione was prepared from 5-aminobenzotriazole according to Procedure A in 6% yield: $^1$H NMR (DMSO-$d_6$): δ 7.04 (d, J=8.4 Hz, 1H), 7.97 (d, J=2.2 Hz, 1H), 8.01 (dd, J=2.2,8.4 Hz, 1H), 8.20 (s, 1H), 9.26 (s, 1H), 11.19 (bs, 1H); APCI-MS m/z 215 (M+1)$^+$. 3,6-Dihydro[1,2,3]triazolo[4,5-e]indole-7,8-dione (47 mg, 0.25 mmol) was combined with 4-methoxyphenylhydrazine hydrochloride (52 mg, 0.3 mmol) in 2 ml of ethanol and heated at 70° C. for 3 hrs. The product was collected by filtration of the hot solution, washing with ethanol and diethyl ether, to give 39 mg (50%) of the title compound as a dark red solid. NMR showed ~1:1 Z/E mixture. $^1$H NMR (DMSO-$d_6$): δ 3.80 (s, 3H); 7.0 (m, 3H); 7.24 (d, J=8.7 Hz, 0.5H); 7.41 (d, J=8.8 Hz, 0.5H); 7.78 (m, 1.5H); 7.98 (d, J=8.5 Hz, 0.5H); 10.8 (s, 0.5H); 11.3 (s, 0.5H); 12.85 (s, 0.5H); 12.95 (s, 0.5H). APCI-MS m/z 307 (M−1)$^-$.

Procedure I—Method for palladium catalyzed coupling of 6-bromooxindole with alkenyl and aromatic tin reagents: preparation of 6-vinyl oxindole.

To a mixture of 6-bromooxindole (Procedure D, 0.50 g, 2.4 mmol), vinyltributylstannane (0.95 g, 3.0 mmol), lithium chloride (0.03 g, 7.1 mmol), 2,6-di-tert-butyl-4-methylphenol (0.01 g, 0.05 mmol) in acetonitrile (25 ml) stirring at 80° C. was added dichlorobis(triphenylphosphine)palladium (II). The resulting reaction was stirred with heating for 16 h. The reaction was poured into a vigorously stirring mixture of 5M potassium fluoride solution: ethyl acetate/1:1 (250 mL) and stirred for 0.75 h. The resulting biphasic mixture was filtered through a Celite 521 pad and the pad flushed with ethyl acetate (5×200mL). The combined organic phases were washed with water (200 mL), saturated sodium chloride (200 mL) and filtered through Whatman PS 1 paper and evaporated in vacuo to a golden yellow syrup. The syrup was titurated with diethyl ether to yield several crops of tan solid. Pure samples were combined, slurried with diethyl ether, filtered, and air dried to yield 0.12 g (31%) of 6-vinyloxindole: $^1$H NMR (DMSO-$d_6$): δ 10.36 (s, 1H), 7.13 (d, 1H, J=7.7 Hz), 6.98 (d, 1H, J=7.5 Hz), 6.66 (dd, 1H, J=10.9, 17.7 Hz), 5.70 (d, 1H, J=17.6 Hz), 5.18 (d, 1H, J=10.9 Hz), 3.42 (s, 2H).

EXAMPLE 1

6-Bromo-3-{(Z and E)-[4-(4-morpholinyl)anilino]methylidene}-1,3-dihydro-2H-indol-2-one Prepared from the dimethylaminomethylene derivative (Procedure E) of 6-bromo-oxindole (procedure D) and 4-(4-morpholino)aniline according to Procedure G in 87% yield to give ~4:1 isomer mixture. Principal isomer: $^1$H NMR (DMSO-$d_6$): δ 10.67 (d, 1H, J=12.5 Hz), 10.56(s, 1H), 8.57 (d, 1H, J=12.8 Hz), 7.48 (d, 1H, J=7.9 Hz), 7.35–7.29 (m, 2H), 7.11–7.04 (m, 3H), 6.93 (s, 1H), 3.76 (s, 4H), 3.15 (s, 4H); ES-MS m/z 400, 402 (M+1).

EXAMPLE 2

6-Bromo-3-{(Z and E)-[4-(4-pyridinylmethyl)anilino]methylidene}-1,3-dihydro-2H-indol-2-one Prepared according to Example 1 in 26% yield to give ~9:1 isomer mixture. Principal isomer: $^1$H NMR (DMSO-$d_6$): δ 10.72 (d, 1H, J=12.6 Hz), 10.65 (s, 1H), 8.66 (d, 1H, J=12.8 Hz), 8.48 (d, 1H, J=5.9 Hz), 7.55 (d, 1H, 8.1 Hz), 7.40–7.27 (m, 6H), 7.12 (dd, 1H, J=1.8,8.1 Hz), 6.99 (d, 1H, J=1.8 Hz), 3.97 (s, 2H); APCI-MS m/s 404, 406 (M−1).

EXAMPLE 3

8-[(Z and E)-4-Toluidinomethylidene]-6,8-dihydroimidazo[4,5-e]indol-7(3H)-one

Sodium hydride (7.2 g, 60% in mineral oil, 0.18 mol) was added in portions over 30 min to a stirred solution of 5-aminobenzimidazole (15.0 g, 0.105 mol) in dry DMF (100 mL) and the mixture was stirred at room temperature for 30 min. The reaction mixture was cooled to 0° C. and a solution of di-tert-butyl dicarbonate (24.0 g, 0.110 mol) in dry DMF (25 mL)was added over 10 min. The reaction mixture was stirred at room temperature for 18 hours. The solvent was evaporated under reduced pressure and the residue was partitioned between water (200 mL) and diethyl ether (200 mL). The organic phase was separated and the aqueous layer was extracted with diethyl ether. The combined organic extracts were washed with water and brine and dried over anhydrous magnesium sulfate. The drynig agent was removed by filtration through a pad of silica gel and the filtrate evaporated to give a mixture of 5- and 6-amino-1-tert-butoxycarbonylbenzimidazole, 21.5 g (84%). H$^1$ NMR (DMSO-$d_6$): δ 8.40 (s, 1H), 8.23 (s, 1H), 7.55 (d, 1H, J=8.8 Hz), 7.34 (d, 1H, J=8.4 Hz), 7.13 (d, $^1$H, J=1.6 Hz), 6.83 (d, 1H, J=2 Hz), 6.68 (dd, 1H, J=8.8, 1.6 Hz), 6.60 (dd, 1H, J=8.4, 2 Hz), 1.61 (s, 9H), 1.60 (s, 9H).

To a cold (−78° C.) solution of ethyl methylthioacetate (11.87 g, 88 mmol) in dry dichloromethane (300 mL) was added, dropwise, sulfuryl chloride (7.1 mL, 11.93 g, 88 mmol) over 5 min. The solution was stirred for 30 min and then a solution of a mixture of 5- and 6-amino-1-tert-butoxycarbonylbenzimidazole (21.5 g, 88 mmol) and Proton Sponge (18.9 g, 88 mmol) in dry dichloromethane (150 mL) was added dropwise over 30 min. The mixture was stirred at ≈8° C. for about 1 h and then triethylamine (12.3 mL, 8.94 g, 88 mmol) was added dropwise and the mixture was allowed to warm to room temperature over 18 hours. The reaction mixture was washed with water (3×100 mL) and brine and then the organic phase was dried over anhydrous magnesium sulfate. The drying agent was removed by filtration through a pad of silica gel and the filtrate evaporated. The residue was triturated with a small amount of diethyl ether and the resulting solid was collected by filtration. The filtrate was stirred with 2N aqueous HCl (10 mL) for 18 hours to yield further white solid which was collected by filtration. The combined white solids were dried under vacuum to give a mixture of 1 and 3-teff-butoxycarbonyl-8-methylthio-7-oxo-7,8-dihydropyrrolo[2,3-g]benzimidazole, 8.74 g (30%). H$^1$ NMR (DMSO-$d_6$): δ 10.882 (s, 1H), 10.72 (s, 1H), 9.41 (s, 1H), 8.52 (s, 1H), 7.45 (d, 1H, J=8.4 Hz), 7.65 (d, 1H, J=8.4 Hz), 7.11 (d, 1H, J=8.4 Hz), 7.93 (d, 1H, J=8.4 Hz), 4.84 9s, 1H), 4.67 (s, 1H), 1.93 (s, 3H), 1.81 (s, 3H), 1.66 (s, 9H).

A solution of a mixture of 1 and 3-tert-butoxycarbonyl-8 methylthio-7-oxo-7,8-dihydropyrrolo[2,3-g]benzimidazole (2.0 g, 6 mmol) in THF (50 mL) was stirred at room temperature and a saturated aqueous solution of ammonium chloride (50 mL) was added. Activated zinc dust (8.0 g) was added and the resulting mixture was stirred vigorously for about 18 hours. The solids were removed by filtration through a pad of Celite and the organic layer was separated. The organic phase was dried over anhydrous magnesium sulfate, filtered and the solvent evaporated under reduced pressure to leave a yellow solid. Trituration with a small amount of solid gave a pale solid which was collected by filtration and dried under vacuum to give a mixture of 1 and 3-tert-butoxycarbonyl-7-oxo-7,8-dihydropyrrolo[2,3-g]benzimidazole, 1.32 g (77%). H$^1$ NMR (DMSO-$d_6$): δ 10.51 (br s, 1H), 10.21 (br s, 1H), 8.46 (s, 1h), 8.02 (s, 1H), 7.67 (m, 1H), 7.55 (d, 1H), 6.87 (d, 1H), 6.70 (m, 1H), 3.84 (s, 2H), 1.62 (s, 9H).

Dimethylformamide di-tert-butyl acetal (0.34 mL, 0.29 g, 1.4 mmol) was added dropwise to a stirred solution of a mixture of 1 and 3-tert-butoxycarbonyl-7-oxo-7,8-dihydropyrrolo[2,3-g]benzimidazole (0.2 g, 0.7 mmol) in dry DMF (2 mL) and the mixture was stirred at room temperature for about 6 hours. The solvent was evaporated under reduced pressure. The residue was dissolved in chloroform:methanol (10:1, 10 mL) and passed through a pad of silica gel. The filtrate was evaporated to give a mixture of 1 and 3-tert-butoxycarbonyl-8-(dimethylaminomethylidinyl)-7-oxo-7H-pyrrolo[2,3-g]benzimidazole as a brown solid, 0.042 g (17%). $^1$H NMR (DMSO-d$_6$): δ 10.10 (s, 1H), 8.40 (s, 1H), 7.40 (s, 1H), 7.22 (d, 1H, J=8.4 Hz), 6.82 (d, 1H, J=8.4 Hz), 1.64 (s, 9H).

A solution of a mixture of 1 and 3-tert-butoxycarbonyl-8-(dimethylaminomethylidinyl)-7-oxo-7H-pyrrolo[2,3-g] benzimidazole (0.02g, 0.061 mmol) and p-toluidine (0.01 g, 0.089 mmol) in acetic acid (1 mL) was heated at 120° C. for 3 hours. The solvent was evaporated under vacuum and the residue was purified using silica gel chromatography with chloroform:methanol (10:1) as eluent to afford the title compound as a mixture of E/Z isomers, 0.012 g (68%). $^1$H NMR of principal isomer (DMSO-d$_6$): δ 12.57 (s, 1H), 12.38 (d, 1H, J=12.8 Hz), 10.01 (s, 1H), 8.33 (s, 1H), 7.95 (d, 1H, J=12.8 Hz), 7.24 (m, 5H), 6.80 (d, 1H, J=8 Hz), 2.28 (s, 3H). MS (AP$^-$) 289 (100) (M$^+$–H).

EXAMPLE 4

8-[(Z and E)-(3-Methyl-4-nitroanilino)methylidene]-3,6-dihydro[1,2,3]triazolo[4,5-e]indol-7-one Prepared as a 1:1 mixture of Z and E isomers in 95% yield from 8-dimethylaminomethylene-1-tert-butyloxycarbonyl-1,6-dihydro[1,2,3]triazolo[4,5-e]indol-7-one and 3-methyl-4-nitroaniline according to the procedure of Example 5. $^1$H NMR (DMSO-d$_6$): δ 2.65 (s, 6H); 7.07 (d, J=8.5 Hz, 0.5H); 7.18 (d, J=8.5 Hz, 0.5H); 7.44 (dd, J=9.0 Hz and 1.5 Hz, 0.5H); 7.53 (m, 1H); 7.6 (m, 1H); 7.78 (brd d, J=8.2 Hz, 0.5H); 8.17 (d, J=9.0 Hz, 0.5H); 8.19 (d, J=9.5 Hz, 0.5H); 8.29 (brd d, J=12.6 Hz, 0.5H); 8.70 (d, J=12.1 Hz, 0.5H); 10.49 (s, 0.5H); 11.0 (s, 0.5H); 11.16 (d, J=12 Hz, 0.5H); 11.8 (brd d, J~8 Hz, 0.5H). APCI-MS: m/z 335 (M–H)$^-$.

EXAMPLE 5

8-{(E/Z)-[4-nitro-3-(trifluoromethyl)anilino]methylidene}-1,6-dihydro[1,2,3]triazolo[4,5-e]indol-7-one 5-Aminobenzotriazole (Lancaster Chemical, 10.14 g, 75 mmol) was dissolved in 200 ml of anhydrous DMF under nitrogen and 3.00 g (75 mmol) of sodium hydride (60% oil dispersion) was added in one portion. Hydrogen evolution and mild exothermicity was observed. The reaction was stirred at room temperature for 20 minutes and then cooled in an ice bath. A solution of di-tert-butyidicarbonate (16.4 g, 75 mmol) in 100 ml of anhydrous DMF was added via siphon. Stirring was continued for 2 hrs at ice bath temperature. The solvent was removed by rotary evaporation under high vacuum at 50° C. to give 32 g of viscous liquid. The crude product was dissolved in a minimum volume of chloroform and filtered through a short column of 600 ml silica gel, eluting with 10% methanol in chloroform. The collected product was evaporated to dryness, redissolved in 400 ml of diethyl ether, and washed three times with water and once with saturated sodium chloride solution. The ether solution was dried over magnesium sulfate and the solvent was removed to give 17.7 g of a mixture of 1- and 3-tert-butyloxycarbonyl-5-aminobenzotriazole contaminated with approx. 1 g of residual mineral oil. This material was then cyclized to the corresponding 3-methylthio-oxindole by the method of Procedure (Gassman). The resultant product (9.6 g of gray solid) was shown to be partially deprotected by NMR. This material was dissolved 200 ml of THF and treated with 50 g of zinc dust (activated by stirring for 10 min in 150 ml of 1 M HCl, followed by washing with three 100 ml portions of water). Saturated aqueous ammonium chloride (150 ml) was added and the reaction was stirred overnight at room temperature. The solution was filtered through Celite, washing with THF and ethyl acetate to give 4.0 g of gray solid which was primarily 1-tert-butyloxycarbonyl-1,6-dihydro[1,2,3]triazolo[4,5-e]indol-7-one. This material (2.04 g, 7.4 mmol) was suspended in 10 ml of anhydrous DMF under nitrogen, cooled in an ice bath, and treated with 4.0 ml (3.4 g, 2.2 equiv) of dimethylformamide di-tert-butyl acetal. The reaction was allowed to warm to room temperature and was stirred overnight. The solvent was removed by rotary evaporation under high vacuum. The residue was filtered through a short column of 100 ml silica gel with 30% ethanol in dichloromethane. Evaporation of solvent provided 1.74 g of yellow solid which was primarily 8-dimethylaminomethylene-1-tert-butyloxycarbonyl-1,6-dihydro[1,2,3]triazolo[4,5-e]indol-7-one containing some product lacking the tert-butyloxycarbonyl protecting group.

The dimethylamino-oxindole derivative from above (33 mg, ~0.1 mmol) was combined in a reaction vial with 4-nitro-3-trifluoromethylaniline (25 mg, 0.12 mmol) in 1–2 ml of glacial acetic acid and stirred overnight in an oil bath at 110° C. The residue was triturated with 2 ml of ethanol, heating briefly to reflux. After cooling to room temperature, 2–3 ml of diethyl ether was added and the resulting precipitate was collected by filtration to give 7.8 mg (20%) of the title compound as a brown solid that was shown by NMR to be ~1:1 mixture of E/Z isomers. $^1$H NMR (DMSO-d$_6$): δ 7.07 (d, J=9 Hz, 0.5H); 7.20 (d, J=8 Hz, 0.5H); 7.63 (d, J=8 Hz, 0.5H); 7.8–8.0 (m, 2H); 8.13 (s, 0.5H); 8.25–8.42 (m, 1.5H); 8.67 (d, J=11 Hz, 0.5H); 10.53 (s, 0.5H); 11.0 (s, 0.5H); 11.24 (d, J=11 Hz); 12.0 (brd d, J~9 Hz, 0.5H). APCI-MS: m/z 389 (M–H)$^-$.

EXAMPLE 6

8-[(Z and E)-(3-Chloro-4-nitroanilino)methylidene]-1,6-dihydro[1,2,3]triazolo[4,5-e]indol-7-one Prepared as a ~1:1 mixture of Z and E isomers in 70% yield from 8-dimethylaminomethylene-1-tert-butyloxycarbonyl-1,6-dihydro[1,2,3]triazolo[4,5-e]indol-7-one and 3-chloro-4-nitroaniline according to the procedure of Example 5. $^1$H NMR (DMSO-d$_6$): δ 7.06 (d, J=8.8 Hz, 0.5H); 7.20 (d, J=8.5 Hz, 0.5H); 7.3–7.66 (m, 1.5H); 7.80 (brd m, 0.5H); 7.85 (d, J=2.5 Hz, 0.5H); 7.91 (d, J=2.5 Hz, 0.5H); 8.23 (d, J=9.1 Hz, 1H); 8.32 (brd m, 0.5H); 8.63 (d, J=11.7 Hz, 0.5H); 10.5 (s 0.5H); 11.0 (s, 0.5H); 11.1 (d, J=11.7 Hz, 0.5H); 11.8 (brd, 0.5H). APCI-MS: m/z 355 (M–H)$^-$.

EXAMPLE 7

8-[(Z and E)-(3,5-Dimethyl-4-nitroanilino)methylidene]-1,6-dihydro[1,2,3]triazolo[4,5-e]indol-7-one Prepared as a ~1:1 mixture of Z and E isomers in 74% yield from 8-dimethylaminomethylene-1-tert-butyloxycarbonyl-1,6-dihydro[1,2,3]triazolo[4,5-e]indol-7-one and 3,5-dimethyl-4-nitroaniline according to the procedure of Example 5. $^1$H NMR (DMSO-d$_6$): δ 2.36 (s, 6H); 7.07 (d, J=8.5 Hz, 0.5H); 7.17 (d, J=8.5 Hz, 0.5H); 7.37 (s, 2H); 7.57 (d, J=8.5 Hz, 0.5H); 7.76 (brd d, J=8.5 Hz, 0.5H); 8.24 (brd d, J=12 Hz, 0.5H); 8.69 (brd d, J=12 Hz, 0.5H); 10.44 (s, 0.5H); 10.97 (s, 0.5H); 11.07 (brd d, J=12 Hz, 0.5H); 11.6 (brd d, J=12 Hz, 0.5H). APCI-MS: m/z 349 (M–H)⁻.

EXAMPLE 8

8-((Z and E)-{4-[2,2,2-Trifluoro-1-hydroxy-1-(trifluoromethyl)ethyl]anilino}methylidene)-1,6-dihydro[1,2,3]triazolo[4,5-e]indol-7-one The title compound was prepared as a ~1:1 mixture of Z and E isomers in 54% yield from 8-dimethylaminomethylene-1-tert-butyloxycarbonyl-1,6-dihydro[1,2,3]triazolo[4,5-e]indol-7-one and 4-[2,2,2-trifluoro-1-hydroxy-1-(trifluoromethyl)ethyl]aniline according to the procedure of Example 5. $^1$H NMR (DMSO-$d_6$): δ 7.07 (d, J=8.7 Hz, 0.5H); 7.17 (d, J=8.7 Hz, 0.5H); 7.56 (d, J=8.7 Hz, 0.5H); 7.6 and 7.75 (2 overlapping Abq, 4H); 8.22 (d, J=13 Hz, 0.5H); 8.75 (m, 1H); 10.4 (s, 0.5H); 10.9 (s, 0.5H); 11.08 (d, J=13 Hz, 0.5H); 11.7 (brd d, J=13 Hz, 0.5H). APCI-MS: m/z 442 (M–H)⁻.

EXAMPLE 9

8-{(Z and E)-[4-(2-Hydroxyethyl)anilino]methylidene}-1,6-dihydro[1,2,3]triazolo[4,5-e]indol-7-one The acetate ester of the title compound was obtained as a ~1:1 mixture of Z and E isomers in 71% yield (26 mg) from 8-dimethylaminomethylene-1-tert-butyloxycarbonyl-1,6-dihydro[1,2,3]triazolo[4,5-e]indol-7-one (25 mg) and 4-(2-hydroxyethyl)aniline (17 mg) in acetic acid according to the procedure of Example 5. The product was stirred in 4 ml methanol with 0.2 ml of 2M NaOH overnight at room temperature. The reaction solution was acidified with 0.2 ml of 2M sulfuric acid, and ethanol and diethyl ether were added. The resulting precipitate was collected by filtration and stirred in 3 ml of water for several hours to dissolve Na$_2$SO$_4$, then filtered and dried to give the title compound (16 mg dark green solid, 70%). $^1$H NMR (DMSO-$d_6$): δ 2.69 (t, J~6 Hz, 2H); 3.58 (m, 2H); 4.62 (m, 1H); 7.01 (d, J=8.5 Hz, 0.5H); 7.12 (d, J=8.5 Hz, 0.5H); 7.26 and 7.32 (overlapping Abq, 4H); 7.46 (d, J=8.5 Hz, 0.5H); 7.64 (brd, 0.5H); 8.13 (d, J=13 Hz, 0.5H); 10.3 (s, 0.5H); 10.8 (s, 0.5H); 11.0 (d, J=13 Hz, 0.5H); 11.45 (brd, 0.5H). APCI-MS: m/z 320 (M–H)⁻.

EXAMPLE 10

8-{(Z)-[4-(Methylsulfanyl)anilino]methylidene}-6H-[1,3]thiazolo[5,4-e]indol-7-one This compound was prepared with 4-methylthioaniline according to Procedure G on a 0.5 mmol scale. The yield was 0.089 grams (53%) for C$_{17}$H$_{13}$N$_3$O$_1$S$_2$. $^1$H NMR (400 MHz, DMSO-$d_6$) δ: 10.9 (d, 1H), 10.78 (s, 1H), 9.21 (s, 1H), 7.9 (d, 1H), 7.7 (d, 1H), 7.25 (d, 2H), 7.1 (d, 1H), 6.8 (d, 2H), 2.4 (s, 3H). ESI-MS m/z 338 (M–1).

EXAMPLE 11

8-[(Z)-(3,5-Dimethoxyanilino)methylidene]-6H-[1,3]thiazolo[5,4-e]indol-7-one

This compound was prepared 3,5-dimethoxyaniline according to Procedure G on a 0.5 mmol scale. The yield was 0.076 grams (43%) for C$_{18}$H$_{15}$N$_3$O$_3$S$_1$. $^1$H NMR (400 MHz, DMSO-$d_6$) δ: 10.9 (d, 1H), 10.83 (s, 1H), 9.21 (s, 1H), 7.98 (d, 1H), 7.77 (d, 1H), 7.08 (d, 1H), 6.59 (s, 2H), 6.25 (s, 1H), 3.77 (s, 6H). ESI-MS m/z 352 (M–1).

EXAMPLE 12

8-[(Z)-(4-Hydroxyanilino)methylidene]H-[1,3]thiazolo[5,4-e]indol-7-one

This compound was prepared with 4-hydroxyaniline according to Procedure G on a 0.5 mmol scale. The yield was 0.081 grams (53%) for C$_{16}$H$_{11}$N$_3$O$_2$S$_1$. $^1$H NMR (400 MHz, DMSO-$d_6$) δ: 10.95 (d, 1H), 10.75 (s, 1H), 9.42 (s, 1H), 9.2 (s, 1H), 7.91 (d, 1H), 7.72 (d, 1H), 7.23 (d, 2H), 7.07 (d, 1H), 6.79 (d, 2H). ESI-MS m/z 308 (M–1).

EXAMPLE 13

1-[(Z)-(3-Methoxyanilino)methylidene]-1,3-dihydro-2H-pyrrolo[3,2-f]quinolin-2-one Prepared from the dimethylaminomethylene derivative (Procedure E) of 1,3-dihydro-2H-pyrrolo[3,2-f]quinolin-2-one (Procedure C) with 3-methoxyaniline according to Procedure G to give the title compound in 63% yield. $^1$H NMR (DMSO-$d_6$) δ: 3.80 (s, 3H); 6.68 (dd, J=1.8, 8.2 Hz, 1H); 7.06 (brd d, J=8.0 Hz, 1H); 7.11 (brd s, 1H); 7.29 (t, J=8.1 Hz, 1H); 7.40 (d, J=8.8 Hz, 1H); 7.46 (dd, J=8.5,4.1 Hz, 1H); 7.71 (d, J=8.8 Hz, 1H); 8.70 (d, J=4.1 Hz, 1H); 8.8 (2 overlapping d, J=8.5, 12 Hz, 2H); 10.94 (s, 1H); 11.74 (d, J=12 Hz, 1H). ES-MS: m/z 316 (M–H)⁻.

EXAMPLE 14

3-{[(Z)-(2-Oxo-2,3-dihydro-1H-pyrrolo[3,2-f]quinolin-1-ylidene)methyl]amino}benzonitrile Prepared from the dimethylaminomethylene derivative (Procedure E) of 1,3-dihydro-2H-pyrrolo[3,2-f]quinolin-2-one (Procedure C) with 3-aminobenzonitrile according to Procedure G in acetic acid to give the title compound in 78% yield as the acetate salt. $^1$H NMR (DMSO-$d_6$) δ: 1.88 (s, 3H); 7.39 (d, J=8.5 Hz, 1H); 7.45–7.6 (m, 3H); 7.78 (m, 2H); 8.20 (s, 1H); 8.75 (d, J=4 Hz, 1H); 8.8–8.9 (m, 2H); 11.0 (s, 1H); 11.8 (d, J=12 Hz, 1H); 11.95 (s, 1H). ES-MS: m/z 313 (M+H)⁺.

EXAMPLE 15

1-[(Z)-4-Toluidinomethylidene]-1,3-dihydro-2H-pyrrolo[3,2-f]quinolin-2-one

Prepared from the dimethylaminomethylene derivative (Procedure E) of 1,3-dihydro-2H-pyrrolo[3,2-f]quinolin-2-one (Procedure C) with p-toluidine according to Procedure G to give the title compound in 98% yield. $^1$H NMR (DMSO-$d_6$) δ: 2.25 (s, 3H); 7.2 (m, 2H); 7.35–7.5 (m, 4H); 7.70 (d, J=8.5 Hz, 1H); 8.70 (d, J=4.0 Hz, 1H); 7.8 (m, 2H); 10.9 (s, 1H); 11.8 (d, J=12 Hz, 1H). ES-MS: m/z 302 (M+H)⁺.

EXAMPLE 16

1-[(Z)-(4-Methoxyanilino)methylidene]-1,3-dihydro-2H-pyrrolo[3,2-f]quinolin-2-one Prepared from the dimethylaminomethylene derivative (Procedure E) of 1,3-dihydro-2H-pyrrolo[3,2-f]quinolin-2-one (Procedure C) with 4-methoxyaniline according to Procedure G in acetic acid to give the title compound in 54% yield as the acetate salt. $^1$H NMR (DMSO-d$_6$) δ: 1.88 (s, 3H); 3.75 (s, 3H); 6.97 (d, J=8.9 Hz, 2H); 7.39 (d, J=8.7 Hz, 1H); 7.43–7.5 (m, 3H); 7.68 (d, J=8.5 Hz, 1H); 8.70 (d, J=4.0 Hz, 1H); 8.75–8.82 (m, 2H); 10.9 (s, 1H); 11.75 (d, J=12 Hz, 1H); 11.9 (s, 1H). ES-MS: m/z 318 (M+H)$^+$.

EXAMPLE 17

3-({[(Z and E)-7-Oxo-6,7-dihydro[1,2,3]triazolo[4,5-e]indol-8(1H)-ylidene]methyl}amino)benzonitrile Prepared as a ~3:2 mixture of geometrical isomers in 88% yield from 8-dimethylaminomethylene-1-tert-butyloxycarbonyl-1,6-dihydro[1,2,3]triazolo[4,5-e]indol-7-one and 3-aminobenzonitrile according to the procedure of Example 5. $^1$H NMR (DMSO-d$_6$): δ 6.88 and 7.02 (2 d, 3:2 ratio, J=8.7 Hz, 1H); 7.45–7.6 (m, ~2.6H); 7.65–7.8 (m, ~1.4H); 7.90 and 7.95 (2 s, 1H); 8.15 and 8.83 (2 s, 1H); 10.2 and 10.85 (2 s, 1H). ES-MS: m/z 303 (M+H)$^+$.

EXAMPLE 18

8-[(Z and E)-4-Toluidinomethylidene]-1,6-dihydro[1,2,3]triazolo[4,5-e]indol-7-one Prepared as a ~1:1 mixture Z and E isomers in 78% yield from 8-dimethylaminomethylene-1-tert-butyloxycarbonyl-1,6-dihydro[1,2,3]triazolo[4,5-e]indol-7-one and p-toluidine according to the procedure of Example 5. $^1$H NMR (DMSO-d$_6$): δ 2.28 (s, 3H); 7.01 and 7.11 (2 d, 1:1 ratio, J=8.4 Hz, 1H); 7.22 and 7.32 (2 overlapping ABq, 4H); 7.45 and 7.64 (2 d, 1.1 ratio, J=8.4 Hz, 1H); 8.11 and 8.68 (2 d, 1:1 ratio, J=13 Hz, 1H); 10.3 and 10.8 (2 s, 1:1 ratio, 1H); 11.0 and 11.45 (2 d, 1:1 ratio, J=13 Hz, 1H). ES-MS: m/z 292 (M+H)$^+$.

EXAMPLE 19

8-[(Z and E)-(4-Methoxyanilino)methylidene]-1,6-dihydro[1,2,3]triazolo[4,5-e]indol-7-one Prepared as a ~1:1 mixture Z and E isomers in 88% yield from 8-dimethylaminomethylene-1-tert-butyloxycarbonyl-1,6-dihydro[1,2,3]triazolo[4,5-e]indol-7-one and 4-methoxyaniline according to the procedure of Example 5. $^1$H NMR (DMSO-d$_6$): δ 3.78 (s, 3H); 6.95–7.1 (m, 3H); 7.3–7.45 (m, 2.5H); 7.60 (d, J=8.5 Hz, 0.5H); 8.05 and 8.65 (2 d, J=12 Hz, 1H), 10.2 and 10.75 (2 s, 1H); 10.95 and 11.55 (2 brd d, J=12 Hz, 1H). ES-MS: m/z 308 (M+H)$^+$.

EXAMPLE 20

8-{(Z)-[4-(4-Morpholinyl)anilino]methylidene}-6H-[1,3]thiazolo[5,4-e]indol-7-one Prepared according to Procedure G with 4-(4-morpholino)aniline in 78% yield. $^1$H NMR (DMSO-d$_6$): δ 10.96 (d, 1H, J=12.6 Hz), 10.76 (s, 1H), 9.20 (s, 1H), 7.95 (d, 1H, J=12.5 Hz), 7.74 (d, 1H, J=8.4 Hz), 7.31 (d, 2H, J=8.8 Hz), 7.08 (d, 1H, J=8.4 Hz), 6.99 (d, 2H, J=9.0 Hz), 3.72 (t, 4H, J=4.7 Hz), 3.07 (t, 4H, J=4.8 Hz); ES-MS m/z 379 (M+H).

EXAMPLE 21

N-(4-{[(Z)-(7-Oxo-6,7-dihydro-8H-[1,3]thiazolo[5,4-e]indol-8-ylidene)methyl]amino}phenyl)acetamide Prepared according to Procedure G with N-(4-aminophenyl)acetamide in 87% yield. $^1$H NMR (DMSO-d$_6$): δ 11.01 (d, 1H, J=12.5 Hz), 10.80 (s, 1H), 9.95 (s, 1H), 9.22 (s, 1H), 7.99 (d, 1H, J=12.5 Hz), 7.75 (d, 1H, J=8.4 Hz), 7.60 (d, 2H, J=8.8 Hz), 7.35 (d, 2H, J=8.8 Hz), 7.09 (d, 1H, J=8.4 Hz), 2.01 (s, 3H).

EXAMPLE 22

8-{(Z)-[4-(2-Hydroxyethyl)anilino]methylidene}-6H-[1,3]thiazolo[5,4-e]indol-7-one Prepared according to Procedure G with 4-(2-hydroxyethyl)aniline in 41% yield. $^1$H NMR (DMSO-d$_6$): δ 10.98 (d, 1H, J=12.5 Hz), 10.81 (s, 1H), 9.22 (s, 1H), 8.00 (d, 1H, J=112.5 Hz), 7.76 (d, 1H, J=8.4 Hz), 7.31 (d, 2H, J=8.4 Hz), 7.24 (d, 2H, J=8.4 Hz), 7.09 (d, 1H, J=8.4 Hz), 4.62 (t, 1H, J=5.1 Hz), 3.59–3.54 (m, 2H), 2.69 (t, 2H, J=7.0 Hz); ES-MS m/z 338 (M+H).

EXAMPLE 23

8-{(Z)-[4-(4-Pyridinylmethyl)anilino]methylidene}-6H-[1,3]thiazolo[5,4-e]indol-7-one Prepared according to Procedure G with 4-(4-pyridylmethyl)aniline in 66% yield. $^1$H NMR (DMSO-d$_6$): δ 10.99 (d, 1H, J=12.5 Hz), 10.84 (s, 1H), 9.23 (s, 1H), 8.74 (d, 2H, J=6.4 Hz), 8.00 (d, 1H, J=12.3 Hz), 7.82 (d, 2H, J=6.2 Hz), 7.77 (d, 1H, J=8.4 Hz), 7.40 (d, 2H, J=8.6 Hz), 7.35 (d, 2H, J=8.4 Hz) 7.09 (s, 1H), 4.20 (s, 2H); ES-MS m/z 384 (M+H).

EXAMPLE 24

4-{[(Z)-(7-Oxo-6,7-dihydro-8H-[1,3]thiazolo[5,4-e]indol-8-ylidene)methyl]amino}benzamide Prepared according to Procedure G with 4-aminobenzamide in 73% yield. $^1$H NMR (DMSO-d$_6$): δ 11.14 (d, 1H, J=12.3 Hz), 10.90 (s, 1H), 9.27 (s, 1H), 8.10 (d, 1H, J=12.3 Hz), 7.93 (d, 3H, J=8.4 Hz), 7.82 (d, 1H, J=8.4 Hz), 7.49 (d, 2H, J=8.6 Hz), 7.30 (s, 1H), 7.12 (d, 1H, J=8.4 Hz); ES-MS m/z 337 (M+H).

EXAMPLE 25

6-Bromo-3-{(Z and E)-[4-(4-morpholinyl)anilino]methylidene}-1,3-dihydro-2H-indol-2-one Prepared according to Example 1 in 87% yield to give ~4:1 isomer mixture. Principal isomer: $^1$H NMR (DMSO-d$_6$): δ 10.67 (d, 1H, J=12.5 Hz), 10.56(s, 1H), 8.57 (d, 1H, J=12.8 Hz), 7.48 (d, 1H, J=7.9 Hz), 7.35–7.29 (m, 2H), 7.11–7.04 (m, 3H), 6.93 (s, 1H), 3.76 (s, 4H), 3.15 (s, 4H); ES-MS m/z 400, 402 (M+1).

EXAMPLE 26

4-{[(Z)-(6-Bromo-2-oxo-1,2-dihydro-3H-indol-3-ylidene)methyl]amino}benzamide

Prepared according to Example I with 4-aminobenzamide in 70% yield. $^1$H NMR (DMSO-d$_6$): δ 10.75 (d, 1H, J=12.5 Hz), 10.65 (s, 1H), 8.69 (d, 1H, J=12.5 Hz), 7.87 (d, 3H, J=8.6 Hz), 7.54 (d, 1H. J=7.9 Hz), 7.44 (d, 2H, J=8.6 Hz), 7.24 (s, 1H), 7.09 (d, 1H, J=8.2 Hz), 6.95 (d, 1H, J=1.4 Hz); ES-MS m/z 356, 358 (M−1).

EXAMPLE 27

N-(4-{[(Z and E)-(6-Bromo-2-oxo-1,2-dihydro-3H-indol-3-ylidene)methyl]amino}phenyl)acetamide Prepared according to Example 1 with N-(4-aminophenyl)acetamide in 79% yield to give ~9:1 isomer mixture. Principal isomer: $^1$H NMR (DMSO-$d_6$): δ 10.75 (d, 1H, J=12.5 Hz), 10.65 (s, 1H), 8.69 (d, 1H, J=12.5 Hz), 7.87 (d, 3H, J=8.6 Hz), 7.54 (d, 1H, J=7.9 Hz), 7.44 (d, 2H, J=8.6 Hz), 7.24 (s, 1H), 7.09 (d, 1H, J=8.2 Hz), 6.95 (d, 1H, J=1.4 Hz); ES-MS m/z 370, 372 (M−1).

EXAMPLE 28

6-Bromo-3-{(Z)-[4-(2-hydroxyethyl)anilino]methylidene}-1,3-dihydro-2H-indol-2-one Prepared according to Example 1 with 4-(2-hydroxyethyl)aniline in 85% yield. $^1$H NMR (DMSO-$d_6$): δ 10.67 (d, 1H, J=12.8 Hz), 10.58 (s, 1H), 8.61 (d, 1H, J=12.6 Hz), 7.50 (d, 1H, J=8.2 Hz), 7.29 (d, 2H, J=8.4 Hz), 7.19 (d, 2H, J=8.2 Hz), 7.06 (d, 1H, J=8.1 Hz), 6.93 (d, 1H, J=1.5 Hz), 4.60 (t, 1H, J=5.1 Hz), 3.55 (m, 2H), 2.66 (t, 2H, J=7.0 Hz); MS-ES m/z 357, 359 (M−1).

EXAMPLE 29

1-{(Z)-[4-(4-Morpholinyl)anilino]methylidene}-1,3-dihydro-2H-pyrrolo[3,2-f]quinolin-2-one Prepared according to Example 13 with 4-(4-morpholino)aniline in 65% yield. $^1$H NMR (DMSO-$d_6$): δ 11.77 (d, 1H, J=12.3 Hz), 10.88 (s, 1H), 8.77 (m, 2H), 8.69 (d, 1H, J=4.0 Hz), 7.67 (d, 1H, J=8.6 Hz), 7.5–7.4 (m, 4H), 6.98 (d, 2H, J=8.8 Hz), 3.72 (t, 4H, J=4.5 Hz), 3.07 (t, 4H, J=4.6 Hz); ES-MS m/z 373 (M+H).

EXAMPLE 30

1-{(Z)-[4-(4-Pyridinylmethyl)anilino]methylidene}-1,3-dihydro-2H-pyrrolo[3,2-f]quinolin-2-one Prepared according to Example 13 with 4-(4-pyridylmethyl)aniline in 59% yield. $^1$H NMR (DMSO-$d_6$): δ 11.74 (d, 1H, J=12.1 Hz), 10.93 (s, 1H), 8.80–8.75 (m, 2H), 8.70 (d, 1H, J=3.9 Hz), 8.44 (d, 2H, J=5.3 Hz), 7.70 (d, 1H, J=8.6 Hz), 7.47–7.43 (m, 3H), 7.39 (d, 1H, J=8.8 Hz), 7.28 (d, 2H, J=8.1 Hz), 7.24 (d, 2H, J=5.1 Hz), 3.95 (s, 2H); ES-MS m/z 379 (M+H).

EXAMPLE 31

N-(4-{[(Z)-(2-Oxo-2,3-dihydro-1H-pyrrolo[3,2-f]quinolin-1-ylidene)methyl]amino}phenyl)acetamide Prepared according to Example 13 with N-(4-aminophenyl)acetamide in 72% yield. $^1$H NMR (DMSO-$d_6$): δ 11.77 (d, 1H, J=12.1 Hz), 10.92 (s, 1H), 9.95 (s, 1H), 8.8–8.77 (m, 2H), 8.70 (d, 1H, J=3.5 Hz), 7.69 (d, 1H, J=8.8 Hz), 7.60 (d, 2H, J=9.0 Hz), 7.5–7.43 (m, 3H), 7.39 (d, 1H, J=8.6 Hz), 2.01 (s, 3H); ES-MS m/z 345 (M+H).

EXAMPLE 32

1-{(Z)-[4-(2-Hydroxyethyl)anilino]methylidene}-1,3-dihydro-2H-pyrrolo[3,2-f]quinolin-2-one Prepared according to Example 13 with 4-(2-hydroxyethyl)aniline in 75% yield. $^1$H NMR (DMSO-$d_6$): δ 11.75 (d, 1H, J=12.1 Hz), 10.92 (s, 1H), 8.82–8.79 (m, 2H), 8.70 (d, 1H, J=3.9 Hz), 7.70 (d, 1H, J=8.6 Hz), 7.5–7.4 (m 4H), 7.23 (d, 2H, J=8.2 Hz), 4.62 (t, 1H, J=5.1 Hz), 3.6–3.55 (m, 2H), 2.70 (t, 2H, J=7.0 Hz); ES-MS m/z 332 (M+H).

EXAMPLE 33

4-{[(Z)-(2-Oxo-2,3-dihydro-1H-pyrrolo[3,2-f]quinolin-1-ylidene)methyl]amino}benzamide Prepared according to Example 13 with 4-aminobenzamide in 54% yield. $^1$H NMR (DMSO-$d_6$): δ 11.90 (d, 1H, J=11.9 Hz), 11.03 (s, 1H), 8.87–8.83 (m, 2H), 8.76 (d, 1H, J=4.0 Hz), 7.93–7.89 (m, 3H), 7.78 (d, 1H, J=8.8 Hz), 7.61 (d, 2H, J=8.6 Hz), 7.52 (dd, 1H, J=4.1,8.5 Hz), 7.45 (d, 1H, J=8.8 Hz), 7.3 (s, 1H); ES-MS m/z 331 (M+H).

EXAMPLE 34

1-[(Z)-(4-Hydroxyanilino)methylidene]-1,3-dihydro-2H-pyrrolo[3,2-f]quinolin-2-one Prepared according to Example 13 with 4-hydroxyaniline in 84% yield. $^1$H NMR (DMSO-$d_6$): δ 11.76 (d, 1H, J=12.3 Hz), 10.90 (s, 1H), 9.44 (s, 1H), 8.77–8.68 (m, 3H), 7.71 (d, 1H, J=8.8 Hz), 7.44–7.33 (m, 4H), 6.83 (d, 2H, J=8.6 Hz); ES-MS m/z 304 (M+H).

EXAMPLE 35

6-(2-Furyl)-3-{(Z)-[4-(4-morpholinyl)anilino]methylidene}-1,3-dihydro-2H-indol-2-one Prepared from the dimethylaminomethylene derivative (Procedure E) of 6-(2-furyl)oxindole (prepared according to Procedure I) with 4-(4-morpholino)aniline according to Procedure G in 90% yield. $^1$H NMR (DMSO-$d_6$): δ 10.66 (d, 1H, J=12.6 Hz), 10.51 (s, 1H), 8.51 (d, 1H, J=12.8 Hz), 7.65 (s, 1H), 7.56 (d, 1H, J=7.9 Hz), 7.29–7.25 (m, 3H), 7.1 (s, 1H), 6.95 (d, 2H, J=8.8 Hz), 6.77 (d, 1H, J=2.9 Hz), 6.52 (s, 1H), 3.71 (s, 4H), 3.05 (s, 4H); ES-MS m/z 388 (M+H).

EXAMPLE 36

N-[4-({(Z and E)-[6-(2-Furyl)-2-oxo-1,2-dihydro-3H-indol-3-ylidene]methyl}amino)phenyl]acetamide Prepared according to Example 35 with N-(4-aminophenyl)acetamide in 29% yield. $^1$H NMR (DMSO-$d_6$): δ 10.68 (d, 1H, J=12.6 Hz), 10.55 (s, 1H), 9.91 (s, 1H), 8.53 (d, 1H, J=12.6 Hz), 7.66 (s, 1H), 7.57–7.54 (m, 3H), 7.32–7.27 (m, 3H), 7.10 (s, 1H), 6.78 (d, 1H, J=2.9 Hz), 6.53 (s, 1H), 2.00 (s, 3H); ES-MS m/z 358 (M−H).

EXAMPLE 37

6-(2-Furyl)-3-{(Z)-[4-(2-hydroxyethyl)anilino]methylidene}-1,3-dihydro-2H-indol-2-one Prepared according to Example 35 with 4-(2-hydroxyethyl)aniline in 63% yield. $^1$H NMR (DMSO-$d_6$): δ 10.68 (d, 1H, J=12.5 Hz), 10.56 (s, 1H), 8.57 (d, 1H, J=12.6 Hz), 7.66 (s, 1H), 7.58 (d, 1H, J=7.9 Hz), 7.28 (br s, 3H), 7.19 (d, 2H, J=8.1 Hz), 7.11 (s, 1H), 6.78 (s, 1H), 6.53 (s, 1H), 4.61 (t, 1H, J=4.9 Hz), 3.58–3.55 (m, 2H), 2.67 (t, 2H, J=6.9 Hz); ES-MS m/z 345 (M−H).

EXAMPLE 38

3-{(Z)-[4-(4-Morpholinyl)anilino]methylidene}-6-vinyl-1,3-dihydro-2H-indol-2-one Prepared according to Procedure G with the dimethylaminomethylene derivative (Procedure E) of 6-vinyloxindole (Procedure I) and 4-(4-morpholino)aniline in 75% yield. $^1$H NMR (DMSO-d$_6$): δ 10.65 (d, 1H, J=2.8 Hz), 10.43 (s, 1H), 8.48 (d, 1H, J=12.5 Hz), 7.48 (d, 1H, J=7.9 Hz), 7.27 (d, 2H, J=8.9 Hz), 7.00 (d, 1H, J=7.9 Hz), 6.95 (d, 2H, J=8.9 Hz), 6.89 (s, 1H), 6.87–6.62 (m, 1H), 5.64 (d, 1H, J=17.84 Hz), 5.08 (d, 1H, J=11.1 Hz), 3.71 (t, 4H, J=4.6 Hz), 3,05 (t, 4H, J=4.6 Hz); ES-MS m/z 346 (M–H).

EXAMPLE 39

3-{(Z)-[4-(4-Pyridinylmethyl)anilino]methylidene}-6-vinyl-1,3-dihydro-2H-indol-2-one Prepared according to Example 38 with 4-(4-pyridylmethyl)aniline in 51% yield. $^1$H NMR (DMSO-d$_6$): δ 10.66 (d, 1H, J=12.5 Hz), 10.49 (s, 1H), 8,53 (d, 1H, J=12.5 Hz), 8.43 (d, 2H, J=5 Hz), 7.50 (d, 1H, J=7.9 Hz), 7.32 (d, 2H, J=8.6 Hz), 7.24–7.21 (m, 4H), 7.01 (d, 1H, J=7.9 Hz), 6,89 (s, 1H), 6.70–6.63 (m, 1H), 5.65 (d, 1H, J=17.5 Hz), 5.10 (d, 1H, J=11.1 Hz), 3.91 (s, 2H); ES-MS m/z 352 (M–H).

EXAMPLE 40

N-(4-{(Z)-[(2-Oxo-6-vinyl-1,2-dihydro-3H-indol-3-ylidene)methyl]amino}phenyl)acetamide Prepared according to Example 38 with N-(4-aminophenyl)acetamide in 42% yield. $^1$H NMR (DMSO-d$_6$): δ 10.67 (d, 1H, J=12.5 Hz), 10.47 (s, 1H), 9.90 (s, 1H), 8.50 (d, 1H, J=12.5 Hz), 7.55 (d, 2H, J=8.6 Hz), 7.49 (d, 1H, J=7.85 Hz), 7.30 (d, 2H, J=8.9 Hz), 7.01 (d, 1H, J=7.9 Hz), 6.89 (s, 1H), 6.70–6.63 (m, 1H), 5.65 (d, 1H, J=17.5 Hz), 5.09 (d, 1H, J=11.1 Hz), 2.00 (s, 3H); ES-MS m/z 318 (M–H).

EXAMPLE 41

3-{(Z)-[4-(2-Hydroxyethyl)anilino]methylidene}-6-vinyl-1,3-dihydro-2H-indol-2-one Prepared according to Example 38 with 4-(2-hydroxyethyl)aniline in 55% yield. $^1$H NMR (DMSO-d$_6$): δ 10.66 (d, 1H, J=12.5 Hz), 10.48 (s, 1H), 8.54 (d, 1H, J=12.5 Hz), 7.51 (d, 1H, J=7.9 Hz), 7.28 (d, 2H, J=8.2 Hz), 7.19 (d, 2H, J=8.2 Hz), 7.01 (d, 1H, J=7.9 Hz), 6.9 (s, 1H), 6.88–6.63 (m, 1H), 5.65 (d, 1H, J=17.5 Hz), 5.09 (d, 1H, J=11.1 Hz), 4.60 (t, 1H, J=5.0 Hz), 3.58–3.53,(m, 2H), 2.66 (t, 2H, J=7.0 Hz); ES-MS m/z 305 (M–H).

EXAMPLE 42

6-(2-Furyl)-3-{(Z)-[4-(4-pyridinylmethyl)anilino]methylidene}-1,3-dihydro-2H-indol-2-one Prepared according to Example 35 with 4-(4-pyridylmethyl)aniline in 42% yield. $^1$H NMR (DMSO-d$_6$): δ 10.67 (d, 1H, J=112.6 Hz), 10.56 (s, 1H), 8.56 (d, 1H, J=12.6 Hz), 8.43 (d, 2H, J=5.3 Hz), 7.66 (s, 1H), 7.57 (d, 1H, J=8.1 Hz), 7.34–7.22 (m, 7H), 7.10 (s, 1H), 6.79 (d, 1H, J=3.3 Hz), 6.53 (s, 1H), 3.91 (s, 2H); ES-MS m/z 391 (M–H)

EXAMPLE 43

6-(2-Furyl)-3-[(Z)-(4-hydroxyanilino)methylidene]-1,3-dihydro-2H-indol-2-one Prepared according to Example 35 with 4-hydroxyaniline in 44% yield. $^1$H NMR (DMSO-d$_6$): δ 10.63 (d, 1H, J=12.8 Hz), 10.49 (s, 1H), 9.32 (s, 1H), 8.46 (d, 1H, J=12.8 Hz), 7.65 (s, 1H), 7.54 (d, 1H, J=7.9 Hz), 7.26 (d, 1H, J=7.9 Hz), 7.21 (d, 2H, J=8.8 Hz), 7.01 (s, 1H), 6.77–6.74 (m, 3H), 6.52 (s, 1H); ES-MS m/z 317 (M–H).

EXAMPLE 44

3-{(Z)-[4-(4-Morpholinyl)anilino]methylidene}-6-(2-thienyl)-1,3-dihydro-2H-indol-2-one Prepared from the dimethylaminomethylene derivative (Procedure E) of 6-(2-thienyl)oxindole (prepared according to Procedure I) with 4-(4-morpholino)aniline according to Procedure G in 47% yield. $^1$H NMR (DMSO-d$_6$): δ 10.67 (d, 1H, J=12.9 Hz), 10.65 (s, 1H), 8.52 (d, 1H, J=12.8 Hz), 7.55 (d, 1H, J=7.9 Hz), 7.42 (d, 1H, J=5.1 Hz), 7.36 (d, 1H. J=3.3 Hz), 7.29 (2H, 8.8 Hz), 7.22 (d, 1H, J=7.9 Hz), 7.08–7.07 (m, 1H), 7.04 (s, 1H), 6.95 (d, 2H, J=9.0 Hz), 3.71 (t, 4H, J=4.5 Hz), 3.05 (t, 4H, J=4.6 Hz).

EXAMPLE 45

N-[4-({(Z)-[2-Oxo-6-(2-thienyl)-1,2-dihydro-3H-indol-3-ylidene]methyl}amino)phenyl]acetamide Prepared according to Example 44 with N-(4-aminophenyl)acetamide in 33% yield. $^1$H NMR (DMSO-d$_6$): δ 10.68 (d, 1H, J=12.6 Hz), 10.52 (s, 1H), 9.91 (s, 1H), 8.53 (d, 1H, J=12.6 Hz), 7.55 (d, 3H, J=8.4 Hz), 7.43 (d, 1H, J=5.1 Hz), 7.37 (d, 1H, J=3.1 Hz), 7.32 (d, 2H, J=8.8 Hz), 7.23 (d, 1H, J=9.2 Hz), 7.07 (t, 1H, J=4.3 Hz), 7.04 (s, 1H), 2.00 (s, 3H); ES-MS m/z 374 (M–H).

EXAMPLE 46

6-Bromo-3-{(Z)-[3-(hydroxymethyl)anilino]methylidene}-1,3-dihydro-2H-indol-2-one Prepared according to Example 1 with 3-(hydroxymethyl)aniline in 54% yield. $^1$H NMR (DMSO-d$_6$): δ 10.74 (d, 1H, J=12.8 Hz), 10.60 (s, 1H), 8.67 (d, 1H, J=12.8 Hz), 7.53 (d, 1H, J=8.2 Hz), 7.30 (d, 2H, J=7.3 Hz), 7.24 (d, 1H, J=8.2 Hz), 7.07 (d, 1H, J=9.3 Hz), 7.02 (d, 1H, 7.3 Hz), 6.94 (s, 1H), 5.23 (t, 1H, J=5.7 Hz), 4.48 (d, 2H, J=5.7 Hz); ES-MS m/z 343, 345 (M–1).

EXAMPLE 47

6-Bromo-3-{(Z and E)-[4-(5-methyl-3-oxo-2,3-dihydro-1H-pyrazol-1-yl)anilino]methylidene}-1,3-dihydro-2H-indol-2-one Prepared according to Example 1 with 2-(4-aminophenyl)-3-methyl-pyrazoline-5-one in 45% yield as ~9:1 isomer mixture. Major isomer: $^1$H NMR (DMSO-d$_6$): δ 10.73 (d, 1H, J=12.6 Hz), 10.60(s, 1H), 9.82 (s, 1H), 8.65 (d, 1H, J=12.6 Hz), 7.52 (d, 1H, J=8.1 Hz), 7.47 (d, 2H, J=8.8 Hz), 7.42 (d, 2H, J=8.8 Hz), 7.08 (d, 1H, J=8.1 Hz), 6.94 (s, 1H), 5.54 (s, 1H), 2.23 (s, 3H); ES-MS m/z 411, 413 (M+1).

EXAMPLE 48

3-Ethyl-3-(4-{(Z)-[(7-oxo-6,7-dihydro-8H-[1,3]thiazolo[5,4-e]indol-8-ylidene)methyl]amino}phenyl)-2,6-piperidinedione A mixture of 8-dimethylamino-methylene-6,8-dihydro-1-thia-3,6-diaza-as-indacen-7-one (Procecure E, 0.040 g, 0.163 mmol), DL-aminoglutethimide (0.055 g, 0.237 mmol) in absolute ethanol (5 ml) was heated with stirring at 90° C. for 16 h. The reaction was diluted with ethanol and diethyl ether and the product collected by filtration to yield 0.038 g (54%) of the title compound. $^1$H NMR (DMSO-$d_6$): δ 11.00 (d, 1H, J=12.5 Hz), 10.88 (s, 1H), 10.83 (s, 1H), 9.23 (s, H), 8.02 (d, 1H, J=12.5 Hz), 7.77 (d, 1H, J=8.6 Hz), 7.42 (d, 2H, J=8.9 Hz), 7.31 (d, 2H, J=8.9 Hz), 7.09 (d, 1H, J=8.2 Hz), 2.44–2.34 (m, 2H), 2.15–2.13 (m, 2H), 1.86–1.02 (m, 2H), 0.75 (t, 3H, J=7.3 Hz); ES-MS m/z 431 (M–H).

EXAMPLE 49

8-[(Z)-(4-Phenoxyanilino)methylidene]-6H-[1,3]thiazolo[5,4-e]indol-7-one

Prepared according to Procedure G with 4-phenoxyaniline in 86% yield. $^1$H NMR (DMSO-$d_6$): δ 11.02 (d, 1H, J=12.5 Hz), 10.81 (s, 1H), 9.22 (s, 1H), 7.99 (d, 1H, J=12.3 Hz), 7.76 (d, 1H, J=8.42 Hz), 7.46 (d, 2H, J=9.0 Hz), 7.37 (t, 2H, J=7.9 Hz), 7.12–7.06 (m, 4H), 6.98 (d, 2H, J=8.1 Hz); ES-MS m/z 384 (M–H).

EXAMPLE 50

8-{(Z)-[4-(Benzyloxy)anilino]methylidene}-6H-[1,3]thiazolo[5,4-e]indol-7-one

Prepared according to Procedure G with 4-(benzyloxy)aniline in 90% yield. $^1$H NMR (DMSO-$d_6$): δ 10.96 (d, 1H, J=12.5 Hz), 10.77 (s, 1H), 9.21 (s, 1H), 7.95 (d, 1H, J=12.5 Hz), 7.74 (d, 1H, J=8.4 Hz), 7.43 (d, 2H, J=7.1 Hz), 7.39–7.35 (m, 4H), 7.32–7.30 (m, 1H), 7.09–7.04 (m, 3H), 5.09 (s, 2H); ES-MS m/z 398 (M–H).

EXAMPLE 51

Methyl 4-(4-{[((Z)-7-oxo-6,7-dihydro-8H-[1,3]thiazolo[5,4-e]indol-8-ylidene)methyl]amino}phenoxy)benzoate Prepared according to Procedure G with methyl 4-(4-aminophenoxy)benzoate in 35% yield. $^1$H NMR (DMSO-$d_6$): δ 11.05 (d, 1H, J=12.3 Hz), 10.83 (s, 1H), 9.22 (s, 1H), 8.01 (d, 1H, 12.3 Hz), 7.95–7.93 (m, 2H), 7.77 (d, 1H, J=8.4 Hz), 7.52 (d, 2H, J=9.0 Hz), 7.19 (d, 2H, J=8.8 Hz), 7.10 (d, 1H, J=8.4 Hz), 7.03 (d, 2H, J=8.8 Hz), 3.80 (s, 3H); ES-MS m/z 442 (M–H).

EXAMPLE 52

Methyl 3-(4-{(Z)-[(7-oxo-6,7-dihydro-8H-[1,3]thiazolo[5,4-e]indol-8-ylidene)methyl]amino}phenoxy)benzoate Prepared according to Procedure G with methyl 3-(4-aminophenoxy)benzoate in 71% yield. $^1$H NMR (DMSO-$d_6$): δ 11.05 (d, 1H, J=12.5 Hz), 10.82 (s, 1H), 9.22 (s, 1H), 8.01 (d, 1H, J=12.3 Hz), 7.77(d, 1H, J=8.4 Hz), 7.68 (d, 1H, J=7.9 Hz), 7.55–7.49 (m, 3H), 7.41 (s, 1H), 7.31 (dd, 1H, J=2.3,8.2 Hz), 7.14 (d, 2H, J=8.8 Hz), 7.09 (d, 1H, J=8.4 Hz), 3.08 (s, 3H); ES-MS m/z 442 (M–H).

EXAMPLE 53

8-{(Z)-[3-(Hydroxymethyl)anilino]methylidene}-6H-[1,3]thiazolo[5,4-e]indol-7-one Prepared according to Procedure G with 3-(hydroxymethyl)aniline in 83% yield. $^1$H NMR (DMSO-$d_6$): δ 11.05 (d, 1H, J=12.5 Hz), 10.84 (s, 1H), 9.23 (s, 1H), 8.05 (d, 1H, 12.3 Hz), 7.77 (d, 1H, J=8.4 Hz), 7.37–7.26 (m, 3H), 7.10 (d, 1H, J=8.4 Hz), 7.06 (d, 1H, J=7.5 Hz), 5.27 (t, 1H, J=5.7 Hz), 4.52 (d, 2H, J=5.9 Hz); ES-MS m/z 322 (M–H).

EXAMPLE 54

3-{(Z)-[(7-Oxo-6,7-dihydro-8H-[1,3]thiazolo[5,4-e]indol-8-ylidene)methyl]amino}benzamide Prepared according to Procedure G with 3-aminobenzamide in 84% yield. $^1$H NMR (DMSO-$d_6$): δ 11.13 (d, 1H, J=12.3 Hz), 10.87 (s, 1H), 9.23 (s, 1H), 8.12–8.07 (m, 2H), 7.84 (s, 1H), 7.78 (d, 1H, J=8.4 Hz), 7.58 (t, 2H, J=7.7 Hz), 7.47 (t, 2H, J=7.8 Hz), 7.10 (d, 1H, J=8.4 Hz); ES-MS m/z 335 (M–H).

EXAMPLE 55

8-{(Z)-[4-(5-Methyl-3-oxo-2,3-dihydro-1H-pyrazol-1-yl)anilino]methylidene}-6H-[1,3]thiazolo[5,4-e]indol-7-one A mixture of 8-dimethylamino-methylene-6,8-dihydro-1-thia-3,6-diaza-as-indacen-7-one (Procedure E, 0.040 g, 0.163 mmol), 2-(4-aminophenyl)-3-methyl-pyrazoline-5-one (0.047 g, 0.248 mmol) in absolute ethanol (5 ml) was heated with stirring at 90° C. for 16 h. The reaction was diluted with ethanol and diethyl ether and the product collected by filtration to yield 0.052 (83%) of the title compound. $^1$H NMR (DMSO-$d_6$): δ 11.08 (d, 1H, J=12.3 Hz), 10.84 (s, 1H), 9.85 (s, 1H), 9.23 (s, 1H), 8.05 (d, 1H, J=12.1 Hz), 7.78 (d, 1H, J=8.2 Hz), 7.51–7.45 (m, 4H), 7.10 (d, 1H, J=8.4 Hz), 5.55 (s, 1H), 2.25 (s, 3H); ES-MS m/z 388 (M–H).

EXAMPLE 56

Methyl 4-{(Z)-[(7-oxo-6,7dihydro-8H-[1,3]thiazolo[5,4-e]indol-8-ylidene)methyl]amino}benzoate Prepared according to Procedure G methyl 4-aminobenzoate in 47% yield. $^1$H NMR (DMSO-$d_6$): δ 11.17 (d, 1H, J=12.1 Hz), 10.91 (s, 1H), 9.25 (s, 1H), 8.07 (d, 1H, 12.1 Hz), 7.95 (d, 2H, J=8.6 Hz), 7.81 (d, 1H, J=8.2 Hz), 7.51(d, 2H, J=8.6 Hz), 7.10 (d, 1H, J=8.4 Hz), 3.81 (s, 3H); ES-MS m/z 350 (M–H).

EXAMPLE 57

4-{(Z)-[(7-Oxo-6,7dihydro-8H-[1,3]thiazolo[5,4-e]indol-8-ylidene)methyl]amino}benzonitrile Prepared according to Procedure G with 4-aminobenzonitrile in 71% yield. $^1$H NMR (DMSO-$d_6$): δ 11.14 (d, 1H, J=11.9 Hz), 10.92 (s, 1H), 9.25 (s, 1H), 8.04 (d, 1H, J=11.9

Hz), 7.82 (dd, 3H, J=2.4, 8.7 Hz), 7.59 (d, 2H, J=8.8 Hz), 7.10 (d, 1H, J=8.4 Hz); ES-MS m/z 317 (M−H).

EXAMPLE 58

N-Methyl-N-(4-{(Z)-[(7-oxo-6,7dihydro-8H-[1,3] thiazolo[5,4-e]indol-8-ylidene)methyl] amino}phenyl)acetamide A mixture of 8-dimethylamino-methylene-6,8-dihydro-1-thia-3,6-diaza-as-indacen-7-one (Procedure E, 0.040 g, 0.163 mmol), 4-amino-N-methylacetanilide (0.040 g, 0.244 mmol) in absolute ethanol (5 ml) was heated with stirring at 90° C. for 16 h. The reaction was diluted with ethanol and diethyl ether and the product collected by filtration to yield 0.038 g (64%) of the title compound. $^1$H NMR (DMSO-d$_6$): δ 11.03 (d, 1H, J=12.3 Hz), 10.84 (s, 1H), 9.23 (s, 1H), 8.02 (d, 1H, J=12.3 Hz), 7.78 (d, 1H, J=8.4 Hz), 7.48 (d, 2H, J=8.2 Hz), 7.35 (d, 2H, J=8.2 Hz), 7.09 (d, 1H, J=8.4 Hz), 3.11 (s, 3H), 1.76 (s, 3H); ES-MS m/z 363 (M−H).

EXAMPLE 59

1-[(Z)-(4-Phenoxyanilino)methylidene]-1,3-dihydro-2H-pyrrolo[3,2-f]quinolin-2-one Prepared according to Example 13 with 4-phenoxyaniline in 79% yield. $^1$H NMR (DMSO-d$_6$): δ 11.78 (d, 1H, J=12.1 Hz), 10.93 (s, 1H), 8.81–8.78 (m, 2H), 8.70 (d, 1H, J=4.0 Hz), 7.70 (d, 1H, J=8.6 Hz), 7.56 (d, 2H, J=8.8 Hz), 7.45 (dd, 1H, J=4.1, 8.5 Hz), 7.41–7.35 (m, 3H), 7.12–7.05 (m, 3H), 6.98 (d, 2H, J=8.2 Hz); ES-MS m/z 378 (M−H).

EXAMPLE 60

1-{(Z)-[4-(Benzyloxy)anilino]methylidene}-1,3dihydro-2H-pyrrolo[3,2-f]quinolin-2-one Prepared according to Example 13 with 4-(benzyloxy) aniline in 59% yield. $^1$H NMR (DMSO-d$_6$): δ 11.80 (d, 1H, J=12.3 Hz), 10.99 (s, 1H), 8.95 (d, 1H, J=8.1 Hz), 8.82–8.77 (m, 2H), 7.73 (d, 1H, J=8.8 Hz), 7.54 (dd, 1H, J=4.1,8.3 Hz), 7.49–7.30 (m, 8H), 7.05 (d, 2H, J=9.0 Hz), 5.11 (s, 2H), ES-MS m/z 394 (M+H).

EXAMPLE 61

Methyl 4-(4-{(Z)-[(2-oxo-2,3-dihydro-1H-pyrrolo[3, 2-f]quinolin-1-ylidene)methyl]amino}phenoxy)benzoate Prepared according to Example 13 with methyl 4-(4-aminophenoxy)benzoate in 69% yield. $^1$H NMR (DMSO-d$_6$): δ 11.80 (d, 1H, J=12.1 Hz), 10.94 (s, 1H), 8.83–8.80 (m, 2H), 8.70 (d, 1H, J=3.9 Hz), 7.95 (d, 2H, J=8.8 Hz), 7.71 (d, 1H, J=8.8 Hz), 7.62 (d, 2H, J=9.0 Hz), 7.45 (dd, 1H, J=4.1, 8.5 Hz), 7.41 (d, 1H, J=8.8 Hz), 7.18 (d, 2H, J=8.8 Hz), 7.03 (d, 2H, J=8.8 Hz), 3.80 (s, 3H); ES-MS m/z 436 (M−H).

EXAMPLE 62

Methyl 3-(4-{(Z)-[(2-oxo-2,3-dihydro-1H-pyrrolo[3, 2-f]quinolin-1-ylidene)methyl]amino}phenoxy)benzoate Prepared according to Example 13 with methyl 3-(4-aminophenoxy)benzoate in 45% yield. $^1$H NMR (DMSO-d$_6$): δ 11.96 (d, 1H, J=12.1 Hz), 11.33 (s, 1H), 9.44 (d, 1H, J=8.2 Hz), 9.01–8.98 (m, 2H), 7.95 (d, 1H, J=8.8 Hz), 7.85 (dd, 1H, J=4.9, 8.4 Hz), 7.72–7.66 (m, 4H), 7.54 (t, 1H, J=8.0 Hz), 7.42 (s, 1H), 7.33 (d, 1H, J=8.2 Hz), 7.17 (d, 2H, J=8.6 Hz), 3.80 (s, 3H); ES-MS m/z 438 (M+H).

EXAMPLE 63

3-Ethyl-3-(4-{(Z)-[(2-oxo-2,3-dihydro-1H-pyrrolo [3,2-f]quinolin-1-ylidene)methyl]amino}phenyl)-2, 6-piperidinedione Prepared according to Example 13 with DL-aminoglutethimide in 81% yield. $^1$H NMR (DMSO-d$_6$): δ 11.72 (d, 1H, J=11.7 Hz), 10.93 (s, 1H), 10.88 (s, 1H), 8.82–8.77 (m, 2H), 8.70 (d, 1H, J=2.9 Hz), 7.71 (d, 1H, J=8.8 Hz), 7.52 (d, 2H, J=8.8 Hz), 7.45 (dd, 1H, J=4.1,8.5 Hz), 7.40 (d, 1H, J=8.8 Hz), 7.30 (d, 2H, J=8.6 Hz), 2.36–2.16 (m, 2H), 2.15–2.12 (m, 2H), 1.90–1.77 (m, 2H), 0.76 (t, 3H, J=7.3 Hz); ES-MS m/z 425 (M−H).

EXAMPLE 64

1-[(Z)-(4-Benzoylanilino)methylidene]-1,3-dihydro-2H-pyrrolo[3,2-f]quinolin-2-one Prepared according to Example 13 with 4-benzoylaniline in 76% yield. $^1$H NMR (DMSO-d$_6$): δ 11.92 (d, 1H, J=11.7 Hz), 11.04 (s, 1H), 8.88 (d, 1H, J=11.7 Hz), 8.84 (d, 1H, J=8.6 Hz), 8.73 (d, 1H, J=3.1 Hz), 7.80–7.53 (m, 10H), 7.49 (dd, 1H, J=4.1, 8.5 Hz), 7.42 (d, 1H, J=8.8 Hz); ES-MS m/z 390 (M−H).

EXAMPLE 65

1-{(Z)-[3-Hydroxymethyl)anilino]methylidene}-1,3-dihydro-2H-pyrrolo[3,2-f]quinolin-2-one Prepared according to Example 13 with 3-(hydroxymethyl)aniline in 78% yield. $^1$H NMR (DMSO-d$_6$): δ 11.84 (d, 1H, J=12.1 Hz), 10.36 (s, 1H), 8.86–8.80 (m, 2H), 8.72 (d, 1H, J=4.0 Hz), 7.72 (d, 1H, J=8.7 Hz), 7.48 (dd, 1H, J=4.1,8.5 Hz), 7.43–7.33 (m, 4H), 7.07 (d, 1H, J=7.5 Hz), 5.25 (s, 1H), 4.53 (dd, 2H, J=4.5 Hz); ES-MS m/z 316(M−H).

EXAMPLE 66

1-{(Z)-[4-(5-Methyl-3-oxo-2,3-dihydro-1H-pyrazol-1-yl)anilino]methylidene}-1H-pyrrolo[3,2-f]quinolin-2(3H)-one Prepared according to Example 13 with 2-(4-aminophenyl)-3-methyl-pyrazoline-5-one in 69% yield. $^1$H NMR (DMSO-d$_6$): δ 11.83 (d, 1H, J=11.9 Hz), 10.05 (s, 1H), 9.84 (s, 1H), 8.86–8.82 (m, 2H), 8.71 (d, 1H, J=2.9 Hz), 7.72 (d, 1H, J=8.8 Hz), 7.60 (d, 2H, J=8.8 Hz), 7.48–7.44 (m, 3H), 7.41 (d, 1H, J=8.8 Hz), 5.55 (s, 1H), 2.25 (s, 3H); ES-MS m/z 382 (M−H).

EXAMPLE 67

1-((E)-{4-[(E)-2-(4-Hydroxyphenyl)ethenyl] anilino}-methylidene)-1,3-dihydro-2H-pyrrolo[3,2-f] quinolin-2-one Prepared according to Example 13 with 2-(4-hydroxyphenyl)ethenyl]aniline in 90% yield. $^1$H NMR (DMSO-d$_6$): δ 11.86 (d, 1H, J=11.9 Hz), 10.95 (s, 1H), 9.53 (s, 1H), 8.86–8.83 (m, 2H), 8.71 (d, 1H, J=3.3 Hz), 7.71 (d, 1H, J=8.6 Hz), 758–7.45 (m, 5H), 7.42–7.38 (m, 3H), 7.12–6.98 (m, 2H), 6.74 (d, 2H, J=8.6 Hz); ES-MS m/z 404 (M−H).

EXAMPLE 68

3-{(Z)-[(2-Oxo-2,3-dihydro-1H-pyrrolo[3,2-f]quinolin-1-ylidene)methyl]amino}benzamide Prepared according to Example 13 with 3-aminobenzamide in 66% yield. $^1$H NMR (DMSO-$d_6$): δ 11.86 (d, 1H, J=11.9 Hz), 10.98 (s, 1H), 8.89–8.80 (m, 2H), 8.72 (d, 1H, J=2.9 Hz), 8.06 (s, 1H), 7.88 (s, 1H) 7.74–7.69 (m, 2H), 7.59 (d, 1H, J=7.7 Hz), 7.51–7.45 (m, 3H), 7.41 (d, 1H, J=8.8 Hz); ES-MS m/z 329 (M−H).

EXAMPLE 69

4-{(Z)-[(2-Oxo-2,3-dihydro-1H-pyrrolo[3,2-f]quinolin-1-ylidene)methyl]amino}benzonitrile Prepared according to Example 13 with 4-aminobenzonitrile in 82% yield. $^1$H NMR (DMSO-$d_6$): δ 11.84 (d, 1H, J=11.7 Hz), 11.03 (s, 1H), 8.84–8.73 (m, 2H), 8.72 (dd, 1H, J=1.2,4.1 Hz), 7.82 (d, 2H, J=8.6 Hz), 7.76 (d, 1H, J=8.8 Hz), 7.69 (d, 2H, J=8.8 Hz), 7.48 (dd, 1H, J=4.1,8.5 Hz), 7.41 (d, 1H, J=8.6 Hz); ES-MS m/z 311 (M−H).

EXAMPLE 70

Methyl 4-{(Z)-[(2-oxo-2,3-dihydro-1H-pyrrolo[3,2-f]quinolin-1-ylidene)methyl]amino}benzoate Prepared according to Example 13 with methyl 4-aminobenzoate in 44% yield. $^1$H NMR (DMSO-$d_6$): δ 11.91 (d, 1H, J=11.8 Hz), 11.03 (s, 1H), 8.88–8.83 (m, 2H), 8.72 (dd, 1H, J=1.3, 4.1 Hz), 7.95 (d, 2H, J=8.6 Hz), 7.75 (d, 1H, J=8.9 Hz), 7.63 (d, 2H, J=8.6 Hz), 7.49 (dd, 1H, J=3.9,8.6 Hz), 7.41 (d, 1H, J=8.6 Hz), 3.82 (s, 3H); ES-MS m/z 344 (M−H).

EXAMPLE 71

8-[(Z)-(4-{[2-(Diethylamino)ethyl]sulfonyl}anilino) methylidene]-6H-[1,3]thiazolo[5,4-e]indol-7-one Prepared according to Procedure G with 4-[2-(diethylamino)ethylsulfonyl]aniline in 18% yield. $^1$H NMR (DMSO-$d_6$): δ 11.20 (d, 1H, J=11.9 Hz), 10.93 (s, 1H), 9.26 (s, 1H), 8.08 (d, 1H, J=11.9 Hz), 7.87 (d, 2H, J=8.6 Hz), 7.82 (d, 1H, J=8.42 Hz), 7.63 (d, 2H, J=8.6 Hz), 7.11 (d, 1H, J=8.24 Hz), 3.46–3.38 (m, 2H), 2.8–2.7 (m, 2H), 2.3–2.2 (m, 4H), 0.80 (t, 6H, J=7.0 Hz); ES-MS m/z 455 (M−H).

EXAMPLE 72

1-[(Z)-(4-{[2-(Diethylamino)ethyl]sulfonyl}anilino) methylidene]-1H-pyrrolo[3,2-f]quinolin-2(3H)-one Prepared according to Example 13 with 4-[2-(diethylamino)ethylsulfonyl]aniline in 64% yield. $^1$H NMR (DMSO-$d_6$): δ 11.91 (d, 1H, J=11.5 Hz), 11.04 (s, 1H), 8.88–8.84 (m, 2H), 8.73 (d, 1H, J=3.3 Hz), 7.87 (d, 2H, J=8.6 Hz), 7.78–7.72 (m, 3H), 7.50 (dd, 1H, J=4.1,8.5 Hz), 7.41 (d, 1H, J=8.6 Hz), 3.45–3.38 (m, 2H), 2.71–2.67 (m, 2H), 2.32 (q, 4H, J=7.0 Hz), 0.80 (t, 6H, J=7.1 Hz); ES-MS m/z 449 (M−H).

EXAMPLES 73–88

Are Described in Procedure J (vide infra)

EXAMPLE 89

3,6-Dihydro[1,2,3]triazolo[4,5-e]indole-7,8-dione 8-[N-(4-methoxyphenyl)hydrazone]

See Procedure H.

EXAMPLE 90

3,6-Dihydro[1,2,3]triazolo[4,5-e]indole-7,8-dione 8-{N-[4-(1,3-oxazol-5-yl)phenyl]hydrazone}

Prepared according to Procedure H with 4-(1,3-oxazol-5-yl)phenylhydrazine hydrochloride in 61% yield as ~2:1 mixture of geometric isomers. $^1$H NMR (DMSO-$d_6$): δ 7.09 and 7.26 (2 d, 1:2 ratio, J=8.6 Hz, 1H); 7.55 and 7.85 (ABq, J=8.7 Hz, 4H); 7.65 (s, 1H); 7.85 and 7.98 (2 d, 2:1 ratio, partially obscured by ABq, J=8.6 Hz, 1H); 8.45 (s, 1H); 10.87 and 11.33 (2 s, ~2:1 ratio, 1H). 12.95 (brd, 1H). APCI-MS m/z 344 (M−H)$^-$.

EXAMPLE 91

3,6-Dihydro[1,2,3]triazolo[4,5-e]indole-7,8-dione 8-[N-(4-methylphenyl)hydrazone]

Prepared according to Procedure H with 4-methylphenylhydrazine hydrochloride in 18% yield as ~1:1 mixture of E and Z isomers. $^1$H NMR (DMSO-$d_6$): δ 2.28 (s, 3H); 7.19 (d, J=8.4 Hz, 0.5H); 7.15–7.35 (m, 3.5H); 7.62 (d, J=8.4 Hz, 1H); 7.76 (d, J=8.4 Hz, 0.5H); 7.93 (d, J=8.4 Hz, 0.5H); 10,7 (s, 0.5H); 11.2 (s, 1H); 12.3 and 12.35 2 s, 1H). APCI-MS m/z 291 (M−H)$^-$.

EXAMPLE 92

3,6-Dihydro[1,2,3]triazolo[4,5-e]indole-7,8-dione 8-(N-{4-[(E)-2-(2-pyridinyl)ethenyl] phenyl}hydrazone)

Prepared according to Procedure H with 4'-hydrazino-2-stilbazole dihydrochloride (TCI, Inc.) in 89% yield as ~1:1 mixture of E and Z isomers as the hydrochloride salt. $^1$H NMR (DMSO-$d_6$): δ 7.10 and 7.26 (2 d, J=8.6 Hz, 1H); 7.37 and 7.41 (2 d, J=16 Hz, 1H); 7.55 (d, J=8.6 Hz, 1H); 7.68 (m, 1H); 7.74–7.9 (m, 3.5H); 7.99 (d, J=16 Hz, 1H); 7.99 (d, J=8.6 Hz, 0.5H); 8.16 (t, J=8.6 Hz, 1H); 8.34 (m, 1H); 8.74 (d, J=5.5 Hz, 1H); 10.9 and 11.4 (2 s, 1H); 13.0 (s, 1H). APCI-MS m/z 380 (M−H)$^-$.

EXAMPLE 93

6H-[1,3]Thiazolo[5,4-e]indole-7,8-dione 8-[N-(3-methoxyphenyl)hydrazone]

Prepared according to Procedure H using 6H-[1,3]thiazolo[5,4-e]indole-7,8-dione (Procedure A) and 3-methoxyphenylhydrazine hydrochloride in 44% yield. APCI-MS m/z 323 (M−H)$^-$.

EXAMPLE 94

5-Hydroxy-4,6-dimethyl-1H-indole-2,3-dione 3-[N-(4-methylphenyl)hydrazone]

5-Hydroxy-4,6-dimethyl-1H-indole-2,3-dione was prepared from 3,5-dimethyl-4-hydroxyaniline according to Procedure A: $^1$H NMR (DMSO-$d_6$): δ 2.17 (s, 3H), 2.30 (s, 3H), 6.45 (s, 1H), 8.29 (s, 1H), 10.65 (s, 1H); ESI-MS m/z 190 (M−H)$^-$. The isatin was combined with 4-methylphenylhydrazine hydrochloride according to Procedure H to provide the title compound in 41% yield. $^1$H NMR (DMSO-$d_6$): δ 2.15 (s, 3H), 2.24 (s, 3H), 2.43 (s, 3H), 6.46 (s, 1H), 7.16 (m, 4H), 7.88 (s, 1H), 10.64 (s, 1H), 12.85 (s, 1H). APCI-MS m/z 294 (M−H, 45%).

EXAMPLE 95

(Z)-3,6-Dihydro[1,2,3]triazolo[4,5-e]indole-7,8-dione 8-{N-[4-(trifluoromethyl)phenyl]hydrazone}

Prepared according to Procedure H with 4-trifluoromethylphenylhydrazine hydrochloride in 32% yield. $^1$H NMR (DMSO-$d_6$): δ 7.26 (d, J=8.7 Hz, 1H); 7.59 and 7.83 (ABq, J=8.4 Hz, 4H); 7.89 (brd d, J=8.7 Hz, 1H); 10.9 (s, 1H); 13.0 (s, 1H). APCI-MS m/z 345 (M−H)$^-$.

EXAMPLE 96

6H-[1,3]Thiazolo[5,4e]indole-7,8-dione 8-[N-(3-fluorophenyl)hydrazone] (Z-isomer)

6H-1-Thia-3,6-diaza-as-indacen-7,8-dione (Procedure A, 50 mg, 0.25 mmol) was combined with 3-fluorophenylhydrazine hydrochloride (50 mg, 0.3 mmol) in 2 ml of ethanol and heated at 70° C. for 6 hrs. The product was collected by filtration of the hot solution, washing with ethanol and diethyl ether, to give 47 mg (60%) of the title compound as a brown solid. $^1$H NMR (DMSO-$d_6$): δ 6.82 (t, J=8.7 Hz, 1H); 7.10 (d, J=8.6 Hz, 1H); 7.37 (m, 2H); 7.41 (dd, 1H); 7.97 (d, J=8.6 Hz, 1H); 9.25 (s, 1H); 11.2 (s, 1H). ES-MS m/z 311 (M−1)$^-$.

EXAMPLE 97

(Z)-6H-[1,3]Thiazolo[5,4e]indole-7,8-dione 8-[N-(4-fluorophenyl)hydrazone]

Prepared according to Example 96 with 6H-1-thia-3,6-diaza-as-indacen-7,8-dione (Procedure A) and 4-fluorophenylhydrazine hydrochloride in 49% yield. $^1$H NMR (DMSO-$d_6$): δ 7.11 (d, J=8.6 Hz, 1H); 7.25 (t, J=8.8 Hz, 2H); 7.52 (dd, J=4.8, 8.8 Hz, 2H); 7.94 (d, J=8.6 Hz, 1H); 9.27 (s, 1H); 11.2 (s, 1H); 12.6 (s, 1H). ES-MS m/z 311 (M−1)$^-$.

EXAMPLE 98

(Z)-6H-[1,3]Thiazolo[5,4-e]indole-7,8-dione 8-[N-(4-bromophenyl)hydrazone]

Prepared according to Example 96 with 6H-1-thia-3,6-diaza-as-indacen-7,8-dione (Procedure A) and 4-bromophenylhydrazine hydrochloride in 62% yield. $^1$H NMR (DMSO-$d_6$): δ 7.16 (d, J=8.5 Hz, 1H); 7.50 and 7.62 (Abq, J=8.8 Hz, 4H); 8.02 (d, J=8.5 Hz, 1H); 9.33 (s, 1H); 11.3 (s, 1H); 12.6 (s, 1H). ES-MS m/z 371, 373 (M−1)$^-$.

Procedure J—Method for preparation of a solution phase library containing compounds of the invention.

Set forth below are a selected number of synthesis examples that illustrate the solution library techniques that can be used to obtain the compounds formulae E1, E2, E3 and E4 of the invention. It is believed that one of ordinary skill in the art can follow this procedure or modify it accordingly without undue experimentation in order to obtain the substitutions disclosed above. The following examples are illustrative examples of the solution phase synthesis, not intended to limit the scope of the invention in any way. Certain compounds found in the following solution library are not compounds of the invention and are not listed in Tables 1–5 above, nor are they included in the enumerated Examples. Such compounds are included by way of demonstration only.

Synthesis of Intermediates:

5-Bromo-7-azaoxindole a) 3,3,5 Tribromooxindole

A solution of 3,3-dibromo-7-azaoxindole (5.0 g, 13.4 mmol) in tert-BuOH (100 mL) and water (100 mL) is stirred at room temperature and bromine (5.5 g, 34.3 mmol) is added dropwise over 20 min. A saturated aqueous solution of sodium bicarbonate (approx. 15 mL) is added dropwise over 30 min to raise the pH of the solution to 6.5. The yellow solid formed is collected by filtration. The filtrate is condensed to approx. 100 mL and extracted with $CHCl_3$ (2×50 mL). The combined organic extracts are dried over anhydrous magnesium sulfate and the solvent is evaporated under reduced pressure to leave a yellow solid. The solids are combined and dried under vacuum to give 3,3,5 tribromooxindole as a yellow solid, 6.25 g (98%). $^1$H NMR ($CDCl_3$) δ 9.4 (br s, 1H), 8.28 (d, 1H, J=2 Hz), 7.95 (d, 1H, J=2 Hz).

b) 5-Bromo-7-azaoxindole

A solution of 3,3,5-tribromooxindole (5.0 g, 13.4 mmol) in fresh THF (100 mL) is stirred at room temperature and a saturated aqueous solution of ammonium chloride (100 mL) is added. The flask is placed in a water bath and activated zinc dust (15.0 g, 230 mmol) is added. The mixture is stirred for 20 min and the zinc is removed by filtration through a pad of diatomaceous earth. The organic layer is separated and the aqueous layer is extracted with THF (20 mL). The combined organic layers were washed with saturated brine solution, dried over anhydrous magnesium sulfate and the solvent removed under reduced pressure. The brown residue is triturated with water (20 mL) and the tan solid is collected by filtration and dried under vacuum to give 5-bromo-7-azaoxindole as a tan solid, 2.02 g (71%). $^1$H NMR (DMSO-$d_6$) δ 11.13 (s, 1H), 8.15 (s, 1H), 8.76 (s, 1H), 3.57 (s, 2H). MS (AP−ve) 211 (100) (M−H).

5-Phenyl-7-azaoxindole

To a stirred mixture of 5-bromo-7-azaoxindole (213 mg, 1 mmol) and phenylboronic acid (183 mg, 1.5 mmol) in toluene (6 ml) and ethanol (6 ml) were added 1 M sodium carbonate solution (2.5 ml, 2.5 mmol), lithium chloride (127 mg, 3 mmol) and dichlorobis(triphenylphosphine)palladium (II) (35 mg, 0.05 mmol) under $N_2$ atmosphere. The reaction mixture was heated to reflux at 95° C. for 18 hours. The reaction mixture was diluted with chloroform (50 ml) and washed with brine (20 ml). The aqueous layer was thoroughly extracted with chloroform. The combined organic layers were dried over anhydrous $MgSO_4$, filtered and evaporated under vacuum to give crude product. Trituation of the crude product with diethyl ether yielded 5-phenyl-7- azaoxindole as a yellow solid (108 mg, 51.4%). $^1$H NMR (DMSO-d$_6$): δ 11.04 (s, 1H), 8.32 (s, 1H), 7.83 (s, 1H), 7.60 (d, 2H, J=7.4 Hz), 7.44 (t, 2H, J=7.4 Hz), 7.32 (t, 1H, J=7.4 Hz), 3.58 (s, 2H). MS (−ve APCI): 210 (48, M+), 209 (100, M−H).

5-(Furan-2-yl)-7-aza-oxindole

5-Bromo-7-azaoxindole (0.75 g, 3.52 mmol), 2-tributyltinfuran (1.26 g, 3.52 mmol), tetraethylammonium chloride hydrate (1.94 g, 10.6 mmol) were combined and dissolved in acetonitrile (10 mL) at room temperature under an atmosphere of nitrogen. Bistriphenylphosphine dichloropalladium (II) (0.25 g, 0.35 mmol) was added and the reaction was warmed to 85° C. for 16 hours. The reaction was cooled to room temperature and diluted with aqueous KF (10%, 60 mL). This was stirred for 20 minutes and then diluted with EtOAc (60 mL). The biphasic system was passed through celite, the layers separated, and the volatiles removed in vacuo. The resulting residue was triturated with diethyl ether and the solids were collected by filtration to afford a light yelow solid (0.28 g, 36% yield). $^1$H NMR 300 MHz (DMSO-d$_6$) δ 11.18 (bs, 1H); 8.45 (s, 1H); 7.92 (s, 1H); 7.79 (s, 1H); 6.95 (d, 1H); 6.60 (d, 1H); 3.64 (s, 2H). APCI m/z 201 (M+1).

5-(3-Thienyl)-7-azaoxindole

5-Bromo-7-azaoxindole (0.20 g, 0.94 mmol), 3-tributyltinthiophene (0.42 g, 1.12 mmol), tetraethylammonium chloride hydrate (0.16 g, 0.94 mmol) were combined and dissolved in acetonitrile (10 mL) at room temperature under nitrogen. Bistriphenylphosphine dichloropalladium (II) (0.033 g, 0.047 mmol) was added and the reaction was warmed to 85° C. for 20 hours. Fresh catalyst was added to the reaction mixture, Bistriphenylphosphine dichloropalladium (II) (0.033 g, 0.047 mmol) and the reaction continued to stir at 85° C. for 24 hours. The reaction was cooled to room temperature and diluted with water (20 mL) and EtOAc (20 ml). The biphasic system was passed through celite and the layers were separated. The organic layer was washed with brine (10 mL) and dried over sodium sulfate. The volatiles ere removed in vacuo. The resulting residue was triturated with diethyl ether and collected by filtration (0.16 g, 80% yield). $^1$H NMR 400 MHz (DMSO-d$_6$) δ 11.03 (bs, 1H); 8.43 (s, 1H); 7.92 (s, 1H); 7.84 (s, 1H); 7.60 (m, 1H); 7.53 (d, 1H); 3.58 (s, 2H).

5-Carboethoxy-7-azaoxindole

To a mixture of 5-bromo-7-azaoxindole (213 mg, 1 mmol) in dimethylsulfoxide (1 ml) and ethanol (5 ml) in Parr bomb were added triethylamine (0.31 ml, 2.25 mmol), palladium acetate (33.7 mg, 0.15 mmol), and 1,3-(bisdiphenylphosphino)propane (61.9 mg, 0.15 mmol). Carbon monoxide gas (40 atm) was applied and the reaction mixture was heated at 95° C. for 18 hours with vigorously stirring. The reaction mixture was diluted with diethyl ether (50 ml) and washed with water (10 ml). The aqueous layer was thoroughly extracted with diethyl ether. The combined organic layers were dried over anhydrous MgSO$_4$, filtered and evaporated under vacuum to give crude product. Trituation of the crude product with methanol yielded 5-(carboethoxy)-7-azaoxindole as a tan solid (53 mg, 25.7%). $^1$H NMR (DMSO-d$_6$): δ 11.39 (s, 1H), 8.62 (s, 1H), 7.95 (s, 1H), 4.27 (q, 2H, J=7 Hz), 3.59 (s, 2H), 1.28 (t, 3H, J=7 Hz). MS (−ve APCI): 205 (4, M−H).

6-Chloro-7-azaoxindole a) 6-Chloro-7-aza-3,3-dibromooxindole

6-Chloro-7-azaindole was prepared according to the procedure of Minakata et al; Synthesis, 1992, 661–663. To a stirred solution of 1.32 g (8.7 mmol) of 6-chloro-7-azaindole in tert-butanol (80 mL) was added 9.9 g (28 mmol) of 90% pyridine hydrobromide perbromide reulting in a thick yellow precipitate forming immediately. The reaction was concentrated and the crude chromatographed on silica gel eluting with hexane to 90% hexane/10% EtOAc gradient to give 2.36 g of the title compound as a white solid, containing about 30% of 5-bromo-6-chloro-7-aza-3,3-dibromooxindole as an inseparable impurity. $^1$H NMR (CDCl$_3$) δ 7.16 (d, J=8.0 Hz, 1H), 7.81 (d, J=8.0 Hz, 1H), 9.0 (bs, 1H). (5-Bromo-6-chloro-7-aza-3,3-dibromooxindole, 8.05 (s, 1H), 9.0 (bs, 1H).

b) 6-Chloro-7-azaoxindole

A solution of 2.36 g (7.26 mmol) of the mixture of 6-chloro-7-aza-3,3-dibromooxindole and 5-bromo-6-chloro-7-aza-3,3-dibromooxindole in THF (70 mL) and saturated ammonium chloride solution (70 mL) was treated with 6 g (92 mmol) of powdered zinc. After stirring for 2 h another 6 g (92 mmol) portion of zinc was added and stirring continued another 2 h. The zinc was filtered off and washed with ether. Ether phase separated and the aqueous phase washed twice with a 1:1 mixture of THF/ether. Combined ether fractions were dried over magnesium sulfate, filtered and concentrated. The crude was loaded onto 7.5 g of silica gel and chromatographed on silica gel eluting with 90% hexane/10% ethyl acetate to a 66% hexane/33% ethyl acetate gradient to give 0.647 g of the title compound, plus 0.243 g of 5-bromo-6-chloro-7-azaoxindole. $^1$H NMR (DMSO-d$_6$): δ 3.57 (s, 2H), 7.04 (d, J=7.6 Hz, 1H), 7.61 (d, J=7.6 Hz, 1H), 11.2 (bs, 1H).

7-Azaoxindole a) 3,3-Dibromo-7-azaoxindole

A solution of 7-azaindole (4.0 g, 34 mmol) in tert-BuOH (200 mL) is stirred at room temperature and pyridinium perbromide (32.5 g, 0.1 mol) is added in portions over 30 min. and the reaction mixture is stirred for 3 hours. Pyridinium perbromide (10.8 g, 33 mmol) is added and the mixture is stirred for a further 2 hours. The tert-BuOH is evaporated under educed pressure and the residue is partitioned between water (300 mL) and EtOAc (300 mL). The organic layer is separated and the aqueous layer is extracted with EtOAc. The combined organic layers are washed with water (2×50 mL), and brine. The organic layer is dried over anhydrous MgSO$_4$, filtered and the solvent evaporated. Trituration of the residue with CH$_2$Cl$_2$ gives a white solid which is collected by filtration and dried under vacuum to give 3,3-dibromo-7-azaoxindole, 8.35 g. $^1$H-NMR (DMSO-d$_6$) δ 11.99 (s, 1H), 8.21 (dd, 1H, J=5.1,1.5 Hz), 8.00 (dd, 1H, J=7.5,1.5 Hz), 7.17 (dd, 1H, J=7.5, 5.1 Hz). MS (+ve ES) 293 (28), (M+H), 147 (100).

b) 7-Azaoxindole

A solution of 3,3-dibromo-7-azaoxindole (2.0 g, 7.2 mmol) in THF (50 mL) is stirred at room temperature and a saturated aqueous solution of NH$_4$Cl is added. Activated zinc powder is added and the reaction mixture is stirred for 2 hours. The zinc is removed by filtration through a pad of diatomaceous earth and the organic layer is separated. The aqueous layer is extracted with THF (10 mL) and the combined organic layers are dried over anhydrous MgSO$_4$, filtered and evaporated. The residue is slurried in 10:1 CHCl$_3$:MeOH (15 mL) and filtered through a pad of silica gel and the filtrate is evaporated. The residue is triturated with water and the solid is collected by filtration and dried under vacuum to give 7-azaoxindole, 0.668 g (70%). $^1$H NMR (DMSO-d$_6$) δ 10.94 (s, 1H), 8.02 (d, 1H, J=5.2 Hz), 7.52 (d, 1H, J=6.8 Hz), 6.90 (dd, 1H, J=6.8, 5.2 Hz), 3.53 (s, 2H). MS(AP−ve) 133 (100) (M−H)

4-Aza-oxindole

Diethyl (3-nitropyrid in-2-yl)-malonate

Sodium hydride (60% dispersion in oil, 5.57 g, 0.14 mol) was carefully washed with hexanes under nitrogen before the addition of DMSO (115 mL). Diethyl malonate (22.3 g, 0.14 mol) was added dropwise over 20 min and the mixture was stirred for an additional 30 min at room temperature. 2-Chloro-3-nitropyridine (10 g, 0.06 mol) was added to the reaction and the reaction was placed in a pre-heated oil bath set to 100° C. for 15 min. The reaction was cooled to room temperature and poured into aqueous ammonium chloride (saturated solution, 150 mL). The aqueous solution was extracted with EtOAc:Hexanes (1:1) four times (200 mL each) and the organic layers were combined. The organics were concentrated to afford a solid that was recrystallized from a minimal amount of EtOAc:Hexanes (1:1) (12.5 g, 70% yield). APCI MS m/z 281 (M−1).

Ethyl 2-(3-nitro-pyridin-2-yl)-acetate

Diethyl (3-nitropyridin-2-yl)-malonate (12.5 g, 0.044 mol) was dissolved in DMSO (150 mL) and water (0.79 mL, 0.044 mol) and lithium chloride (4.65 g, 0.11 mol) were added at room temperature under nitrogen. The reaction was warmed to 100° C. 12 hours and more lithium chloride (1 g) was added to the reaction. The reaction was heated for another 5 hours and cooled to room temperature. Brine (150 mL) was added to the reaction before extracting with EtOAc (3×, 275 mL each). The organics were combined and dried over sodium sulfate, then concentrated in vacuo. The resulting residue was triturated with diethyl ether and collected by filtration (8.6 g, 92% yield). $^1$H NMR 400 MHz (DMSO-d6) δ 8.83 (m, 1H); 8.53 (m, 1H); 7.65 (m, 1H); 4.23 (s, 2H); 4.07 (m, 2H); 1.16 (m, 3H).

Ethyl 2-(3-amino-pyridin-2-yl)-acetate

Under an atmosphere of nitrogen, Pd/C (10%, 1.36 g) was charged to a round bottom flask. Ethyl 2-(3-nitro-pyridin-2-yl)-acetate (8.6 g, 0.41 mol) was dissolved in ethanol (200 mL) and added to the reaction vessel. The reaction was placed under an atmosphere of hydrogen and stirred at room temperature for 30 min. The reaction was filtered through celite and the filtrate was concentrated in vacuo to afford the product as a tan solid (6.94 g, 94% yield).

4-Azaoxindole

Ethyl 2-(3-amino-pyridin-2-yl)-acetate (6.94 g, 0.038 mol) was dissolved in diethyl ether (100 mL) at room temperature. Hydrochloric acid (2M, 35 mL) was added and the reaction was stirred for 30 minutes. The volatiles were removed to afford a brown solid that was re-crystallized from ethanol and diethyl ether (4.0 g, 62% yield). $^1$H NMR 400 MHz (DMSO-d$_6$) δ 12.35 (s, 1H); 8.12 (m, 1H); 7.90 (m, 1H); 7.14 (m, 1H); 5.75 (s, 2H). Electrospray MS m/z 135 (M+1).

6-(Furan-2-yl)-oxindole

6-Bromo-oxindole (0.40 g, 1.88 mmol), 2-tributyltinfuran (0.71 mL, 2.26 mmol), and tetraethylammonium chloride hydrate (0.31 g, 1.88 mmol) were combined and dissolved in acetonitrile (15 mL). The palladium catalyst, bistriphenylphosphinedichloropalladium (II) (0.66 g, 0.09 mmol) was added and the reaction was warmed to 85° C. under nitrogen for 20 hours. The reaction was cooled to room temperature and diluted with water (15 mL) before passing the mixture through celite. The pad of celite was washed with EtOAc and the filtrates were combined and separated. The aqueous layer was washed with EtOAc (2×20 mL each). The combined organic phases were washed with brine and dried over sodium sulfate. The volatiles ere removed in vacuo. The resulting residue was triturated with diethyl ether and the solid was collected by filtration (0.13 g, 34%). $^1$H NMR 300 MHz (DMSO-d6) δ 10.5 (s, 1H); 7.75 (s, 1H); 7.30 (m, 2H); 7.11 (s, 1H); 6.91 (m, 1H); 6.60 (m, 1H); 3.52 (s, 2H).

Synthesis of Monomers:

Monomer 6: 5-Carboethoxy-3-ethoxymethylene-7-azaoxindole (Procedure J-1)

5-Carboethoxy-7-azaoxindole (0.040 g, 0.19 mmol) and diethoxymethylacetate (0.16 mL, 0.97 mmol) were combined and dissolved in acetic acid (1 mL). The reaction was warmed to 110° C. and stirred at this temperature for 1 hour. The reaction was cooled to room temperature and diethyl ether was added to precipitate a beige solid that was collected by filtration (35 mg, 69% yield). $^1$H NMR 400 MHz (DMSO-d6) δ 11.30 (s, 1H); 8.58 (s, 1H); 8.05 (s, 1H); 7.93 (s, 1H); 4.44 (m, 2H); 4.28 (m, 2H); 1.35 (m, 3H); 1.28 (m, 3H).

Monomer 7: 3-Dimethylaminomethylene-6-phenyloxindole (Procedure J-2)

6-Phenyloxindole (0.053 mg, 0.25 mmol) and dimethylformamide di-t-butylacetal (0.08 mL, 0.32 mmol) were combined and dissolved in DMF. The reaction mixture was stirred at room temperature for 4 hours. The volatiles were removed in vacuo and the resulting residue was triturated with diethyl ether. The solids were collected by filtration (50 mg, 75% yield). $^1$H NMR 400 MHz (DMSO-d6) mixture of E and Z isomers: δ 10.09 (s, 1H); 10.02 (s, 1H); 7.59–7.51 (m, 4H); 7.45–7.22 (m, 10H); 7.10–7.05 (m, 2H); 6.98 (s, 1H); 6.91 (s, 1H); 3.29 (s, 12H).

Monomer 1: 3-Ethoxymethylene-5-phenyl-7-azaoxindole

Synthesized according to Procedure J-1. $^1$H NMR 400 MHz (DMSO-d6) δ 10.93 (s, 1H); 8.24 (s, 1H); 7.86–7.82 (m, 2H); 7.62–7.56 (m, 2H); 7.44 (m, 2H); 7.34 (m, 1H); 4.40 (m, 2H); 1.35 (m, 3H).

Monomer 2: 3-Ethoxymethylene-5-(2-furanyl)-7-azaoxindole

Synthesized according to Procedure J-1. $^1$H NMR 400 MHz (DMSO-d6) δ 10.96 (s, 1H); 8.36 (s, 1H); 7.87–7.84 (m, 2H); 7.72 (s, 1H); 6.87 (d, 1H); 6.56 (m, 1H); 4.42 (m, 2H); 1.36 (m, 3H).

Monomer 3: 3-Ethoxymethylene-5-(3-thienyl)-7-azaoxindole

Synthesized according to Procedure J-1. $^1$H NMR 400 MHz (DMSO-d6) δ 10.89 (s, 1H); 8.33 (s, 1H); 7.88 (s, 1H); 7.84 (s, 1H); 7.79 (s, 1H); 7.62 (m, 1H); 7.49 (d, 1H); 4.40 (m, 2H); 1.36 (m, 3H).

Monomer 4: 5-Bromo-3-ethoxymethylene-7-azaoxindole

Synthesized according to Procedure J-1. $^1$H NMR 400 MHz (DMSO-d6) δ 11.02 (s, 1H); 8.07 (s, 1H); 7.88 (s, 1H); 7.71 (s, 1H); 4.40 (m, 2H); 1.34 (m, 3H).

Monomer 5: 6-Chloro-3-ethoxymethylene-7-azaoxindole

Synthesized according to Procedure J-1. $^1$H NMR 400 MHz (DMSO-d6) δ 11.06 (s, 1H); 7.84 (s, 1H); 7.63 (d, 1H); 6.98 (d, 1H); 4.39 (m, 2H); 1.32 (m, 3H).

Monomer 8: 3-Dimethylaminomethylene-6-(2-furanyl)oxindole

Synthesized according to Procedure J-2. $^1$H NMR 400 MHz (DMSO-d6) mixture of E and Z isomers: δ 10.10 (s, 1H); 10.03 (s, 1H); 7.64 (s, 1H); 7.61 (s, 1H); 7.56 (s, 1H); 7.38 (s, 1H); 7.37 (d, 1H); 7.26 (d, 1H); 7.14 (s, 1H); 7.12

(s, 1H); 7.03 (s, 1H); 6.96 (s, 1H); 6.72 (d, 1H); 6.67 (d, 1H); 6.52 (s, 1H); 6.49 (s, 1H); 3.29 (s, 12H)

Monomer 9: 3-Dimethylaminomethylene-7-azaoxindole

This monomer was generated in situ (during library synthesis) from 7-aza-oxindole and dimethylformamide di-t-butylacetal in DMF.

Monomer 10: 3-Dimethylaminomethylene-4-azaoxindole

This monomer was generated in situ (during library synthesis) from 4-aza-oxindole and dimethylformamide di-t-butylacetal in DMF.

Representative Amine Monomers are shown in Table 6.

| MONOMER CODE | STRUCTURE |
|---|---|
| A | 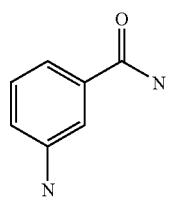 |
| B | 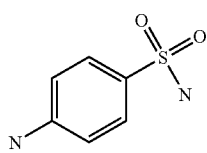 |
| C | 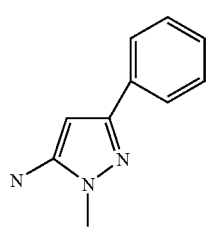 |
| D | 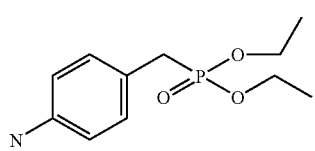 |
| E | 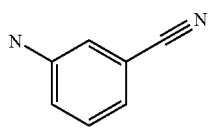 |
| F | 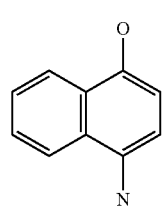 |
| G | 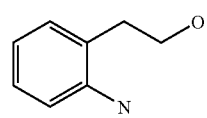 |

-continued

Representative Amine Monomers are shown in Table 6.

| MONOMER CODE | STRUCTURE |
|---|---|
| H | 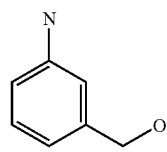 |
| I | 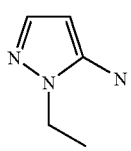 |
| J | 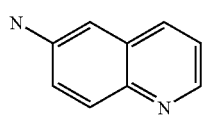 |
| K | 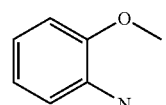 |
| L | 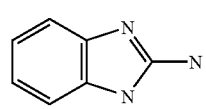 |
| M | 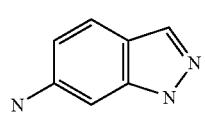 |
| N | 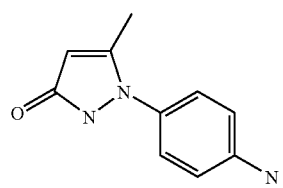 |
| O | 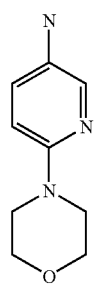 |
| P | 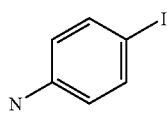 |

Solution Phase Library Synthesis:

Stock solutions (0.037M) were prepared for each set of monomers. For example, 35 mg of Monomer 1 was dissolved in 3.5 mL of ethanol. Each monomer was prepared in a separate solution and carefully labeled 1 through 8. For the amine set, a slight excess of stock solution was prepared. For example, 20.4 mg was dissolved in 4.0 mL of methanol. Each amine was prepared in a separate solution and carefully labeled A through P.

Monomer 9 and Monomer 10 were generated in situ by preparing stock solutions of the corresponding aza-oxindole. For example, 20.1 mg of 4-aza-oxindole was dissolved in 4.0 mL of ethanol. Both of the precursors for monomers 9 and 10 were transferred (0.20 ml/well) to a 96-well dry heating block (vwrBRAND Dry Block Heater, cat #13259-066) according to the map below where M represents the monomer and A represents the amine. The ethanol was evaporated off at 50° C. until it was clear that there was no solvent remaining. DMF (0.20 mL) was added followed by the addition of dimethylformamide di-t-butylacetal (0.003 mL) and this remained at room temperature for 1 hour.

Monomers 1 through 8 (0.20 mL/well) were transferred to the appropriate wells in the dry block heater according to the plate map below. After the in situ conversion of monomer 9 and 10 was complete, the aniline set (0.20 mL/well) was transferred to the appropriate wells according to the plate map below. The plates were heated to 70° C. for 4 hours and then the reaction was cooled to 40° C. and heating was continued for another 16 hours. Ethanol was added as necessary to keep a constant reaction volume in the wells.

Plate 1

| M1 | M1 | M2 | M2 | M3 | M3 | M4 | M4 | M5 | M5 |
|----|----|----|----|----|----|----|----|----|----|
| -A | -AI | — | -AI | — | -AI | — | -AI | — | -AI |
| A | AA | | AA | | AA | | AA | | |
| M1 | M1 | M2 | M2 | M3 | M3 | M4 | M4 | M5 | M5 |
| -A | -A | — | — | — | — | — | — | — | — |
| B | J | AB | AJ | AB | AJ | AB | AJ | AB | AJ |
| M1 | M1 | M2 | M2 | M3 | M3 | M4 | M4 | M5 | M5 |
| -A | -A | — | — | — | — | — | — | — | — |
| C | K | AC | AK | AC | AK | AC | AK | AC | AK |
| M1 | M1 | M2 | M2 | M3 | M3 | M4 | M4 | M5 | M5 |
| -A | -A | — | — | — | — | — | — | — | — |
| D | L | AD | AL | AD | AL | AD | AL | AD | AL |
| M1 | M1 | M2 | M2 | M3 | M3 | M4 | M4 | M5 | M5 |
| -A | -A | — | — | — | — | — | — | — | — |
| E | M | AE | AM | AE | AM | AE | AM | AE | AM |
| M1 | M1 | M2 | M2 | M3 | M3 | M4 | M4 | M5 | M5 |
| -A | -A | — | — | — | — | — | — | — | — |
| F | N | AF | AN | AF | AN | AF | AN | AF | AN |
| M1 | M1 | M2 | M2 | M3 | M3 | M4 | M4 | M5 | M5 |
| -A | -A | — | — | — | — | — | — | — | — |
| G | O | AG | AO | AG | AO | AG | AO | AG | AO |
| M1 | M1 | M2 | M2 | M3 | M3 | M4 | M4 | M5 | M5 |
| -A | -A | — | — | — | — | — | — | — | — |
| H | P | AH | AP | AH | AP | AH | AP | AH | AP |

Plate 2

| M6 | M6 | M7 | M- | M8 | M8 | M9 | M9 | M1 | M1 |
|----|----|----|----|----|----|----|----|----|----|
| — | -AI | — | 7A | — | -AI | — | -AI | 0- | 0- |
| AA | | AA | I | AA | | AA | | AA | AI |
| M6 | M6 | M7 | M7 | M8 | M8 | M9 | M9 | M1 | M1 |
| — | — | — | — | — | — | — | — | 0- | 0- |
| AB | AJ | AB | AJ | AB | AJ | AB | AJ | AB | AJ |
| M6 | M6 | M7 | M7 | M8 | M8 | M9 | M9 | M1 | M1 |
| — | — | — | — | — | — | AC | — | 0- | 0- |
| AC | AK | AC | AK | AC | AK | | AK | AC | AK |
| M6 | M6 | M7 | M7 | M8 | M8 | M9 | M9 | M1 | M1 |
| — | — | — | — | — | — | — | — | 0- | 0- |
| AD | AL | AD | AL | AD | AL | AD | AL | AD | AL |
| M6 | M6 | M7 | M7 | M8 | M8 | M9 | M9 | M1 | M1 |
| — | — | — | — | — | — | — | — | 0- | 0- |
| AE | AM | AE | AM | AE | AM | AE | AM | AE | AM |
| M6 | M6 | M7 | M7 | M8 | M8 | M9 | M9 | M1 | M1 |
| — | — | — | — | — | — | — | — | 0- | 0- |
| AF | AN | AF | AN | AF | AN | AF | AN | AF | AN |
| M6 | M6 | M7 | M7 | M8 | M8 | M9 | M9 | M1 | M1 |

-continued

| — | — | — | — | — | — | — | — | 0- | 0- |
|----|----|----|----|----|----|----|----|----|----|
| AG | AO | AG | AO | AG | AO | AG | AO | AG | AO |
| M6 | M6 | M7 | M7 | M8 | M8 | M9 | M9 | M1 | M1 |
| — | — | — | — | — | — | — | — | 0- | 0- |
| AH | AP | AH | AP | AH | AP | AH | AP | AH | AP |

Upon completion of the reaction, methanol (1.0 mL) was added to each well. Using a multi-pipettor, the contents of the reaction wells were transferred to the appropriate wells of a 96-well (Beckmann) plate. The volatiles were removed using a nitrogen flow to substantially reduce the volume of solvent, followed by placing the plates in a vacuum drying oven at 70° C. under 15 mmHg of pressure. The average weight of product determined for plate 1 was 1.91 mg/well (70% conversion). The average weight of product determined for plate 2 was 1.78 mg/mL (70% conversion). All of the wells were analysed by LC-MS.

A Micromass Platform II mass spectrometer equipped with an electrospray ion source was used to acquire low resolution LC-MS data for the samples. The system software runs on a PC computer with the Microsoft operating system, and consists of Masslynx v3.1 and Openlynx v3.1 software packages. The mass spectrometer inlet system was comprised of a Hewlett Packard 11100 HPLC Chromatograph, a Gilson 215 autosampler, and a Hewlett Packard 11100 photo-diode array detector. A Supelco ABZ+ 5 cm column was used to provide separations prior to electrospray ionization. The HPLC was programmed as follows:

| Time | % A | % B | Flow Rate |
|------|-----|-----|-----------|
| 0.0 min | 85 | 15 | 0.6 ml/min |
| 3.0 min | 25 | 75 | 0.6 ml/min |
| 4.0 min | 0 | 100 | 0.6 ml/min |
| 5.0 min | 0 | 100 | 0.6 ml/min |

The data were processed automatically using standard peak detection parameters provided by the Openlynx software.

A Micromass LCT bench-top mass spectrometer equipped with an electrospray ionization source was used to obtain accurate mass (high resolution) data. The LCT utilizes two hexapole RF lenses to transfer ions from the source to an orthogonal acceleration time-of-flight (TOF) analyser. The ions emerging from the analyser are detected using a dual microchannel plate detector and ion counting system. The system software runs on a PC computer with the Microsoft operating system, and consists of Masslynx v3.2 and Openlynx v3.2 software packages. The mass spectrometer inlet system is comprised of a Waters Alliance 2690 Separations Module, Waters 2700 autosampler, Waters 996 photo-diode array detector and Valco column switching device. A mobile phase flow rate of 1 ml/min exits the Alliance 2690 and is reduced to a mass spectrometer flow rate of 20 μl/min using an Acurate flow splitter. A lock mass solution at a flow rate of 4 μl/min is added to the spectrometer flow via a Harvard syringe pump and a tee piece placed immediately before the electrospray probe. The instrument resolution was determined by acquiring a spectrum and measuring the full peak width t half peak height (FWHH). The instrument was tuned to provide a resolution of 4600 to 5000 (FWHH). The instrument was calibrated using the ions of polyethylene glycol (PEG) as reference standards.

The lock mass used [3,5-DiI-Tyr, Ala, N-Me-Phe, Gly-01] Enkephalin (MH+ $C_{26}H_{34}I_2N_5O_6$=766.0599) at a concentration of 5 ng/µl.

The following Table lists examples of the invention prepared in the solution phase library with accompanying high resolution or low resolution mass spectral data.

| No. | IUPAC NAME | DATA |
|---|---|---|
| 73 | 3-{[(Z and E)-(2-Oxo-6-phenyl-1,2-dihydro-3H-indol-3-ylidene)methyl]amino}benzamide | Accurate mass M + H = 356.1388 (mmu error 1.0) |
| 74 | Diethyl 4-{[(Z and E)-(2-oxo-6-phenyl-1,2-dihydro-3H-indol-3-ylidene)methyl]amino}benzylphosphonate | Accurate mass M + H = 463.1952 (mmu error 3.4) |
| 75 | 3-{[(Z and E)-(2-Oxo-6-phenyl-1,2-dihydro-3H-indol-3-ylidene)methyl]amino}benzonitrile | Accurate mass M + H = 338.1289 (mmu error 0.3) |
| 76 | 3-{(Z and E)-[2-(2-Hydroxyethyl)anilino]-methylidene}-6-phenyl-1,3-dihydro-2H-indol-2-one | Accurate mass M + H = 357.1595 (mmu error 0.7) |
| 77 | 3-{(Z and E)-[3-(Hydroxymethyl)anilino]-methylidene}-6-phenyl-1,3-dihydro-2H-indol-2-one | Accurate mass M + H = 343.1438 (mmu error 0.7) |
| 78 | 3-[(Z and E)-(2-Methoxyanilino)methylidene]-6-phenyl-1,3-dihydro-2H-indol-2-one | Accurate mass M + H = 343.1442 (mmu error 0.3) |
| 79 | 3-{(Z and E)-[4-(5-Methyl-3-oxo-2,3-dihydro-1H-pyrazol-1-yl)anilino]methylidene}-6-phenyl-1H-indol-2-one | Accurate mass M + H = 409.1645 (mmu error 1.9) |
| 80 | 3-[(Z and E)-(4-Iodoanilino)methylidene]-6-phenyl-1H-indol-2-one | Accurate mass M + H = 439.0246 (mmu error 1.9) |
| 81 | 3-({(Z and E)-[6-(2-Furyl)-2-oxo-1,2-dihydro-3H-indol-3-ylidene]methyl}amino)benzamide | Accurate mass M + H = 346.1188 (mmu error 0.2) |
| 82 | Diethyl 4-({(Z and E)-[6-(2-furyl)-2-oxo-1,2-dihydro-3H-indol-3-ylidene]methyl}amino)-benzylphosphonate | Accurate mass M + H = 453.1755 (mmu error 2.3) |
| 83 | 3-({(Z and E)-[6-(2-Furyl)-2-oxo-1,2-dihydro-3H-indol-3-ylidene]methyl}amino)benzonitrile | LC-ES-MS (M + H) = 328 |
| 84 | 6-(2-Furyl)-3-{(Z and E)-[2-(2-hydroxyethyl)anilino]methylidene}-1,3-dihydro-2H-indol-2-one | Accurate mass M + H = 347.1377 (mmu error 1.7) |
| 85 | 6-(2-Furyl)-3-{(Z and E)-[3-(hydroxymethyl)anilino]methylidene}-1,3-dihydro-2H-indol-2-one | Accurate mass M + H = 333.1227 (mmu error 1.0) |
| 86 | 6-(2-Furyl)-3-[(Z and E)-(2-methoxyanilino)-methylidene]-1,3-dihydro-2H-indol-2-one | Accurate mass M + H = 333.1234 (mmu error 0.4) |
| 87 | 6-(2-Furyl)-3-{(Z and E)-[4-(5-methyl-3-oxo-2,3-dihydro-1H-pyrazol-1-yl)anilino]methylidene}-1H-indol-2-one | Accurate mass M + H = 399.1444 (mmu error 1.1) |
| 88 | 6-(2-Furyl)-3-[(Z and E)-(4-iodoanilino)-methylidene]-1H-indol-2-one | Accurate mass M + H = 429.0031 (mmu error 2.7) |
| 99 | 3-{[(2-Oxo-5-phenyl-1,2-dihydro-3H-pyrrolo[2,3-b]pyridin-3-ylidene)methyl]amino}benzamide | Accurate mass M + H = 357.1339 (mmu error 1.2) |
| 100 | Diethyl 4-{[(2-oxo-5-phenyl-1,2-dihydro-3H-pyrrolo[2,3-b]pyridin-3-ylidene)methyl]amino}-benzylphosphonate | Accurate mass M + H = 464.1918 (mmu error 2.0) |
| 101 | 3-{[(2-Oxo-5-phenyl-1,2-dihydro-3H-pyrrolo[2,3-b]pyridin-3-ylidene)methyl]amino}benzonitrile | Accurate mass M + H = 339.1237 (mmu error 0.8) |
| 102 | 3-{[2-(2-Hydroxyethyl)anilino]methylidene}-5-phenyl-1,3-dihydro-2H-pyrrolo[2,3-b]pyridin-2-one | Accurate mass M + H = 358.1534 (mmu error 2.1) |
| 103 | 3-{[3-(Hydroxymethyl)anilino]methylidene}-5-phenyl-1,3-dihydro-2H-pyrrolo[2,3-b]pyridin-2-one | Accurate mass M + H = 344.1377 (mmu error 2.1) |
| 104 | 3-[(2-Methoxyanilino)methylidene]-5-phenyl-1,3-dihydro-2H-pyrrolo[2,3-b]pyridin-2-one | Accurate mass M + H = 344.1386 (mmu error 1.2) |
| 105 | 3-{[4-(5-Methyl-3-oxo-2,3-dihydro-1H-pyrazol-1-yl)anilino]methylidene}-5-phenyl-1H-pyrrolo[2,3-b]pyridin-2-one | Accurate mass M + H = 410.1597 (mmu error 1.9) |
| 106 | 3-[(4-Iodoanilino)methylidene]-5-phenyl-1H-pyrrolo[2,3-b]pyridin-2-one | Accurate mass M + H = 440.0218 (mmu error 0.0) |

-continued

| No. | IUPAC NAME | DATA |
|---|---|---|
| 107 | 3-({[5-(2-Furyl)-2-oxo-1,2-dihydro-3H-pyrrolo[2,3-b]pyridin-3-ylidene]methyl}amino)benzamide | Accurate mass M + H = 347.1135 (mmu error 0.8) |
| 108 | Diethyl 4-({[5-(2-furyl)-2-oxo-1,2-dihydro-3H-pyrrolo[2,3-b]pyridin-3-ylidene]methyl}amino)benzylphosphonate | Accurate mass M + H = 454.1724 (mmu error 0.7) |
| 109 | 3-({[5-(2-Furyl)-2-oxo-1,2-dihydro-3H-pyrrolo[2,3-b]pyridin-3-ylidene]methyl}amino)benzonitrile | Accurate mass M + H = 329.1017 (mmu error 2.1) |
| 110 | 5-(2-Furyl)-3-{[2-(2-hydroxyethyl)anilino]methylidene}-1,3-dihydro-2H-pyrrolo[2,3-b]pyridin-2-one | Accurate mass M + H = 348.1333 (mmu error 1.4) |
| 111 | 5-(2-Furyl)-3-{[3-(hydroxymethyl)anilino]methylidene}-1,3-dihydro-2H-pyrrolo[2,3-b]pyridin-2-one | Accurate mass M + H = 334.1168 (mmu error 2.3) |
| 112 | 5-(2-Furyl)-3-[(2-methoxyanilino)methylidene]-1,3-dihydro-2H-pyrrolo[2,3-b]pyridin-2-one | Accurate mass M + H = 334.1177 (mmu error 1.4) |
| 113 | 5-(2-Furyl)-3-{[4-(5-methyl-3-oxo-2,3-dihydro-1H-pyrazol-1-yl)anilino]methylidene}-1H-pyrrolo[2,3-b]pyridin-2-one | Accurate mass M + H = 400.1394 (mmu error 1.5) |
| 114 | 5-(2-Furyl)-3-[(4-iodoanilino)methylidene]-1H-pyrrolo[2,3-b]pyridin-2-one | Accurate mass M + H = 430.0008 (mmu error 0.3) |
| 115 | 3-({[2-Oxo-5-(3-thienyl)-1,2-dihydro-3H-pyrrolo[2,3-b]pyridin-3-ylidene]methyl}amino)benzamide | Accurate mass M + H = 363.0903 (mmu error 1.2) |
| 116 | Diethyl 4-({[2-oxo-5-(3-thienyl)-1,2-dihydro-3H-pyrrolo[2,3-b]pyridin-3-ylidene]methyl}amino)benzylphosphonate | Accurate mass M + H = 470.1497 (mmu error 0.6) |
| 117 | 3-({[2-Oxo-5-(3-thienyl)-1,2-dihydro-3H-pyrrolo[2,3-b]pyridin-3-ylidene]methyl}amino)benzonitrile | Accurate mass M + H = 345.0800 (mmu error 0.9) |
| 118 | 3-{[2-(2-Hydroxyethyl)anilino]methylidene}-5-(3-thienyl)-1,3-dihydro-2H-pyrrolo[2,3-b]pyridin-2-one | Accurate mass M + H = 364.1098 (mmu error 2.1) |
| 119 | 3-{[3-(Hydroxymethyl)anilino]methylidene}-5-(3-thienyl)-1,3-dihydro-2H-pyrrolo[2,3-b]pyridin-2-one | Accurate mass M + H = 350.0959 (mmu error 0.4) |
| 120 | 3-[(2-Methoxyanilino)methylidene]-5-(3-thienyl)-1,3-dihydro-2H-pyrrolo[2,3-b]pyridin-2-one | Accurate mass M + H = 350.0946 (mmu error 1.7) |
| 121 | 3-{[4-(5-Methyl-3-oxo-2,3-dihydro-1H-pyrazol-1-yl)anilino]methylidene}-5-(3-thienyl)-1,3-dihydro-2H-pyrrolo[2,3-b]pyridin-2-one | Accurate mass M + H = 416.1172 (mmu error 0.8) |
| 122 | 3-[(4-Iodoanilino)methylidene]-5-(3-thienyl)-1H-pyrrolo[2,3-b]pyridin-2-one | Accurate mass M + H = 445.9771 (mmu error 1.2) |
| 123 | 3-{[(5-Bromo-2-oxo-1,2-dihydro-3H-pyrrolo[2,3-b]pyridin-3-ylidene)methyl]amino}benzamide | Accurate mass M + H = 359.0134 (mmu error 0.9) |
| 124 | Diethyl 4-{[(5-Bromo-2-oxo-1,2-dihydro-3H-pyrrolo[2,3-b]pyridin-3-ylidene)methyl]amino}benzylphosphonate | Accurate mass M + H = 466.0730 (mmu error 0.0) |
| 125 | 3-{[(5-Bromo-2-oxo-1,2-dihydro-3H-pyrrolo[2,3-b]pyridin-3-ylidene)methyl]amino}benzonitrile | Accurate mass M + H = 341.0033 (mmu error 0.4) |
| 126 | 5-Bromo-3-{[2-(2-hydroxyethyl)anilino]methylidene}-1,3-dihydro-2H-pyrrolo[2,3-b]pyridin-2-one | Accurate mass M + H = 360.0337 (mmu error 1.0) |
| 127 | 5-Bromo-3-{[3-(hydroxymethyl)anilino]methylidene}-1,3-dihydro-2H-pyrrolo[2,3-b]pyridin-2-one | Accurate mass M + H = 346.0176 (mmu error 1.4) |
| 128 | 5-Bromo-3-[(2-methoxyanilino)methylidene]-1,3-dihydro-2H-pyrrolo[2,3-b]pyridin-2-one | Accurate mass M + H = 346.0169 (mmu error 2.1) |
| 129 | 5-Bromo-3-{[4-(5-methyl-3-oxo-2,3-dihydro-1H-pyrazol-1-yl)anilino]methylidene}-1,3-dihydro-2H-pyrrolo[2,3-b]pyridin-2-one | Accurate mass M + H = 412.0388 (mmu error 2.0) |
| 130 | 5-Bromo-3-[(4-iodoanilino)methylidene]-1H-pyrrolo[2,3-b]pyridin-2-one | Accurate mass M + H = 441.9002 (mmu error 0.8) |
| 131 | 3-{[(6-Chloro-2-oxo-1,2-dihydro-3H-pyrrolo[2,3-b]pyridin-3-ylidene)methyl]amino}benzamide | Accurate mass M + H = 315.0633 (mmu error 1.5) |

-continued

| No. | IUPAC NAME | DATA |
|---|---|---|
| 132 | Diethyl 4-{[(6-chloro-2-oxo-1,2-dihydro-3H-pyrrolo[2,3-b]pyridin-3-ylidene)methyl]amino}benzylphosphonate | Accurate mass M + H = 422.1234 (mmu error 0.2) |
| 133 | 3-{[(6-Chloro-2-oxo-1,2-dihydro-3H-pyrrolo[2,3-b]pyridin-3-ylidene)methyl]amino}benzonitrile | Accurate mass M + H = 297.0532 (mmu error 1.0) |
| 134 | 6-Chloro-3-{[2-(2-hydroxyethyl)anilino]methylidene}-1,3-dihydro-2H-pyrrolo[2,3-b]pyridin-2-one | Accurate mass M + H = 316.0836 (mmu error 1.6) |
| 135 | 6-Chloro-3-{[3-(hydroxymethyl)anilino]methylidene}-1,3-dihydro-2H-pyrrolo[2,3-b]pyridin-2-one | Accurate mass M + H = 302.0683 (mmu error 1.3) |
| 136 | 6-Chloro-3-[(2-methoxyanilino)methylidene]-1,3-dihydro-2H-pyrrolo[2,3-b]pyridin-2-one | Accurate mass M + H = 302.0667 (mmu error 2.9) |
| 137 | 6-Chloro-3-{[4-(5-methyl-3-oxo-2,3-dihydro-1H-pyrazol-1-yl)anilino]methylidene}-1,3-dihydro-2H-pyrrolo[2,3-b]pyridin-2-one | Accurate mass M + H = 368.0894 (mmu error 1.9) |
| 138 | 6-Chloro-3-[(4-iodoanilino)methylidene]-1H-pyrrolo[2,3-b]pyridin-2-one | Accurate mass M + H = 397.9504 (mmu error 1.2) |
| 139 | Ethyl 3-{[3-(aminocarbonyl)anilino]methylidene}-2-oxo-2,3-dihydro-1H-pyrrolo[2,3-b]pyridine-5-carboxylate | Accurate mass M + H = 353.1242 (mmu error 0.7) |
| 140 | Ethyl 3-({4-[(diethoxyphosphoryl)methyl]anilino}methylidene)-2-oxo-1,2-dihydro-3H-pyrrolo[2,3-b]pyridine-5-carboxylate | Accurate mass M + H = 460.1826 (mmu error 1.0) |
| 141 | Ethyl 3-[(3-cyanoanilino)methylidene]-2-oxo-2,3-dihydro-1H-pyrrolo[2,3-b]pyridine-5-carboxylate | Accurate mass M + H = 335.1127 (mmu error 1.6) |
| 142 | Ethyl 3-{[2-(2-hydroxyethyl)anilino]methylidene}-2-oxo-2,3-dihydro-1H-pyrrolo[2,3-b]pyridine-5-carboxylate | Accurate mass M + H = 354.1434 (mmu error 1.9) |
| 143 | Ethyl 3-{[3-(hydroxymethyl)anilino]methylidene}-2-oxo-2,3-dihydro-1H-pyrrolo[2,3-b]pyridine-5-carboxylate | Accurate mass M + H = 340.1287 (mmu error 0.9) |
| 144 | Ethyl 3-[(2-methoxyanilino)methylidene]-2-oxo-2,3-dihydro-1H-pyrrolo[2,3-b]pyridine-5-carboxylate | Accurate mass M + H = 340.1285 (mmu error 1.1) |
| 145 | Ethyl 3-{[4-(5-methyl-3-oxo-2,3-dihydro-1H-pyrazol-1-yl)anilino]methylidene}-2-oxo-1,2-dihydro-3H-pyrrolo[2,3-b]pyridine-5-carboxylate | Accurate mass M + H = 406.1499 (mmu error 1.5) |
| 146 | Ethyl 3-[(4-iodoanilino)methylidene]-2-oxo-1,2-dihydro-3H-pyrrolo[2,3-b]pyridine-5-carboxylate | Accurate mass M + H = 436.0103 (mmu error 1.3) |
| 147 | 3-{[(2-Oxo-1,2-dihydro-3H-pyrrolo[2,3-b]pyridin-3-ylidene)methyl]amino}benzamide | Accurate mass M + H = 281.1024 (mmu error 1.4) |
| 148 | Diethyl 4-{[(2-oxo-1,2-dihydro-3H-pyrrolo[2,3-b]pyridin-3-ylidene)methyl]amino}benzyl phosphonate | Accurate mass M + H = 388.1607 (mmu error 1.8) |
| 149 | 3-{[(2-Oxo-1,2-dihydro-3H-pyrrolo[2,3-b]pyridin-3-ylidene)methyl]amino}benzonitrile | Accurate mass M + H = 263.0923 (mmu error 0.9) |
| 150 | 3-{[2-(2-Hydroxyethyl)anilino]methylidene}-1,3-dihydro-2H-pyrrolo[2,3-b]pyridin-2-one | Accurate mass M + H = 282.1229 (mmu error 1.2) |
| 151 | 3-{[3-(Hydroxymethyl)anilino]methylidene}-1,3-dihydro-2H-pyrrolo[2,3-b]pyridin-2-one | Accurate mass M + H = 268.1082 (mmu error 0.3) |
| 152 | 3-[(2-Methoxyanilino)methylidene]-1,3-dihydro-2H-pyrrolo[2,3-b]pyridin-2-one | Accurate mass M + H = 268.1082 (mmu error 0.3) |
| 153 | 3-{[4-(5-Methyl-3-oxo-2,3-dihydro-1H-pyrazol-1-yl)anilino]methylidene}-1H-pyrrolo[2,3-b]pyridin-2-one | Accurate mass M + H = 334.1301 (mmu error 0.2) |
| 154 | 3-[(4-Iodoanilino)methylidene]-1H-pyrrolo[2,3-b]pyridin-2-one | Accurate mass M + H = 363.9898 (mmu error 0.7) |
| 155 | 3-{[(2-Oxo-1,2-dihydro-3H-pyrrolo[3,2-b]pyridin-3-ylidene)methyl]amino}benzamide | Accurate mass M + H = 281.1035 (mmu error 0.3) |

| No. | IUPAC NAME | DATA |
|---|---|---|
| 156 | Diethyl 4-{[(2-oxo-1,2-dihydro-3H-pyrrolo[3,2-b]pyridin-3-ylidene)methyl]amino}benzyl phosphonate | LC-ES-MS (M + H) = 388 |
| 157 | 3-{[(2-Oxo-1,2-dihydro-3H-pyrrolo[3,2-b]pyridin-3-ylidene)methyl]amino}benzonitrile | Accurate mass M + H = 263.0912 (mmu error 2.0) |
| 158 | 3-{[2-(2-Hydroxyethyl)anilino]methylidene}-1,3-dihydro-2H-pyrrolo[3,2-b]pyridin-2-one | Accurate mass M + H = 282.1241 (mmu error 0.0) |
| 159 | 3-{[3-(Hydroxymethyl)anilino]methylidene}-1,3-dihydro-2H-pyrrolo[3,2-b]pyridin-2-one | Accurate mass M + H = 268.1079 (mmu error 0.6) |
| 160 | 3-[(2-Methoxyanilino)methylidene]-1,3-dihydro-2H-pyrrolo[3,2-b]pyridin-2-one | Accurate mass M + H = 268.1083 (mmu error 0.2) |
| 161 | 3-{[4-(5-Methyl-3-oxo-2,3-dihydro-1H-pyrazol-1-yl)anilino]methylidene}-1H-pyrrolo[3,2-b]pyridin-2-one | Accurate mass M + H = 334.1301 (mmu error 0.2) |
| 162 | 3-[(4-Iodoanilino)methylidene]-1H-pyrrolo[3,2-b]pyridin-2-one | Accurate mass M + H = 363.9896 (mmu error 0.9) |
| 163 | 3-{(Z and E)-[(1-methyl-3-phenyl-1H-pyrazol-5-yl)amino]methylidene}-5-phenyl-1,3-dihydro-2H-pyrrolo[2,3-b]pyridin-2-one | Accurate mass M + H = 394.1645 (mmu error 2.2) |
| 164 | 3-{(Z and E)-[(4-Hydroxy-1-naphthyl)amino]-methylidene}-5-phenyl-1,3-dihydro-2H-pyrrolo[2,3-b]pyridin-2-one | Accurate mass M + H = 380.1388 (mmu error 1.0) |
| 165 | 3-{(Z and E)-[(1-Ethyl-1H-pyrazol-5-yl)amino]-methylidene}-5-phenyl-1,3-dihydro-2H-pyrrolo[2,3-b]pyridin-2-one | Accurate mass M + H = 332.1508 (mmu error 0.3) |
| 166 | 3-[(Z and E)-(1H-Benzimidazol-2-ylamino)-methylidene]-5-phenyl-1H-pyrrolo[2,3-b]pyridin-2-one | Accurate mass M + H = 354.1336 (mmu error 1.8) |
| 167 | 3-((Z and E)-{[6-(4-Morpholinyl)-3-pyridinyl]-amino}methylidene)-5-phenyl-1,3-dihydro-2H-pyrrolo[2,3-b]pyridin-2-one | Accurate mass M + H = 400.1754 (mmu error 1.9) |
| 168 | 5-(2-Furyl)-3-{(Z and E)-[(1-methyl-3-phenyl-1H-pyrazol-5-yl)amino]methylidene}-1,3-dihydro-2H-pyrrolo[2,3-b]pyridin-2-one | Accurate mass M + H = 384.1455 (mmu error 0.5) |
| 169 | 5-(2-Furyl)-3-{(Z and E)-[(4-hydroxy-1-naphthyl)amino]methylidene}-1,3-dihydro-2H-pyrrolo[2,3-b]pyridin-2-one | Accurate mass M + H = 370.1189 (mmu error 0.2) |
| 170 | 3-{(Z and E) [(1-Ethyl-1H-pyrazol-5-yl)amino]-methylidene}-5-(2-furyl)-1,3-dihydro-2H-pyrrolo[2,3-b]pyridin-2-one | Accurate mass M + H = 322.1297 (mmu error 0.6) |
| 171 | 3-[(Z and E)-(1H-Benzimidazol-2-ylamino)-methylidene]-5-(2-furyl)-1H-pyrrolo[2,3-b]pyridin-2-one | LC-ES-MS (M + H) = 344 |
| 172 | 5-(2-Furyl)-3-((Z and E)-{[6-(4-morpholinyl)-3-pyridinyl]amino}methylidene)-1,3-dihydro-2H-pyrrolo[2,3-b]pyridin-2-one | Accurate mass M + H = 390.1556 (mmu error 0.9) |
| 173 | 3-{(Z and E)-[(1-Methyl-3-phenyl-1H-pyrazol-5-yl)amino]methylidene}-5-(3-thienyl)-1,3-dihydro-2H-pyrrolo[2,3-b]pyridin-2-one | Accurate mass M + H = 400.1231 (mmu error 0.0) |
| 174 | 3-{(Z and E)-[(4-Hydroxy-1-naphthyl)amino]-methylidene}-5-(3-thienyl)-1,3-dihydro-2H-pyrrolo[2,3-b]pyridin-2-one | Accurate mass M + H = 386.0960 (mmu error 0.3) |
| 175 | 3-{(Z and E)-[(1-Ethyl-1H-pyrazol-5-yl)amino]-methylidene}-5-(3-thienyl)-1,3-dihydro-2H-pyrrolo[2,3-b]pyridin-2-one | Accurate mass M + H = 338.1060 (mmu error 1.5) |
| 176 | 3-[(Z and E)-(1H-Benzimidazol-2-ylamino)-methylidene]-5-(3-thienyl)-1,3-dihydro-2H-pyrrolo[2,3-b]pyridin-2-one | Accurate mass M + H = 360.0915 (mmu error 0.3) |
| 177 | 3-((Z and E)-{[6-(4-Morpholinyl)-3-pyridinyl]amino}methylidene)-5-(3-thienyl)-1,3-dihydro-2H-pyrrolo[2,3-b]pyridin-2-one | Accurate mass M + H = 406.1321 (mmu error 1.6) |
| 178 | 5-Bromo-3-{(Z and E)-[(1-methyl-3-phenyl-1H-pyrazol-5-yl)amino]methylidene}-1,3-dihydro-2H-pyrrolo[2,3-b]pyridin-2-one | Accurate mass M + H = 396.0442 (mmu error 1.7) |
| 179 | 5-Bromo-3-{(Z and E)-[(4-hydroxy-1-naphthyl)-amino]methylidene}-1,3-dihydro-2H-pyrrolo[2,3-b]pyridin-2-one | Accurate mass M + H = 382.0187 (mmu error 0.3) |
| 180 | 5-Bromo-3-{(Z and E)-[(1-ethyl-1H-pyrazol-5-yl)amino]methylidene}-1,3-dihydro-2H-pyrrolo[2,3-b]pyridin-2-one | Accurate mass M + H = 334.0297 (mmu error 0.5) |

-continued

| No. | IUPAC NAME | DATA |
|---|---|---|
| 181 | 3-[(Z and E)-(1H-Benzimidazol-2-ylamino)-methylidene]-5-bromo-1,3-dihydro-2H-pyrrolo[2,3-b]pyridin-2-one | Accurate mass M + H = 356.0134 (mmu error 1.2) |
| 182 | 5-Bromo-3-((Z and E)-{[6-(4-morpholinyl)-3-pyridinyl]amino}methylidene)-1,3-dihydro-2H-pyrrolo[2,3-b]pyridin-2-one | Accurate mass M + H = 402.0556 (mmu error 0.8) |
| 183 | 6-Chloro-3-{(Z and E)-[(1-methyl-3-phenyl-1H-pyrazol-5-yl)amino]methylidene}-1,3-dihydro-2H-pyrrolo[2,3-b]pyridin-2-one | Accurate mass M + H = 352.0957 (mmu error 0.7) |
| 184 | 6-Chloro-3-{(Z and E)-[(4-hydroxy-1-naphthyl)amino]methylidene}-1,3-dihydro-2H-pyrrolo[2,3-b]pyridin-2-one | Accurate mass M + H = 338.0669 (mmu error 2.7) |
| 185 | 6-Chloro-3-{(Z and E)-[(1-ethyl-1H-pyrazol-5-yl)amino]methylidene}-1,3-dihydro-2H-pyrrolo[2,3-b]pyridin-2-one | Accurate mass M + H = 290.0808 (mmu error 0.0) |
| 186 | 3-[(Z and E)-(1H-Benzimidazol-2-ylamino)-methylidene]-6-chloro-1,3-dihydro-2H-pyrrolo[2,3-b]pyridin-2-one | Accurate mass M + H = 312.0633 (mmu error 1.8) |
| 187 | 6-Chloro-3-((Z and E)-{[6-(4-morpholinyl)-3-pyridinyl]amino}methylidene)-1,3-dihydro-2H-pyrrolo[2,3-b]pyridin-2-one | Accurate mass M + H = 358.1053 (mmu error 1.7) |
| 188 | Ethyl 3-{(Z and E)-[(1-methyl-3-phenyl-1H-pyrazol-5-yl)amino]methylidene}-2-oxo-2,3-dihydro-1H-pyrrolo[2,3-b]pyridine-5-carboxylate | Accurate mass M + H = 390.1556 (mmu error 0.9) |
| 189 | Ethyl 3-{(Z and E)-[(4-hydroxy-1-naphthyl)-amino]methylidene}-2-oxo-2,3-dihydro-1H-pyrrolo[2,3-b]pyridine-5-carboxylate | Accurate mass M + H = 376.1289 (mmu error 0.7) |
| 190 | Ethyl 3-{(Z and E)-[(1-ethyl-1H-pyrazol-5-yl)amino]methylidene}-2-oxo-2,3-dihydro-1H-pyrrolo[2,3-b]pyridine-5-carboxylate | Accurate mass M + H = 328.1403 (mmu error 0.5) |
| 191 | Ethyl 3-[(Z and E)-(1H-benzimidazol-2-ylamino)methylidene]-2-oxo-1,2-dihydro-3H-pyrrolo[2,3-b]pyridine-5-carboxylate | Accurate mass M + H = 350.1241 (mmu error 1.1) |
| 192 | Ethyl 3-((Z and E)-{[6-(4-morpholinyl)-3-pyridinyl]amino}methylidene)-2-oxo-2,3-dihydro-1H-pyrrolo[2,3-b]pyridine-5-carboxylate | Accurate mass M + H = 396.1655 (mmu error 1.6) |
| 193 | 3-{(Z and E)-[(1-Methyl-3-phenyl-1H-pyrazol-5-yl)amino]methylidene}-6-phenyl-1,3-dihydro-2H-indol-2-one | Accurate mass M + H = 393.1691 (mmu error 2.3) |
| 194 | 3-{(Z and E)-[(4-Hydroxy-1-naphthyl)amino]methylidene}-6-phenyl-1,3-dihydro-2H-indol-2-one | Accurate mass M + H = 379.1430 (mmu error 1.5) |
| 195 | 3-{(Z and E)-[(1-Ethyl-1H-pyrazol-5-yl)amino]methylidene}-6-phenyl-1,3-dihydro-2H-indol-2-one | Accurate mass M + H = 331.1552 (mmu error 0.6) |
| 196 | 3-[(Z and E)-(1H-Benzimidazol-2-ylamino)methylidene]-6-phenyl-1H-indol-2-one | Accurate mass M + H = 353.1388 (mmu error 1.4) |
| 197 | 3-((Z and E)-{[6-(4-Morpholinyl)-3-pyridinyl]amino}methylidene)-6-phenyl-1,3-dihydro-2H-indol-2-one | Accurate mass M + H = 399.1809 (mmu error 1.1) |
| 198 | 6-(2-Furyl)-3-{(Z and E)-[(1-methyl-3-phenyl-1H-pyrazol-5-yl)amino]methylidene}-1,3-dihydro-2H-indol-2-one | Accurate mass M + H = 383.1498 (mmu error 0.9) |
| 199 | 6-(2-Furyl)-3-{(Z and E)-[(4-hydroxy-1-naphthyl)amino]methylidene}-1,3-dihydro-2H-indol-2-one | |
| 200 | 3-{(Z and E)-[(1-Ethyl-1H-pyrazol-5-yl)amino]methylidene}-6-(2-furyl)-1,3-dihydro-2H-indol-2-one | Accurate mass M + H = 321.1342 (mmu error 0.8) |
| 201 | 3-[(Z and E)-(1H-Benzimidazol-2-ylamino)methylidene]-6-(2-furyl)-1H-indol-2-one | Accurate mass M + H = 343.1192 (mmu error 0.2) |
| 202 | 6-(2-Furyl)-3-((Z and E)-{[6-(4-morpholinyl)-3-pyridinyl]amino}methylidene)-1,3-dihydro-2H-indol-2-one | Accurate mass M + H = 389.1604 (mmu error 0.8) |
| 203 | 3-{(Z and E)-[(1-Methyl-3-phenyl-1H-pyrazol-5-yl)amino]methylidene}-1,3-dihydro-2H-pyrrolo[2,3-b]pyridin-2-one | Accurate mass M + H = 318.1347 (mmu error 0.6) |
| 204 | 3-{(Z and E)-[(4-Hydroxy-1-naphthyl)amino]methylidene}-1,3-dihydro-2H-pyrrolo[2,3-b]pyridin-2-one | |
| 205 | 3-{(Z and E)-[(1-Ethyl-1H-pyrazol-5-yl)amino]methylidene}-1,3-dihydro-2H-pyrrolo[2,3-b]pyridin-2-one | Accurate mass M + H = 256.1195 (mmu error 0.2) |

-continued

| No. | IUPAC NAME | DATA |
|---|---|---|
| 206 | 3-[(Z and E)-(1H-Benzimidazol-2-ylamino)-methylidene]-1H-pyrrolo[2,3-b]pyridin-2-one | |
| 207 | 3-((Z and E)-{[6-(4-Morpholinyl)-3-pyridinyl]-amino}methylidene)-1,3-dihydro-2H-pyrrolo[2,3-b]pyridin-2-one | Accurate mass M + H = 324.1453 (mmu error 0.7) |
| 208 | 3-{(Z and E)-[(1-Methyl-3-phenyl-1H-pyrazol-5-yl)amino]methylidene}-1,3-dihydro-2H-pyrrolo[3,2-b]pyridin-2-one | Accurate mass M + H = 318.1347 (mmu error 0.7) |
| 209 | 3-{(Z and E)-[(4-Hydroxy-1-naphthyl)amino]-methylidene}-1,3-dihydro-2H-pyrrolo[3,2-b]pyridin-2-one | |
| 210 | 3-{(Z and E)-[(1-Ethyl-1H-pyrazol-5-yl)amino]-methylidene}-1,3-dihydro-2H-pyrrolo[3,2-b]pyridin-2-one | Accurate mass M + H = 256.1178 (mmu error 1.9) |
| 211 | 3-[(Z and E)-(1H-Benzimidazol-2-ylamino)-methylidene]-1H-pyrrolo[3,2-b]pyridin-2-one | |
| 212 | 3-((Z and E)-{[6-(4-Morpholinyl)-3-pyridinyl]amino}methylidene)-1,3-dihydro-2H-pyrrolo[3,2-b]pyridin-2-one | Accurate mass M + H = 324.1449 (mmu error 1.0) |

Although it is preferred to administer the CDK2 inhibitor agents in the practice of the present invention via topical application to susceptible skin areas for preventing/reducing the severity of alopecia incident to chemotherapy and/or radiation therapy, and via mouthwash formulation or lozenge for preventing/reducing the severity of mucositis incident to chemotherapy and/or radiation therapy, the CDK2 inhibitor agents in the practice of the invention can be otherwise administered in oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to combat the alopecia and/or mucositis condition.

Oral dosages of the present invention, when used for the indicated effects, will range between about 0.01 to about 100 mg/kg of body weight per day, and particularly about 0.1 to 10 mg/kg of body weight per day. Oral dosage units will generally be administered in the range of from 0.1 to about 250 mg and more preferably from about 25 to about 250 mg. The daily dosage for a 70 kg mammal will generally be in the range of about 70 mg to 7 grams of a compound of the present invention.

The dosage to be administered is based on the usual conditions such as the physical condition of the patient, age, body weight, past medical history, route of administrations, severity of the conditions and the like. In some cases, a relatively lower dose is sufficient and, in some cases, a relatively higher dose or increased number of doses may be necessary. Topical application may be once or more than once per day depending on the course of chemotherapy and/or radiation therapy treatment. Advantageously, compounds of the present invention may be administered in a single daily dose, or the total daily dosage may be administered in divided doses of two, three or four times daily.

The compounds of the invention can be prepared in a range of concentrations for topical use of about 0.1 to about 5 mg/ml of suitable solvent. A preferred volume for application to the scalp is about 2 to 20 ml, resulting in an effective dosage delivered to the patient of about 0.2 to about 100 mg.

For treatment of chemotherapy-induced alopecia, administration 1 to 2 times prior to chemotherapy administration is preferred, with additional applications administered as needed. A similar regimen can be pursued for treatment of alopecia induced by radiation therapy. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing about 0.01 to about 99.5%, more particularly, about 0.5 to about 90% of a kinase inhibitor in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The inhibitory activity of various illustrative compounds was determined against CDK2 kinase, as well as against other kinases for comparison purposes (VEGFR2, Tie-2, and c-fms) by the assay techniques described below.

VEGFR-2

The peptide substrate used in the VEGFR-2 assay was biotin-aminohexyl-EEEEYFELVAKKKK-NH$_2$. The kinase domain of the enzyme was purified to homogeneity from a baculovirus expression system. The enzyme was preactivated on ice for 15 min in the presence of 100 µM ATP and 20 mM MgCl$_2$, and stored at −80° C. until needed for assay. The activated enzyme was diluted to 0.4 nM into a 60 µl reaction containing 100 mM HEPES, pH 7.5, 5 µM ATP, 10 mM MgCl$_2$, 5 µM peptide, 0.1 mM DTT, 0.05 mg/ml BSA, and an inhibitor at varying concentrations. The controls were reactions in the presence (negative controls) or absence (positive controls) of 50 mM EDTA. Reactions were incubated for 30 min at room temperature, and then quenched by the addition of EDTA to 60 mM in 210 µl. The quenched samples (190 µl) were transferred to a neutravidin-coated plate (Pierce) and incubated at room temperature for 40 min to allow biotinylated peptide to bind to the neutravidin. The unbound components of the reaction were removed by washing with a plate washer, then 200 µl HRP-PY20 anti-phosphotyrosine antibody conjugate was added to each well. After incubation for 40 min, the plate was washed to remove any unbound anitbody. A HRP substrate, K-blue (Neogen) was added and the reaction was quenched with Red Stop (Neogen) after 20 min. The absorbance of the wells was read at $A_{650}$ in a plate reader. IC$_{50}$ values were obtained by fitting raw data to $A_{650}=V_{MAX}*(1-[I]/IC_{50}+[I])))+b$, where b is background.

CDK1 and CDK2

Cyclin dependent protein kinase assays utilized the peptides Biotin-aminohexyl-MKAKKTPKKAKK and Biotin-aminohexyl-ARRPMSPKKKA-NH$_2$ as phosphoryl group acceptors. CDK1 and CDK2 were both expressed utilizing a baculovirus expression system and were partially purified to comprise 20–80% of total protein, with no detectable competing reactions present. Typically, assays were performed by incubating either enzyme (0.2–10 nM), with and without inhibitor, one of the two peptide substrates (1–10 nM), [γ-$^{32}$P]ATP (1–20 nM), and 10–20 mM Mg$^{2+}$ for periods of time generally within the range 10–120 min. Reactions were terminated with 0.2–2 volumes of either 20% acetic acid or 50–100 mM EDTA buffered to pH 7 (substrate consumption<20%). The buffer employed in enzyme assays was either 30 mM HEPES 7.4 containing 0.15 M NaCl and 5% DMSO, the buffer 50 mM MOPS 7.0 containing 0.15 M NaCl and 5% DMSO, or the buffer 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM=V$_{max}$*(1−([I]/(K+[I])))+nsb, or pIC50s were determined by a fit to the equation CPM=nsb+(V$_{max}$−nsb)/(1+(x/10$^x$−pIC50)), where nsb are the background counts.

Tie-2

The peptide substrate used in the Tie-2 assay was biotin-aminohexyl-LEAREYRWLGGKKKamide. The kinase domain of the enzyme was purified to homogeneity from a baculovirus expression system. The enzyme was diluted to 10 nM into a 60 µl reaction containing 100 mM HEPES, pH 7.5, 500 µM ATP, 10 mM MgCl$_2$, 2 µM peptide, 1 mM DTT, 0.05 mg/ml BSA, and an inhibitor at varying concentrations. The controls were reactions in the presence (negative controls) or absence (positive controls) of 50 mM EDTA. Reactions were incubated for 30 min at room temperature, and then quenched by stopped by 80 µl of 0.15 M EDTA. The quenched samples (125 µl) were transferred to a Neutravidin plates # 15128 and incubated at room temperature for 30–60 minutes, allowing the biotinylated peptide to bind to the neutravidin on the plates. The neutravidin plates were then washed with water for 5 times. Europium conjugated anti-phosphotyrosine antibody, (EG & G Wallac, # CR04-100) (1 mg/ml) was diluted 1:10,000 in 1% BSA-0.05% Tween 20-TBS, and 150 µl of the diluted antibody was added to each well of the neutravidin plate, so the phosphorylated peptide was bound with the Europium labelled antibody. After another 30–60 min incubation at room temperature, the plates were washed again with water for 5 times. 150 ul of Enhancemant solution was then added to each well, dissociating Eu$^{3+}$ from solid phase bound antibodies to form a homogeneous and highly fluorescent Eu-(2-NTA)$_3$(TOPO)$_{2-3}$ micellar chelate solution. The plates were incubated for 10 minutes at room temperature to allow the above process, and fluorescent signal for each well was determined in a Wallac 1420 Victor Multilabel Counter with "Europium" protocol.

The kinase activity of all wells was calculated as % S, the percentage of the fluorescent counts vs. positive controls after substraction of negative controls, as in eq. 1.

$$\% \ S = 100 * \frac{Counts_{sample} - Counts_{negative}}{Counts_{positive} - Counts_{negative}} \quad (1)$$

Plots of compound concentration versus % S were constructed. IC50s (K, expressed in units of molarity), the compound concentration at which the enzyme activity was inhibited by 50%, were determined from nonlinear least squares fits of the data to the simple competitive binding model of eq. 2.

$$\% \ S = \% \ S_{max}*(1-(X/(K+X)))+Y2 \quad (2)$$

Where % S is the experimentally observed count rate at sample compound concentration X, % S$_{max}$ is the best fit value for the maximum amplitude of the concentration-response curve, Y$_2$ is the count rate observed at infinitely high inhibitor concentration.

c-Fms c-fms protein kinase assays utilized the peptide substrate, biotin-EAIYAAPFAKKK-NH$_2$, as the phosphoryl group acceptor. The c-fms intracellular domain was expressed from a baculovirus expression system, as an amino-terminal GST fusion protein, and purified to homogeneity using Glutathione agarose from Sigma Chemical Co. Maximum activation of the enzyme was achieved by preactivation at room temperature for 120 min in the presence of 100 µM ATP and 15 mM MgCl$_2$, This enzyme stock was diluted to 150 nM prior to using in the assay. Typically assays were performed in white, opaque, 96-well plates in a 45 ul assay volume including 15 ul 6% DMSO, with or without compounds, 15 ul of the preactivated, diluted enzyme, and 15 ul of a substrate mixture. Reactions contained 50 mM HEPES, pH 7.5, 1.7 μM ATP, 15 mM MgCl$_2$, 3 μM peptide, 2.5 mM DTT, 50 mM NaCl and 0.15 uCi/assay [$^{32}$P]ATP. The controls were reactions in the presence (negative controls) or absence (positive controls) of 50 mM EDTA. Reactions were allowed to proceed for 90 min at room temperature. The reaction products were quantified using Scintillation Proximity technolgy. The reactions were quenched by the addition of 200 ul of a solution containing 0.3 mg streptavidin SPA beads from Amersham, 50 mM EDTA, 0.1% TX-100, 50 uM ATP, in PBS, pH 7.2 (phosphate buffered solution). Plates were sealed and counted in a Packard Topcount scintillation counter. IC50 values were obtained by fitting raw data to the equation $$y = V\max*(1-(x/(k+x))).$$

The results shown in Table 7 illustrate the inhibitory activity of illustrative compounds against CDK2 as well as (for comparison) several other kinases (VEGFR2, Tie-2, and c-fms).

TABLE 7

Kinase inhibition data of representative compounds

| Compound | VEGFR2 | CDK2 | Tie-2 | c-fms |
|---|---|---|---|---|
| Example 24 | +++ | ++ | + | + |
| Example 29 | +++ | + | + | + |
| Example 30 | +++ | +++ | + | + |
| Example 32 | +++ | ++ | + | + |
| Example 48 | ++++ | +++ | + | + |
| Example 55 | ++++ | +++ | + | + |
| Example 58 | +++ | +++ | + | |
| Example 63 | ++++ | | + | |
| Example 66 | ++++ | | + | |
| Example 71 | +++ | | + | |
| Example 72 | ++++ | | + | |

Key (IC$_{50}$, nM)
1–10: ++++
11–50: +++
51–100: ++
>100: +

Another category of compositions including CDK2 inhibitor compounds that may be usefully employed in the practice of the invention include compounds of the formula (F):

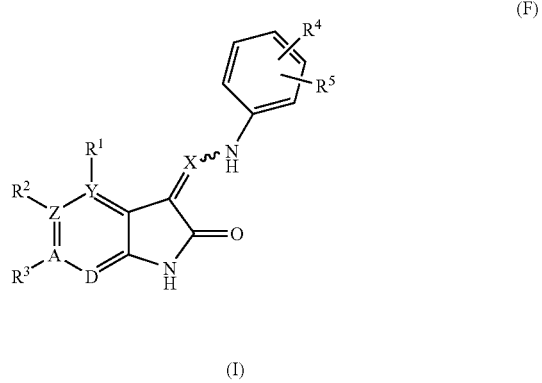

(F)

wherein
X is selected from the group consisting of: N, CH, CCF$_3$, and C(C$_{1-12}$ aliphatic);

Y is C or N, with the proviso that when Y is N, R$^1$ is absent, and Z, A and D are each C;

Z is C or N, with the proviso that when Z is N, R$^2$ is absent, and Y, A and D are each C;

A is C or N, with the proviso that when A is N, R$^3$ is absent, and Y, Z and D are each C;

D is C or N, with the proviso that when D is N, then Y, Z and A are each C;

R$^1$ is selected from the group consisting of: hydrogen, C$_{1-12}$ aliphatic, thiol, hydroxy, hydroxy-C$_{1-12}$ aliphatic, Aryl, Aryl-C$_{1-12}$ aliphatic, R$^6$-Aryl-C$_{1-12}$ aliphatic, Cyc, Cyc-C$_{1-6}$ aliphatic, Het, Het-C$_{1-12}$ aliphatic, C$_{1-12}$ alkoxy, Aryloxy, amino, C$_{12}$ aliphatic amino, di-C$_{1-12}$ aliphatic amino, di-C$_{1-12}$ aliphatic aminocarbonyl, di-C$_{1-12}$ aliphatic aminosulfonyl, C$_{1-12}$ alkoxycarbonyl, halogen, cyano, sulfonamide and nitro, where R$^6$, Aryl, Cyc and Het are as defined below;

R$^2$ is selected from the group consisting of: hydrogen, C$_{1-12}$ aliphatic, N-hydroxyimino-C$_{1-12}$ aliphatic, C$_{1-12}$ alkoxy, hydroxy-C$_{1-12}$ aliphatic, C$_{12}$ alkoxycarbonyl, carboxyl C$_{1-12}$ aliphatic, Aryl, R$^6$-Aryl-oxycarbonyl, R$^6$-oxycarbonyl-Aryl, Het, aminocarbonyl, C$_{1-12}$ aliphatic-aminocarbonyl, Aryl-C$_{1-12}$ aliphatic-aminocarbonyl, R$^6$-Aryl-C$_{1-12}$ aliphatic-aminocarbonyl, Het-C$_{1-12}$ aliphatic-aminocarbonyl, hydroxy-C$_{1-12}$ aliphatic-aminocarbonyl, C$_{1-12}$-alkoxy-C$_{1-12}$ aliphatic-aminocarbonyl, C$_{1-12}$ alkoxy-C$_{1-12}$ aliphatic-amino, di-C$_{1-12}$ aliphatic amino, di-C$_{1-12}$ aliphatic aminocarbonyl, di-C$_{1-12}$ aliphatic aminosulfonyl, halogen, hydroxy, nitro, C$_{1-12}$ aliphatic-sulfonyl, aminosulfonyl and C$_{1-12}$ aliphatic-aminosulfonyl, where R$^6$ Aryl and Het are as defined below;

R$^1$ and R$^2$ are optionally joined to form a fused ring selected from the group as defined for Het below, and said fused ring is optionally substituted by one or more substituents selected from the group consisting of: C$_{1-12}$ aliphatic, halogen, nitro, cyano, C$_{1-12}$ alkoxy, carbonyl-C$_{1-12}$ alkoxy and oxo;

R$^3$ is selected from the group consisting of: hydrogen, C$_{1-12}$ aliphatic, hydroxy, hydroxy C$_{1-12}$ aliphatic, di-C$_{1-12}$ aliphatic amino, di-C$_{1-12}$ aliphatic aminocarbonyl, di-C$_{1-12}$ aliphatic aminosulfonyl, C$_{1-12}$ alkoxy, Aryl, Aryloxy, hydroxy-Aryl, Het, hydroxy-Het, Het-oxy and halogen, where Aryl and Het are as defined below;

R$^2$ and R$^3$ are optionally joined to form a fused ring selected from the group as defined for Het below, and said fused ring is optionally substituted by C$_{1-6}$ aliphatic and/or C$_{1-6}$ aliphatic-carbonyl;

R$^4$ is selected from the group consisting of: sulfonic acid, C$_{1-12}$ aliphatic-sulfonyl, sulfonyl-C$_{1-12}$ aliphatic, C$_{1-12}$ aliphatic-sulfonyl-C$_{1-6}$ aliphatic, C$_{1-6}$ aliphatic-amino, R$^7$-sulfonyl, R$^7$-sulfonyl-C$_{1-12}$ aliphatic, R$^7$-aminosulfonyl, R$^7$-aminosulfonyl-C$_{1-12}$ aliphatic, R$^7$-sulfonylamino, R$^7$-sulfonylamino-C$_{1-12}$ aliphatic, aminosulfonylamino, di-C$_{1-12}$ aliphatic amino, di-C$_{1-12}$ aliphatic aminocarbonyl, di-C$_{1-12}$ aliphatic aminosulfonyl, di-C$_{1-12}$ aliphatic amino, di-C$_{1-12}$ aliphatic aminocarbonyl, di-C$_{1-12}$ aliphatic aminosulfonyl-C$_{1-12}$ aliphatic, (R$^8$)$_{1-3}$-Arylamino, (R$^3$)$_{1-3}$-Arylsulfonyl, (R$^3$)$_{1-3}$-Aryl-aminosulfonyl, (R$^{11}$)$_{1-3}$-Aryl-sulfonylamino, Het-amino, Het-sulfonyl, Het-aminosulfonyl, aminoiminoamino and aminoiminoaminosulfonyl, where R$^7$, R$^8$, Aryl and Het are as defined below;

R$^5$ is hydrogen or R$^4$ and R$^5$ are optionally joined to form a fused ring selected from the group as defined for Het below, and said fused ring is optionally substituted by one or more substituents selected from the group consisting of: C$_{1-12}$ aliphatic, oxo and dioxo;

R⁶ is selected from the group consisting of: $C_{1-12}$ aliphatic, hydroxy, $C_{1-12}$ alkoxy and halogen;
R⁷ is selected from the group consisting of: hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic,
Aryl-$C_{1-12}$-alkoxy, Aryl-carbonyl, $C_{1-18}$ alkoxyalkoxyalkoxyalkoxyaliphatic and hydroxyl, where Het and Aryl are as defined below;
R⁸ is selected from the group consisting of: hydrogen, nitro, cyano, $C_{1-12}$ alkoxy, halo, carbonyl-$C_{1-12}$ alkoxy and halo-$C_{1-12}$ aliphatic;
Aryl is selected from the group consisting of: phenyl, naphthyl, phenanthryl and anthracenyl;
Cyc is selected from the group consisting of: cyclopropyl, cyclobutyl, cyclopentyl, cyclohexyl, cycloheptyl and cyclooctyl, and optionally has one or more degrees of unsaturation;
Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, quinoline, tetrahydrofuran, tetrazine, thidiazine, thiadiazole, thiatriazole, thiazine, thiazole, thiomorpholine, thiophene, thiopyran, triazine and triazole;
and the salts, esters, amides, carbamates solvates, hydrates, affinity reagents and/or prodrugs thereof, in either crystalline or amorphous form. The esters, amides and and carbamates are preferably hydrolyzable and are more preferably biohydrolyzable. The salts are preferably pharmaceutically acceptable salts.

Another category of compositions including CDK2 inhibitor compounds that may be usefully employed in the practice of the invention include compounds of the formula (F): defined as follows:

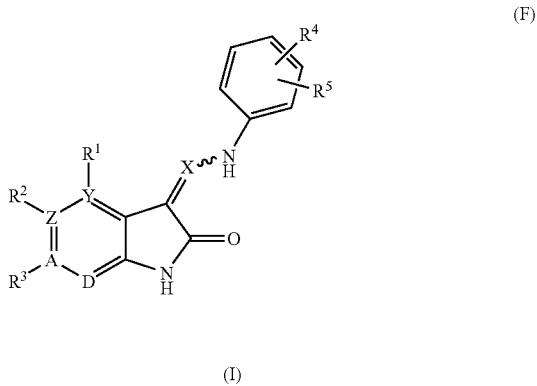

wherein
X is selected from the group consisting of: N, CH and C($C_{1-6}$ aliphatic);
Y is C or N. with the proviso that when Y is N. R¹ is absent, and Z, A and D are each C;
Z is C or N, with the proviso that when Z is N, R² is absent, and Y, A and D are each C;
A is C or N, with the proviso that when A is N, R₃ is absent, and Y, Z and D are each C;
D is C or N, with the proviso that when D is N, then Y, Z and A are C;
R¹ is selected from the group consisting of: hydrogen, $C_{1-6}$ aliphatic, hydroxy-$C_{1-6}$ aliphatic, Aryl-$C_{1-6}$ aliphatic, R⁶-Aryl-$C_{1-6}$ aliphatic, Cyc-$C_{1-6}$ aliphatic, Het-$C_{1-6}$ aliphatic, $C_{1-6}$ alkoxy, Aryloxy, aminocarbonyl, di-$C_{1-6}$ aliphatic amino, di-$C_{1-6}$ aliphatic aminocarbonyl, di-$C_{1-6}$ aliphatic aminosulfonyl, $C_{1-6}$ alkoxycarbonyl, halogen and nitro, where R⁶, Aryl, Cyc and Het are as defined below;
R² is selected from the group consisting of: hydrogen, $C_{1-6}$ aliphatic, R⁷-$C_{1-6}$ aliphatic, $C_{1-6}$ alkoxy, hydroxy-$C_{1-6}$ aliphatic, $C_{1-6}$ alkoxycarbonyl, carboxyl $C_{1-6}$ aliphatic, Aryl, R⁶-Aryl-oxycarbonyl, R⁶-oxycarbonyl-Aryl, Het, aminocarbonyl, $C_{1-6}$ aliphatic-aminocarbonyl, Aryl-$C_{1-6}$ aliphatic-aminocarbonyl, R⁶-Aryl-$C_{1-6}$ aliphatic-aminocarbonyl, Het-$C_{1-6}$ aliphatic-aminocarbonyl, hydroxy-$C_{1-6}$ aliphatic-aminocarbonyl, $C_{1-6}$-alkoxy-$C_{1-6}$ aliphatic-aminocarbonyl, $C_{1-6}$ alkoxy-$C_{1-6}$ aliphatic-amino, di-$C_{1-6}$ aliphatic amino, di-$C_{1-6}$ aliphatic aminocarbonyl, di-$C_{1-6}$ aliphatic aminosulfonyl, halogen, hydroxy, nitro, sulfo, $C_{1-6}$ aliphatic-sulfonyl, aminosulfonyl, $C_{1-6}$ aliphatic-aminosulfonyl and quaternary ammonium, where R⁶, R⁷, Aryl and Het are as defined below;
R¹ and R² are optionally joined to form a fused ring selected from the group as defined for Het below, and said fused ring is optionally substituted by halogen and/or oxo;
R³ is selected from the group consisting of: hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-6}$ aliphatic aminosulfonyl, $C_{1-6}$ alkoxy, Aryl, Aryloxy, hydroxy-Aryl, Het, hydroxy-Het, Het-oxy and halogen, where Aryl and Het are as defined below;
R² and R³ are optionally joined to form a fused ring selected from the group as defined for Het below, and said fused ring is optionally substituted by $C_{1-6}$ aliphatic or $C_{1-6}$ aliphatic-carbonyl;
R⁴ is selected from the group consisting of: sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, R⁷-sulfonyl, R⁷-sulfonyl-$C_{1-12}$ aliphatic, R⁷-aminosulfonyl, R⁷-aminosulfonyl-$C_{1-12}$ aliphatic, R⁷-sulfonylamino, R⁷-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, (R⁸)$_{1-3}$-Arylamino, (R⁸)$_{1-3}$-Arylsulfonyl, (R⁸)$_{1-3}$-Aryl-aminosulfonyl, (R⁸)$_{1-3}$-Aryl-sulfonylamino, Het-amino, Het-sulfonyl, Het-aminosulfonyl, aminoiminoamino and aminoiminoaminosulfonyl, where R⁷,
R⁸, Aryl and Het are as defined below;
R⁵ is hydrogen;
R⁴ and R⁵ are optionally joined to form a fused ring selected from the group as defined for Het below, and said fused ring is optionally substituted by oxo or dioxo;
R⁶ is selected from the group consisting of: hydrogen, $C_{1-6}$ aliphatic, hydroxy, $C_{1-6}$ alkoxy and halogen;
R⁷ is selected from the group consisting of: hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic and hydroxyl, where Het and Aryl are as defined below;

$R^8$ is hydrogen and/or halo-$C_{1-6}$ aliphatic;

Aryl is phenyl or naphthyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole; and the salts, esters, amides, carbamates, solvates, hydrates, affinity reagents and/or prodrugs thereof, in either crystalline or amorphous form. The esters, amides and carbamates are preferably hydrolyzable and are more preferably biohydryzeable. The salts are preferably pharmaceutically acceptable salts.

A highly preferred group of compounds including CDK2 inhibitor compounds that may be usefully employed in the practice of the invention include compounds of the formula (F), defined as follows:

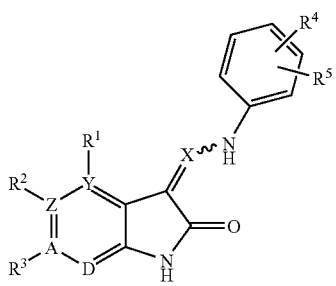

(F)

(I)

wherein

X is selected from the group consisting of: N, CH and $CCH_3$;

Y is C or N, with the proviso that when Y is N, $R^1$ is absent, and Z, A and D are each C;

Z is C or N, with the proviso that when Z is N, $R^2$ is absent, and Y, A and D are each C;

A is C or N, with the proviso that when A is N, $R^3$ is absent, and X, Y and D are each C;

D is C or N, with the proviso that when D is N, then Y, Z and A are each C;

$R^1$ is selected from the group consisting of: hydrogen, $C_{1-6}$ aliphatic, hydroxy-$C_{1-6}$ aliphatic, di-$C_{1-6}$ aliphatic amino, di-$C_{1-6}$ aliphatic aminocarbonyl, di-$C_{1-6}$ aliphatic aminosulfonyl, Aryl-$C_{1-6}$ aliphatic, $R^6$-Aryl-$C_{1-6}$ aliphatic, Cyc-$C_{1-6}$ aliphatic, Het-$C_{1-6}$ aliphatic, $C_{1-6}$ alkoxy, Aryloxy, aminocarbonyl, $C_{1-6}$ alkoxycarbonyl, halogen and nitro, where $R^6$, Aryl, Cyc and Het are as defined below;

$R^2$ is selected from the group consisting of: hydrogen, $C_{1-6}$ aliphatic, N-hydroxyimino-$C_{1-6}$ aliphatic, $C_{1-6}$ alkoxy, $C_{1-6}$ alkoxycarbonyl, Aryl, $R^6$-Aryloxycarbonyl, Het, aminocarbonyl, $C_{1-6}$ aliphatic aminocarbonyl, Aryl-$C_{1-6}$ aliphatic aminocarbonyl, $R^6$-Aryl-$C_{1-6}$ aliphatic aminocarbonyl, Het-$C_{1-6}$ aliphatic aminocarbonyl, di-$C_{1-6}$ aliphatic amino, di-$C_{1-6}$ aliphatic aminocarbonyl, di-$C_{1-6}$ aliphatic aminosulfonyl, hydroxy-$C_{1-6}$ aliphatic aminocarbonyl, $C_{1-6}$-alkoxy-$C_{1-6}$ aliphatic aminocarbonyl, $C_{1-6}$ alkoxy-$C_{1-6}$ aliphatic amino, halogen, hydroxy, nitro, $C_{1-6}$ aliphatic sulfonyl, aminosulfonyl and $C_{1-6}$ aliphatic aminosulfonyl, where $R^6$, Aryl and Het are as defined below;

$R^1$ and $R^2$ are optionally joined to form a fused ring selected from the group as defined for Het below, and said fused ring is optionally substituted by halogen and/or oxo;

$R^3$ is selected from the group consisting of: hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-6}$ aliphatic aminosulfonyl $C_{1-6}$ alkoxy, Aryloxy, Het and halogen, where Aryl and Het are as defined below;

$R^2$ and $R^3$ are optionally joined to form a fused ring selected from the group as defined for Het below, and said fused ring is optionally substituted by $C_{1-6}$ alkyl and/or $C_{1-6}$ alkylcarbonyl;

$R^4$ is selected from the group consisting of: $R^7$-sulfonyl, $R^7$-sulfonyl $C_{1-6}$-aliphatic, $C_{1-6}$ aliphatic sulfonyl-$C_{1-6}$ aliphatic, $R^7$-aminosulfonyl, di-$C_{1-6}$ aliphatic amino, di-$C_{1-6}$ aliphatic aminocarbonyl, di-$C_{1-6}$ aliphatic aminosulfonyl, di-$C_{1-6}$ aliphatic aminosulfonyl-$C_{1-6}$ aliphatic, $R^7$-aminosulfonyl $C_{1-6}$ aliphatic, aminosulfonylamino, $R^7$-$C_{1-6}$ aliphatic aminosulfonyl-$C_{1-6}$ aliphatic, Aryl, Het, $R^8$-Aryl-aminosulfonyl, Het-aminosulfonyl and aminoiminoaminosulfonyl, where $R^7$, $R^8$, Aryl and Het are as defined below;

$R^5$ is hydrogen;

$R^4$ and $R^5$ are optionally joined to form a fused ring selected from the group as defined for Het below, and said used ring is optionally substituted by oxo or dioxo;

$R^6$ is selected from the group consisting of: hydroxy, $C_{1-6}$ alkoxy and halogen;

$R^7$ is selected from the group consisting of: hydrogen, $C_{1-6}$ aliphatic, hydroxy $C_{1-6}$-alkoxy, hydroxy-$C_{1-6}$ aliphatic, $C_{1-6}$ aliphatic carbonyl, Aryl-carbonyl, $C_{1-12}$ alkoxyalkoxyalkoxyalkyl, hydroxyl, Aryl, Aryl-$C_{1-6}$-alkoxy, Aryl-$C_{1-6}$-aliphatic, Het, Het-$C_{1-6}$-alkoxy, di-Het-$C_{1-6}$-alkoxy, Het-$C_{1-6}$-aliphatic and di-Het-$C_{1-6}$-aliphatic;

$R^8$ is trifluoromethyl;

Aryl is phenyl;

Cyc is cyclobutyl;

Het is a saturated or unsaturated heteroatom ring system selected from the group consisting of: benzimidazole, dihydrothiophene, dioxolane, furan, imidazole, morpholine, oxazole, pyridine, pyrrole, pyrrolidine, thiadiazole, thiazole, thiophene, and triazole;

and the salts, esters, amides, carbamates, solvates, hydrates, affinity reagents and/or prodrugs thereof, in either crystalline or amorphous form. The esters, amides and carbamates are preferably hydrolyzable and are more preferably biohydrolyzable. The salts are preferably pharmaceutically acceptable salts.

A preferred group of compositions with respect to the substitutions at $R^4$ including CDK2 inhibitor compounds that may be usefully employed in the practice of the invention include compounds of the formula (F):

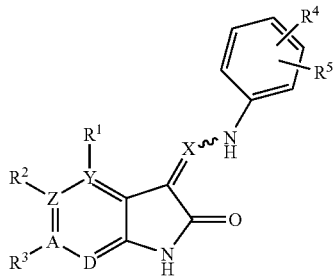

(F)

(I)

wherein

X is N or CH;

Y is C or N, with the proviso that when Y is N, $R^1$ is absent, and Z, A and D are each C;

Z is C or N, with the proviso that when Z is N, $R^2$ is absent, and Y, A and D are each C;

A is C or N, with the proviso that when A is N, $R^3$ is absent, and Y, Z and D are each C;

D is C or N, with the proviso that when D is N, Y, Z and A are each C;

$R^1$ is selected from the group consisting of: hydrogen, $C_{1-12}$ aliphatic, thiol, hydroxy, hydroxy-$C_{1-12}$ aliphatic, Aryl, Aryl-$C_{1-12}$ aliphatic, $R^6$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, halogen, cyano, sulfonamide and nitro, where $R^6$, Aryl, Cyc and Het are as defined below;

$R^2$ is selected from the group consisting of: hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Aryl-oxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl and $C_{1-12}$ aliphatic-aminosulfonyl, where $R^6$, Aryl and Het are as defined below;

$R^1$ and $R^2$ are optionally joined to form a fused ring selected from the group as defined for Het below, and said fused ring is optionally substituted by one or more substituents selected from the group consisting of: halogen, nitro, cyano, $C_{1-12}$ alkoxy, carbonyl-$C_{1-12}$ alkoxy and oxo;

$R^3$ is selected from the group consisting of: hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

$R^2$ and $R^3$ are optionally joined to form a fused ring selected from the group as defined for Het below, and said fused ring is optionally substituted by $C_{1-6}$ aliphatic and/or $C_{1-6}$ aliphatic-carbonyl;

$R^4$ is selected from the group consisting of: $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic aminosulfonyl, di-$C_{1-12}$ aliphatic aminosulfonyl-$C_{1-12}$ aliphatic, $(R^8)_{1-3}$-Aryl-aminosulfonyl, $(R^8)_{1-3}$Aryl-sulfonylamino and aminoiminoaminosulfonyl, where $R^7$, $R^8$, Aryl and Het are as defined below;

$R^5$ is hydrogen;

$R^4$ and $R^5$ are optionally joined to form a fused ring selected from the group as defined for Het below, and said fused ring is optionally substituted by oxo or dioxo;

$R^6$ is selected from the group consisting of: $C_{1-12}$ aliphatic, hydroxy, $C_{1-12}$ alkoxy and halogen;

$R^7$ is selected from the group consisting of: hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic and hydroxyl, where Het and Aryl are as defined below;

$R^8$ is selected from the group consisting of: hydrogen, nitro, cyano, $C_{1-12}$ alkoxy, halo, carbonyl-$C_{1-12}$ alkoxy and halo-$C_{1-12}$ aliphatic; and Aryl is selected from the group consisting of: phenyl, naphthyl, phenanthryl and anthracenyl;

Cyc is selected from the group consisting of: cyclopropyl, cyclobutyl, cyclopentyl, cyclohexyl, cycloheptyl and cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole;

and the salts, esters, amides, carbamates, solvates, hydrates, affinity reagents and/or prodrugs thereof, in either crystalline or amorphous form. The esters, amides and carbamates are preferably hydrolyzable and are more preferably biohydrolyzeable. The salts are preferably pharmacetically acceptable salts.

A highly preferred group of compounds with respect to the substitutions at $R^4$, including CDK2 inhibitor compounds that may be usefully employed in the practice of the invention, include compounds of the formula (F):

wherein

X is CH;

Y is C or N, with the proviso that when Y is N, $R^1$ is absent, and Z, A and D are each C;

Z is C or N, with the proviso that when Z is N, $R^2$ is absent, and Y, A and D are each C;

A is C or N, with the proviso that when A is N, $R^3$ is absent, and Y, Z and D are each C;

D is C or N, with the proviso that when D is N, Y, Z and A are each C;

$R^1$ is hydrogen;

$R^2$ is selected from the group consisting of: hydrogen, $C_{1-12}$ alkoxycarbonyl, Aryl, Het and halogen, where Aryl and Het are as defined below;

$R^3$ is hydrogen or halogen;

$R^4$ is selected from the group consisting of: $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic aminosulfonyl, di-$C_{1-12}$ aliphatic aminosulfonyl-$C_{1-12}$ aliphatic, $(R^8)_{1-3}$-Aryl-aminosulfonyl, $(R^8)_{1-3}$-Aryl-sulfonylamino and aminoiminoaminosulfonyl, where $R^7$, $R^8$, Aryl and Het are as defined below;

$R^5$ is hydrogen;

$R^4$ and $R^5$ are optionally joined to form a fused ring selected from the group as defined for Het below, and said used ring is optionally substituted by oxo or dioxo;

$R^7$ is selected from the group consisting of: hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic and hydroxyl, where Het and Aryl are as defined below;

$R^8$ is selected from the group consisting of: hydrogen, nitro, cyano, $C_{1-12}$ alkoxy, halo, carbonyl-$C_{1-12}$ alkoxy and halo-$C_{1-12}$ aliphatic;

Aryl is selected from the group consisting of: phenyl, naphthyl, phenanthryl and anthracenyl;

Cyc is selected from the group consisting of: cyclopropyl, cyclobutyl, cyclopentyl, cyclohexyl, cycloheptyl or cyclooctyl, and optionally has one or more degrees of unsaturation;

Het is a saturated or unsaturated heteroatom ring system selected from the group consisting of: benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole;

and the salts, esters, amides, carbamates solvates, hydrates, affinity reagents and/or prodrugs thereof, in either crystalline or amorphous form. The esters, amides and carbamates are preferably hydrolyzable and are more preferably biohydrolyzable. The salts are preferably pharmaceutically acceptable salts.

Due to the presence of an oxindole exocyclic double bond, the compounds specified include their respective pure E and Z geometric isomers as well as mixtures of E and Z isomers. Thus, for example, compound number 1A in the tables below is disclosed and claimed as the E geometric thereof, the Z geometric isomer thereof, and a mixture of the E and Z geometric isomers thereof, but it is not limited by any given ratio(s).

Likewise, it is understood that compounds may exist in tautomeric forms other than that shown in the formula.

Certain of the compounds as described will contain one or more chiral, or asymmetric, centers and will therefore be capable of existing as optical isomers that are either dextrorotatory or levorotatory. Also included in the compounds are the respective dextrorotatory or levorotatory pure preparations, and mixtures thereof.

Certain compounds may exist in stereoisomeric forms (e.g. they may contain one or more asymmetric carbon atoms or may exhibit cis-trans isomerism). The individual stereoisomers (enantiomers and diastereoisomers) and mixtures of these are included. Likewise, it is understood that compounds may exist in tautomeric forms other than that shown in the formula and these are also included within the scope of the disclosure.

Various illustrative compounds are listed in Tables 1A and 2A below. Compounds are identified by the numbers shown in the first column; variables below in the rest of the columns are with reference to the generic structure. Corresponding IUPAC nomenclature are disclosed in Table 2A. Since all substituents at each point of substitution are capable of independent synthesis of each other, the tables are to be read as a matrix in which any combination of substituents is within the scope of the description.

TABLE 1A

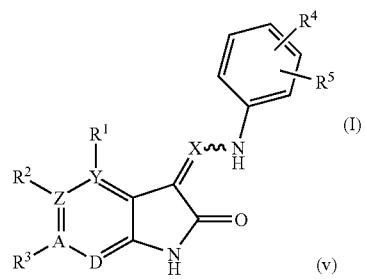

(F)
(I)
(v)

| Example | Y | Z | A | D | R¹ | R² | R³ | R⁴ | R⁵ | X |
|---|---|---|---|---|---|---|---|---|---|---|
| 1A | C | N | C | C | H | — | H | 4'-SO₂NH₂ | H | CH |
| 2A | C | C | N | C | H | H | — | 4'-SO₂NH₂ | H | CH |
| 3A | N | C | C | C | — | H | H | 4'-CH=NN(H)-5' | | CH |
| 4A | N | C | C | C | — | H | H | 4'-N=CH—CH=CH-5' | | CH |
| 5A | C | C | C | N | H | H | H | 4'-SO₂NH₂ | H | CH |
| 6A | C | C | C | N | H | H | H | 4'-CH=NN(H)-5' | | CH |
| 7A | C | C | C | N | H | H | H | 4'-N=CH—CH=CH-5' | | CH |
| 8A | C | C | C | N | H | phenyl | H | 4'-SO₂NH₂ | H | CH |

TABLE 1A-continued (F), (I), (v)

| Example | Y | Z | A | D | R¹ | R² | R³ | R⁴ | R⁵ | X |
|---|---|---|---|---|---|---|---|---|---|---|
| 9A | C | C | C | N | H | phenyl | H | 4'-CH=NN(H)-5' | | CH |
| 10A | C | C | C | N | H | phenyl | H | 4'-N=CH—CH=CH-5' | | CH |
| 11A | C | C | C | N | H | 2-furanyl | H | 4'-SO$_2$NH$_2$ | H | CH |
| 12A | C | C | C | N | H | 2-furanyl | H | 4'-CH=NN(H)-5' | | CH |
| 13A | C | C | C | N | H | 2-furanyl | H | 4'-N=CH—CH=CH-5' | | CH |
| 14A | C | C | C | N | H | 3-thiophenyl | H | 4'-SO$_2$NH$_2$ | H | CH |
| 15A | C | C | C | N | H | 3-thiophenyl | H | 4'-CH=NN(H)-5' | | CH |
| 16A | C | C | C | N | H | 3-thiophenyl | H | 4'-N=CH—CH=CH-5' | | CH |
| 17A | C | C | C | N | H | Br | H | 4'-SO$_2$NH$_2$ | H | CH |
| 18A | C | C | C | N | H | Br | H | 4'-CH=NN(H)-5' | | CH |
| 19A | C | C | C | N | H | Br | H | 4'-N=CH—CH=CH-5' | | CH |
| 20A | C | C | C | N | H | H | Cl | 4'-SO$_2$NH$_2$ | H | CH |
| 21A | C | C | C | N | H | H | Cl | 4'-CH=NN(H)-5' | | CH |
| 22A | C | C | C | N | H | H | Cl | 4'-N=CH—CH=CH-5' | | CH |
| 23A | C | C | C | N | H | carbethoxy | H | 4'-SO$_2$NH$_2$ | H | CH |
| 24A | C | C | C | N | H | carbethoxy | H | 4'-CH=NN(H)-5' | | CH |
| 25A | C | C | C | N | H | carbethoxy | H | 4'-N=CH—CH=CH-5' | | CH |

Standard accepted nomenclature corresponding to the subsequent Examples is set forth below. In some cases nomenclature is given for one or more possible isomers.

TABLE 2A

IUPAC Nomenclature of Examples

| EXAMPLE | IUPAC NAME |
|---|---|
| 1A | 4-{[(2-Oxo-1,2-dihydro-3H-pyrrolo[3,2-c]pyridin-3-ylidene)methyl]amino}benzenesulfonamide |
| 2A | 4{[(2-Oxo-1,2-dihydro-3H-pyrrolo[2,3-c]pyridin-3-ylidene)methyl]amino}benzenesulfonamide |
| 3A | 3[-(1H-Indazol-6-ylamino)methylidene]-1H-pyrrolo[3,2-b]-pyridin-2-one |
| 4A | 3-[(6-Quinolinylamino)methylidene]-1,3-dihydro-2H-pyrrolo-[3,2-b]pyridin-2-one |
| 5A | 4-{[(2-Oxo-1,2-dihydro-3H-pyrrolo[2,3-b]pyridin-3-ylidene)methyl]amino}benzenesulfonamide |
| 6A | 3-[(1H-Indazol-6-ylamino)methylidene]-1H-pyrrolo[2,3-b]-pyridin-2-one |
| 7A | 3-[(6-Quinolinylamino)methylidene]-1,3-dihydro-2H-pyrrolo[2,3-b]pyridin-2-one |
| 8A | 4-{[(2-Oxo-5-phenyl-1,2-dihydro-3H-pyrrolo[2,3-b]pyridin-3-ylidene)methyl]amino}benzenesulfonamide |

TABLE 2A-continued

IUPAC Nomenclature of Examples

| EX-AMPLE | IUPAC NAME |
|---|---|
| 9A | 3-[(1H-Indazol-6-ylamino)methylidene]-5-phenyl-1H-pyrrolo-[2,3-b]pyridin-2-one |
| 10A | 5-Phenyl-3-[(6-quinolinylamino)methylidene]-1,3-dihydro-2H-pyrrolo[2,3-b]pyridin-2-one |
| 11A | 4-({[5-(2-Furyl)-2-oxo-1,2-dihydro-3H-pyrrolo[2,3-b]pyridin-3-ylidene]methyl}amino)benzenesulfonamide |
| 12A | 5-(2-Furyl)-3-[(1H-indazol-6-ylamino)methylidene]-1H-pyrrolo-[2,3-b]pyridin-2-one |
| 13A | 5-(2-Furyl)-3-[(6-quinolinylamino)methylidene]-1,3-dihydro-2H-pyrrolo[2,3-b]pyridin-2-one |
| 14A | 4-({[2-Oxo-5-(3-thienyl)-1,2-dihydro-3H-pyrrolo[2,3-b]-pyridin-3-ylidene]methyl}amino)benzenesulfonamide |
| 15A | 3-[(1H-Indazol-6-ylamino)methylidene]-5-(3-thienyl)-1,3-dihydro-2H-pyrrolo[2,3-b]pyridin-2-one |
| 16A | 3-[(6-Quinolinylamino)methylldene]-5-(3-thienyl)-1,3-dihydro-2H-pyrrolo[2,3-b]pyridin-2-one |
| 17A | 4-{[(5-Bromo-2-oxo-1,2-dihydro-3H-pyrrolo[2,3-b]pyridin-3-ylidene)methyl]amino}benzenesulfonamide |
| 18A | 5-Bromo-3-[(1H-indazol-6-ylamino)methylidene]-1,3-dihydro-2H-pyrrolo[2,3-b]pyridin-2-one |
| 19A | 5-Bromo-3-[(6-quinolinylamino)methylidene]-1,3-dihydro-2H-pyrrolo[2,3-b]pyridin-2-one |
| 20A | 4-{[(6-Chloro-2-oxo-1,2-dihydro-3H-pyrrolo[2,3-b]pyridin-3-ylidene)methyl]amino}benzenesulfonamide |
| 21A | 6-Chloro-3-[(1H-indazol-6-ylamino)methylidene]-1,3-dihydro-2H-pyrro[2,3-b]pyridin-2-one |
| 22A | 6-Chloro-3-[(6-quinolinylamino)methylidene]-1,3-dihydro-2H-pyrrolo[2,3-b]pyridin-2-one |
| 23A | Ethyl 3-{[4-(aminosulfonyl)anilino]methylidene}-2-oxo-1,2-dihydro-3H-pyrrolo[2,3-b]pyridine-5-carboxylate |
| 24A | Ethyl 3-[(1H-indazol-6-ylamino)methylidene]-2-oxo-1,2-dihydro-3H-pyrrolo[2,3-b]pyridine-5-carboxylate |
| 25A | Ethyl 2-oxo-3-[(6-quinolinylamino)methylidene]-2,3-dihydro-1H-pyrrolo[2,3-b]pyridine-5-carboxylate |

The compounds of formula (F) can be prepared readily according to the following reaction Synthesis Schemes (in which all variables are as defined before) and examples or modifications thereof using readily available starting materials, reagents and conventional synthesis procedures. In these reactions, it is also possible to make use of variants which are themselves known to those of ordinary skill in this art, but are not mentioned in greater detail.

Synthesis Schemes

Scheme 1. Preparation of pyrrolo[3,2-b]pyridin-2-ones

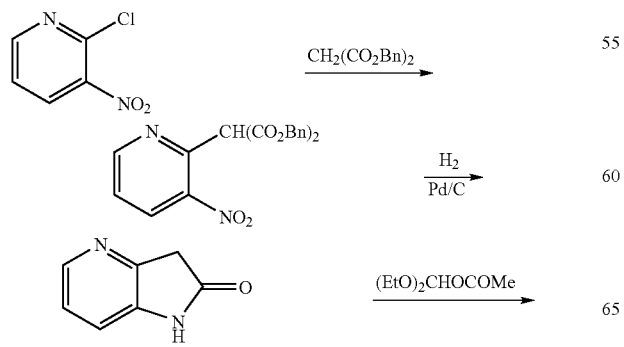

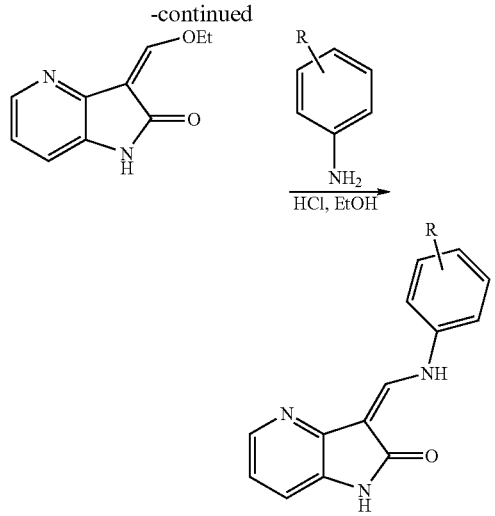

Scheme 2. Preparation of pyrrolo[3,2-c]pyridin-2-ones.

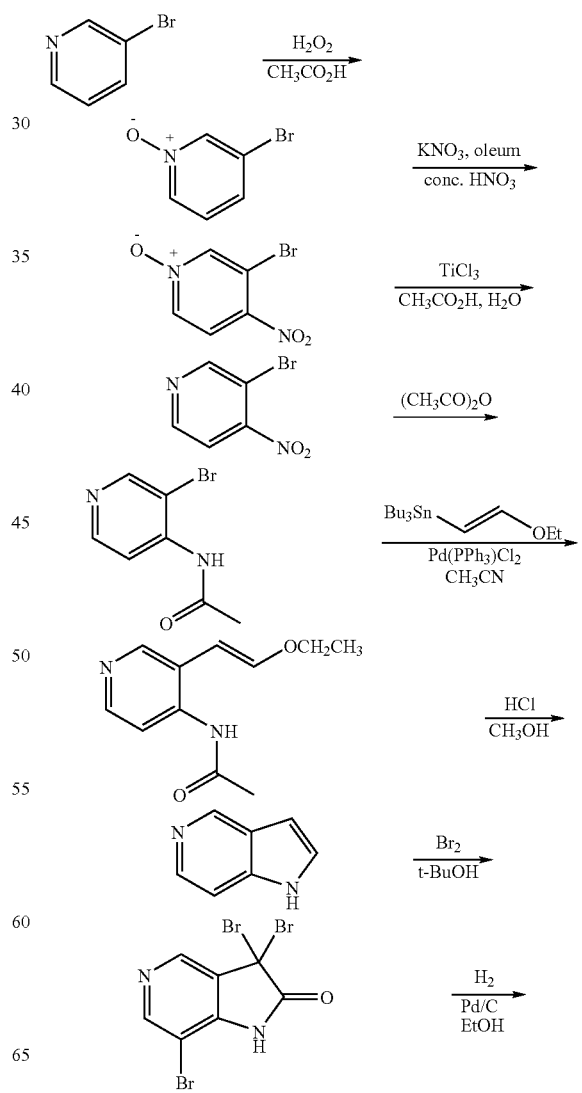

-continued
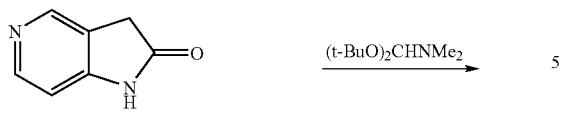
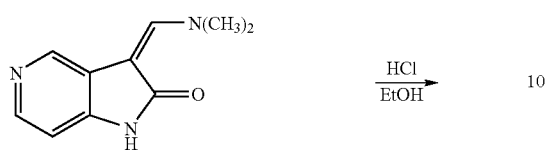
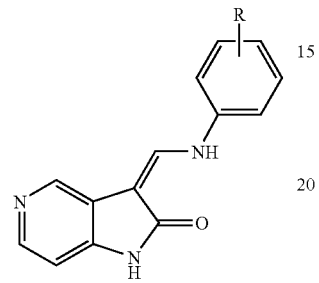
Scheme 3. Preparation of pyrrolo[2,3-c]pyridin-2-ones.
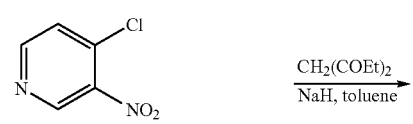
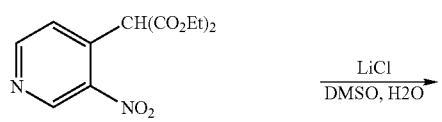
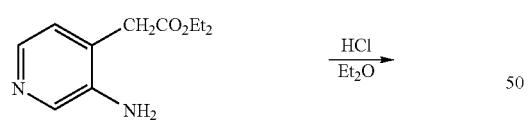
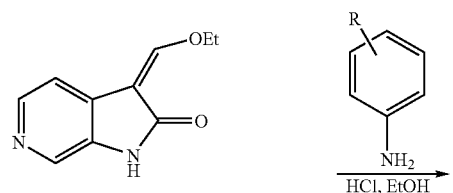
-continued
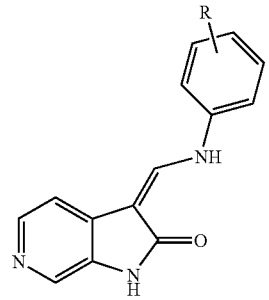
Scheme 4. Preparation of pyrrolo[2,3-b]pyridin-2-ones.
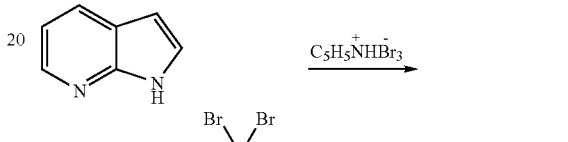
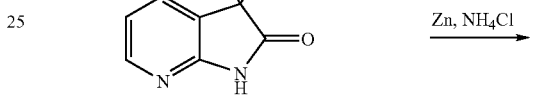
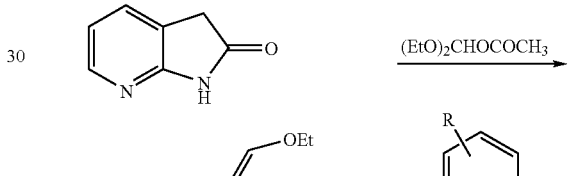
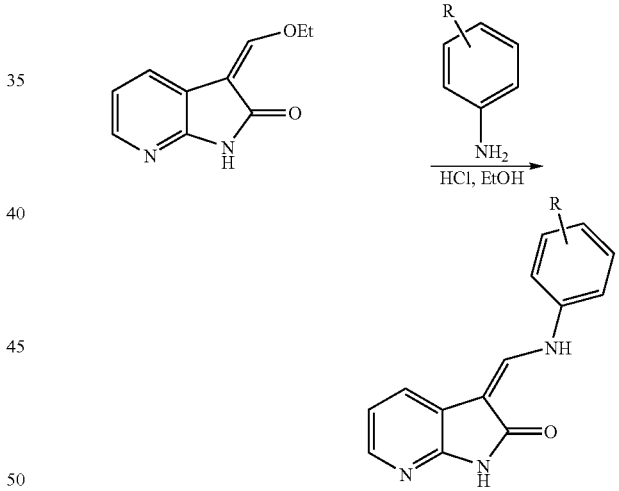
Scheme 5. Preperation of 6-chloropyrrolo[2,3-b]pyridin-2-ones.
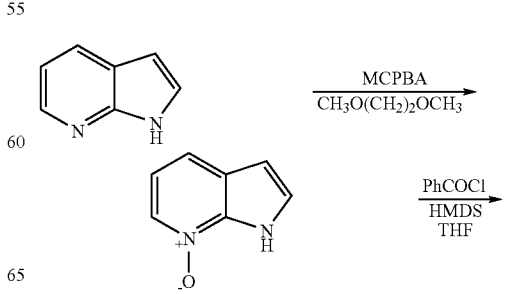

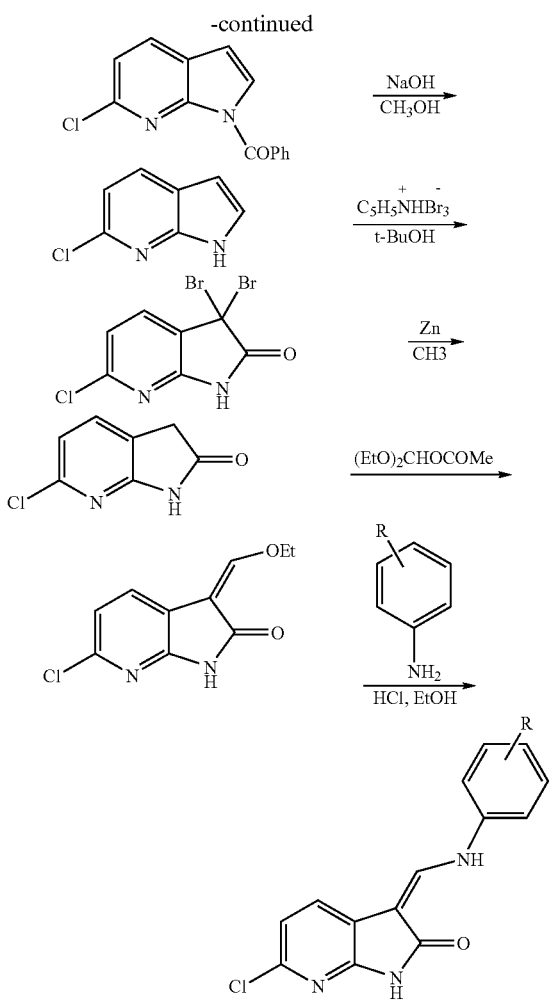

In the foregoing Schemes 1–5, R is $R^4$ and/or $R^5$ as described herein.

Scheme 6. Preparation of 5-substituted-1,3-dihydro-2H-pyrrolo[2,3-b]pyridin-2-ones

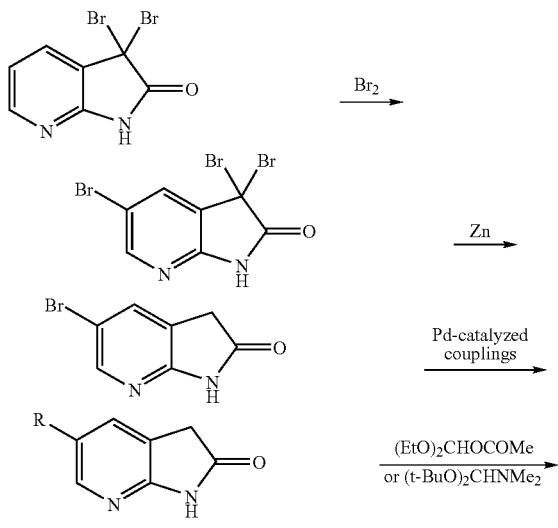

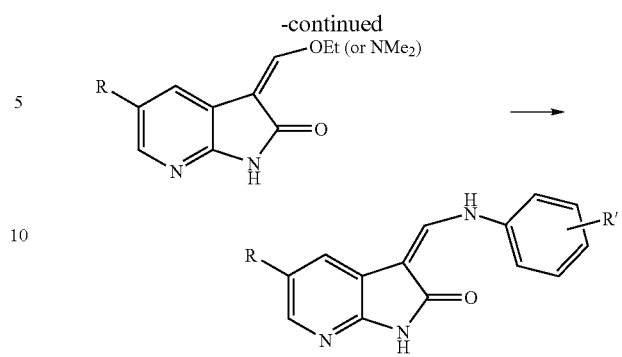

wherein R is Het, Ar or $CO_2Et$, where Het and Ar are as described herein, and R' is $R^4$ or $R^5$, as those are previously described.

The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the following Examples are as follows:

g=grams
mg=milligrams
L=liters
mL=milliliters
M=molar
N=normal
mM=millimolar
i.v.=intravenous
p.o.=per oral
s.c.=subcutaneous
Hz=hertz
mol=moles
mmol=millimoles
mbar=millibar
psi=pounds per square inch
rt=room temperature
min=minutes
h=hours
mp=melting point
TLC=thin layer chromatography
$R_f$=relative TLC mobility
MS=mass spectrometry
NMR=nuclear magnetic resonance spectroscopy
APCI=atmospheric pressure chemical ionization
ESI=electrospray ionization
m/z=mass to charge ratio
$t_r$=retention time
Pd/C=palladium on activated carbon
ether=diethyl ether
MeOH=methanol
EtOAc=ethyl acetate
TEA=triethylamine
DIEA=diisopropylethylamine
THF=tetrahydrofuran
DMF=N,N-dimethylformamide
DMSO=dimethylsulfoxide
DDQ=2,3-dichloro-5,6-dicyano-1,4-benzoquinone
LAH=lithium aluminum hydride TFA=trifluoroacetic acid
LDA=lithium diisopropylamide
THP=tetrahydropyranyl
NMM=N-methylmorpholine, 4-methylmorpholine
HMPA=hexamethylphosphoric triamide
DMPU=1,3-dimethypropylene urea
d=days
ppm=parts per million
kD=kiloDalton
LPS=lipopolysaccharide
PMA=phorbol myristate acetate
SPA=scintillation proximity assay
EDTA=ethylenediamine tetraacetic acid
FBS=fetal bovineserum
PBS=phosphate buffered saline solution
BrdU=bromodeoxyuridine
BSA=bovine serum albumin
FCS=fetal calf serum
DMEM=Dulbecco's modified Eagle's medium
pfu=plaque forming units
MOI=multiplicity of infection Reagents are commercially available or are prepared according to procedures in the literature. The physical data given for the compounds exemplified is consistent with the assigned structure of those compounds. $^1$H NMR spectra were obtained on VARIAN Unity Plus NMR spectrophotometers at 300 or 400 Mhz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterisation, and to follow the progess of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure.

A Micromass Platform II mass spectrometer equipped with an electrospray ion source was used to acquire low resolution LC-MS data for the samples that were prepared in library format. The system software runs on a PC computer with the Microsoft operating system, and consists of Masslynx v3.1 and Openlynx v3.1 software packages. The mass spectrometer inlet system was comprised of a Hewlett Packard 1100 HPLC Chromatograph, a Gilson 215 autosampler, and a Hewlett Packard 1100 photo-diode array detector. A Supelco ABZ+5 cm column was used to provide separations prior to electrospray ionization. The HPLC was programmed as follows:

| Time | % A | % B | Flow Rate |
|---|---|---|---|
| 0.0 min | 85 | 15 | 0.6 ml/min |
| 3.0 min | 25 | 75 | 0.6 ml/min |
| 4.0 min | 0 | 100 | 0.6 ml/min |
| 5.0 min | 0 | 100 | 0.6 ml/min |

The data were processed automatically using standard peak detection parameters provided by the Openlynx software.

Micromass LCT bench-top mass spectrometer equipped with an electrospray ionization source was used to obtain accurate mass data for the samples that were prepared in library format. The LCT utilizes two hexapole RF lenses to transfer ions from the source to an orthogonal acceleration time-of-flight (TOF) analyser. The ions emerging from the analyser are detected using a dual microchannel plate detector and ion counting system. The system software runs on a PC computer with the Microsoft operating system, and consists of Masslynx v3.2 and Openlynx v3.2 software packages. The mass spectrometer inlet system is comprised of a Waters Alliance 2690 Separations Module, Waters 2700 autosampler, Waters 996 photo-diode array detector and Valco column switching device. A mobile phase flow rate of 1 ml/min exits the Alliance 2690 and is reduced to a mass spectrometer flow rate of 20 ul/min using an Acurate flow splifter. A lock mass solution at a flow rate of 4 ul/min is added to the spectrometer flow via a Harvard syringe pump and a tee piece placed immediately before the electrospray probe. The instrument resolution was determined by acquiring a spectrum and measuring the full peak width t half peak height (FWHH). The instrument was tuned to provide a resolution of 4600 to 5000 (FWHH). The instrument was calibrated using the ions of polyethylene glycol (PEG) as reference standards. The lock mass used [3,5-Dil-Tyr,Ala, N-Me-Phe,Gly-0I] Enkephalin (MH+ C26H34I2N5O6=766.0599) at a concentration of 5 ng/ul.

EXAMPLE 1A

4-{[(2-Oxo-1,2-dihydro-3H-pyrrolo[3,2-c]pyridin-3-ylidene)-methyl]amino}benzenesulfonamide a) 3-Dimethylamino-methylene-1,5-diazainden-2-one:

3-Bromo-4-nitropyridine-1-oxide was prepared according to the procedure of Daisley and Hanbali (Org. Prep. Proced. Int. 1983, 15, 280) and converted to 1,5-diazaindene via the method of Sakamoto et. al. (Heterocycles 1992, 34, 2379). 1,5-Diazaindene was subsequently converted to 1,5-diazainden-2-one hydrobromide via the procedure outlined by Robinson and Donahue (J. Org. Chem. 1991, 56, 4805) and reaction of this with N,N-dimethylformamide-di-t-butyl acetal in DMF gave 3-dimethylamino-methylene-1,5-diazainden-2-one (as described for the preparation of 3-dimethylamino-methylene-1,6-diazainden-2-one): $^1$H NMR (DMSO-$d_6$): δ 3.35 (s, 6H), 7.13 (d, J=6.1 Hz, 1H), 8.09 (s, 1H), 8.20 (d, J=6.1 Hz, 1H), 8.57 (s, 1H), 11.50 (s, 1H); $C_{10}H_{11}N_3O$: APES+MS: m/z 190 (M+H).

b) 4-{[(2-Oxo-1,2-dihydro-3H-pyrrolo[3,2-c]pyridin-3-ylidene)methyl]amino}-benzenesulfonamide (Mixture of E and Z Isomers):

3-Dimethylamino-methylene-1,5-diazainden-2(3H)-one was reacted with sulfanilamide in ethanol with hydrochloric acid to give the title compound (by the method described for Example 2, section f) as a 15:4 mixture of Z:E isomers. $^1$H NMR (DMSO-$d_6$, peak areas normalized using the overlapping peak at δ 8.45 as 1H): δ 7.37 (m, 3H), 7.72 (d, J=8.8 Hz, 2H), 7.86 (d, J=8.8 Hz, 2H), 8.18 E(d, J=14.2 Hz, 0.21H), 8.45 (m, 1H), 8.96 Z (s, 0.79H), 9.14 Z (d, J=13.5 Hz, 0.79H), 9.48 E (s, 0.21H), 10.7 E (m, 0.21H), 10.98 Z (d, J=13.5 Hz, 0.79H), 11.88 E(s, 0.21H), 12.11 Z(s, 0.79H), 14.7 (brs, 1H); $C_{14}H_{12}N_4O_3S$: APES+MS m/z 317 (M+H).

EXAMPLE 2A

4-{[(2-Oxo-1,2-dihydro-3H-pyrrolo[2,3-c]pyridin-3-ylidene)methyl]amino}benzenesulfonamide a) 3-Nitro-4-pyridinyl-propanedioic acid diethyl ester:

To a suspension of 3.05 g of 60% sodium hydride (76.0 mmol) in toluene (50 mL) in a 250 mL RB flask was added 12.2 g of diethyl malonate (76.0 mmol) dropwise. The reaction mixture was stirred for 30 min under nitrogen, and a solution of 10.8 g of 4-chloro-3-nitropyridine (prepared according to the procedure of Houston et al. J. Med. Chem. 1985, 28, 467) in toluene (50 mL) was added dropwise and the resulting mixture refluxed for 4 hours. The reaction mixture was concentrate, and the residue was partitioned between 100 mL each of dilute hydrochloric acid and diethyl ether. The aqueous phase was extracted twice with 100 mL of ether, and the combined ether phases were dried over magnesium sulfate and concentrated to give a dark oil. This was chromatographed on silica gel eluting with a hexane-30% hexane/EtOAc gradient to give 3.5 g of the title compound as a colorless oil which crystallized on standing. $^1$H NMR (DMSO-$d_6$): δ 1.15 (t, J=7.1 Hz, 6H), 4.16 (q, J=7.1 Hz, 4H), 5.55 (s, 1H), 7.59 (d, J=5.1 Hz, 1H), 8.89 (d, J=5.1 Hz, 1H), 9.24 (s, 1H); $C_{12}H_{14}N_2O_6$: APES-MS m/z 281 (M−H).

b) 3-Nitro-4-pyridineacetic acid ethyl ester:

To a 100 ml RB flask was added 1.5 g (5.3 mmol) of 3-nitro-4-pyridinyl-propanedioic acid diethyl ester, 0.450 g (10.6 mmol) of lithium chloride, 0.095 g (5.3 mmol) of water and 35 mL of DMSO. The solution was heated at 100° C. for 4 h. The cooled reaction mixture was diluted with ethyl acetate (50 mL) and washed successively with water (50 mL) and brine (50 mL). The organic phase was dried over sodium sulfate, filtered and concentrated, and the residue was chromatographed on silica gel eluting with a hexane-10% EtOAc/hexane gradient to give 0.76 g of the title compound as a yellow solid. $^1$H NMR (DMSO-$d_6$): δ 1.14 (t, J=7.1 Hz, 3H), 4.06 (q, J=7.1 Hz, 2H), 4.12 (s, 2H), 7.63 (d, J=4.9 Hz, 1H), 8.82 (d, J=4.9 Hz, 1H), 9.21 (s, 1H); $C_9H_{10}N_2O_4$: APES+MS m/z 211 (M+H).

c) 3-Amino-4-pyridineacetic acid ethyl ester:

To a 250-ml Parr flask was added 0.30 g (1.4 mmol) of 3-nitro-4-pyridineacetic acid ethyl ester, 50 mg of 10% palladium on charcoal and 100 mL of ethanol. The mixture was subjected to hydrogenation using a Parr hydrogenator at 40 PSI for 15 min. The mixture was filtered through celite, and the filtrate was concentrated to give an oil which crystallised under a high vacuum to afford 0.282 g of the title compound as a yellow solid. $^1$H NMR (DMSO-$d_6$): δ 1.15 (t, J=7.2 Hz, 3H), 3.52 (s, 2H), 4.05 (q, J=7.2 Hz, 2H), 5.11 (s, 2H), 6.89 (d, J=4.8 Hz, 1H), 7.67 (d, J=4.8 Hz, 1H), 7.92 (s, 1H).

d) 1,6-diazainden-2(3H)-one hydrochloride:

To a 50-ml round-bottom flask was added 0.36 g (2.0 mmol) of 3-amino-4-pyridineacetic acid ethyl ester, 15 mL of ether and 10 mL of 10% hydrochloric acid. The resulting biphasic solution was stirred for 16 hours at room temperature. The two phases were separated, and the ether phase was washed with 5 mL of water. The combined aqueous phases were evaporated to dryness to yield 0.285 g of the title compound as a brown solid. $^1$H NMR (DMSO-$d_6$): δ 5.93 (s, 1H), 7.59 (d, J=5.6 Hz, 1H), 8.02 (s, 1H), 8.49 (d, J=5.6 Hz, 1H), 12.54 (s, 1H), 14.0 (bs, 1H); $C_8H_6N_2O$: APCI+MS: m/z 135 (M+H).

e) 3-Dimethylamino-methylene-1,6-diazainden-2(3H)-one:

To a suspension of 0.080 g (0.47 mmol) of 1,6-diazainden-2(3H)-one in 10 mL of DMF was added 1.2 g (6.0 mmol) of N,N-dimethylformamide-di-t-butyl acetal. The mixture was stirred at ambient temperature for 2 hours, and a dark oil deposited. The DMF was removed under high vacuum, and the residue was passed through a silica gel pad, eluting with ethyl acetate:methanol (1:1). The yellow fractions were pooled, and removal of solvent in vacuo left a brown solid (0.12 g): $^1$H NMR (DMSO-$d_6$): δ 3.3 (s, 6H), 7.35 (d, J=5.0, 1H), 7.80 (bs, 1H), 7.91 (s, 1H), 7.95 (d, J=5.0, 1H), 10.32 (bs, 1H); $C_{10}H_{11}N_3O$: APES+MS: m/z 190 (M+H).

f) 4-{[(2-Oxo-1,2-dihydro-3H-pyrrolo[2,3-c]pyridin-3-ylidene)methyl]amino}-benzenesulfonamide:

To a 25-ml round-bottom flask was added 0.12 g (0.47 mmol) of 3-dimethylaminomethylene-1,6-diazainden-2 (3H)-one, 0.081 g (0.47 mmol) of sulfanilamide, 10 ml of ethanol and two drops of concentrated hydrochloric acid. The reaction mixture was refluxed using an oil bath with stirring for 3 hours, then cooled and filtered. The collected solid was dissolved in a minimum volume of hot methanol. Upon cooling, a dark material deposited. The methanol solution was decanted and diluted to twice its volume with ethyl acetate. A light brown solid deposited after standing for 48 hours. The solid was isolated by filtration, dried, and redissolved in hot methanol (30 mL). The solution was concentrated to 20 mL and diluted with an equal volume of ethyl acetate. On cooling, a tan solid formed. The solid was isolated by filtration and washed with methanol/ethyl acetate to give 25 mg (17%) of the title compound. $^1$H NMR (DMSO-$d_6$): δ 7.42 (s, 2H), 7.82 (d, J=8.5 Hz, 2H), 7.90 (d, J=8.5 Hz, 2H), 8.28 (s, 1H), 8.11 (d, J=6.0 Hz, 1H), 8.38 (d, J=6.0 Hz, 1H), 9.35 (d, J=13.5 Hz, 1H), 11.53 (s, 1H), 11.60 (d, J=13.5 Hz, 1H), 14.6 (brs, 1H); $C_{14}H_{12}N_4O_3S$: APCI-MS m/z 315 (M−H).

EXAMPLE 3A

4-{[(2-Oxo-1,2-dihydro-3H-pyrrolo[2,3-b]pyridin-3-ylidene)methyl]amino}benzenesulfonamide Dimethylformamide di-tert-butyl acetal (180 mg, 0.89 mmol) was added to a solution of 1,2-dihydro-3H-pyrrolo[2,3-b]pyridin-2-one (70 mg, 0.52 mmol) in 0.25 ml DMF, and the reaction mixture was slowly warmed to 100° C. The cooled solution was then diluted with 5 ml of ethanol. Sulfanilamide (172 mg, 1.00 mmol) and methanesulfonic acid (60 mg, 0.63 mmol) were added, and the reaction mixture was stirred at reflux for 2 hours. The cooled solution was diluted with 4 ml of water, treated with $NaHCO_3$ (70 mg, 0.83 mmol) and stirred 10 min. The resulting solid was filtered, washed with water and ethanol, and then suspended in boiling methanol and filtered upon cooling. Inorganics were removed by filtration through a short silica gel column, eluting with DMF. The resulting solution was diluted with an equal volume of ice water, and the suspension was refrigerated overnight. The solid was isolated by filtration and dried to give 36 mg (21%) of the title compound as a yellow solid: $^1$H NMR (400 MHz, DMSO-$d_6$) (4:1 ratio of Z:E isomers): δ (Z) 11.07 (s, 1H), 10.76 (d, J=12.4 Hz, 1H), 8.67 (d, J=12.5 Hz, 1H), 7.92 (d, J=5.1 Hz, 1H), 7.84 (d, J=7.3 Hz,

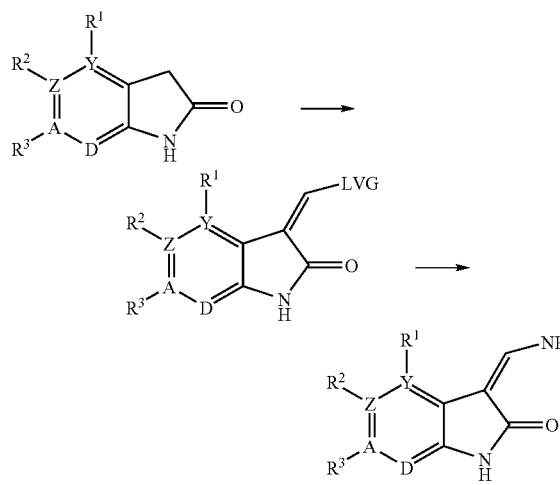

1H), 7.77 (d, J=8.7 Hz, 2H), 7.55 (d, J=8.6 Hz, 2H), 7.25 (s, 2H), 6.93 (dd, J=7.3, 5.1 Hz, 1H); (E) 10.79 (s, 1H), 9.70 (d, J=13.4 Hz, 1H), 8.23 (d, J=7.3 Hz, 1H). ESI-MS m/z 315 (M−H). Anal. Calcd. for $C_{14}H_{12}N_4O_3S \cdot 0.5H_2O$: C, 51.68; H, 4.03; N, 17.03. Found: C, 51.75; H, 3.95; N, 17.26.

Compounds Prepared Via Solution Phase Library Techniques (Parallel Synthesis)

We now set forth a selected number of synthesis examples that illustrate the solution library techniques that can be used to obtain the compounds of Formula (F) of the invention. It is believed that one of ordinary skill in the art will, in view of the synthesis scheme set forth below (Scheme A), be able to follow this procedure or modify it accordingly without undue experimentation in order to obtain any of the substitutions disclosed above. The following examples are illustrative examples of the solution phase synthesis, not intended to limit the scope of the invention in any way.

Scheme A. Preparation of Pyrrolopyridinones Via Solution Phase Library Techniques We refer now to formulae (I), (II), and (III) above, wherein $R^1$, $R^2$, $R^3$, Y, Z, A, D and Ar are as defined hereinabove, and wherein LVG is a leaving group selected form the group consisting of: $OCH_3$, $OCH_2CH_3$, OH, and $N(CH_3)_2$.

Synthesis of Intermediates:

5-Bromo-1,3-dihydro-2H-pyrrolo[2,3-b]pyridin-2-one a) 3,3,5-Tribromo-1,3-dihydro-2H-pyrrolo[2,3-b]pyridin-2-one A solution of 3,3-dibromo-1,3-dihydro-2H-pyrrolo[2,3-b]pyridin-2-one (5.0 g, 13.4 mmol) in tert-BuOH (100 mL) and water (100 mL) was stirred at room temperature and bromine (5.5 g, 34.3 mmol) was added dropwise over 20 min. A saturated aqueous solution of sodium bicarbonate (approx. 15 mL) was added dropwise over 30 min to raise the pH of the solution to 6.5. The yellow solid formed was collected by filtration. The filtrate was condensed to approx. 100 mL and extracted with $CHCl_3$ (2×50 mL). The combined organic extracts were dried over anhydrous magnesium sulfate, and the solvent was evaporated under reduced pressure to leave a yellow solid. The solids were combined and dried under vacuum to give 3,3,5-tribromo-1,3-dihydro-2H-pyrrolo[2,3-b]pyridin-2-one as a yellow solid, 6.25 g (98%). $^1$H NMR ($CDCl_3$) δ 9.4 (br s, 1H), 8.28 (d, 1H, J=2 Hz), 7.95 (d, 1H, J=2 Hz).

b) 5-Bromo-1,3-dihydro-2H-pyrrolo[2,3-b]pyridin-2-one

A solution of 3,3,5-tribromo-1,3-dihydro-2H-pyrrolo[2,3-b]pyridin-2-one (5.0 g, 13.4 mmol) in fresh THF (100 mL) was stirred at room temperature, and a saturated aqueous solution of ammonium chloride (100 mL) was added. The flask was placed in a water bath, and activated zinc dust (15.0 g, 230 mmol) was added. The mixture was stirred for 20 min, and the zinc was removed by filtration through a pad of diatomaceous earth. The organic layer was separated, and the aqueous layer was extracted with THF (20 mL). The combined organic layers were washed with saturated brine solution and dried over anhydrous magnesium sulfate. Solvent was removed under reduced pressure. The brown residue was triturated with water (20 mL), and the tan solid was collected by filtration and dried under vacuum to give the title compound as a tan solid, 2.02 g (71%). $^1$H NMR ($d_6$-DMSO) δ 11.13 (s, 1H), 8.15 (s, 1H), 8.76 (s, 1H), 3.57 (s, 2H). MS (AP −ve) 211 (100) (M−H).

5-Phenyl-1,3-dihydro-2H-pyrrolo[2,3-b] pyrid in-2-one

To a stirred mixture of 5-bromo-1,3-dihydro-2H-pyrrolo [2,3-b]pyridin-2-one (213 mg, 1 mmol) and phenylboronic acid (183 mg, 1.5 mmol) in toluene (6 ml) and ethanol (6 ml) were added 1 M sodium carbonate solution (2.5 ml, 2.5 mmol), lithium chloride (127 mg, 3 mmol) and dichlorobis (triphenylphosphine)-palladium(II) (35 mg, 0.05 mmol) under $N_2$ atmosphere. The reaction mixture was heated to reflux at 95° C. for 18 hours. The reaction mixture was diluted with chloroform (50 ml) and washed with brine (20 ml). The aqueous layer was thoroughly extracted with chloroform. The combined organic layers were dried over anhydrous $MgSO_4$, filtered and evaporated under vacuum to give crude product. Trituation of the crude product with diethyl ether yielded 5-phenyl-1,3-dihydro-2H-pyrrolo[2,3-b]pyridin-2-one as a yellow solid (108 mg, 51.4%). $^1$H NMR ($d_6$-DMSO): δ 11.04 (s, 1H), 8.32 (s, 1H), 7.83 (s, 1H), 7.60 (d, 2H, J=7.4 Hz), 7.44 (t, 2H, J=7.4 Hz), 7.32 (t, 1H, J=7.4 Hz), 3.58 (s, 2H). MS (−ve APCI): 210 (48, M$^+$), 209 (100, M−H).

5-(2-Furyl)-1,3-dihydro-2H-pyrrolo[2,3-b]pyridin-2-one

5-Bromo-1,3-dihydro-2H-pyrrolo[2,3-b]pyridin-2-one (0.75 g, 3.52 mmol), 2-tributyltinfuran (1.26 g, 3.52 mmol), tetraethylammonium chloride hydrate (1.94 g, 10.6 mmol) were combined and dissolved in acetonitrile (10 mL) at room temperature under an atmosphere of nitrogen. Bistriphenylphosphine dichloropalladium (II) (0.25 g, 0.35 mmol) was added, and the reaction was warmed to 85° C. for 16 hours. The reaction was cooled to room temperature and diluted with aqueous KF (10%, 60 mL). This was stirred for 20 minutes and then diluted with EtOAc (60 mL). The biphasic system was passed through celite, the layers separated, and the volatiles removed in vacuo. The resulting residue was triturated with diethyl ether, and the solids were collected by filtration to afford the title compound as a light yelow solid (0.28 g, 36% yield). $^1$H NMR 300 MHz (DMSO-$d_6$): δ 11.18 (bs, 1H); 8.45 (s, 1H); 7.92 (s, 1H); 7.79 (s, 1H); 6.95 (d, 1H); 6.60 (d, 1H); 3.64 (s, 2H). APCI m/z 201 (M+1).

5-(3-thienyl)-1,3-dihydro-2H-pyrrolo[2,3-b]pyridin-2-one

5-Bromo-1,3-dihydro-2H-pyrrolo[2,3-b]pyridin-2-one (0.20 g, 0.94 mmol), 3-tributyltinthiophene (0.42 g, 1.12 mmol), tetraethylammonium chloride hydrate (0.16 g, 0.94 mmol) were combined and dissolved in acetonitrile (10 mL)

at room temperature under nitrogen. Bistriphenylphosphine dichloropalladium (II) (0.033 g, 0.047 mmol) was added, and the reaction was warmed to 85° C. for 20 hours. Fresh catalyst (bistriphenylphosphine dichloropalladium (II), 0.033 g, 0.047 mmol) was added to the reaction mixture, and the reaction was stirred at 85° C. for 24 hours. The reaction was cooled to room temperature and diluted with water (20 mL) and EtOAc (20 ml). The biphasic system was passed through celite, and the layers were separated. The organic layer was washed with brine (10 mL) and dried over sodium sulfate. The volatiles were removed in vacuo. The resulting residue was triturated with diethyl ether and collected by filtration to provide the title compound (0.16 g, 80% yield). $^1$H NMR 400 MHz (DMSO-d$_6$) δ 11.03 (bs, 1H); 8.43 (s, 1H); 7.92 (s, 1H); 7.84 (s, 1H); 7.60 (m, 1H); 7.53 (d, 1H); 3.58 (s, 2H).

Ethyl 2-oxo-2,3-dihydro-1H-pyrrolo[2,3-b]pyridine-5-carboxylate

To a mixture of 5-bromo-1,3-dihydro-2H-pyrrolo[2,3-b]pyridin-2-one (213 mg, 1 mmol) in dimethylsulfoxide (1 ml) and ethanol (5 ml) in Parr bomb were added triethylamine (0.31 ml, 2.25 mmol), palladium acetate (33.7 mg, 0.15 mmol), and 1,4-(bisdiphenylphosphino)propane (61.9 mg, 0.15 mmol). Carbon monoxide gas (40 atm) was applied and the reaction mixture was heated at 95° C. for 18 hours with vigorous stirring. The reaction mixture was diluted with diethyl ether (50 ml) and washed with water (10 ml). The aqueous layer was thoroughly extracted with diethyl ether. The combined organic layers were dried over anhydrous MgSO$_4$, filtered and evaporated under vacuum to give crude product. Trituration of the crude product with methanol provided the title compound as a tan solid (53 mg, 26%). $^1$H NMR (d$_6$-DMSO): δ 11.39 (s, 1H), 8.62 (s, 1H), 7.95 (s, 1H), 4.27 (q, 2H, J=7 Hz), 3.59 (s, 2H), 1.28(t, 3H, J=7 Hz). MS(−ve APCI): 205 (4, M−H).

1,3-Dihydro-2H-pyrrolo[2,3-b]pyridin-2-one a) 3,3-dibromo-1,3-dihydro-2H-pyrrolo[2,3-b]pyridin-2-one A solution of pyrrolo[2,3-b]pyridine (4.0 g, 34 mmol) in tert-BuOH (200 mL) was stirred at room temperature and pyridinium perbromide (32.5 g, 0.1 mol) was added in portions over 30 min, and the reaction mixture was stirred for 3 hours. Pyridinium perbromide (10.8 g, 33 mmol) was added, and the mixture was stirred for a further 2 hours. The tert-BuOH was evaporated under reduced pressure, and the residue was partitioned between water (300 mL) and EtOAc (300 mL). The organic layer was separated, and the aqueous layer was extracted with EtOAc. The combined organic layers were washed with water (2×50 mL) and brine The organic layer was dried over anhydrous MgSO$_4$ and filtered, and the solvent was evaporated. Trituration of the residue with CH$_2$Cl$_2$ gave a white solid which was collected by filtration and dried under vacuum to provide 8.35 g of the title compound. $^1$H NMR (d$_6$-DMSO) δ 11.99 (s, 1H), 8.21 (dd, 1H, J=5.1,1.5 Hz), 8.00 (dd, 1H, J=7.5, 1.5 Hz), 7.17 (dd, 1H, J=7.5, 5.1 Hz). MS (+ve ES) 293 (28), (M+H) 147 (100).

b) 1,3-Dihydro-2H-pyrrolo[2,3-b]pyridin-2-one

A solution of 3,3-dibromo-1,3-dihydro-2H-pyrrolo[2,3-b]pyridin-2-one (2.0 g, 7.2 mmol) in THF (50 mL) was stirred at room temperature, and a saturated aqueous solution of NH$_4$Cl was added. Activated zinc powder was added, and the reaction mixture was stirred for 2 hours. The zinc was removed by filtration through a pad of diatomaceous earth, and the organic layer was separated. The aqueous layer was extracted with THF (10 mL), and the combined organic layers were dried over anhydrous MgSO$_4$, filtered and evaporated. The residue was slurried in 10:1 CHCl$_3$:MeOH (15 mL) and filtered through a pad of silica gel, and the filtrate was evaporated. The residue was triturated with water, and the solid was collected by filtration and dried under vacuum to give the title compound, 0.668 g (70%). $^1$H NMR (d$_6$-DMSO) δ 10.94 (s, 1H), 8.02 (d, 1H, J=5.2 Hz), 7.52 (d, 1H, J=6.8 Hz), 6.90 (dd, 1H, J=6.8, 5.2 Hz), 3.53 (s, 2H). MS (AP−ve) 133 (100) (M−H)

1,3-Dihydro-2H-pyrrolo[3,2-b]pyridin-2-one a) Diethyl (3-nitropyridin-2-yl)-malonate Sodium hydride (60% dispersion in oil, 5.57 g, 0.14 mol) was carefully washed with hexanes under nitrogen before the addition of DMSO (115 mL). Diethyl malonate (22.3 g, 0.14 mol) was added dropwise over 20 min, and the mixture was stirred for an additional 30 min at room temperature. 2-Chloro-3-nitropyridine (10 g, 0.06 mol) was added to the reaction, and the reaction was placed in a pre-heated oil bath set to 100° C. for 15 min. The reaction was cooled to room temperature and poured into aqueous ammonium chloride (saturated solution, 150 mL). The aqueous solution was extracted with EtOAc:hexanes (1:1) four times (200 mL each), and the organic layers were combined. The organics were concentrated to afford a solid that was recrystallized from a minimal amount of EtOAc:hexanes (1:1) to provide the title compound (12.5 g, 70% yield). APCI MS m/z 281 (M−H).

b) Ethyl 2-(3-nitro-pyridin-2-yl)-acetate

Diethyl (3-nitropyridin-2-yl)-malonate (12.5 g, 0.044 mol) was dissolved in DMSO (150 mL), and water (0.79 mL, 0.044 mol) and lithium chloride (4.65 g, 0.11 mol) were added at room temperature under nitrogen. The reaction was warmed to 100° C. for 12 hours, and more lithium chloride (1 g) was added to the reaction. The reaction was heated for another 5 hours and cooled to room temperature. Brine (150 mL) was added, and the reaction mixture was extracted with EtOAc (3×275 mL). The extracts were combined, dried over sodium sulfate and concentrated in vacuo. The resulting residue was triturated with diethyl ether and collected by filtration to yield the title compound (8.6 g, 92% yield). $^1$H NMR 400 MHz (DMSO-d$_6$): δ 8.83 (m, 1H); 8.53 (m, 1H); 7.65 (m, 1H); 4.23 (s, 2H); 4.07 (m, 2H); 1.16 (m, 3H).

c) Ethyl 2-(3-amino-pyridin-2-yl)-acetate

Under an atmosphere of nitrogen, Pd/C (10%, 1.36 g) was added to a round bottom flask. Ethyl 2-(3-nitro-pyridin-2-yl)-acetate (8.6 g, 0.41 mol) was dissolved in ethanol (200 mL) and added to the reaction vessel. The reaction was placed under an atmosphere of hydrogen and stirred at room temperature for 30 min. The reaction was filtered through celite, and the filtrate was concentrated in vacuo to afford the title compound as a tan solid (6.94 g, 94% yield).

d) 1,3-Dihydro-2H-pyrrolo[3,2-b]pyridin-2-one

Ethyl 2-(3-amino-pyridin-2-yl)-acetate (6.94 g, 0.038 mol) was dissolved in diethyl ether (100 mL) at room temperature. Hydrochloric acid (2M, 35 mL) was added, and the reaction was stirred for 30 minutes. The volatiles were removed to afford a brown solid that was recrystallized from ethanol and diethyl ether to provide the title compound (4.0 g, 62% yield). $^1$H NMR 400 MHz (DMSO-d$_6$): δ 12.35 (s, 1H); 8.12 (m, 1H); 7.90 (m, 1H); 7.14 (m, 1H); 5.75 (s, 2H).

Electrospray MS m/z 135 (M+H).

6-Chloro-1,3-dihydro-2H-pyrrolo[2,3-b] pyridin-2-one a) 3,3-Dibromo-6-chloro-1,3-dihydro-2H-pyrrolo[2,3-b]pyridin-2-one To a stirred solution of 1.32 g (8.7 mmol) of 6-chloro-1H-pyrrolo[2,3-b]pyridine (Minakata et al., Synthesis 1992, 661–663) in tert-butanol (80 mL) was added 9.9 g (28 mmol) of 90% pyridine hydrobromide perbromide, resulting in immediate formation of a thick yellow precipitate. The reaction was concentrated, and the crude residue was chromatographed on silica gel, eluting with a hexane to 90% hexane/10% EtOAc gradient, to give 2.36 g of the title compound as a white solid [$^1$H NMR (CDCl$_3$): δ 7.16 (d, J=8.0 Hz, 1H), 7.81 (d, J=8.0 Hz, 1H), 9.0 (bs, 1H)] containing about 30% of 3,3,5-tribromo-6-chloro-1,3-dihydro-2H-pyrrolo[2,3-b]pyridin-2-one as an inseparable impurity [$^1$H NMR δ 8.05 (s, 1H), 9.0 (bs, 1H)].

b) 6-Chloro-1,3-dihydro-2H-pyrrolo[2,3-b]pyridin-2-one

A solution of 2.36 g (7.26 mmol) of the mixture of 3,3-dibromo-6-chloro-1,3-dihydro-2H-pyrrolo[2,3-b]pyridin-2-one and 3,3,5-tribromo-6-chloro-1,3-dihydro-2H-pyrrolo[2,3-b]pyridin-2-one in THF (70 mL) and saturated ammonium chloride solution (70 mL) was treated with 6 g (92 mmol) of powdered zinc. The mixture was stirred for 2 hours, and another 6 g (92 mmol) portion of zinc was added. Stirring was continued another 2 hours. The zinc was filtered off and washed with ether. The ether phase was separated, and the aqueous phase was extracted twice with a 1:1 mixture of THF/ether. The combined organic extracts were dried over magnesium sulfate, filtered and concentrated. The crude residue was loaded onto 7.5 g of silica gel and chromatographed on silica gel, eluting with a 90% hexane/10% ethyl acetate to 66% hexane/33% ethyl acetate gradient to give 0.647 g of the title compound. $^1$H NMR (DMSO-d$_6$): δ 3.57 (s, 2H), 7.04 (d, J=7.6 Hz, 1H), 7.61 (d, J=7.6 Hz, 1H), 11.2 (bs, 1H).

Synthesis of Monomers:

Ethyl 3-[(Z)-ethoxymethylidene]-2-oxo-1,2-dihydro-3H-pyrrolo[2,3-b]pyridine-5-carboxylate (Procedure A)

Ethyl 2-oxo-2,3-dihydro-1H-pyrrolo[2,3-b]pyridine-5-carboxylate (0.040 g, 0.19 mmol) and diethoxymethyl acetate (0.16 mL, 0.97 mmol) were combined and dissolved in acetic acid (1 mL). The reaction was warmed to 110° C. and stirred at this temperature for 1 hour. The reaction was cooled to room temperature, and diethyl ether was added to precipitate the title compound as a beige solid that was collected by filtration (35 mg, 69% yield). $^1$H NMR 400 MHz (DMSO-d$_6$): δ 11.30 (s, 1H); 8.58 (s, 1H); 8.05 (s, 1H); 7.93 (s, 1H); 4.44 (m, 2H); 4.28 (m, 2H); 1.35 (m, 3H); 1.28 (m, 3H).

3-[Ethoxymethylidene]-5-phenyl-1H-pyrrolo[2,3-b]pyridin-2-one

This compound was synthesized from 5-phenyl-1,3-dihydro-2H-pyrrolo[2,3-b]pyridin-2-one and diethoxymethyl acetate according to Procedure A. $^1$H NMR 400 MHz (DMSO-d$_6$): δ 10.93 (s, 1H); 8.24 (s, 1H); 7.86–7.82 (m, 2H); 7.62–7.56 (m, 2H); 7.44 (m, 2H); 7.34 (m, 1H); 4.40 (m, 2H); 1.35 (m, 3H).

3-[Ethoxymethylid ene]-5-(2-furyl)-1H-pyrrolo[2,3-b]pyridin-2-one

This compound was synthesized from 5-(2-furyl)-1,3-dihydro-2H-pyrrolo[2,3-b]pyridin-2-one and diethoxymethyl acetate according to Procedure A. $^1$H NMR 400 MHz (DMSO-d$_6$): δ 10.96 (s, 1H); 8.36 (s, 1H); 7.87–7.84 (m, 2H); 7.72 (s, 1H); 6.87 (d, 1H); 6.56 (m, 1H); 4.42 (m, 2H); 1.36 (m, 3H).

3-[Ethoxymethylidene]-5-(3-thienyl)-1H-pyrrolo[2,3-b]pyridin-2-one

This compound was synthesized from 5-(3-thienyl)-1H-pyrrolo[2,3-b]pyridin-2-one and diethoxymethyl acetate according to Procedure A. $^1$H NMR 400 MHz (DMSO-d$_6$): δ 10.89 (s, 1H); 8.33 (s, 1H); 7.88 (s, 1H); 7.84 (s, 1H); 7.79 (s, 1H); 7.62 (m, 1H); 7.49 (d, 1H); 4.40 (m, 2H); 1.36 (m, 3H).

5-Bromo-3-[ethoxymethylidene]-1H-pyrrolo[2,3-b]pyridin-2-one

This compound was synthesized from 5-bromo-1H-pyrrolo[2,3-b]pyridin-2-one and and diethoxymethyl acetate according to Procedure A. $^1$H NMR 400 MHz (DMSO-d$_6$): δ 11.02 (s, 1H); 8.07 (s, 1H); 7.88 (s, 1H); 7.71 (s, 1H); 4.40 (m, 2H); 1.34 (m, 3H).

6-Chloro-3-[ethoxymethylidene]-1H-pyrrolo[2,3-b] pyridin-2-one

This compound was synthesized from 6-chloro-1H-pyrrolo[2,3-b]pyridin-2-one and diethoxymethyl acetate according to Procedure A. $^1$H NMR 400 MHz (DMSO-d$_6$): δ 11.06 (s, 1H); 7.84 (s, 1H); 7.63 (d, 1H); 6.98 (d, 1H); 4.39 (m, 2H); 1.32 (m, 3H).

3-[(Dimethylamino)methylidene]-1H-pyrrolo[2,3-b]pyridin-2-one

This compound was prepared in situ (during library synthesis) from 1,3-dihydro-2H-pyrrolo[2,3-b]pyridin-2-one and dimethylformamide di-t-butylacetal in DMF.

3-[(Dimethylamino)methylidene]-1H-pyrrolo[3,2-b]pyridin-2-one

This monomer was generated in situ (during library synthesis) from 1,3-dihydro-2H-pyrrolo[3,2-b]pyridin-2-one and dimethylformamide di-t-butylacetal in DMF.

Solution Phase Library Synthesis:

The compounds of Formula (F) described here were prepared as part of a larger library of related compounds using the following procedure. Stock solutions (0.037M in ethanol) were prepared for each set of pyrrolopyridinone monomers. For the aniline set (4-aminobenzenesulfonamide, 1H-indazol-6-amine, and 6-quinolinamine), a slight excess of stock solution was prepared.

3-[(Dimethylamino)methylidene]-1H-pyrrolo[2,3-b]pyridin-2-one and 3-[(dimethylamino)methylidene]-1H-pyrrolo[3,2-b]pyridin-2-one were generated in situ by preparing stock solutions of the corresponding pyrrolopyridinone. For example, 20.1 mg of 1,3-dihydro-2H-pyrrolo[3,2-b]pyridinone was dissolved in 4.0 mL of ethanol. Both of the pyrrolopyridinones were transferred (0.20 ml/well) to a 96-well dry heating block (vwrBRAND Dry Block Heater, cat #13259–066). The ethanol was evaporated off at 50° C. until it was clear that there was no solvent remaining. DMF (0.20 mL) was added followed by the addition of dimethylformamide di-t-butylacetal (0.003 mL), and this remained at room temperature for 1 hour.

The ethoxymethylidenepyrrolopyridinones (0.20 mL/well) were transferred to wells in the dry block heater. The aniline set (0.20 mL/well) was transferred to the appropriate wells such that each pyrrolopyridinone was reacted with each aniline. The plates were heated to 70° C. for 4 hours, and then the reaction was cooled to 40° C. and heating was continued for another 16 hours. Ethanol was added as necessary to keep a constant reaction volume in the wells.

Upon completion of the reaction, methanol (1.0 mL) was added to each well. Using a multi-pipettor, the contents of the reaction wells were transferred to the appropriate wells of a 96-well (Beckmann) plate. The volatiles were removed using a nitrogen flow to substantially reduce the volume of solvent, followed by placing the plates in a vacuum drying oven at 70° C. under 15 mm Hg of pressure. All of the wells were analysed by LC-MS.

EXAMPLE 3A

3-[(1H-Indazol-6-ylamino)methylidene]-1H-pyrrolo[3,2-b]pyridin-2-one

High resolution masspec: calc. for $C_{15}H_{11}N_5O$, 278.1042 (M+H); found, 278.1036.

EXAMPLE 4A

3-[(6-Quinolinylamino)methylidene]-1,3-dihydro-2H-pyrrolo[3,2-b]pyridin-2-one

High resolution masspec: calc. for $C_{17}H_{12}N_4O$, 289.1089 (M+H); found, 289.1085.

EXAMPLE 6A

3-[(1H-Indazol-6-ylamino)methylidene]-1H-pyrrolo[2,3-b]pyridin-2-one

High resolution masspec: calc. for $C_{15}H_{11}N_5O$, 278.1042 (M+H); found, 278.1033.

EXAMPLE 7A

3-[(6-Quinolinylamino)methylidene]-1,3-dihydro-2H-pyrrolo[2,3-b]pyridin-2-one

High resolution masspec: calc. for $C_{17}H_{12}N_4O$, 289.1089 (M+H); found, 289.1079.

EXAMPLE 8A

4-{[(2-Oxo-5-phenyl-1,2-dihydro-3H-pyrrolo[2,3-b]pyridin-3-ylidene)methyl]amino}benzenesulfonamide High resolution masspec: calc. for $C_{20}H_{16}N_4O_3S$, 393.1021 (M+H); found, 393.1003.

EXAMPLE 9A

3-[(1H-Indazol-6-ylamino)methylidene]-5-phenyl-1H-pyrrolo[2,3-b]pyridin-2-one

High resolution masspec: calc. for $C_{21}H_{15}N_5O$, 354.1355 (M+H), found, 354.1336.

EXAMPLE 10A

5-Phenyl-3-[(6-quinolinylamino)methylidene]-1,3-dihydro-2H-pyrrolo[2,3-b]pyridin-2-one High resolution masspec: calc. for $C_{23}H_{16}N_4O$, 365.1402 (M+H); found, 365.1396.

EXAMPLE 11A 4-({[5-(2-Furyl)-2-oxo-1,2-dihydro-3H-pyrrolo[2,3-b]pyridin-3-ylidene]methyl}amino)benzenesulfonamide High resolution masspec: calc. for $C_{18}H_{14}N_4O_4S$, 383.0814 (M+H); found, 383.0800.

EXAMPLE 12A 5-(2-Furyl)-3-[(1H-indazol-6-ylamino)methylidene]-1H-pyrrolo[2,3-b]pyridin-2-one Low resolution masspec: 344 (M+H).

EXAMPLE 13A 5-(2-Furyl)-3-[(6-quinolinylamino)methylidene]-1,3-dihydro-2H-pyrrolo[2,3-b]pyridin-2-one High resolution masspec: calc. for $C_{21}H_{14}N_4O_2$, 355.1195 (M+H); found, 355.1182.

EXAMPLE 14A 4-({[2-Oxo-5-(3-thienyl)-1,2-dihydro-3H-pyrrolo[2,3-b]pyridin-3-ylidene]methyl}amino)benzenesulfonamide Low resolution masspec: 399 (M+H).

EXAMPLE 15A

3-[(1H-Indazol-6-ylamino)methylidene]-5-(3-thienyl)-1,3-dihydro-2H-pyrrolo[2,3-b]pyridin-2-one High resolution masspec: calc. for $C_{11}H_{13}N_5OS$, 360.0919 (M+H); found, 360.0903.

EXAMPLE 16A

3-[(6-Quinolinylamino)methylidene]-5-(3-thienyl)-1,3-dihydro-2H-pyrrolo[2,3-b]pyridin-2-one High resolution masspec: calc. for $C_{21}H_{14}N_4OS$, 371.0966 (M+H); found, 371.0956.

EXAMPLE 17A

4-{[(5-Bromo-2-oxo-1,2-dihydro-3H-pyrrolo[2,3-b]pyridin-3-ylidene)methyl]amino}benzenesulfonamide High resolution masspec: calc. for $C_{14}H_{11}BrN_4O_3S$, 394.9813 (M+H); found, 394.9792.

EXAMPLE 18A

5-Bromo-3-[(1H-indazol-6-ylamino)methylidene]-1,3-dihydro-2H-pyrrolo[2,3-b]pyridin-2-one High resolution masspec: calc. for $C_{15}H_{10}BrN_5O$, 356.0146 (M+H); found, 356.0135.

EXAMPLE 19A

5-Bromo-3-[(6-quinolinylamino)methylidene]-1,3-dihydro-2H-pyrrolo[2,3-b]pyridin-2-one High resolution masspec: calc. for $C_{17}H_{11}BrN_4O$, 367.0194 (M+H); found, 367.0177.

EXAMPLE 20A

4-{[(6-Chloro-2-oxo-1,2-dihydro-3H-pyrrolo[2,3-b]pyridin-3-ylidene)methyl]amino}benzenesulfonamide High resolution masspec: calc. for $C_{14}H_{11}ClN_4O_3S$, 351.0318 (M+H); found, 351.0315.

EXAMPLE 21A

6-Chloro-3-[(1H-indazol-6-ylamino)methylidene]-1,3-dihydro-2H-pyrrolo[2,3-b]pyridin-2-one High resolution masspec: calc. for $C_{15}H_{10}ClN_5O$, 312.0652 (M+H); found, 312.0628.

EXAMPLE 22A

6-Chloro-3-[(6-quinolinylamino)methylidene]-1,3-dihydro-2H-pyrrolo[2,3-b]pyridin-2-one High resolution masspec: calc. for $C_{17}H_{11}ClN_4O$, 323.0699 (M+H); found, 323.0697.

EXAMPLE 23A

Ethyl 3-{[4-(aminosulfonyl)anilino]methylidene}-2-oxo-1,2-dihydro-3H-pyrrolo[2,3-b]pyridine-5-carboxylate High resolution masspec: calc. for $C_{17}H_{16}N_4O_5S$, 389.0919 (M+H); found, 389.0914.

EXAMPLE 24A

Ethyl 3-[(1H-indazol-6-ylamino)methylidene]-2-oxo-1,2-dihydro-3H-pyrrolo[2,3-b]pyridine-5-carboxylate High resolution masspec: calc. for $C_{18}H_{11}N_5O_3$, 350.1253 (M+H); found, 350.1241.

EXAMPLE 25A

Ethyl 2-oxo-3-[(6-quinolinylamino)methylidene]-2,3-dihydro-1H-pyrrolo[2,3-b]pyridine-5-carboxylate High resolution masspec: calc. for $C_{20}H_{16}N_4O_3$, 361.1300 (M+H); found, 361.1299.

Compounds of formula (F) are effective at inhibiting the CDK2 enzyme at concentrations which range from 0.01 to 3 UM and additionally show specificity relative to other kinases. Substrate phosphorylation assays were carried out as previously described, with the results set out in Table 3A below, illustrating the inhibitory activity of compounds of formula (F) against three different kinases (CDK2, c-fms, and VEGFR2).

TABLE 3A

Kinase inhibition data of representative compounds of formula (F)

| Example | CDK2 | C-FMS | VEGFR2 |
|---|---|---|---|
| 1A | +++ | | + |
| 2A | +++ | | |
| 3A | | | + |
| 4A | | | + |
| 5A | ++ | | + |
| 6A | | + | ++ |
| 7A | | | + |
| 8A | + | | |
| 9A | | + | |
| 10A | | + | |
| 11A | +++ | ++ | + |
| 12A | + | + | ++ |
| 13A | | + | + |
| 14A | ++ | ++ | ++ |
| 15A | ++ | + | + |
| 16A | | ++ | + |
| 17A | +++ | + | ++ |
| 18A | +++ | + | ++ |
| 19A | +++ | + | ++ |
| 20A | ++ | | ++ |
| 21A | ++ | + | ++ |
| 22A | | + | + |
| 23A | +++ | + | ++ |
| 24A | +++ | + | +++ |
| 25A | ++ | | ++ |

Key ($IC_{50}$, µM)
0.01–0.1: +++
0.1–1.0: ++
1.0–10: +

When the CDK2 inhibitor compounds are used to combat alopecia and/or mucositis in conjunction with the administration of chemotherapeutic agents or radiation therapy for cancer treatment, the CDK 2 inhibitor compounds may be utilized to provide a secondary means of suppressing tumor growth either when administered simultaneously with the chemotherapeutic agents, or in an alternating regimen to suppress tumor growth between chemotherapeutic or radiation treatments.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for cancer conditions, or for other indications for the compounds of the invention as indicated above. Likewise, the specific pharmacologic responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

While the invention has been described herein with reference to specific features, aspects and embodiments, it will be appreciated that the scope of the invention is not thus limited, but rather extends to and encompasses other variations, modifications and other embodiments. Accordingly, the invention is to be correspondingly interpreted and constructed as including all such variations, modifications and other embodiments within its spirit and scope as hereinafter claimed.

BIBLIOGRAPHY

Throughout this specification various references have been cited, and the disclosures of all such references, as well as the following references, are incorporated herein by reference.

Cline, B. W., Prevention of chemotherapy-induced alopecia: A review of the literature, Cancer Nursing/June 1984, pp. 221–227.

Gray, N. S., et al., Exploiting Chemical Libraries, Structure, and Genomics in the Search for Kinase Inhibitors, Science, Vol. 284, 24 July 1998, pp. 533–538.

Hussein, A. M., Chemotherapy-induced Alopecia: New Developments, Southern Medical Journal, May 1993, Vol. 86, No. 5, pp. 489496.

Hussein, A. M., et al., Protection from Chemotherapy-Induced Alopecia in a Rat Model, Science, Vol.249, Sep. 28, 1990, pp. 1564–1566.

Lauer, A. C., et al., Transfollicular Drug Delivery, Pharmaceutical Research, Vol. 12, No. 2, 1995, pp. 179–186.

Li, L., et al., The feasibility of targeted selective gene therapy of the hair follicle, Nature Medicine, Volume 1, No. 7, July 1995, pp. 705–706.

Palumbo, Giuseppe A., et al., The Tyrphostin AG17 Induces Apoptosis and Inhibition of cdk2 Activity in a Lymphoma Cell Line That Overexpresses bcl-2, Cancer Research 57, 2434–2339, Jun. 15, 1997.

Roberts, James M., et al., U.S. Pat. No. 5,861,259 issued Jan. 19, 1999.

Sawaya, M. E., Alopecia—the search for novel agents continues, Exp. Opin. Ther. Patents (1997) 7(8):859–872, Ashley Publications Ltd.

Sedlacek, Hans H., et al., Flavopiridol (L86 82875; NSC 649890), a new kinase inhibitor for tumor therapy, International Journal of Oncology 9: 1143–1168, 1996.

Toledo, Leticia M., et al., Structures of staurosporine bound to CDK2 and cAPK—new tools for structure-based design of protein kinase inhibitors, Structure 1997, Vol. 5 No. 12, pp. 1551–1556.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for cancer conditions, or for other indications for the compounds of the invention as indicated above. Likewise, the specific pharmacologic responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

The invention claimed is:

1. A method of treating the severity of alopecia side-effects of chemotherapy and/or radiation therapy, in a subject receiving such therapy, comprising administering to said subject an effective amount of a cyclin-dependent kinase II inhibitor, wherein said inhibitor is a compound of the formula (I)

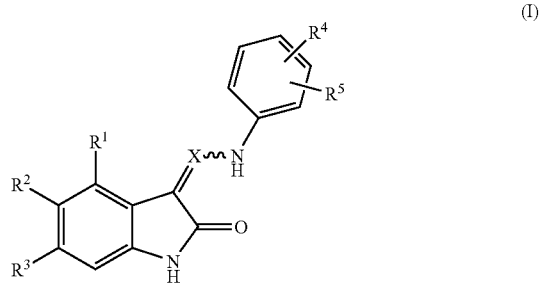

wherein

X is N, CH, $CCF_3$, or $C(C_{1-12}$ aliphatic);

$R^1$ is hydrogen, $C_{1-12}$ aliphatic, thiol, hydroxy, hydroxy-$C_{1-12}$ aliphatic, Aryl, Aryl-$C_{1-12}$ aliphatic, $R^6$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $c_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, halogen, cyano, sulfonamide, or nitro, where $R^6$, Aryl, Cyc and Het are as defined below;

$R^2$ is hydrogen, $C_{1-12}$ aliphatic, N-hydroxymino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Aryl-oxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl, or $C_{1-12}$ aliphatic-aminosulfonyl, where Aryl and Het are as defined below;

further wherein $R^1$ and $R^2$ are optionally joined to form a fused ring, said fused ring selected from the group as defined for Het below, or any of said fused rings optionally substituted by halogen, nitro, cyano, $C_{1-12}$ alkoxy, carbonyl-$C_{1-12}$ alkoxy or oxo;

$R^3$ is hydrogen, $C_{1-12}$ aliphatic, hydroxy, hydroxy $C_{1-12}$ aliphatic, di-$C_{1-12}$ aliphatic amino, di-$_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

further wherein $R^2$ and $R^3$ are optionally joined to form a fused ring, said fused ring selected from the group as defined for Het below, or any of said fused rings optionally substituted by $C_{1-6}$ aliphatic or $C_{1-6}$ aliphatic-carbonyl;

with the proviso that $R^1$, $R^2$ and $R^3$ cannot simultaneously be H;

$R^4$ is sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, $R^7$-sulfonyl, $R^7$-sulfonyl-$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Aryl-aminosulfonyl, $(R^8)_{1-3}$-Aryl-sulfonylamino, Het-amino, Het-sulfonyl, Het-aminosulfonyl, aminoiminoamino, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring selected from the group as defined for Het below, or any of said used rings optionally substituted by $C_{1-12}$ aliphatic, oxo or dioxo;

$R^6$ is $C_{1-12}$ aliphatic, hydroxy, $C_{1-12}$ alkoxy, or halogen;

$R^7$ is hydrogen, $C_{1-12}$ aliphatic, $C_{1-12}$ alkoxy, hydroxy-$C_{1-12}$alkoxy, hydroxy-$C_{1-12}$ aliphatic, carboxylic acid, $C_{1-12}$ aliphatic-carbonyl, Het, Het-$C_{1-12}$ aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic, or hydroxyl where Het and Aryl are as defined below;

$R^6$ is hydrogen, nitro, cyano, $C_{1-12}$ alkoxy, halo, carbonyl-$C_{1-12}$ alkoxy or halo-$C_{1-12}$ aliphatic;

Aryl is phenyl, naphthyl, phenanthryl or anthracenyl;

Cyc is cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatrizole, thiazine, thiazole, thiomorpholine, thiophene, thiopyran, triazine and triazole with the proviso that when $R^2$ is thiadiazine, then $R^4$ cannot be methylsulfone;

and the pharmaceutically acceptable salts, biohydrolyzable esters, biohydrolyzable amides, biahydrolyzable carbamates solvates, hydrates, affinity reagents or prodrugs thereof in either crystalline or amorphous form.

2. The method of claim 1, wherein said cyclin-dependent kinase II inhibitor is topically administered to the scalp to prevent/reduce the severity of chemotherapy-induced alopecia.

3. The method of claim 1, wherein said cyclin-dependent kinase II inhibitor is topically administered to the scalp to prevent/reduce the severity of radiation therapy-induced alopecia.

4. The method of claim 1, wherein said cyclin-dependent kinase II inhibitor is characterised by at least one of the following IC50 characteristics:

(a) an IC50 value of less than 2.5 nanoMolar against CDK2; and (b) an IC50 value of less than 1.5 micromolar in a G1 checkpoint assay.

5. The method of claim 1, wherein said administration of the cyclin-dependent kinase II inhibitor comprises non-systemic administration.

* * * * *

UNITED STATES PATENT AND TRADEMARK OFFICE
CERTIFICATE OF CORRECTION

PATENT NO. : 7,105,529 B2  
APPLICATION NO. : 09/999331  
DATED : September 12, 2006  
INVENTOR(S) : Davis et al.

Page 1 of 1

It is certified that error appears in the above-identified patent and that said Letters Patent is hereby corrected as shown below:

On the Title page:

Item (56) should be inserted as follows:

(56) References Cited
OTHER PUBLICATIONS (cont'd)
-- Zindy *et al.*, Biochemical & Biophysical Research Communications, 1992, 182, pp. 1144-1154. --

In the Claims:

Claim 1 (Column 230, Line 28) should read as follows:

-- $R^2$ is hydrogen, $C_{1-12}$ aliphatic, N-hydroxyimino-$C_{1-12}$ --

Claim 1 (Column 230, Line 48) should read as follows:

-- aliphatic, di-$C_{1-12}$ aliphatic amino, di-$C_{1-12}$ aliphatic --

Claim 1 (Column 231, Line 22) should read as follows:

-- $R^8$ is hydrogen, nitro, cyano, $C_{1-12}$ alkoxy, halo, carbonyl- --

Claim 4 (Column 232, Line 25) should read as follows:

-- (b) an IC50 value of less than 1.5 microMolar in a G1 --

Signed and Sealed this

Fourth Day of December, 2007

JON W. DUDAS  
*Director of the United States Patent and Trademark Office*